(12) United States Patent
Jayyosi et al.

(10) Patent No.: US 7,005,440 B1
(45) Date of Patent: Feb. 28, 2006

(54) THERAPEUTIC USES OF TRI-ARYL ACID DERIVATIVES

(75) Inventors: Zaid Jayyosi, Flemington, NJ (US); Gerard M. McGeehan, Chester Springs, PA (US); Michael F. Kelley, West Chester, PA (US); Richard F. Labaudiniere, Collegeville, PA (US); Litao Zhang, Kennett Square, PA (US); Robert D. Groneberg, Boulder, CO (US); Daniel G. McGarry, King of Prussia, PA (US); Thomas J. Caulfield, Paris (FR); Anne Minnich, Flemington, NJ (US); Mark Bobko, Exton, PA (US); Robert Morris, Wayne, PA (US)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 306 days.

(21) Appl. No.: 09/724,496

(22) Filed: Nov. 28, 2000

Related U.S. Application Data

(63) Continuation of application No. PCT/US00/11490, filed on Apr. 28, 2000.

(60) Provisional application No. 60/131,454, filed on Apr. 28, 1999.

(51) Int. Cl.
  *A01N 43/76* (2006.01)

(52) U.S. Cl. ............ 514/375; 514/279; 514/247; 514/248; 548/217; 544/242; 544/249

(58) Field of Classification Search ............. 548/236, 548/217; 514/374, 252.01, 824, 866, 375, 514/279, 247, 248; 544/242, 249
See application file for complete search history.

(56) References Cited

U.S. PATENT DOCUMENTS

| | | | |
|---|---|---|---|
| 4,920,131 A | * | 4/1990 | Huang et al. ............ 514/311 |
| 5,051,427 A | * | 9/1991 | Huang et al. ............ 514/311 |
| 5,508,408 A | | 4/1996 | von Sprecher et al. |
| 6,376,512 B1 | * | 4/2002 | Jayyosi et al. ............ 514/311 |

FOREIGN PATENT DOCUMENTS

| | | |
|---|---|---|
| EP | 0 643 045 | 3/1995 |
| WO | WO 89/04303 | 5/1989 |
| WO | WO 89/05294 | 6/1989 |
| WO | WO 89/12629 | 12/1989 |
| WO | WO 92/22533 | 12/1992 |
| WO | WO 97/24331 | 7/1997 |
| WO | WO 97/27857 | 8/1997 |
| WO | WO 97/28149 | 8/1997 |
| WO | WO 97/31907 | 9/1997 |
| WO | WO 9731907 A1 * | 9/1997 |
| WO | WO 98/27974 | 7/1998 |
| WO | WO 99/07357 | 2/1999 |
| WO | WO 99/08501 | 2/1999 |
| WO | WO 99/20275 | 4/1999 |
| WO | WO 00/64888 | 11/2000 |

OTHER PUBLICATIONS

Co-pending U.S. Appl. No. 09/490,897, filed on Jan. 27, 2000.
Co-pending U.S. Appl. No. 09/622,649, filed on Sep. 14, 2000.

* cited by examiner

*Primary Examiner*—James O. Wilson
*Assistant Examiner*—Matthew L. Fedowitz
(74) *Attorney, Agent, or Firm*—Finnegan, Henderson, Farabow, Garrett & Dunner, L.L.P.

(57) ABSTRACT

The use of triaryl acid derivatives of formula (I)

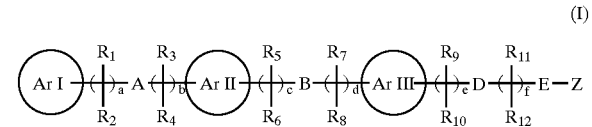

and their pharmaceutical compositions as PPAR ligand receptor binders. The PPAR ligand receptor binders of this invention are useful as agonists or antagonists of the PPAR receptor.

56 Claims, No Drawings

THERAPEUTIC USES OF TRI-ARYL ACID DERIVATIVES

CROSS-REFERENCE TO RELATED APPLICATIONS

This application is a continuation of International Application No. PCT/US00/11490, filed on Apr. 28, 2000, which application, in turn, claims priority from U.S. Provisional Application No. 60/131,454, filed on Apr. 28, 1999.

BACKGROUND OF THE INVENTION

This invention is directed to the use of triaryl acid derivatives and their pharmaceutical compositions as PPAR ligand receptor binders. The PPAR ligand receptor binders of this invention are useful as agonists or antagonists of the PPAR receptor.

FIELD OF THE INVENTION

Peroxisome proliferator-activated receptors (PPAR) can be subdivided into three subtypes, namely: PPARα, PPARδ, and PPARγ. These are encoded by different genes (Motojima, Cell Structure and Function, 18:267–277, 1993). Moreover, 2 isoforms of PPARγ also exist, PPARγ$_1$, and γ$_2$. These 2 proteins differ in their NH$_2$-terminal-30 amino acids and are the result of alternative promoter usage and differential mRNA splicing (Vidal-Puig, Jimenez, Linan, Lowell, Hamann, Hu, Spiegelman, Flier, Moller, J. Clin. Invest., 97:2553–2561, 1996).

Biological processes modulated by PPAR are those modulated by receptors, or receptor 24 combinations, which are responsive to the PPAR receptor ligands described herein. These processes include, for example, plasma lipid transport and fatty acid catabolism, regulation of insulin sensitivity and blood glucose levels, which are involved in hypoglycemia/hyperinsulinism (resulting from, for example, abnormal pancreatic beta cell function, insulin secreting tumors and/or autoimmune hypoglycemia due to autoantibodies to insulin, the insulin receptor, or autoantibodies that are stimulatory to pancreatic beta cells), macrophage differentiation which lead to the formation of atherosclerotic plaques, inflammatory response, carcinogenesis, hyperplasia or adipocyte differentiation.

Obesity is an excessive accumulation of adipose tissue. Recent work in this area indicates that PPARγ plays a central role in the adipocyte gene expression and differentiation. Excess adipose tissue is associated with the development of serious medical conditions, for example, non-insulin-dependent diabetes mellitus (NIDDM), hypertension, coronary artery disease, hyperlipidemia and certain malignancies. The adipocyte may also influence glucose homeostasis through the production of tumor necrosis factor α (TNFα) and other molecules.

Non-insulin-dependent diabetes mellitus (NIDDM), or Type II diabetes, is the more common form of diabetes, with 90–95% of hyperglycemic patients experiencing this form of the disease. In NIDDM there appears to be a reduction in the pancreatic β-cell mass, several distinct defects in insulin secretion or a decrease in tissue sensitivity to insulin. The symptoms of this form of diabetes include fatigue, frequent urination, thirst, blurred vision, frequent infections and slow healing of sores, diabetic nerve damage and renal disease. Resistance to the metabolic actions of insulin is one of the key features of non-insulin dependent diabetes (NIDDM). Insulin resistance is characterised by impaired uptake and utilization of glucose in insulin-sensitive target organs, for example, adipocytes and skeletal muscle, and by impaired inhibition of hepatic glucose output. The functional insulin deficiency and the failure of insulin to supress hepatic glucose output results in fasting hyperglycemia. Pancreatic β-cells compensate for the insulin resistance by secreting increased levels of insulin. However, the β-cells are unable to maintain this high output of insulin, and, eventually, the glucose-induced insulin secretion falls, leading to the deterioration of glucose homeostasis and to the subsequent development of overt diabetes.

Hyperinsulinemia is also linked to insulin resistance, hypertriglyceridaemia and increased plasma concentration of low density lipoproteins. The association of insulin resistance and hyperinsulinemia with these metabolic disorders has been termed "Syndrome X" and has been strongly linked to an increased risk of hypertension and coronary artery disease.

Metformin is known in the art to be used in the treatment of diabetes in humans (U.S. Pat. No. 3,174,901). Metformin acts primarily to decrease liver glucose production. Troglitazone® is known to work primarily on enhancing the ability of skeletal muscle to respond to insulin and take up glucose. It is known that combination therapy comprising metformin and troglitazone can be used in the treatment of abnormalities associated with diabetes (DDT 3:79–88, 1998).

PPARγ activators, in particular Troglitazone®, have been found to convert cancerous tissue to normal cells in liposarcoma, a tumor of fat (PNAS 96:3951–3956, 1999). Furthermore, it has been suggested that PPAR γ activators may be useful in the treatment of breast and colon cancer (PNAS 95:8806–8811, 1998, Nature Medicine 4:1046–1052, 1998).

Moreover, PPARγ activators, for example Troglitazone®, have been implicated in the treatment of polycystic ovary syndrome (PCO). This is a syndrome in women that is characterized by chronic anovulation and hyperandrogenism. Women with this syndrome often have insulin resistance and an increased risk for the development of noninsulin-dependent diabetes mellitus. (Dunaif, Scott, Finegood, Quintana, Whitcomb, J. Clin. Endocrinol. Metab., 81:3299, 1996.

Furthermore, PPARγ activators have recently been discovered to increase the production of progesterone and inhibit steroidogenesis in granulosa cell cultures and therefore may be useful in the treatment of climacteric. (U.S. Pat. No. 5,814,647 Urban et al. Sep. 29, 1998; B. Lohrke et al. Journal of Edocrinology, 159, 429–39, 1998). Climacteric is defined as the syndrome of endocrine, somatic and psychological changes occurring at the termination of the reproductive period in the female.

Peroxisomes are cellular organelles which play a role in controlling the redox potential and oxidative stress of cells by metabolizing a variety of substrates such as hydrogen peroxide. There are a number of disorders associated with oxidative stress. For example, inflammatory response to tissue injury, pathogenesis of emphysema, ischemia-associated organ injury (shock), doxorubicin-induced cardiac injury, drug-induced hepatotoxicity, atherosclerosis, and hyperoxic lung injuries, are each associated with the production of reactive oxygen species and a change in the reductive capacity of the cell. Therefore, it is envisaged that PPARα activators, among other things, regulate the redox potential and oxidative stress in cells, would be effective in the treatment of these disorders (Poynter et al, J. Biol. Chem. 273, 32833–41, 1998).

It has also been discovered that PPARα agonists inhibit NFAB-mediated transcription thereby modulating various inflammatory responses such as the inducible nitric oxide synthase (NOS) and cyclooxygenase-2 (COX-2) enzyme pathways (Pineda-Torra, I. T al, 1999, Curr. Opinion in Lipidology, 10,151–9) and thus can be used in the therapeutic intervention of a wide variety of inflammatory diseases and other pathologies (Colville-Nash, et al., Journal of Immunology, 161, 978–84, 1998; Staels et al, Nature, 393, 790–3, 1998).

Peroxisome proliferators activate PPAR, which in turn, acts as a transcription factor, and causes differentiation, cell growth and proliferation of peroxisomes. PPAR activators are also thought to play a role in hyperplasia and carcinogenesis as well as altering the enzymatic capability of animal cells, such as rodent cells, but these PPAR activators appear to have minimal negative effects in human cells (Green, Biochem. Pharm. 43(3):393, 1992). Activation of PPAR results in the rapid increase of gamma glutamyl transpeptidase and catalase.

PPARα is activated by a number of medium and long-chain fatty acids and is involved in stimulating β-oxidation of fatty acids in tissues such as liver, heart, skeletal muscle, and brown adipose tissue (Isseman and Green, supra; Beck et al., Proc. R. Soc. Lond. 247:83–87, 1992; Gottlicher et al., Proc. Natl. Acad. Sci. USA 89:4653–4657, 1992). Pharmacological PPARα activators, for example fenofibrate, clofibrate, genfibrozil, and bezafibrate, are also involved in substantial reduction in plasma triglycerides along with moderate reduction in LDL cholesterol, and they are used particularly for the treatment of hypertriglyceridemia, hyperlipidemia and obesity. PPARα is also known to be involved in inflammatory disorders. (Schoonjans, K., Current Opionion in Lipidology, 8, 159–66, 1997).

The human nuclear receptor PPARδ has been cloned from a human osteosarcoma cell cDNA library and is fully described in A. Schmidt et al., Molecular Endocrinology, 6:1634–1641 (1992), the contents of which are hereby incorporated herein by reference. It should be noted that PPARδ is also referred to in the literature as PPARβ and as NUC1, and each of these names refers to the same receptor. For example, in A. Schmidt et al., Molecular Endocrinology, 6: pp. 1634–1641, 1992, the receptor is referred to as NUC1. PPARδ is observed in both embryo and adult tissues. This receptor has been reported to be involved in regulating the expression of some fat-specific genes, and plays a role in the adipogenic process (Amri, E. et al., J. Biol. Chem. 270, 2367–71, 1995).

Atherosclerotic disease is known to be caused by a number of factors, for example, hypertension, diabetes, low levels of high density lipoprotein (HDL), and high levels of low density lipoprotein (LDL). In addition to risk reduction via effects on plasma lipid concentrations and other risk factors, PPARα agonists exert direct atheroprotective effects (Frick, M. H., et al. 1997. Circulation 96:2137–2143, de Faire, et al. 1997. Cardiovasc. Drugs Ther. 11 Suppl 1:257–63:257–263).

It has recently been discovered that PPARδ agonists are useful in raising HDL levels and therefore useful in treating atherosclerotic diseases. (Leibowitz et al.; WO/9728149). Atherosclerotic diseases include vascular disease, coronary heart disease, cerebrovascular disease and peripheral vessel disease. Coronary heart disease includes CHD death, myocardial infarction, and coronary revascularization. Cerebrovascular disease includes ischemic or hemorrhagic stroke and transient ischemic attacks.

PPARγ subtypes are involved in activating adipocyte differentiation, and are not involved in stimulating peroxisome proliferation in the liver. Activation of PPARγ is implicated in adipocyte differentiation through the activation of adipocyte-specific gene expression (Lehmann, Moore, Smith-Oliver, Wilkison, Willson, Kliewer, J. Biol. Chem., 270:12953–12956, 1995). The DNA sequences for the PPARγ receptors are described in Elbrecht et al., BBRC 224;431437 (1996). Although peroxisome proliferators, including fibrates and fatty acids, activate the transcriptional activity of PPAR's, only prostaglandin $J_2$ derivatives such as the arachidonic acid metabolite 15-deoxy-delta$^{12}$, 14-prostaglandin $J_2$ (15d-PGJ$_2$) have been identified as natural ligands specific for the PPARγ subtype, which also binds thiazolidinediones. This prostaglandin activates PPARγ-dependent adipogenesis, but activates PPARα only at high concentrations (Forman, Tontonoz, Chen, Brun, Spiegelman, Evans, Cell, 83:803–812, 1995; Kliewer, Lenhard, Wilson, Patel, Morris, Lehman, Cell, 83:813–819, 1995). This is further evidence that the PPAR family subtypes are distinct from one another in their pharmacological response to ligands.

It has been suggested that compounds activating both PPARα and PPARγ should be potent hypotriglyceridemic drugs, which could be used in the treatment of dyslipidemia associated with atherosclerosis, non-insulin dependent diabetes mellitus, Syndrome X,. (Staels, B. et al., Curr. Pharm. Des., 3 (1), 1–14 (1997)) and familial combined hyperlipidemia (FCH). Syndrome X is the syndrome characterized by an initial insulin resistant state, generating hyperinsulinaemia, dyslipidaemia and impaired glucose tolerance, which can progress to non-insulin dependent diabetes mellitus (Type II diabetes), characterized by hyperglycemia. FCH is characterized by hypercholesterolemia and hypertriglyceridemia within the same patient and family.

The present invention is directed to a series of compounds that are useful in modulating PPAR receptors, as well as to a number of other pharmaceutical uses associated therewith.

SUMMARY OF THE INVENTION

This invention provides new aromatic compounds and pharmaceutical compositions prepared therewith that are PPAR ligand receptor binders, and which are useful as agonists or antagonists of the PPAR receptors. The invention also includes the discovery of new uses for previously known compounds.

The compounds for use according to the invention, including the new compounds of the present invention, are of Formula I

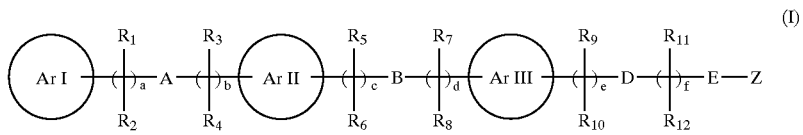

(I)

wherein:

are independently aryl, fused arylcycloalkenyl, fused arylcycloalkyl, fused arylheterocyclenyl, fused arylheterocyclyl, heteroaryl, fused heteroarylcycloalkenyl, fused heteroarylcycloalkyl, fused heteroarylheterocyclenyl, or fused heteroarylheterocyclyl;

A is —O—, —S—, —SO—, —SO$_2$—, —NR$_{13}$—, —C(O)—, —N(R$_{14}$)C(O)—, —C(O)N(R$_{15}$)—, —N(R$_{14}$)C(O)N(R$_{15}$)—, —C(R$_{14}$)=N—,

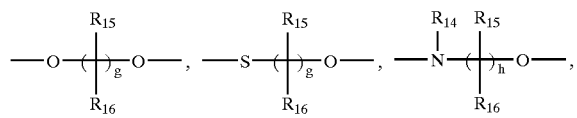

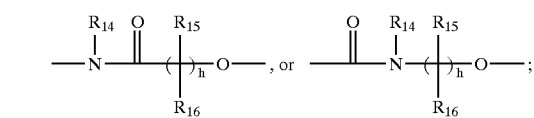

B is —O—, —S—, —SO—, —SO$_2$—, —NR$_{17}$—, a chemical bond, ethynylene, —C(O)—, —N(R$_{18}$)C(O)—, or —C(O)N(R$_{18}$)—;

D is —O—, —S—, —NR$_{19}$—, a chemical bond, ethynylene, —C(O)—, —N(R$_{20}$)C(O)—, or —C(O)N(R$_{20}$)—;

E is a chemical bond or an ethylene group;

a is 0–4;
b is 0–4;
c is 0–4;
d is 0–5;
e is 0–4;
f is 0–6;
g is 1–4;
h is 1–4;

R$_1$, R$_3$, R$_5$, R$_7$, R$_9$, and R$_{11}$, are independently hydrogen, halogen, alkyl, carboxyl, alkoxycarbonyl or aralkyl;

R$_2$, R$_4$, R$_6$, R$_8$, R$_{10}$ and R$_{12}$, are independently —(CH$_2$)$_q$—X;

q is 0–3;

X is hydrogen, halogen, alkyl, alkenyl, cycloalkyl, heterocyclyl, aryl, heteroaryl, aralkyl, heteroaralkyl, hydroxy, alkoxy, aralkoxy, heteroaralkoxy, carboxyl, alkoxycarbonyl, tetrazolyl, acyl, acylHNSO$_2$—, —SR$_{23}$, Y$^1$Y$^2$N— or Y$^3$Y$^4$NCO—;

Y$^1$ and Y$^2$ are independently hydrogen, alkyl, aryl, aralkyl or heteroaralkyl, or one of Y$^1$ and Y$^2$ is hydrogen or alkyl and the other of Y$^1$ and Y$^2$ is acyl or aroyl;

Y$^3$ and Y$^4$ are independently hydrogen, alkyl, aryl, aralkyl or heteroaralkyl;

Z is R$_{21}$O$_2$C—, R$_{21}$OC—, cyclo-imide, —CN, R$_{21}$O$_2$SHNCO—, R$_{21}$O$_2$SHN—, (R$_{21}$)$_2$NCO—, R$_{21}$O—2,4-thiazolidinedionyl, or tetrazolyl; and R$_{19}$ and R$_{21}$, are independently hydrogen, alkyl, aryl, cycloalkyl, or aralkyl;

R$_{13}$, R$_{17}$, R$_{19}$ and R$_{23}$ are independently R$_{22}$OC—, R$_{22}$NHOC—, hydrogen, alkyl, aryl, heteroaryl, cycloalkyl, heterocyclyl, heteroaralkyl, or aralkyl;

R$_{14}$, R$_{15}$, R$_{16}$, R$_{18}$ and R$_{20}$ are independently hydrogen, alkyl, aralkyl, carbonyl, or alkoxycarbonyl;

or R$_{14}$, and R$_{15}$ taken together with the carbon and nitrogen atoms through which they are linked form a 5 or 6-membered azaheterocyclyl group; or when a is 2–4, then vicinal R$_1$ radicals taken together with the carbon atoms to which the R$_1$ radicals are linked form an ethylene group; or when b is 2–4, then vicinal R$_3$ radicals taken together with the carbon atoms to which the R$_3$ radicals are linked form an ethylene group; or when c is 2–4, then vicinal R$_5$ radicals taken together with the carbon atoms to which the R$_5$ radicals are linked form an ethylene group; or when d is 2–5, then vicinal R$_7$ radicals taken together with the carbon atoms to which the R$_7$ radicals are linked form an ethylene group; or when e is 2–4, then vicinal R$_9$ radicals taken together with the carbon atoms to which the R$_9$ radicals are linked form an ethylene group; or when f is 2–6, then vicinal R$_{11}$ radicals taken together with the carbon atoms to which the R$_{11}$ radicals are linked form an ethylene group; and R$_{22}$ is hydrogen, alkyl, aryl, heteroaryl, cycloalkyl, heterocyclyl, heteroaralkyl, or aralkyl; or a pharmaceutically acceptable salt thereof, an N-oxide thereof, a hydrate thereof or a solvate thereof.

DETAILED DESCRIPTION OF THE INVENTION

As employed above and throughout the disclosure, the following terms, unless otherwise indicated, shall be understood to have the following meanings:

Definitions

In the present specification, the term "compounds for use according to the invention", and equivalent expressions, are meant to embrace compounds of general Formula (I) as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

"Prodrug" means a compound which is convertible in vivo by metabolic means (e.g. by hydrolysis) to a compound of Formula (I), including N-oxides thereof. For example an ester of a compound of Formula (I) containing a hydroxy group may be convertible by hydrolysis in vivo to the parent molecule. Alternatively an ester of a compound of Formula (I) containing a carboxy group may be convertible by hydrolysis in vivo to the parent molecule.

"Patient" includes both human and other mammals.

"Chemical bond" means a direct single bond between atoms.

"Acyl" means an H—CO— or alkyl-CO— group wherein the alkyl group is as herein described. Preferred acyls contain a lower alkyl. Exemplary acyl groups include formyl, acetyl, propanoyl, 2-methylpropanoyl, butanoyl and palmitoyl.

"Alkenyl" means an aliphatic hydrocarbon group containing a carbon—carbon double bond and which may be a straight or branched chain having about 2 to about 15 carbon atoms in the chain. Preferred alkenyl groups have 2 to about 12 carbon atoms in the chain and more preferably about 2 to about 4 carbon atoms in the chain. Branched means that one or more lower alkyl groups such as methyl, ethyl or propyl are attached to a linear alkenyl chain. "Lower alkenyl" means about 2 to about 4 carbon atoms in the chain, which may be straight or branched. The alkenyl group is optionally substituted by one or more halo groups. Exemplary alkenyl groups include ethenyl, propenyl, n-butenyl, i-butenyl, 3-methylbut-2-enyl, n-pentenyl, heptenyl, octenyl and decenyl.

"Alkoxy" means an alkyl —O— group wherein the alkyl group is as herein described. Exemplary alkoxy groups include methoxy, ethoxy, n-propoxy, i-propoxy, n-butoxy and heptoxy.

"Alkoxycarbonyl" means an alkyl-O—CO— group, wherein the alkyl group is as herein defined. Exemplary alkoxycarbonyl groups include methoxycarbonyl, ethoxycarbonyl, or t-butyloxycarbonyl.

"Alkyl" means an aliphatic hydrocarbon group which may be a straight or branched chain having about 1 to about 20 carbon atoms in the chain. Preferred alkyl groups have 1 to about 13 carbon atoms in the chain. Branched means that one or more lower alkyl groups such as methyl, ethyl or propyl are attached to a linear alkyl chain. "Lower alkyl" means that there are about 1 to about 4 carbon atoms in the chain, which may be straight or branched. The alkyl is optionally substituted with one or more "alkyl group substituents" which may be the same or different, and include halo, carboxy, cycloalkyl, cycloalkenyl, heterocyclyl, heterocyclenyl, aryl, alkoxy, alkoxycarbonyl, aralkoxycarbonyl, heteroaralkoxycarbonyl, $Y^1Y^2$ NCO—, wherein $Y^1$ and $Y^2$ are independently hydrogen, alkyl, aryl, aralkyl or heteroaralkyl, or —$Y^1$ and $Y^2$ taken together with the nitrogen atom to which Y and $Y^2$ are attached form heterocyclyl. Exemplary alkyl groups include methyl, trifluoromethyl, ethyl, n-propyl, i-propyl, n-butyl, t-butyl, n-pentyl, and 3-pentyl. Preferably, the alkyl group substituent is selected from acyl, halo, carboxy, carboxymethyl, methoxycarbonylethyl, benzyloxycarbonylmethyl, and pyridylmethyloxycarbonylmethyl and alkoxycarbonyl.

"Alkylsulfinyl" means an alkyl-SO— group wherein the alkyl group is as defined above. Preferred groups are those wherein the alkyl group is lower alkyl.

"Alkylsulfonyl" means an alkyl-$SO_2$-group wherein the alkyl group is as defined above. Preferred groups are those wherein the alkyl group is lower alkyl.

"Alkylthio" means an alkyl-S— group wherein the alkyl group is as defined above. Exemplary alkylthio groups include methylthio, ethylthio, i-propylthio and heptylthio.

"Aralkoxy" means an aralkyl-O— group wherein the aralkyl group is as defined herein. Exemplary aralkoxy groups include benzyloxy and 1- and 2-naphthalenemethoxy.

"Aralkoxycarbonyl" means an aralkyl-O—CO— group wherein the aralkyl group is as defined herein. An exemplary aralkoxycarbonyl group is benzyloxycarbonyl.

"Aralkyl" means an aryl-alkyl-group wherein the aryl and alkyl groups are as defined herein. Preferred aralkyls contain a lower alkyl moiety. Exemplary aralkyl groups include benzyl, 2-phenethyl and naphthalenemethyl.

"Aralkylsulfonyl" means an aralkyl-$SO_2$— group wherein the aralkyl group is as defined herein.

"Aralkylsulfinyl" means an aralkyl-SO— group wherein the aralkyl group is as defined herein.

"Aralkylthio" means an aralkyl-S— group wherein the aralkyl group is as defined herein. An exemplary aralkylthio group is benzylthio.

"Aroyl" means an aryl-CO— group wherein the aryl group is as defined herein. Exemplary aroyl groups include benzoyl and 1- and 2-naphthoyl.

"Aryl" means an aromatic monocyclic or multicyclic ring system of about 6 to about 14 carbon atoms, preferably of about 6 to about 10 carbon atoms. The aryl is optionally substituted with one or more "ring system substituents" which may be the same or different, and are as defined herein. Exemplary aryl groups include phenyl, naphthyl, substituted phenyl, and substituted naphthyl.

"Aryldiazo" means an aryl-diazo-group wherein the aryl and diazo groups are as defined herein.

"Fused arylcycloalkenyl" means a fused aryl and cycloalkenyl as defined herein. Preferred fused arylcycloalkenyls are those wherein the aryl thereof is phenyl and the cycloalkenyl consists of about 5 to about 6 ring atoms. A fused arylcycloalkenyl group may be bonded to the rest of the compound through any atom of the fused system capable of such bondage. The fused arylcycloalkenyl may be optionally substituted by one or more ring system substituents, wherein the "ring system substituent" is as defined herein. Exemplary fused arylcycloalkenyl groups include 1,2-dihydronaphthylenyl; indenyl; 1,4-naphthoquinonyl, and the like.

"Fused arylcycloalkyl" means a fused aryl and cycloalkyl as defined herein. Preferred fused arylcycloalkyls are those wherein the aryl thereof is phenyl and the cycloalkyl consists of about 5 to about 6 ring atoms. A fused arylcycloalkyl group may be bonded to the rest of the compound through any atom of the fused system capable of such bonding. The fused arylcycloalkyl may be optionally substituted by one or more ring system substituents, wherein the "ring system substituent" is as defined herein. Exemplary fused arylcycloalkyl and substituted fused arylcycloalkyl groups include 1,2,3,4-tetrahydronaphthyl; 1,4-dimethyl-2,3-dihydronaphthyl; 2,3-dihydro-1,4-naphthoquinonyl, α-tetralonyl, tetralonyl and the like.

"Fused arylheterocyclenyl" means a fused aryl and heterocyclenyl wherein the aryl and heterocyclenyl groups are as defined herein. Preferred fused arylheterocyclenyl groups are those wherein the aryl thereof is phenyl and the heterocyclenyl consists of about 5 to about 6 ring atoms. A fused arylheterocyclenyl group may be bonded to the rest of the compound through any atom of the fused system capable of such bonding. The designation of aza, oxa or thia as a prefix before the heterocyclenyl portion of the fused arylheterocyclenyl means that a nitrogen, oxygen or sulfur atom respectively, is present as a ring atom. The fused arylheterocyclenyl may be optionally substituted by one or more ring system substituents, wherein the "ring system substituent" is as defined herein. The nitrogen atom of a fused arylheterocyclenyl may be a basic nitrogen atom. The nitrogen or sulphur atom of the heterocyclenyl portion of the fused arylheterocyclenyl is also optionally oxidized to the corresponding N-oxide, S-oxide or S,S-dioxide. Exemplary fused arylheterocyclenyl and substituted fused arylheterocyclenyl groups include 3H-indolinyl, 2(1H)quinolinonyl, 4-oxo-1,4-dihydroquinolinyl, 2H-1-oxoisoquinolyl, 1,2-dihydroquinolinyl, (2H)quinolinyl N-oxide, 3,4-dihydroquinolinyl, 1,2-dihydroisoquinolinyl, 3,4-dihydroisoquinolinyl, chromonyl, 3,4-dihydroisoquinoxalinyl, 4(3H) quinazolinonyl, 4H-chromen-2yl, and the like. Preferably, 2(1H)quinolinonyl, 1,2-dihydroquinolinyl, (2H)quinolinyl N-oxide, or 4-(3H)quinazolinonyl.

"Fused arylheterocyclyl" means a fused aryl and heterocyclyl wherein the aryl and heterocyclyl groups are as defined herein. Preferred fused arylheterocyclyls are those wherein the aryl thereof is phenyl and the heterocyclyl consists of about 5 to about 6 ring atoms. A fused arylheterocyclyl may be bonded to the rest of the compound through any atom of the fused system capable of such bonding. The designation of aza, oxa or thia as a prefix before the heterocyclyl portion of the fused arylheterocyclyl means that a nitrogen, oxygen or sulphur atom respectively is present as a ring atom. The fused arylheterocyclyl group may be optionally substituted by one or more ring system substituents, wherein the "ring system substituent" is as defined herein. The nitrogen atom of a fused arylheterocyclyl may be a basic nitrogen atom. The nitrogen or sulphur atom of the heterocyclyl portion of the fused arylheterocyclyl is also optionally oxidized to the corresponding N-oxide, S-oxide or S,S-dioxide. Exemplary fused arylheterocyclyl and substituted fused arylheterocyclyl groups include indolinyl, o-benzoic sulfimidyl, 4-chromanonyl, oxindole, 1,2,3,4-tetrahydroisoquinolinyl, 1,2,3,4-tetrahydroquinolinyl, 1H-2,3-dihydroisoindol-2-yl, 2,3-dihydrobenz[f]isoindol-2-yl, 1,2,3,4-tetrahydrobenz[g]isoquinolin-2-yl, chromanyl, isochromanonyl, 2,3-dihydrochromonyl, 1,4-benzodioxan, 1,2,3,4-tetrahydroquinoxalinyl, and the like. Preferably, 1,2,3,4-tetrahydroisoquinolinyl, 1,2,3,4-tetrahydroquinoxalinyl, and 1,2,3,4-tetrahydroquinolinyl.

"Aryloxy" means an aryl-O— group wherein the aryl group is as defined herein. Exemplary groups include phenoxy and 2-naphthyloxy.

"Aryloxycarbonyl" means an aryl-O—CO— group wherein the aryl group is as defined herein. Exemplary aryloxycarbonyl groups include phenoxycarbonyl and naphthoxycarbonyl.

"Arylsulfonyl" means an aryl-SO₂— group wherein the aryl group is as defined herein.

"Arylsulfinyl" means an aryl-SO— group wherein the aryl group is as defined herein.

"Arylthio" means an aryl-S— group wherein the aryl group is as defined herein. Exemplary arylthio groups include phenylthio and naphthylthio.

"Carbamoyl" is an NH₂—CO— group.

"Carboxy" means a HO(O)C— (carboxylic acid) group.

"Compounds of the invention," and equivalent expressions, are meant to embrace compounds of general Formula (I) as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

"Cycloalkoxy" means an cycloalkyl-O— group wherein the cycloalkyl group is as defined herein. Exemplary cycloalkoxy groups include cyclopentyloxy and cyclohexyloxy.

"Cycloalkenyl" means a non-aromatic mono- or multicyclic ring system of about 3 to about 10 carbon atoms, preferably of about 5 to about 10 carbon atoms, and which contains at least one carbon—carbon double bond. Preferred ring sizes of rings of the ring system include about 5 to about 6 ring atoms. The cycloalkenyl is optionally substituted with one or more "ring system substituents" which may be the same or different, and are as defined herein. Exemplary monocyclic cycloalkenyl include cyclopentenyl, cyclohexenyl, cycloheptenyl, and the like. An exemplary multicyclic cycloalkenyl is norbornylenyl.

"Cycloalkyl" means a non-aromatic mono- or multicyclic ring system of about 3 to about 10 carbon atoms, preferably of about 5 to about 10 carbon atoms. Preferred ring sizes of rings of the ring system include about 5 to about 6 ring atoms. The cycloalkyl is optionally substituted with one or more "ring system substituents" which may be the same or different, and are as defined herein. Exemplary monocyclic cycloalkyl include cyclopentyl, cyclohexyl, cycloheptyl, and the like. Exemplary multicyclic cycloalkyl include 1-decalin, norbornyl, adamant-(1- or 2-)yl, and the like.

"Cycloalkylene" means a bivalent, saturated carbocyclic group having about 3 to about 6 carbon atoms. Preferred cycloalkylene groups include 1,1-, 1,2-, 1,3-, and 1,4-cis or trans-cyclohexylene; and 1,1-, 1,2-, and 1,3-cyclopentylene.

"Cyclo-imide" means a compound of formulae

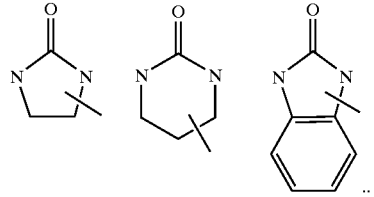

The cyclo-imide moiety may be attached to the parent molecule through either a carbon atom or nitrogen
atom of the carbamoyl moiety. An exemplary imide group is N-phthalimide.

"Diazo" means a bivalent —N=N— radical.

"Halo" means fluoro, chloro, bromo, or iodo. Preferred are fluoro, chloro and bromo, more preferably fluoro and chloro.

"Heteroaralkyl" means a heteroaryl-alkyl-group wherein the heteroaryl and alkyl groups are as defined herein. Preferred heteroaralkyls contain a lower alkyl moiety. Exemplary heteroaralkyl groups include thienylmethyl, pyridylmethyl, imidazolylmethyl and pyrazinylmethyl.

"Heteroaralkythio" means a heteroaralkyl-S— group wherein the heteroaralky group is as defined herein. An exemplary heteroaralkylthio group is 3-pyridinepropanthiol.

"Heteroaralkoxy" means an heteroaralky-O— group wherein the heteroaralkyl group is as defined herein. An exemplary heteroaralkoxy group is 4-pyridylmethyloxy.

"Heteroaroyl" means an means an heteroaryl-CO— group wherein the heteroaryl group is as defined herein. Exemplary heteroaryl groups include thiophenoyl, nicotinoyl, pyrrol-2-ylcarbonyl and 1 and 2-naphthoyl and pyridinoyl.

"Heteroaryldiazo" means an heteroaryl-diazo-group wherein the heteroaryl and diazo groups are as defined herein.

"Heteroaryl" means an aromatic monocyclic or multicyclic ring system of about 5 to about 14 carbon atoms, preferably about 5 to about 10 carbon atoms, in which at least one of the carbon atoms in the ring system is replaced by a hetero atom, i.e., other than carbon, for example nitrogen, oxygen or sulfur. Preferred ring sizes of rings of the ring system include about 5 to about 6 ring atoms. The heteroaryl ring is optionally substituted by one or more "ring system substituents" which may be the same or different, and are as defined herein. The designation of aza, oxa or thia as a prefix before the heteroaryl means that a nitrogen, oxygen or sulfur atom is present, respectively, as a ring atom. A nitrogen atom of an heteroaryl may be a basic nitrogen atom and also may be optionally oxidized to the corresponding N-oxide. Exemplary heteroaryl and substituted heteroaryl groups include pyrazinyl, thienyl, isothiazolyl, oxazolyl, pyrazolyl, cinnolinyl, pteridinyl, benzofuryl, furazanyl, pyrrolyl, 1,2,4-oxadiazolyl, benzoxazole, 1,2,4-thiadiazolyl, pyridazinyl, indazolyl, quinoxalinyl, phthalazinyl, imidazo[1,2-a]pyridine, imidazo[2,1-b]thiazolyl, benzofurazanyl, azaindolyl, benzimidazolyl, benzothienyl, thienopyridyl, thienopyrimidyl, pyrrolopyridyl, imidazopyridyl, naphthyridinyl, benzoazaindole, 1,2,4-triazinyl, benzothiazolyl, furyl, imidazolyl, indolyl, isoindolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl. Preferred heteroaryl and substituted heteroaryl groups include quinolinyl, indazolyl, indolyl, quinazolinyl, pyridyl, pyrimidinyl, furyl, benzothiazolyl, benzoxazole, benzofuryl, quinoxalinyl, benzimidazolyl, 1,2,4-oxadiazolyl, benzothienyl, and isoquinolinyl.

"Fused heteroarylcycloalkenyl" means a fused heteroaryl and cycloalkenyl wherein the heteroaryl and cycloalkenyl groups are as defined herein. Preferred fused heteroarylcycloalkenyls are those wherein the heteroaryl thereof is phenyl and the cycloalkenyl consists of about 5 to about 6 ring atoms. A fused heteroarylcycloalkenyl may be bonded to the rest of the compound through any atom of the fused system capable of such bonding. The designation of aza, oxa or thia as a prefix before the heteroaryl portion of the fused heteroarylcycloalkenyl means that a nitrogen, oxygen or sulfur atom is present, respectively, as a ring atom. The fused heteroarylcycloalkenyl may be optionally substituted by one or more ring system substituents, wherein the "ring system substituent" is as defined herein. The nitrogen atom of a fused heteroarylcycloalkenyl may be a basic nitrogen atom. The nitrogen atom of the heteroaryl portion of the fused heteroarylcycloalkenyl may also be optionally oxidized to the corresponding N-oxide. Exemplary fused heteroarylcycloalkenyl groups include 5,6-dihydroquinolyl; 5,6-dihydroisoquinolyl; 5,6-dihydroquinoxalinyl; 5,6-dihydroquinazolinyl; 4,5-dihydro-1H-benzimidazolyl; 4,5-dihydrobenzoxazolyl; 1,4-naphthoquinolyl, and the like.

"Fused heteroarylcycloalkyl" means a fused heteroaryl and cycloalkyl wherein the heteraryl and cycloalkyl groups are as defined herein. Preferred fused heteroarylcycloalkyls are those wherein the heteroaryl thereof consists of about 5 to about 6 ring atoms and the cycloalkyl consists of about 5 to about 6 ring atoms. A fused heteroarylcycloalkyl may be bonded to the rest of the compoun through any atom of the fused system capable of such bonding. The designation of aza, oxa or thia as a prefix before the heteroaryl portion of the fused heteroarylcycloalkyl means that a nitrogen, oxygen or sulfur atom is present respectively as a ring atom. The fused heteroarylcycloalkyl may be optionally substituted by one or more ring system substituents, wherein the "ring system substituent" is as defined herein. The nitrogen atom of a fused heteroarylcycloalkyl may be a basic nitrogen atom. The nitrogen atom of the heteroaryl portion of the fused heteroarylcycloalkyl may also be optionally oxidized to the corresponding N-oxide. Exemplary fused heteroarylcycloalkyl include 5,6,7,8-tetrahydroquinolinyl; 5,6,7,8-tetrahydroisoquinolyl; 5,6,7,8-tetrahydroquinoxalinyl; 5,6,7,8-tetrahydroquinazolyl; 4,5,6,7-tetrahydro-1H-benzimidazolyl; 4,5,6,7-tetrahydrobenzoxazolyl; 1H-4-oxa-1,5-diazanaphthalen-2-only; 1,3-dihydroimidizole-[4,5]-pyridin-2-only; 2,3-dihydro-1,4-dinaphthoquinonyl and the like, preferably, 5,6,7,8-tetrahydroquinolinyl or 5,6,7,8-tetrahydroisoquinolyl.

"Fused heteroarylheterocyclenyl" means a fused heteroaryl and heterocyclenyl wherein the heteraryl and heterocyclenyl groups are as defined herein. Preferred fused heteroarylheterocyclenyls are those wherein the heteroaryl thereof consists of about 5 to about 6 ring atoms and the heterocyclenyl consists of about 5 to about 6 ring atoms. A fused heteroarylheterocyclenyl may be bonded to the rest of the compound through any atom of the fused system capable of such bonding. The designation of aza, oxa or thia as a prefix before the heteroaryl or heterocyclenyl portion of the fused heteroarylheterocyclenyl means that a nitrogen, oxygen or sulfur atom is present respectively as a ring atom. The fused heteroarylheterocyclenyl may be optionally substituted by one or more ring system substituent, wherein the "ring system substituent" is as defined herein. The nitrogen atom of a fused heteroarylazaheterocyclenyl may be a basic nitrogen atom. The nitrogen or sulphur atom of the heteroaryl or heterocyclenyl portion of the fused heteroarylheterocyclenyl may also be optionally oxidized to the corresponding N-oxide, S-oxide or S,S-dioxide. Exemplary fused heteroarylheterocyclenyl groups include 7,8-dihydro[1,7]naphthyridinyl; 1,2-dihydro[2,7]naphthyridinyl; 6,7-dihydro-3H-imidazo[4,5-c]pyridyl; 1,2-dihydro-1,5-naphthyridinyl; 1,2-dihydro-1,6-naphthyridinyl; 1,2-dihydro-1,7-naphthyridinyl; 1,2-dihydro-1,8-naphthyridinyl; 1,2-dihydro-2,6-naphthyridinyl, and the like.

"Fused heteroarylheterocyclyl" means a fused heteroaryl and heterocyclyl wherein the heteroaryl and heterocyclyl groups are as defined herein. Preferred fused heteroarylheterocyclyls are those wherein the heteroaryl thereof consists of about 5 to about 6 ring atoms and the heterocyclyl consists of about 5 to about 6 ring atoms. A fused heteroarylheterocyclyl may be bonded to the rest of the compound through any atom of the fused system capable of such bonding. The designation of aza, oxa or thia as a prefix before the heteroaryl or heterocyclyl portion of the fused heteroarylheterocyclyl means that a nitrogen, oxygen or sulfur atom is present respectively as a ring atom. The fused heteroarylheterocyclyl may be optionally substituted by one or more ring system substituent, wherein the "ring system substituent" is as defined herein. The nitrogen atom of a fused heteroarylheterocyclyl may be a basic nitrogen atom. The nitrogen or sulphur atom of the heteroaryl or heterocyclyl portion of the fused heteroarylheterocyclyl may also be optionally oxidized to the corresponding N-oxide, S-oxide or S,S-dioxide. Exemplary fused heteroarylheterocyclyl groups include 2,3-dihydro-1H pyrrol[3,4-b]quinolin-2-yl; 1,2,3,4-tetrahydrobenz [b][1,7]naphthyridin-2-yl; 1,2,3,4-tetrahydrobenz [b][1,6]naphthyridin-2-yl; 1,2,3,4-tetrahydro-9H pyrido[3,4-b]indol-2yl; 1,2,3,4-tetrahydro-9H-pyrido[4,3-b]indol-2yl, 2,3,-dihydro-1H-pyrrolo[3,4-b]indol-2-yl; 1H-2,3,4,5-tetrahydroazepino[3,4-b]indol-2-yl; 1H-2,3,4,5-tetrahydroazepino[4,3-b]indol-3-yl; 1H-2,3,4,5-tetrahydroazepino[4,5-b]indol-2 yl, 5,6,7,8-tetrahydro[1,7]napthyridinyl; 1,2,3,4-tetrhydro[2,7]naphthyridyl; 2,3-dihydro[1,4]dioxino[2,3-b]pyridyl; 2,3-dihydro[1,4]dioxino[2,3b]pryidyl; 3,4-dihydro-2H-1-oxa[4,6]diazanaphthalenyl; 4,5,6,7-tetrahydro-3H-imidazo[4,5-c]pyridyl; 6,7-dihydro[5,8]diazanaphthalenyl; 1,2,3,4-tetrahydro[1,5]napthyridinyl; 1,2,3,4-tetrahydro[1,6]

napthyridinyl; 1,2,3,4-tetrahydro[1,7]napthyridinyl; 1,2,3,4-tetrahydro[1,8]napthyridinyl; 1,2,3,4-tetrahydro[2,6]napthyridinyl, and the like.

¹"Heteroarysulfonyl" means an heteroaryl-SO$_2$— group wherein the heteroaryl group is as defined herein. An examplary hetararylsulfonyl groups is 3-pyridinepropansulfonyl.

"Heteroarylsulfinyl" means an heteroaryl —SO— group wherein the heteroaryl group is as defined herein.

"Heteroarylthio" means an heteroaryl —S— group wherein the heteroaryl group is as defined herein. Exemplary heteroaryl thio groups include pyridylthio and quinolinylthio.

"Heterocyclenyl" means a non-aromatic monocyclic or multicyclic hydrocarbon ring system of about 3 to about 10 carbon atoms, preferably about 5 to about 10 carbon atoms, in which at least one or more of the carbon atoms in the ring system is replaced by a hetero atom, for example a nitrogen, oxygen or sulfur atom, and which contains at least one carbon—carbon double bond or carbon-nitrogen double bond. Preferred ring sizes of rings of the ring system include about 5 to about 6 ring atoms. The designation of aza, oxa or thia as a prefix before the heterocyclenyl means that a nitrogen, oxygen or sulfur atom is present respectively as a ring atom. The heterocyclenyl may be optionally substituted by one or more ring system substituents, wherein the "ring system substituent" is as defined herein. The nitrogen atom of an heterocyclenyl may be a basic nitrogen atom. The nitrogen or sulphur atom of the heterocyclenyl is also optionally oxidized to the corresponding N-oxide, S-oxide or S,S-dioxide. Exemplary monocyclic azaheterocyclenyl and substituted monocyclic azaheterocyclenyl groups include 1,2,3,4-tetrahydrohydropyridine, 1,2-dihydropyridyl, 1,4-dihydropyridyl, 1,2,3,6-tetrahydropyridine, 4(3H) pyrimidone, 1,4,5,6-tetrahydropyrimidine, 2-pyrrolinyl, 3-pyrrolinyl, 2-imidazolinyl, 2-pyrazolinyl, and the like. Exemplary oxaheterocyclenyl groups include 3,4-dihydro-2H-pyran, dihydrofuryl, and fluorodihydrofuryl An exemplary multicyclic oxaheterocyclenyl group is 7-oxabicyclo [2.2.1]heptenyl. Exemplary monocyclic thiaheterocycleny rings include dihydrothiophenyl and dihydrothiopyranyl.

"Heterocyclyl" means a non-aromatic saturated monocyclic or multicyclic ring system of about 3 to about 10 carbon atoms, preferably about 5 to about 10 carbon atoms, in which at least one of the carbon atoms in the ring system is replaced by a hetero atom, for example nitrogen, oxygen or sulfur. Preferred ring sizes of rings of the ring system include about 5 to about 6 ring atoms. The designation of aza, oxa or thia as a prefix before the heterocyclyl means that a nitrogen, oxygen or sulfur atom is present respectively as a ring atom. The heterocyclyl may be optionally substituted by one or more "ring system substituents" which may be the same or different, and are as defined herein. The nitrogen atom of an heterocyclyl may be a basic nitrogen atom. The nitrogen or sulphur atom of the heterocyclyl is also optionally oxidized to the corresponding N-oxide, S-oxide or S,S-dioxide. Exemplary monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuryl, tetrahydrothiophenyl, tetrahydrothiopyranyl, and the like. Exemplary multicyclic heterocyclyl rings include 1,4 diazabicyclo-[2.2.2]octane and 1,2-cyclohexanedicarboxylic acid anhydride.

"Ring system substituent" includes hydrogen, alkyl, cycloalkyl, heterocyclyl, aryl, heteroaryl, aralkyl, heteroaralkyl, hydroxy, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, fused cycloalkyl, fused cycloalkenyl, fused heterocyclyl, fused heterocyclenyl, arylazo, heteroarylazo, $R^aR^bN$—, $R^cR^dNCO$—, $R^cO_2CN$—, and $R^cR^dNSO_2$— wherein $R^a$ and $R^b$ are independently hydrogen, alkyl, aryl, aralkyl or heteroaralkyl, or one of $R^a$ and $R^b$ is hydrogen or alkyl and the other of $R^a$ and $R^b$ is aroyl or heteroaroyl. $R^c$ and $R^d$ are independently hydrogen, alkyl, aryl, heteroaryl, cycloalkyl, cycloalkenyl, heterocyclyl, heterocyclenyl, aralkyl or heteroaralkyl. Where the ring is cycloalkyl, cycloalkenyl, heterocyclyl or heterocyclenyl, the ring system substituent may also include methylene ($H_2C$=), oxo (O=), thioxo (S=), on carbon atom(s) thereof. Preferably, the ring substituents are selected from oxo (O=), (lower, alkyl, aryl, alkoxy, aralkoxy, halo, trifluoromethyl, carboxy, alkoxycarbonyl, optionally substituted phenyl, optionally substituted benzyloxy, optionally substituted cyclohexyl, optionally substituted cyclobutyl, optionally substituted heteroaryl, and $R^eO_2CN$—, wherein $R^e$ is cycloalkyl.

"Tetrazolyl" means a group of formula

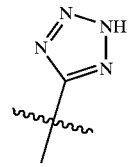

wherein the hydrogen atom thereof is optionally replaced by alkyl, carboxyalkyl or alkoxycarbonylalkyl.

"PPAR ligand receptor binder" means a ligand which binds to the PPAR receptor. PPAR ligand receptor binders of this invention are useful as agonists or antagonists of the PPAR-α, PPAR-δ, or PPAR-γ receptor.

The term "pharmaceutically acceptable salt" refers to a relatively non-toxic, inorganic or organic acid addition salt of a compound of the present invention. A salt can be prepared in situ during the final isolation and purification of a compound or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, laurylsulphonate salts, and the like. (See, for example S. M. Berge, et al., "Pharmaceutical Salts," *J. Pharm. Sci.,* 66: 1–19, 1977, the contents of which are hereby incorporated herein by reference.)

"Treating" means the partial or complete relieving or preventing of one or more physiological or biochemical parameters associated with PPAR activity. The term "modulate" refers to the ability of a compound to either directly (by binding to the receptor as a ligand) or indirectly (as a precursor for a ligand or an inducer which promotes production of a ligand from a precursor) induce expression of gene(s) maintained under hormone control, or to repress expression of gene (s) maintained under such control.

The term "obesity" refers generally to individuals who are at least about 20–30% over the average weight for the person's age, sex and height. Technically, "obese" is defined, for males, as individuals whose body mass index is greater than 27.3 kg/m². Those skilled in the art readily recognize that the invention method is not limited to those who fall within the above criteria. Indeed, the invention method can also be advantageously practiced by individuals who fall outside of these traditional criteria, for example by those who are prone to obesity.

The phrase "amount effective to lower blood glucose levels" refers to levels of a compound sufficient to provide circulating concentrations high enough to accomplish the desired effect. Such a concentration typically falls in the range of about 10 nM up to 2 µM, with concentrations in the range of about 100 nm up to about 500 nM being preferred.

The phrase "amount effective to lower triclyceride levels" refers to levels of a compound sufficient to provide circulating concentrations high enough to accomplish the desired effect. Such a concentration typically falls in the range of about 10 nM up to 2 µM; with concentrations in the range of about 100 nm up to about 500 nM being preferred.

Preferred Embodiments

Preferred embodiments according to the invention includes the use of compounds of Formula I (and their pharmaceutical compositions) as binders for PPAR receptors.

More particularly, the use of compounds of Formula I that bind to the PPAR-α receptor,
compounds of Formula I that bind to the PPAR-δ receptor,
compounds of Formula I that bind to the PPAR-γ receptor,
compounds of Formula I that bind to the PPAR-α and the PPAR-γ receptor,
compounds of Formula I that bind to the PPAR-α and the PPAR-α receptor,
compounds of Formula I that bind to the PPAR-γ and the PPAR-6 receptor,
compounds of Formula I that act as PPAR receptor agonists,
compounds of Formula I that act as PPAR-α receptor agonists,
compounds of Formula I that act as PPAR-δ receptor agonists,
compounds of Formula I that act as PPAR-γ receptor agonists,
compounds of Formula I that act as both PPAR-α and PPAR-γ receptor agonists,
compounds of Formula I that act as both PPAR-γ and PPAR-δ receptor agonists,
compounds of Formula I that act as both PPAR-γ and PPAR-δ receptor agonists,
compounds of Formula I that act as both PPAR-α receptor antagonists and PPAR-γ receptor agonists,
compounds of Formula I that act as both PPAR-α receptor antagonists and PPAR-65 receptor agonists,
compounds of Formula I and act as both PPAR-γ receptor antagonists and PPAR-67 receptor agonists,
compounds of Formula I that act as both PPAR-α receptor agonists and PPAR-γ receptor antagonists,
compounds of Formula I that act as both PPAR-α receptor agonists and PPAR-67 receptor antagonists,
compounds of Formula I that act as both PPAR-α receptor agonists and PPAR-67 receptor antagonists,
compounds of Formula I that act as PPAR receptor antagonists,
compounds of Formula I that act as PPAR-δ receptor antagonists,
compounds of Formula I that act as PPAR-γ receptor antagonists,
compounds of Formula I that act as PPAR-α receptor antagonists,
compounds of Formula I that act as both PPAR-α and PPAR-δ receptor antagonists,
compounds of Formula I that act as both PPAR-α and PPAR-δ receptor antagonists, and
compounds of Formula I that act as both PPAR-γ and PPAR-δ receptor antagonists.

An embodiment according to the invention is directed to treating a patient suffering from a physiological disorder capable of being modulated by a compound of Formula I having PPAR ligand binding activity, comprising administering to the patient a pharmaceutically effective amount of the compound, or a pharmaceutically acceptable salt thereof. Physiological disorders capable of being so modulated include, for example, cell differentiation to produce lipid accumulating cells, regulation of insulin sensitivity and blood glucose levels, which are involved in hypoglycemia/hyperinsulinism (resulting from, for example, abnormal pancreatic beta cell function, insulin secreting tumors and/or autoimmune hypoglycemia due to autoantibodies to insulin, autoantibodies to the insulin receptor, or autoantibodies that are stimulatory to pancreatic beta cells), macrophage differentiation which leads to the formation of atherosclerotic plaques, inflammatory response, carcinogenesis, hyperplasia, adipocyte gene expression, adipocyte differentiation, reduction in the pancreatic β-cell mass, insulin secretion, tissue sensitivity to insulin, liposarcoma cell growth, chronic anovulation, hyperandrogenism, progesterone production, steroidogenesis, redox potential and oxidative stress in cells, nitric oxide synthase (NOS) production, increased gamma glutamyl transpeptidase, catalase, plasma triglycerides, HDL and LDL cholesterol levels and the like.

Another embodiment according to the invention is directed to a method of treating a disease state in a patient with a pharmaceutically effective amount of a compound of Formula I, or a pharmaceutically acceptable salt thereof, wherein the disease is associated with a physiological detrimental blood level of insulin, glucose, free fatty acids (FFA), or triclycerides.

An embodiment according to the invention is directed to treating a patient suffering from a physiological disorder associated with physiologically detrimental levels of triclycerides in the blood, by administering to the patient a pharmaceutically effective amount of the compound, or of a pharmaceutically acceptable salt thereof.

An embodiment according to the invention is the use of compounds of Formula I and their pharmaceutical compositions as anti-diabetic, anti-lipidemic, anti-hypertensive or anti-arteriosclerotic agents, or in the treatment of obesity.

Another embodiment according to the invention is directed to a method of treating hyperglycemia in a patient, by administering to the patient a pharmaceutically effective amount to lower blood glucose levels of a compound of Formula I, or a pharmaceutically acceptable salt thereof. Preferably, the form of hyperglycemia treated in accordance with this invention is Type II diabetes.

Another embodiment according to the invention is directed to a method of reducing triglyceride levels in a patient, comprising administering to the patient a therapeutically effective amount (to lower triglyceride levels) of a compound of Formula I, or a pharmaceutically acceptable salt thereof.

Another embodiment according to the invention is directed to a method of treating hyperinsulinism in a patient, comprising administering to the patient a therapeutically effective amount of a compound of Formula I, or a pharmaceutically acceptable salt thereof.

Another embodiment according to the invention is directed to a method of treating insulin resistance in a patient, comprising administering to the patient a therapeutically effective amount of a compound of Formula I, or a pharmaceutically acceptable salt thereof.

Another embodiment according to the invention is directed to a method of treating cardiovascular disease, such as atherosclerosis in a patient, comprising administering to the patient a therapeutically effective amount of a compound of Formula I, or a pharmaceutically acceptable salt thereof.

Another embodiment according to the invention is directed to treating of hyperlipidemia in a patient, comprising administering to the patient a therapeutically effective amount of a compound of Formula I, or a pharmaceutically acceptable salt thereof.

Another embodiment according to the invention is directed to treating of hypertension in a patient, comprising administering to the patient a therapeutically effective amount of a compound of Formula I, or a pharmaceutically acceptable salt thereof.

Another embodiment according to the invention is directed to treating eating disorders in a patient, comprising administering to the patient a therapeutically effective amount of a compound of Formula I, or a pharmaceutically acceptable salt thereof. Treatment of eating disorders includes the regulation of appetite and or food intake in patients suffering from under-eating disorders such as anorexia nervosa as well as over-eating disorders such as obesity and anorexia bulimia.

Another embodiment according to the invention is directed to treating a disease state associated with low levels of HDL comprising administering to the patient a therapeutically effective amount of a compound of Formula I, or a pharmaceutically acceptable salt thereof. Diseases associated with low levels of HDL include atherosclerotic diseases.

Another embodiment according to the invention is directed to treating polycystic ovary syndrome comprising administering to the patient a therapeutically effective amount of a compound of Formula I, or a pharmaceutically acceptable salt thereof.

Another embodiment according to the invention is directed to treating climacteric comprising administering to the patient a therapeutically effective amount of a compound of Formula I, or a pharmaceutically acceptable salt thereof.

Another embodiment according to the invention is directed to treating inflammatory diseases such as rheumatoid arthritis, chronic obstructive pulmonary disease (emphysema or chronic bronchitis), or asthma comprising administering to the patient a therapeutically effective amount of a compound of Formula I, or a pharmaceutically acceptable salt thereof.

Another aspect of the invention is to provide a novel pharmaceutical composition which is effective, in and of itself, for utilization in a beneficial combination therapy because it includes a plurality of active ingredients which may be utilized in accordance with the invention.

In another aspect, the present invention provides a method for treating a disease state in a patient, wherein the disease is associated with a physiological detrimental level of insulin, glucose, free fatty acids (FFA), or triglycerides, in the blood, comprising administering to the patient a therapeutically effective amount of a compound of Formula I, and also administering a therapeutically effective amount of an additional hypoglycemic agent.

In another aspect, the present invention provides a method for treating a disease state in a patient, wherein the disease is associated with a physiological detrimental level of insulin, glucose, free fatty acids (FFA), or triglycerides, in the blood, comprising administering to the patient a therapeutically effective amount of a compound of Formula I, and also administering a therapeutically effective amount of a biguanidine compound.

In another aspect, the present invention provides a method for treating a disease state in a patient, wherein the disease is associated with a physiological detrimental level of insulin, glucose, free fatty acids (FFA), or triglycerides, in the blood, comprising administering to the patient a therapeutically effective amount of a compound of Formula I, and also administering a therapeutically effective amount of metformin.

The invention also provides kits or single packages combining two or more active ingredients useful in treating the disease. A kit may provide (alone or in combination with a pharmaceutically acceptable diluent or carrier), a compound of Formula (I) and an additional hypoglycaemic agent (alone or in combination with diluent or carrier).

There are many known hypoglycemic agents in the art, for example, insulin; biguanidines, such as metformin and buformin; sulfonylureas, such as acetohexamide, chloropropamide, tolazamide, tolbutamide, glyburide, glypizide and glyclazide; thiazolidinediones, such as troglitazone; α-glycosidase inhibitors, such as acarbose and miglatol; and $B_3$ adrenoreceptor agonists such as CL-316, 243.

Since sulfonylureas are known to be capable of stimulating insulin release, but are not capable of acting on insulin resistance, and compounds of Formula I are able to act on insulin resistance, it is envisaged that a combination of these medicaments could be used as a remedy for conditions associated with both deficiency in insulin secretion and insulin-resistance.

Therefore, the invention also provides a method of treating diabetes mellitus of type II in a patient comprising administering a compound of Formula I and one or more additional hypoglycemic agents selected from the group consisting of sulfonylureas, biguanidines, thiazolidinediones, $B_3$-adrenoreceptor agonists, α-glycosidase inhibitors and insulin.

The invention also provides a method of treating diabetes mellitus of type II in a patient comprising administering a compound of Formula I and a sulfonylurea selected from the group consisting of acetohexamide, chlorpropamide, tolazaride, tolbutamide, glyburide, glypizide and glyclazide.

The invention also provides a method of treating diabetes mellitus of type II in a patient comprising administering a compound of Formula I and a biguanidine selected from the group consisting of metformin and buformin.

The invention also provides a method of treating diabetes mellitus of type II in a patient comprising administering a compound of Formula I and an α-glycosidase inhibitor selected from the group consisting acarbose and miglatol.

The invention also provides a method of treating diabetes mellitus of type II in a patient comprising administering a compound of Formula I and an thiazolidinedione, for example, troglitazone.

As indicated above, a compound of Formula I may be administered alone or in combination with one or more additional hypoglycemic agents. Combination therapy includes administration of a single pharmaceutical dosage formulation which contains a compound of Formula I and one or more additional hypoglycemic agent, as well as administration of the compound of Formula I and each additional hypoglycemic agents in its own separate pharmaceutical dosage formulation. For example, a compound of Formula I and hypoglycemic agent can be administered to the patient together in a single oral dosage composition such as a tablet or capsule, or each agent administered in separate oral dosage formulations. Where separate dosage formulations are used, the compound of Formula I and one or more additional hypoglycemic agents can be administered at essentially the same time, i.e., concurrently, or at separately staggered times, i.e., sequentially.

For example, the compound of Formula I may be administered in combination with one or more of the following additional hypoglycemic agents: insulin; biguanidines such as metformin or buformin; sulfonylureas such as acetohexamide, chloropropamide, tolazamide, tolbutamide, glyburide, glypizide or glyclazide; thiazolidinediones such as troglitazone; α-glycosidase inhibitors such as acarbose or miglatol; or $B_3$ adrenoreceptor agonists such as CL-316, 243.

The compound of Formula I is preferably administered with a biguanidine, in particular, metformin.

The compounds of Formula I contain at least three aromatic or hetero-aromatic rings, which may be designated as shown in Formula II below, and for which their substitution pattern along the chain with respect to each other also is shown below.

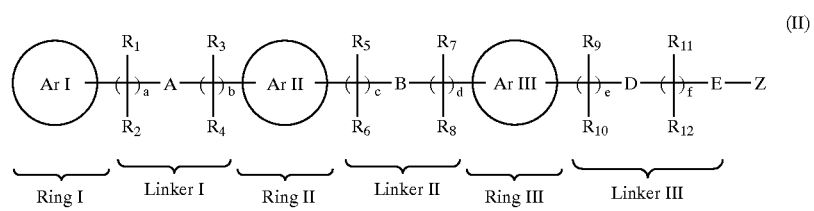

(II)

A preferred aspect of the compounds of Formula II, is a compound wherein (Ar I)

is selected from quinolinyl, benzothiophenyl, benzoimidazolyl, quinazolinyl, benzothiazolyl, quinoxalinyl, naphthyl, pyridyl, 1H-indazolyl, 1,2,3,4-tetrahydroquinolinyl, benzofuranyl, thienyl, or indolyl, and one end of the linker, Linker I, is attached to (Ar I)

preferably at the 2-position of the ring moiety.

Another aspect of the compounds of Formula II is a compound wherein (Ar II)

is a 6 membered aryl or heteroaryl group and Linker I and Linker II are attached to (Ar II)

at positions 1,2-, 1,3-, or 1,4- to each other.

Another aspect of the compounds of Formula II is a compound wherein (Ar II)

is a naphthyl group, Linker I and Linker II are attached to (Ar II)

at positions 1,4-, or 2,4- to each other on the naphthyl moiety.

Another aspect of the compounds of Formula II, is a compound wherein (Ar III)

is 6-membered aryl or heteroaryl, and has a preferred position of attachment of Linker II and Linker III to Ring III at positions 1,2-, to each other.

Another aspect of the compounds of Formula II, is a compound wherein

is 6-membered aryl or heteroaryl, and has a preferred position of attachment of Linker II and Linker III to Ring III at positions 1,2-, 1,3-, to each other.

Another aspect of the compounds of Formula II, is a compound wherein

is 6-membered aryl or heteroaryl, and has a preferred position of attachment of Linker II and Linker III to Ring III at positions 1,4- to each other.

A further preferred aspect of the compound of Formula II is described by Formula V below:

is optionally substituted aryl, optionally substituted heteroaryl, optionally substituted fused arylheterocyclalkyl or optionally substituted fused arylheterocyclenyl.

Another aspect of this invention is a compound of the invention wherein a=1 or 2; $R_1$ and $R_2$ is hydrogen; A is a chemical bond; and b=0.

Another aspect of this invention is a compound of the invention wherein a=0; A is

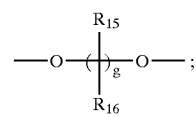

$R_{15}$ and $R_{16}$ are hydrogen; g is 1, 2, or 3; and b=0.

Another aspect of this invention is a compound of the invention wherein a=0; A is —$NR_{13}$—, b=1, $R_3$ and $R_4$ are hydrogen.

Another aspect of this invention is a compound of the invention wherein a=2; vicinal $R_1$ radicals taken together with the carbon atoms to which the $R_1$ radicals are linked form an ethylene group; $R_2$ is hydrogen; A is a chemical bond; and b=0.

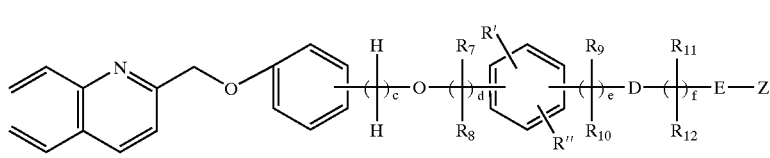

where $R_1$, $R_2$, c, d, e, f, D, E and Z are as defined above, c+d=1–3, and R' and R" are ring system substituents.

Another aspect of this invention is a compound of the invention wherein

is optionally substituted aryl, optionally substituted azaheteroaryl, or optionally substituted fused arylheterocyclenyl;

is optionally substituted aryl, optionally substituted heteroaryl, or optionally substituted fused arylheterocyclenyl; and

Another aspect of this invention is a compound of the invention wherein a=1, 2 or 3; $R_1$ and $R_2$ are hydrogen; A is —O—; and b=0.

Another aspect of this invention is a compound of the invention wherein a=1; $R_1$, $R_2$, $R_3$ and $R_4$ are hydrogen; A is —O—; and b=1.

Another aspect of this invention is a compound of the invention wherein c=1 or 2; $R_5$ and $R_6$ are hydrogen or alkyl; B is a chemical bond; and d=0.

Another aspect of this invention is a compound of the invention wherein c=2; vicinal $R_5$ radicals taken together with the carbon atoms to which the $R_5$ radicals are linked form an ethylene group; $R_6$ is hydrogen; B is a chemical bond; and d=0.

Another aspect of this invention is a compound of the invention wherein c=0 or 1; $R_5$ and $R_6$ are hydrogen; B is —O—; and d=0 or 1.

Another aspect of this invention is a compound of the invention wherein c=0; B is C(O)— or —S(O)$_2$—; d=1 and $R_7$ and $R_8$ are independently hydrogen or alkyl.

Another aspect of this invention is a compound of the invention wherein e=0; f=0; D and E is a chemical bond; Z is $R_{21}O_2SHNCO$—, and $R_2$, is phenyl.

Another aspect of this invention is a compound of the invention wherein e=0; f=0 or 1; and E is a chemical bond; Z is tetrazolyl, $NH_2CO$— or —$CO_2R_{21}$; and $R_{21}$ is hydrogen or lower alkyl.

Another aspect of this invention is a compound of the invention wherein e=0; f=0 or 1; D is —O— or a chemical bond; E is a chemical bond; and Z is tetrazolyl, NH₂CO— or —CO₂R₂₁; and R₂₁ is hydrogen or lower alkyl.

Another aspect of this invention is a compound of the invention wherein e=0; f=1; D is —O— or a chemical bond; E is a chemical bond; R₁₁ and R₁₂ are hydrogen or alkyl; and Z is tetrazolyl, NH₂CO— or —CO₂R₂₁; and R₂₁ is hydrogen or lower alkyl.

Another aspect of this invention is a compound of the invention wherein e=2, then vicinal R₉ radicals taken together with the carbon atoms to which the R₉ radicals are linked form an ethylene group; f=0; D and E is a chemical bond; and Z is —CO₂R₂₁; and R₂₁ is hydrogen.

Another aspect of this invention is a compound of the invention wherein e=0; f=3; D is —O—; E is a chemical bond; R₁₁ and R₁₂ are hydrogen or alkyl, or at least one of R₁₁ is carboxyl or alkoxycarbonyl; Z is tetrazolyl, or —CO₂R₂₁; and R₂₁ is hydrogen or lower alkyl.

Another aspect of this invention is a compound of the invention wherein e=0; f=1, 2, or 3; D is —C(O)—; E is a chemical bond; R₁ and R₁₂ are hydrogen or alkyl; Z is tetrazolyl or CO₂R₂₁; and R₂₁ is hydrogen or lower alkyl.

A preferred aspect of this invention is a compound of the invention wherein

is an optionally substituted quinolinyl, quinoxalinyl, quinazolinyl, isoquinolinyl, N-alkyl-quinolin-4-onyl, quinazolin-4-onyl, benzoxazolyl, benzimidazolyl, benzothiazolyl, benzofuranyl, benzothiophenyl, indolinyl oxazolyl, thiazolyl, oxadiazolyl isoxazolyl, imidazolyl, pyrazol-yl, thiadiazolyl, triazolyl, pyridyl pyrimidinyl, pyrazinyl, pyridazinyl, phenyl, or napthalenyl group, wherein the substituent is a ring system substituent as defined herein, more preferably a substituent selected from the group consisting of phenyl, substituted-phenyl, thienyl, substituted thienyl, cycloalkyl, lower alkyl, branched alkyl, fluoro, chloro, alkoxy, aralkyloxy, trifluoromethyl and trifluoromethyloxy.

A more preferred aspect of this invention is a compound of the invention wherein

is unsubstituted quinolin-2-yl, 3-substituted quinolin-2-yl, 4-substituted quinolin-2-yl, 6-substituted quinolin-2-yl or 7 substituted quinolin-2-yl; an unsubstituted quinozalin-2-yl, 3-substituted quinozalin-2-yl, 6-substituted quinozalin-2-yl or 3,6-disubstituted quinozalin-2-yl; unsubstituted quinazolin-2-yl, 4-substituted quinazolin-2-yl or 6-substituted quinazolin-2-yl; unsubstituted isoquinolin-3-yl, 6-substituted isoquinolin-3-yl or 7-substituted isoquinolin-3-yl; 3-substituted-quinazolin-4-on-2-yl; N-substituted quinolin-4-on-2-yl; 2-substituted-oxazol-4-yl or 2,5 disubstituted-oxazol-4-yl; 4-substituted oxazol-2-yl or 4,5-disubstituted-oxazol-2-yl; 2-substituted thiazol-4-yl or 2,5-disubstituted thiazol-4-yl; 4-substituted thiazol-2-yl or 4,5-disubstituted-thiazol-2-yl; 5-substituted-[1,2,4]oxadiazol-3-yl; 3-substituted-[1,2,4]oxadiazol-5-yl; 5-substituted-imidazol-2-yl or 3,5-disubstituted-imidazol-2-yl; 2-substituted-imidazol-5-yl or 2,3-disubstituted-imidazol-5-yl; 3-substituted-isoxazol-5-yl; 5-substituted-isoxazol-3-yl; 5-substituted-[1,2,4]thiadiazol-3-yl; 3-substituted-[1,2,4]-thiadiazol-5-yl; 2-substituted-[1,3,4]-thiadiazol-5-yl; 2-substituted-[1,3,4]-oxadiazol-5-yl; 1-substituted-pyrazol-3-yl; 3-substituted-pyrazol-5-yl; 3-substituted-[1,2,4]-triazol-5-yl; 1-substituted-[1,2,4]-triazol-3-yl; 3-substituted pyridin-2-yl, 5-substituted pyridin-2-yl, 6-substituted pyridin-2-yl or 3,5-disubstituted pyridin-2-yl; 3-substituted pyrazin-2-yl, 5-substituted pyrazin-2-yl, 6-substituted pyrazin-2-yl or 3,5 disubstituted-pyrazin-2-yl; 5-substituted pyrimidin-2-yl or 6-substituted-pyrimidin-2-yl; 6-substituted-pyridazin-3-yl or 4,6-disubstituted-pyridazin-3-yl; unsubstituted napthalen-2-yl, 3-substituted napthalen-2-yl, 4-substituted napthalen-2-yl, 6-substituted napthalen-2-yl or 7 substituted napthalen-2-yl; 2-substituted phenyl, 4-substituted phenyl or 2,4-disubstituted phenyl; unsubstituted-benzothiazol-2-yl or 5-substituted-benzothiazol-2-yl; unsubstituted benzoxazol-2yl or 5-substituted-benzoxazol-2-yl; unsubstituted-benzimidazol-2-yl or 5-substituted-benzimidazol-2-yl; unsubstituted-thiophen-2-yl, 3-substituted-thiophen-2-yl, 6-substituted-thiophen-2yl or 3,6-disubstituted-thiophen-2yl; unsubstituted-benzofuran-2-y, 3-substituted-benzofuran-2-yl, 6-substituted-benzofuran-2-yl or 3,6-disubstituted-benzofuran-2-yl; 3-substituted-benzofuran-6-yl or 3,7-disubstituted-benzofuran-6-yl, wherein the substituent is a ring system substituent as defined herein, more preferably a substituent selected from the group consisting of phenyl, substituted-phenyl, thienyl, substituted thienyl, cycloalkyl, lower alkyl, branched alkyl, fluoro, chloro, alkoxy, aralkyloxy, trifluoromethyl and trifluoromethyloxy.

Another more preferred aspect of this invention is a compound of the invention wherein R₁ and R₂ are both H, a=1, A is —O— and b=0.

Another more preferred aspect of this invention is a compound of the invention wherein R₁ and R₂ are both H, a=2, A is —O— and b=0.

Another more preferred aspect of this invention is a compound of the invention wherein a=0, A is —O— or —NR₁₃—; R₁₃ is hydrogen or alkyl; R₃ and R₄ are both independently hydrogen; and b=1.

Another more preferred aspect of this invention is a compound of the invention wherein a=0, A is —O— or —NR₁₃—; R₁₃ is hydrogen or alkyl; R₃ and R₄ are both independently hydrogen; b=1; and ArI is 3-substituted quinolin-2-yl, 4-substituted quinolin-2-yl, 6-substituted quinolin-2-yl, 7 substituted quinolin-2-yl, unsubstituted quinoxalin-2-yl, 3-substituted quinoxalin-2-yl, 6-substituted quinoxalin-2-yl, 3,6-disubstituted quinoxalin-2-yl, unsubstituted quinazolin-2-yl, 4-substituted quinazolin-2-yl, 6-substituted quinazolin-2-yl, unsubstituted isoquinolin-3-yl, 6-substituted isoquinolin-3-yl, 7-substituted isoquinolin-3-yl, 4-substituted oxazol-2-yl, 4,5-disubstituted-oxazol-2-yl, 4-substituted-thiazol-2-yl, 4,5-disubstituted-thiazol-2-yl, 5-substituted -imidazol-2-yl, 3,5-disubstituted-imidazol-2-yl, 1-substituted-pyrazol-3-yl, 3-substituted-pyrazol-5-yl, 3-substituted pyridin-2-yl, 5-substituted pyridin-2-yl, 6-substituted pyridin-2-yl or 3,5-disubstituted pyridin-2-yl, 3-substituted pyrazin-2-yl, 5-substituted pyrazin-2-yl, 6-substituted pyrazin-2-yl, 3,5 disubstituted-pyrazin-2-yl, 5-substituted pyrimidin-2-yl, 6-substituted-pyrimidin-2-yl, 6-substituted-pyridazin-3-yl, 4,6-disubstituted-pyridazin-3-yl, unsubstituted-benzothiazol-2-yl, 5-substituted-benzothiazol-2-yl, unsubstituted-benzoxazol-2-yl, 5-substituted-benzoxazol-2-yl, unsubstituted benzimidazol-2-yl, 5-substituted-benzimidazol-2-yl, 3-substituted-benzofuran-6-yl or 3,7-disubstituted-benzofuran-6-yl.

Another aspect of this invention is a compound of formula I as described by formula (Ia) below:

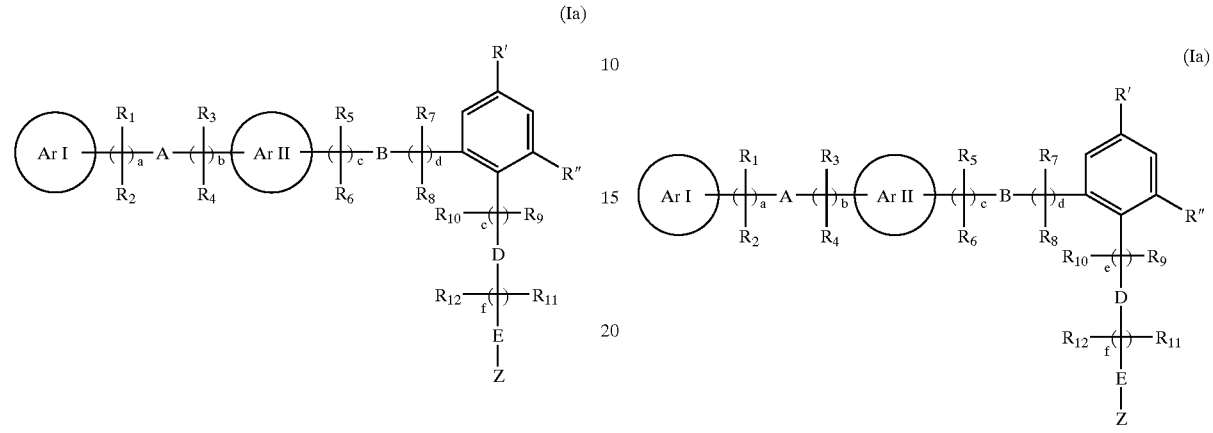
(Ia)

wherein

Ar I and

Ar II are independently aryl, fused arylcycloalkenyl, fused arylcycloalkyl, fused arylheterocyclenyl, fused arylheterocyclyl, heteroaryl, fused heteroarylcycloalkenyl, fused heteroarylcycloalkyl, fused heteroarylheterocyclenyl, or fused heteroarylheterocyclyl;

c+d=1 or 2;

B is —O—;

$R_5$, $R_6$, $R_7$, $R_8$ are independently hydrogen;

e=0;

D and E are a chemical bond;

Z is $R_{21}O_2C$—, $R_{21}OC$—, cyclo-imide, —CN, $R_{21}O_2SHNCO$—, $R_{21}O_2SHN$—, $(R_{21})_2NCO$—, $R_{21}O$-2,4-thiazolidinedionyl, or tetrazolyl;

R' and R" are ring system substituents as defined herein, more preferably, R' is lower alkyl, halo, alkoxy, aryloxy or aralkyl; and R" is lower alkyl or halo.

Another aspect of this invention is a compound of formula I as described by formula (Ia) below:

(Ia)

wherein

Ar I and

Ar II are independently aryl, fused arylcycloalkenyl, fused arylcycloalkyl, fused arylheterocyclenyl, fused arylheterocyclyl, heteroaryl fused heteroarylcycloalkenyl, fused heteroarylcycloalkyl, fused heteroarylheterocyclenyl, or fused heteroarylheterocyclyl;

c+d=1 or 2;

B is —O—;

$R_5$, $R_6$, $R_7$, $R_8$ are independently hydrogen;

e=0;

f=0;

D and E are a chemical bond;

Z is —$CO_2H$;

R' and R" are ring system substituents as defined herein, more preferably, R' is lower alkyl, halo, alkoxy, aryloxy or aralkyl; and R" is lower alkyl or halo.

Another aspect of this invention is a compound of formula I as described by formula (Ia) below:

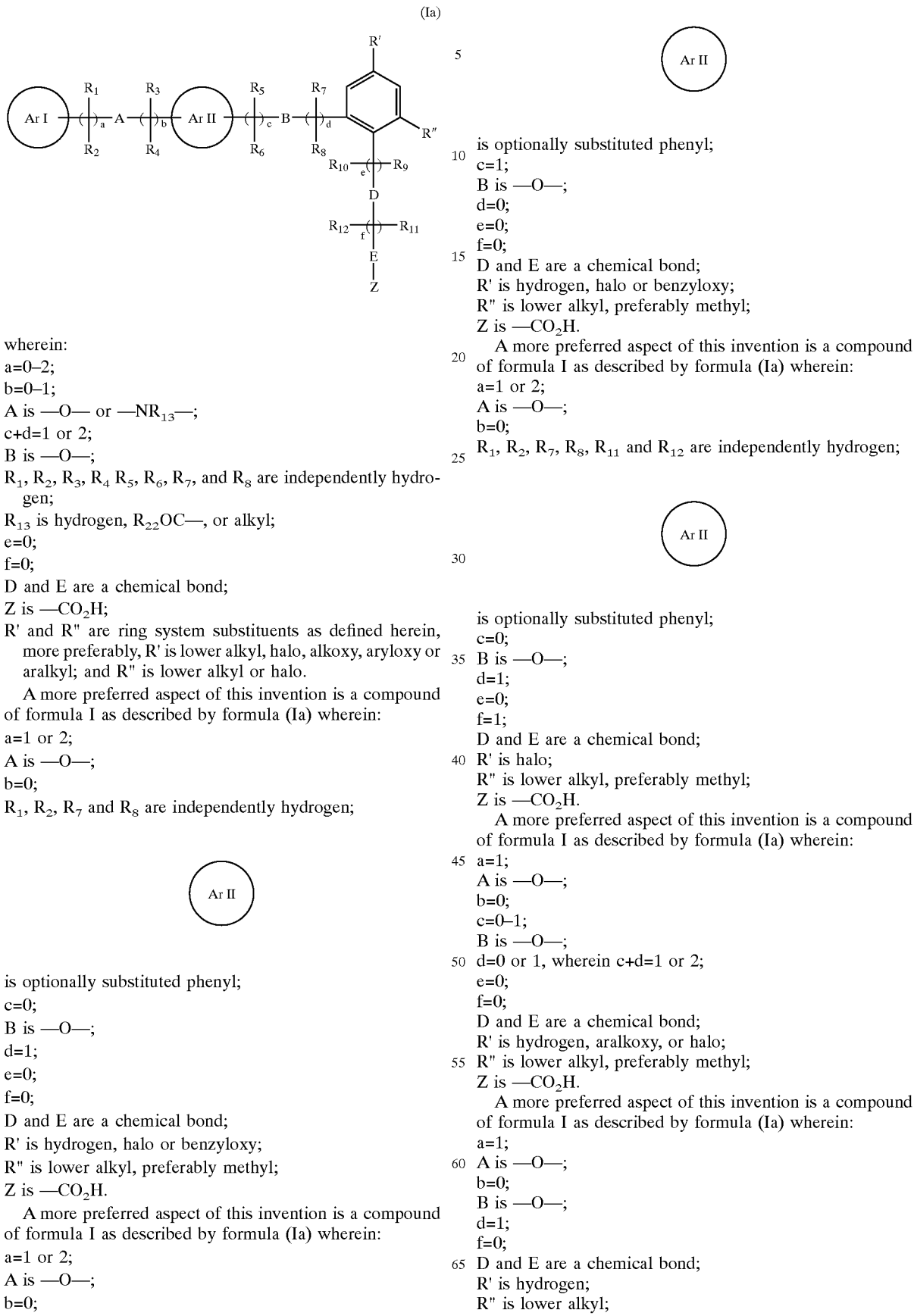

(Ia)

wherein:
a=0–2;
b=0–1;
A is —O— or —NR$_{13}$—;
c+d=1 or 2;
B is —O—;
R$_1$, R$_2$, R$_3$, R$_4$ R$_5$, R$_6$, R$_7$, and R$_8$ are independently hydrogen;
R$_{13}$ is hydrogen, R$_{22}$OC—, or alkyl;
e=0;
f=0;
D and E are a chemical bond;
Z is —CO$_2$H;
R' and R" are ring system substituents as defined herein, more preferably, R' is lower alkyl, halo, alkoxy, aryloxy or aralkyl; and R" is lower alkyl or halo.

A more preferred aspect of this invention is a compound of formula I as described by formula (Ia) wherein:
a=1 or 2;
A is —O—;
b=0;
R$_1$, R$_2$, R$_7$ and R$_8$ are independently hydrogen;

Ar II is optionally substituted phenyl;
c=0;
B is —O—;
d=1;
e=0;
f=0;
D and E are a chemical bond;
R' is hydrogen, halo or benzyloxy;
R" is lower alkyl, preferably methyl;
Z is —CO$_2$H.

A more preferred aspect of this invention is a compound of formula I as described by formula (Ia) wherein:
a=1 or 2;
A is —O—;
b=0;
R$_1$, R$_2$, R$_5$ and R$_6$ are independently hydrogen;

Ar II is optionally substituted phenyl;
c=1;
B is —O—;
d=0;
e=0;
f=0;
D and E are a chemical bond;
R' is hydrogen, halo or benzyloxy;
R" is lower alkyl, preferably methyl;
Z is —CO$_2$H.

A more preferred aspect of this invention is a compound of formula I as described by formula (Ia) wherein:
a=1 or 2;
A is —O—;
b=0;
R$_1$, R$_2$, R$_7$, R$_8$, R$_{11}$ and R$_{12}$ are independently hydrogen;

Ar II is optionally substituted phenyl;
c=0;
B is —O—;
d=1;
e=0;
f=1;
D and E are a chemical bond;
R' is halo;
R" is lower alkyl, preferably methyl;
Z is —CO$_2$H.

A more preferred aspect of this invention is a compound of formula I as described by formula (Ia) wherein:
a=1;
A is —O—;
b=0;
c=0–1;
B is —O—;
d=0 or 1, wherein c+d=1 or 2;
e=0;
f=0;
D and E are a chemical bond;
R' is hydrogen, aralkoxy, or halo;
R" is lower alkyl, preferably methyl;
Z is —CO$_2$H.

A more preferred aspect of this invention is a compound of formula I as described by formula (Ia) wherein:
a=1;
A is —O—;
b=0;
B is —O—;
d=1;
f=0;
D and E are a chemical bond;
R' is hydrogen;
R" is lower alkyl;

Z is —CO$_2$H.

A more preferred aspect of this invention is a compound of formula I as described by formula (Ia) wherein:

(Ar I)

and (Ar II)

are aryl or heteroaryl;
a=1;
A is —O—;
b=0;
c=0;
B is —O—;
d=1;
e=0;
f=0;
D and E are a chemical bond;
R' is hydrogen;
R" is lower alkyl;
Z is —CO$_2$H.

A more preferred aspect of this invention is a compound of formula I as described by formula (Ia) wherein:

(Ar I)

is optionally substituted azaheteroaryl;

(Ar II)

is optionally substituted phenyl;

a=1;
A is —O—;
b=0;
c=0;
B is —O—;
e=0;
f=0;
D and E are a chemical bond;
R' is hydrogen;
R" is lower alkyl;
Z is CO$_2$H.

A more preferred aspect of this invention is a compound of formula I as described by formula (Ia) wherein:

(Ar I)

is optionally substituted quinolinyl, or a 5-membered heteroaryl group wherein the heteroaryl group is substituted by optionally substituted phenyl or optionally substituted cyclohexyl;

(Ar II)

is optionally substituted phenyl;
a=1;
A is —O—;
b=0;
c=0;
B is —O—;
d=1;
e=0;
f=0;
D and E are a chemical bond;
R' is hydrogen;
R" is lower alkyl;
Z is CO$_2$H.

Compounds according to the invention are selected from the group consisting of

;

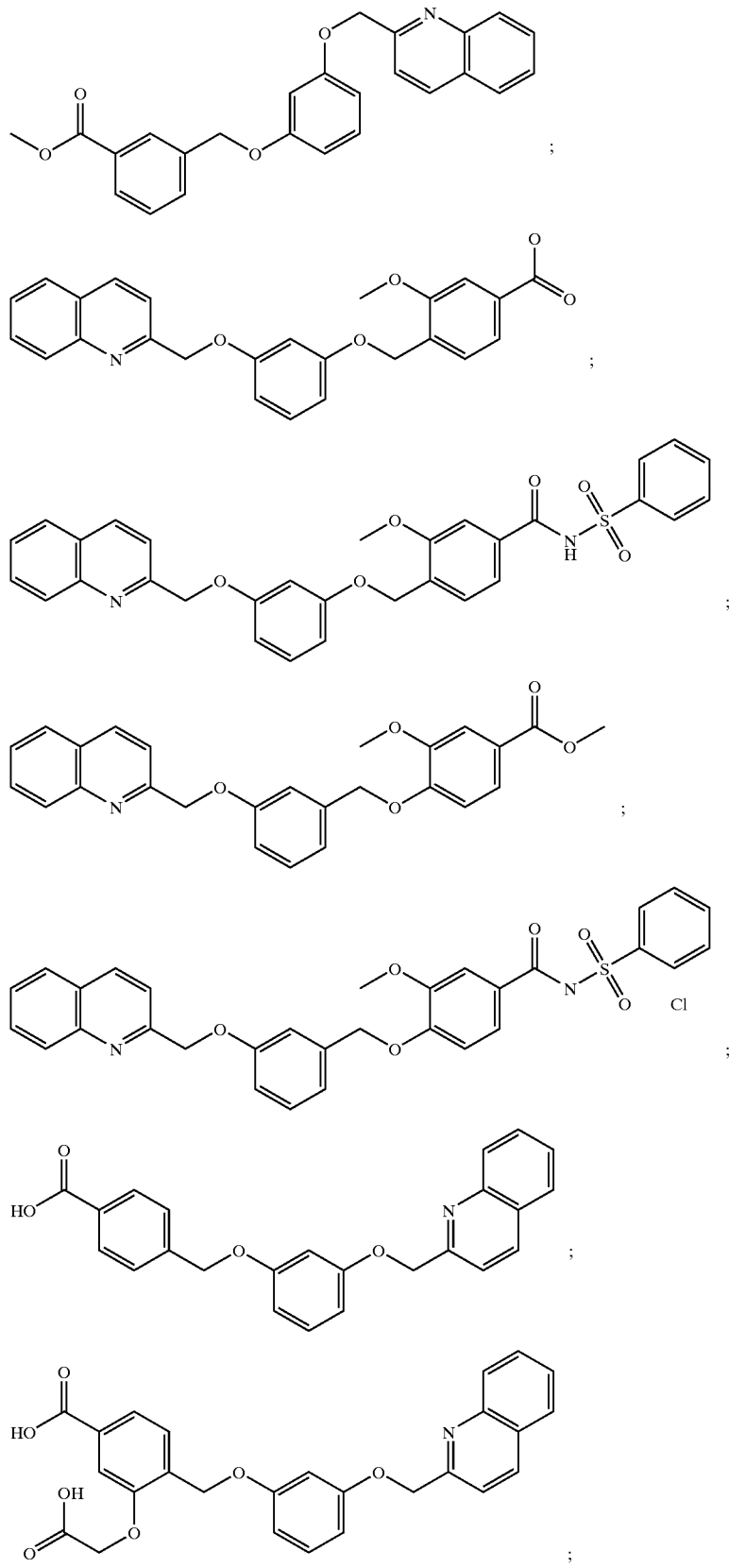

-continued
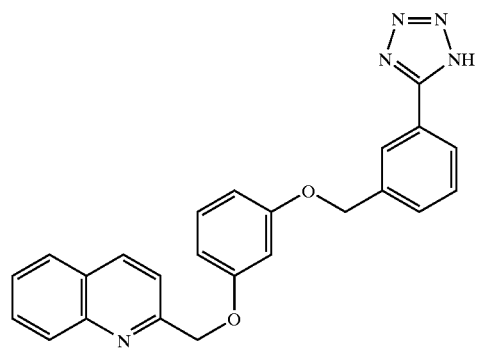
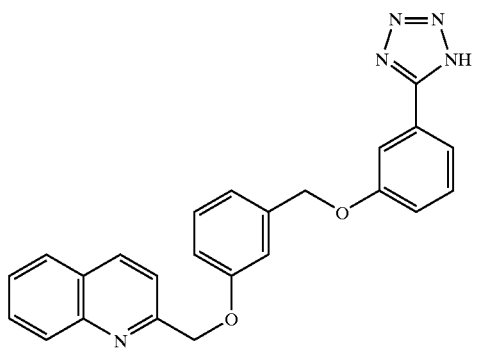
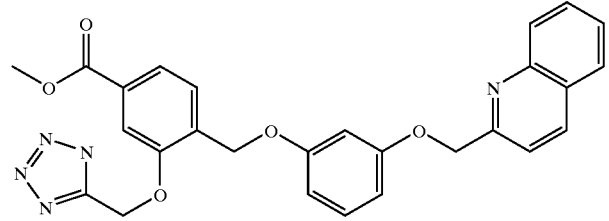
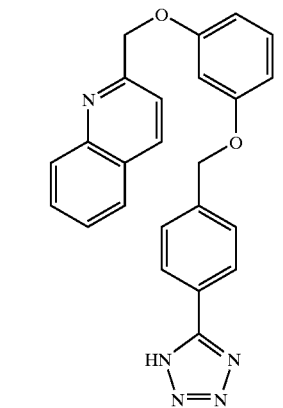
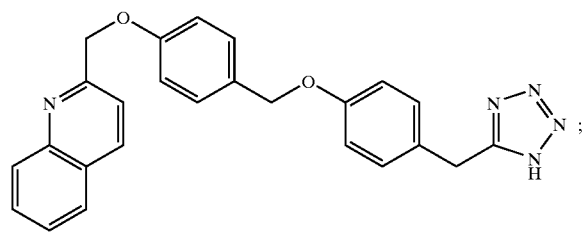
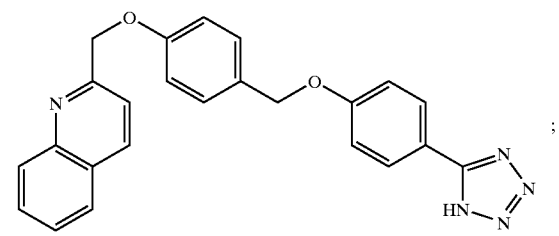
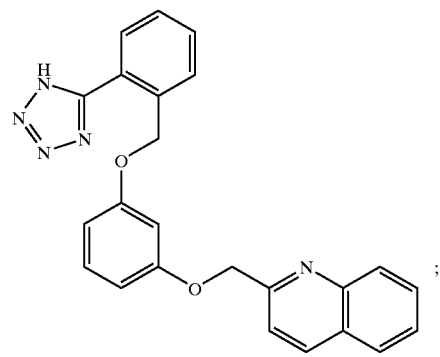
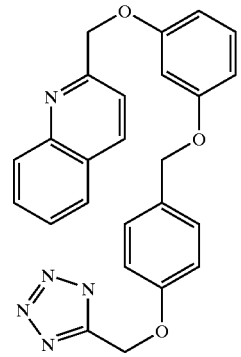
154–156° C.
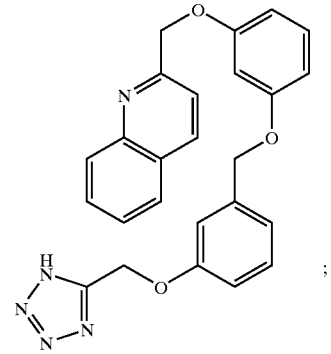

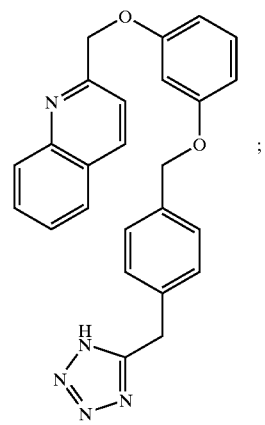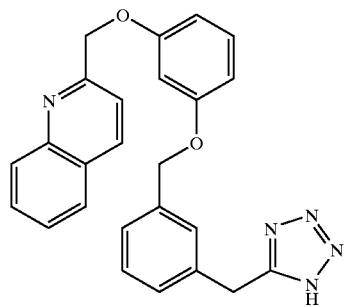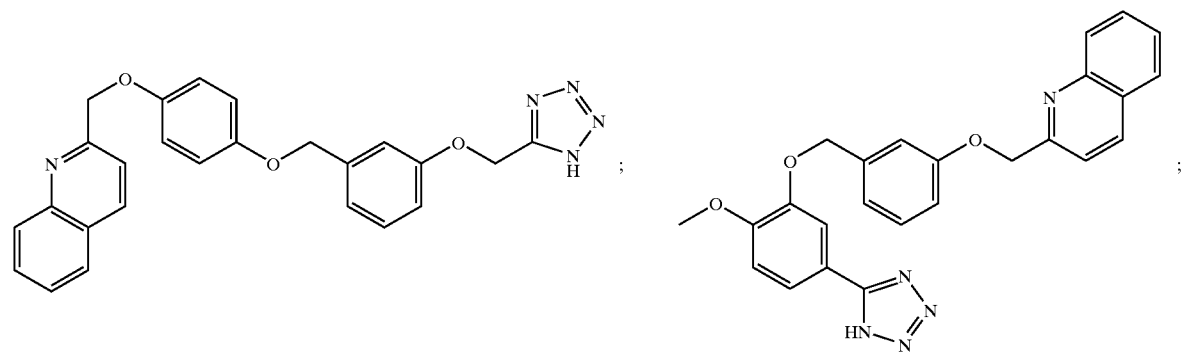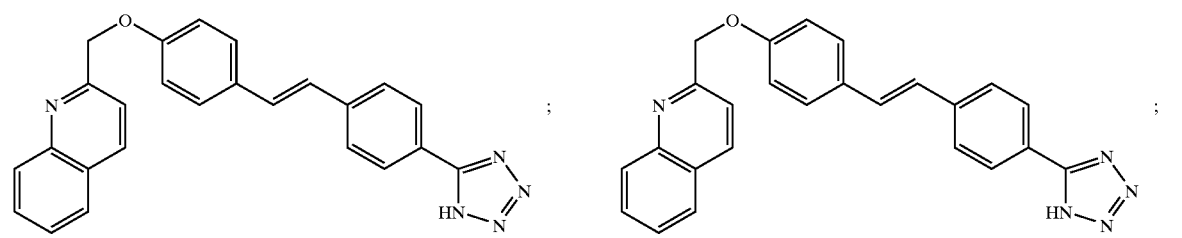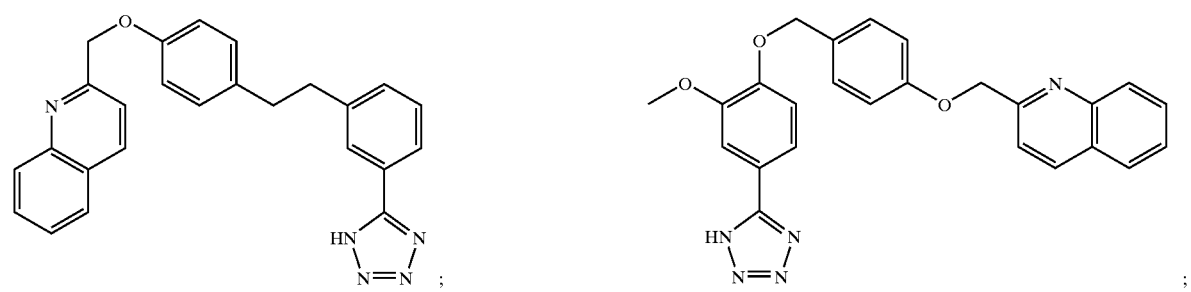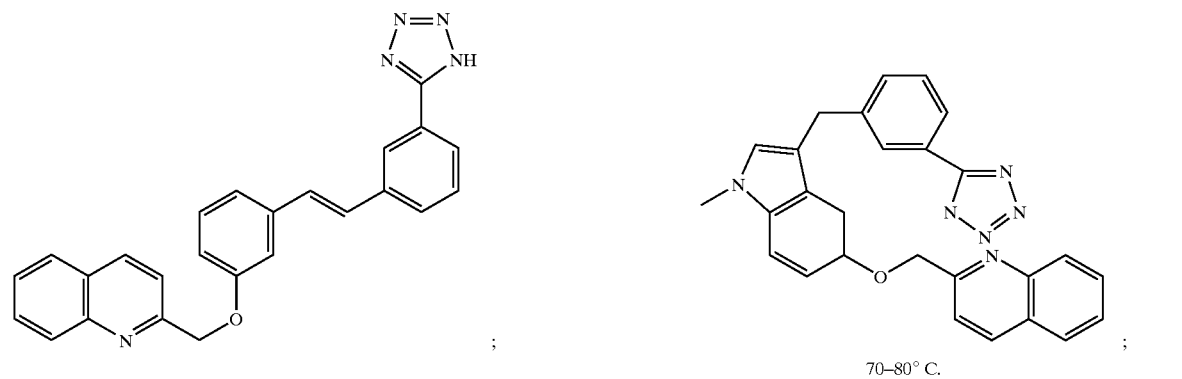

-continued
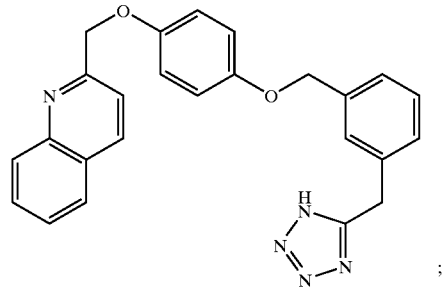
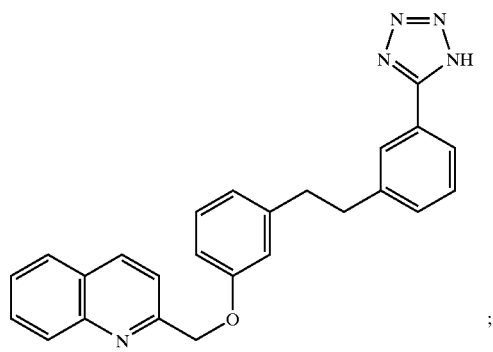
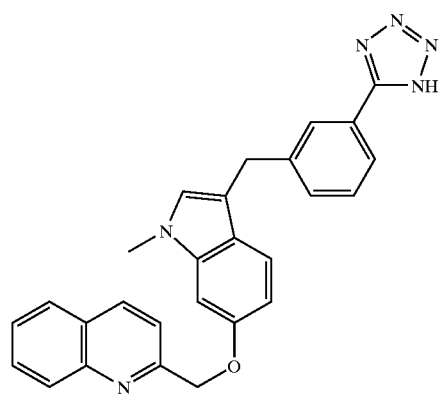
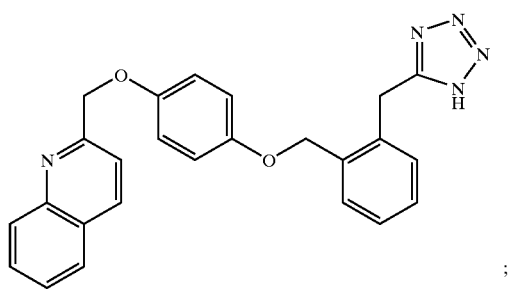
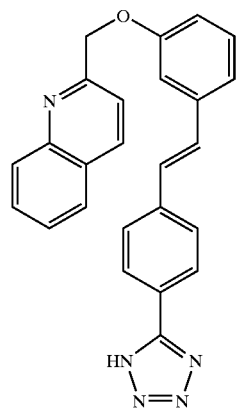
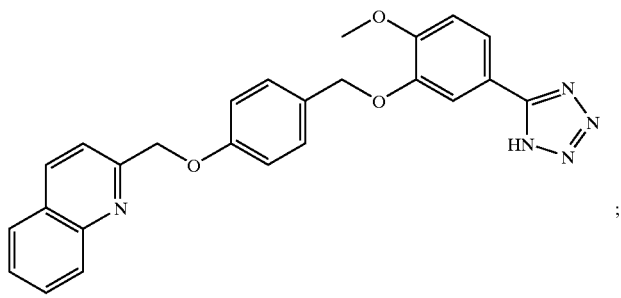
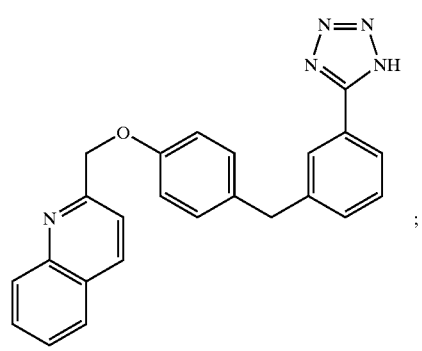
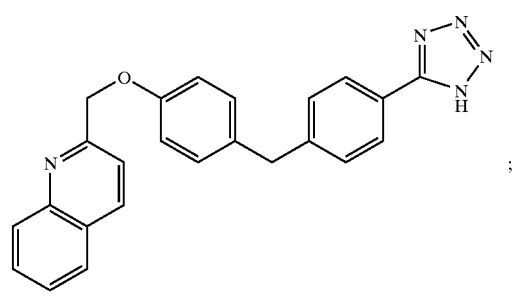

-continued
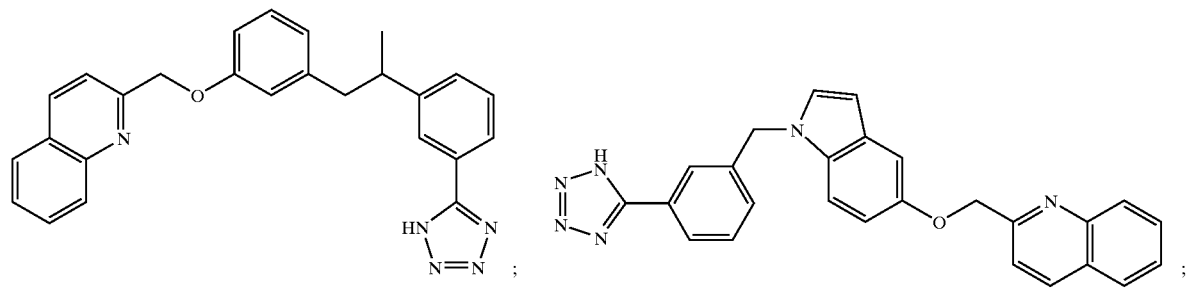
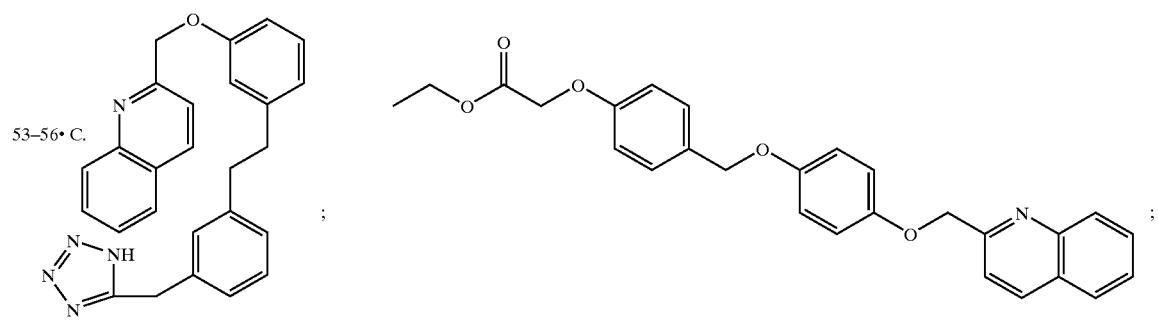
53–56° C.
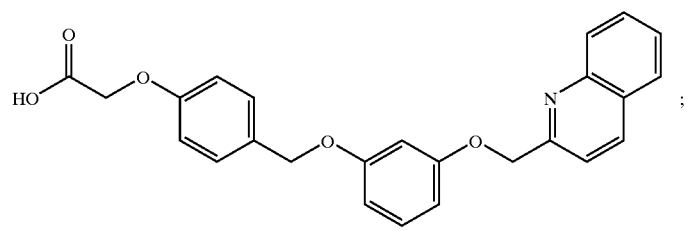
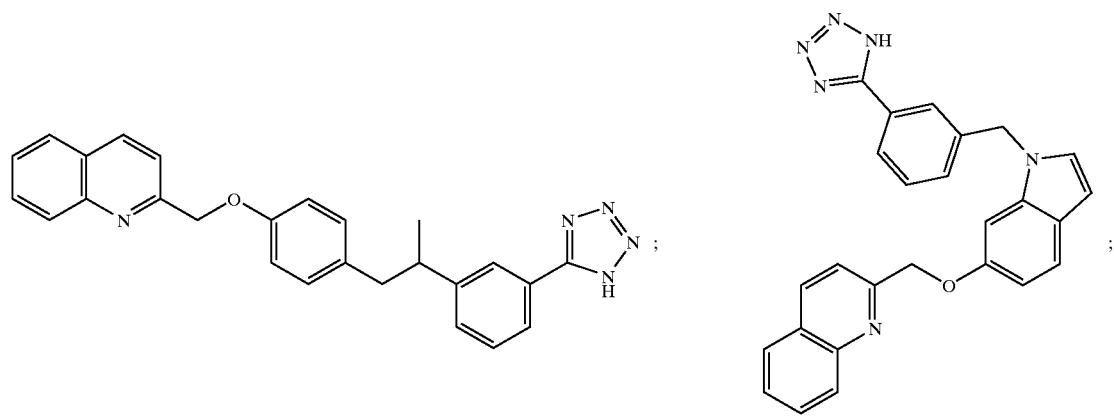
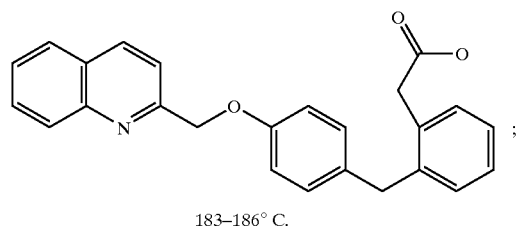
183–186° C.

-continued
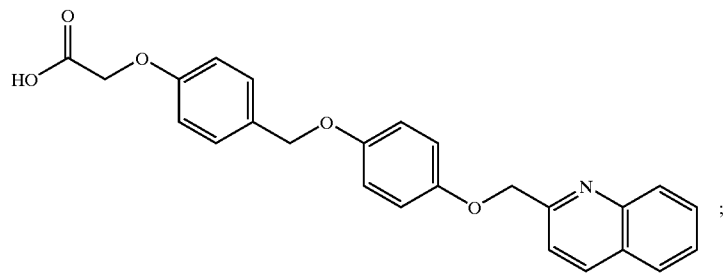
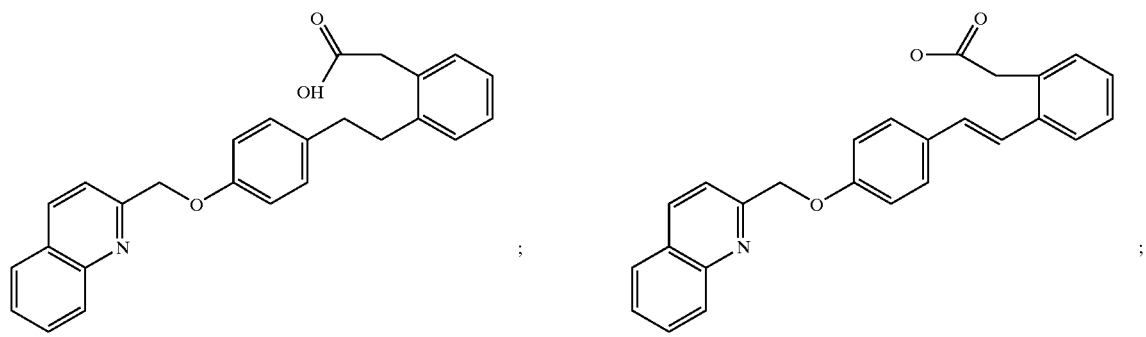
174–176° C.   183–185° C.
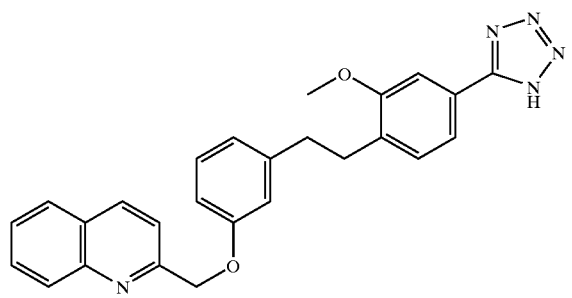
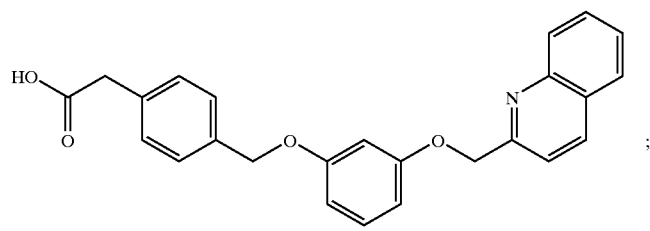
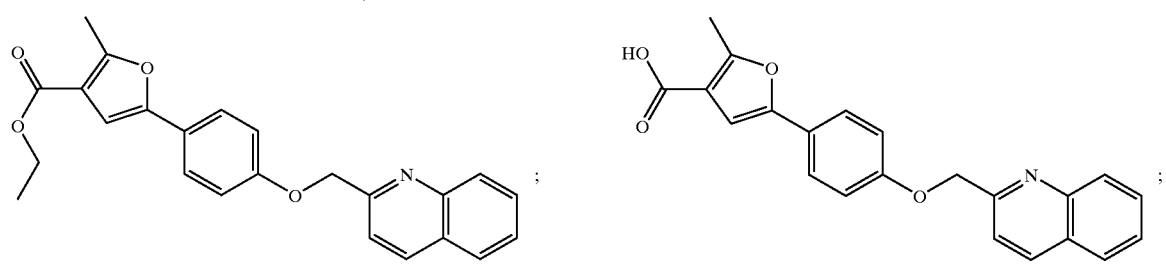

-continued
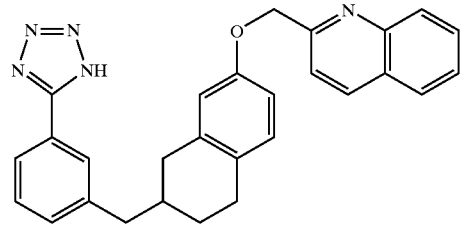
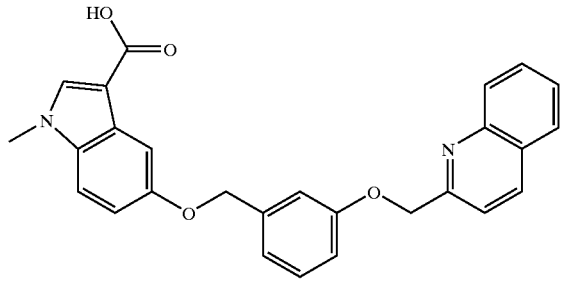
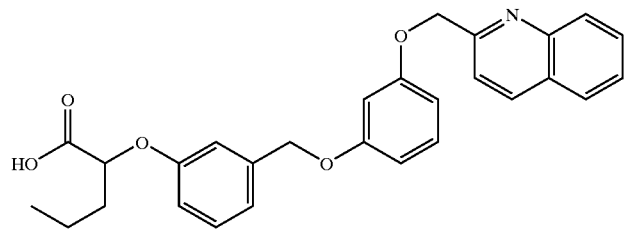
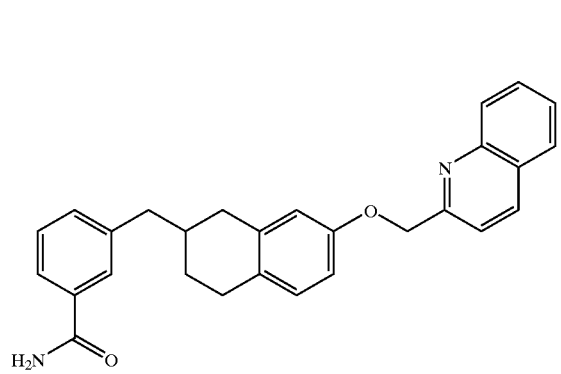
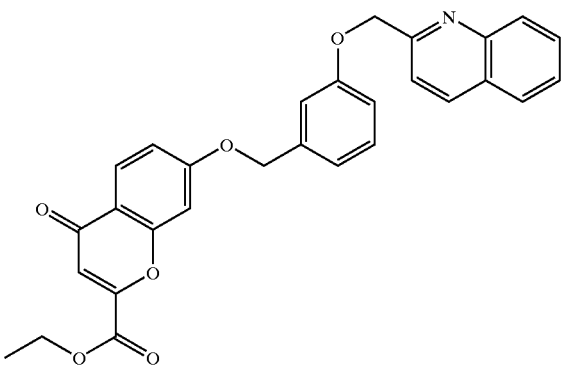
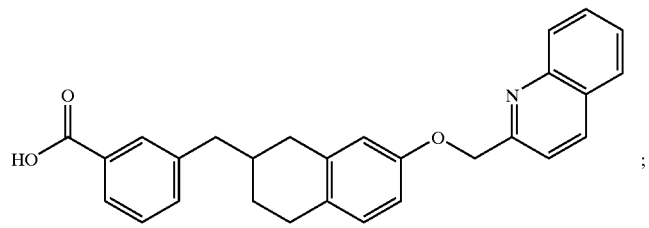
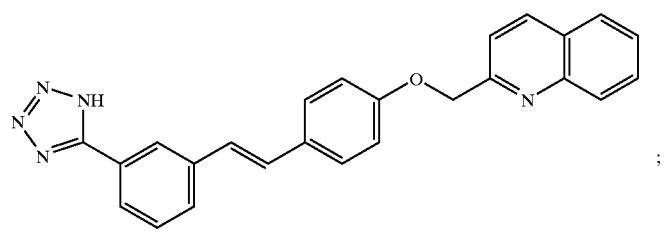
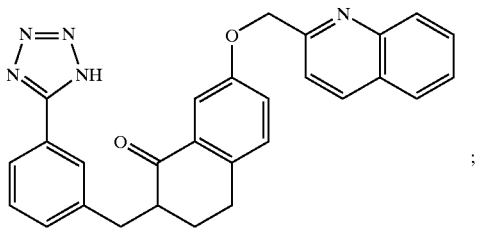

-continued
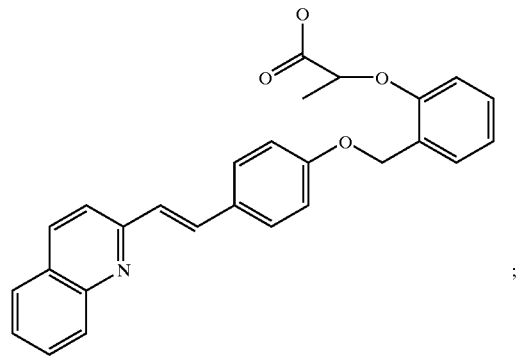
201–203° C.
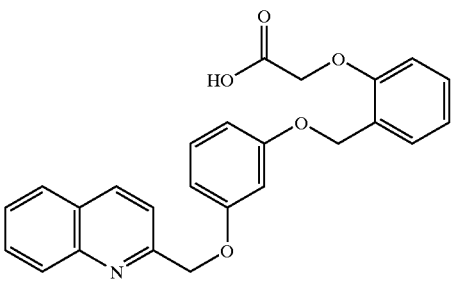
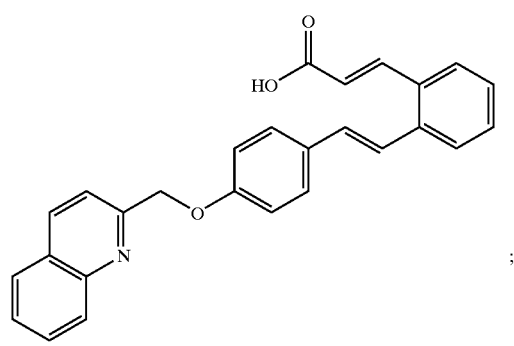
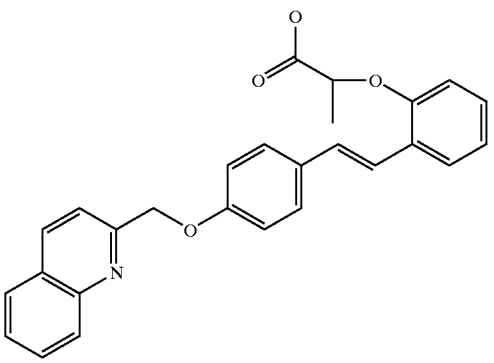
96–97° C.
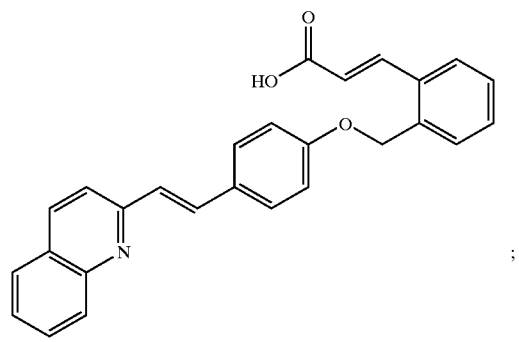
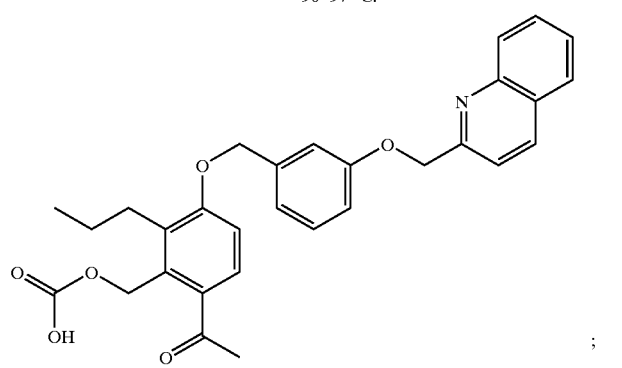
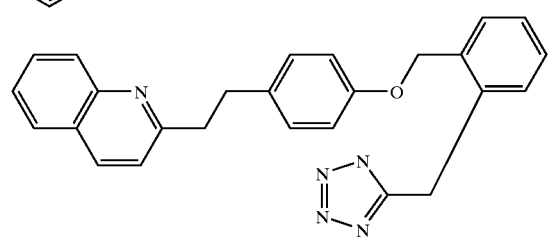
191–196° C.
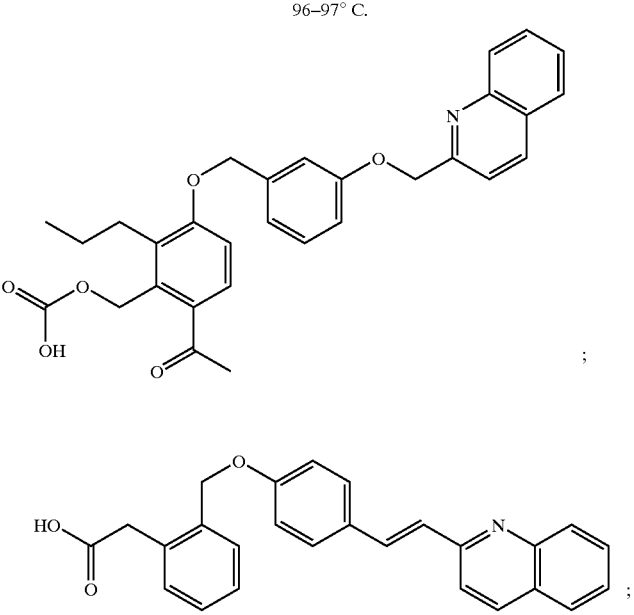
169–173° C.
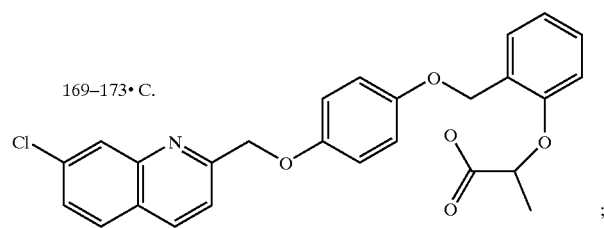

-continued
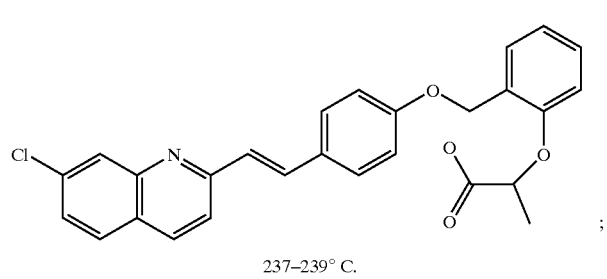
237–239° C.
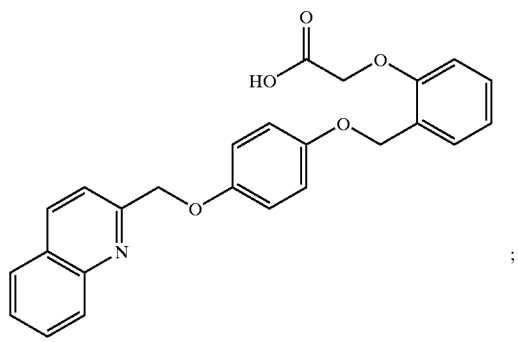
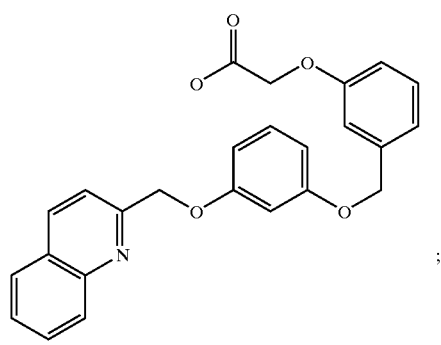
146–151° C.
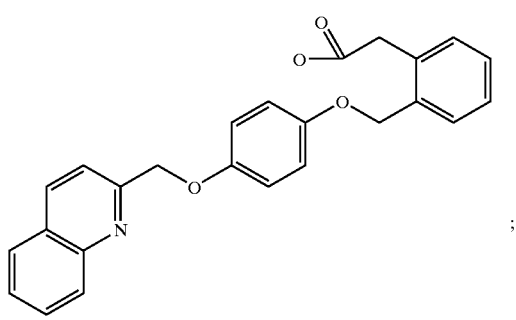
181–183° C.
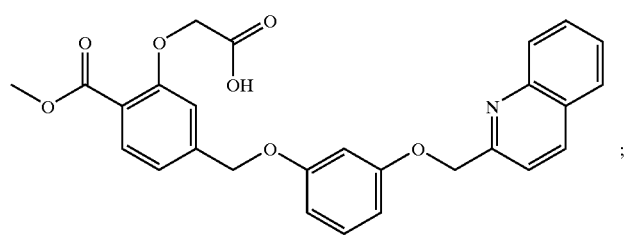
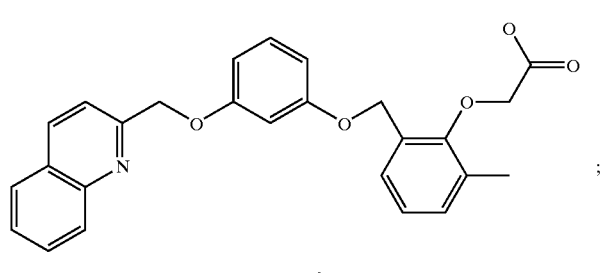
149–153° C.
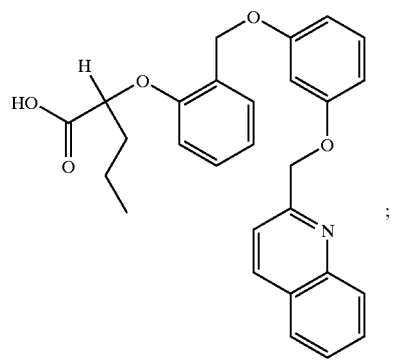

-continued
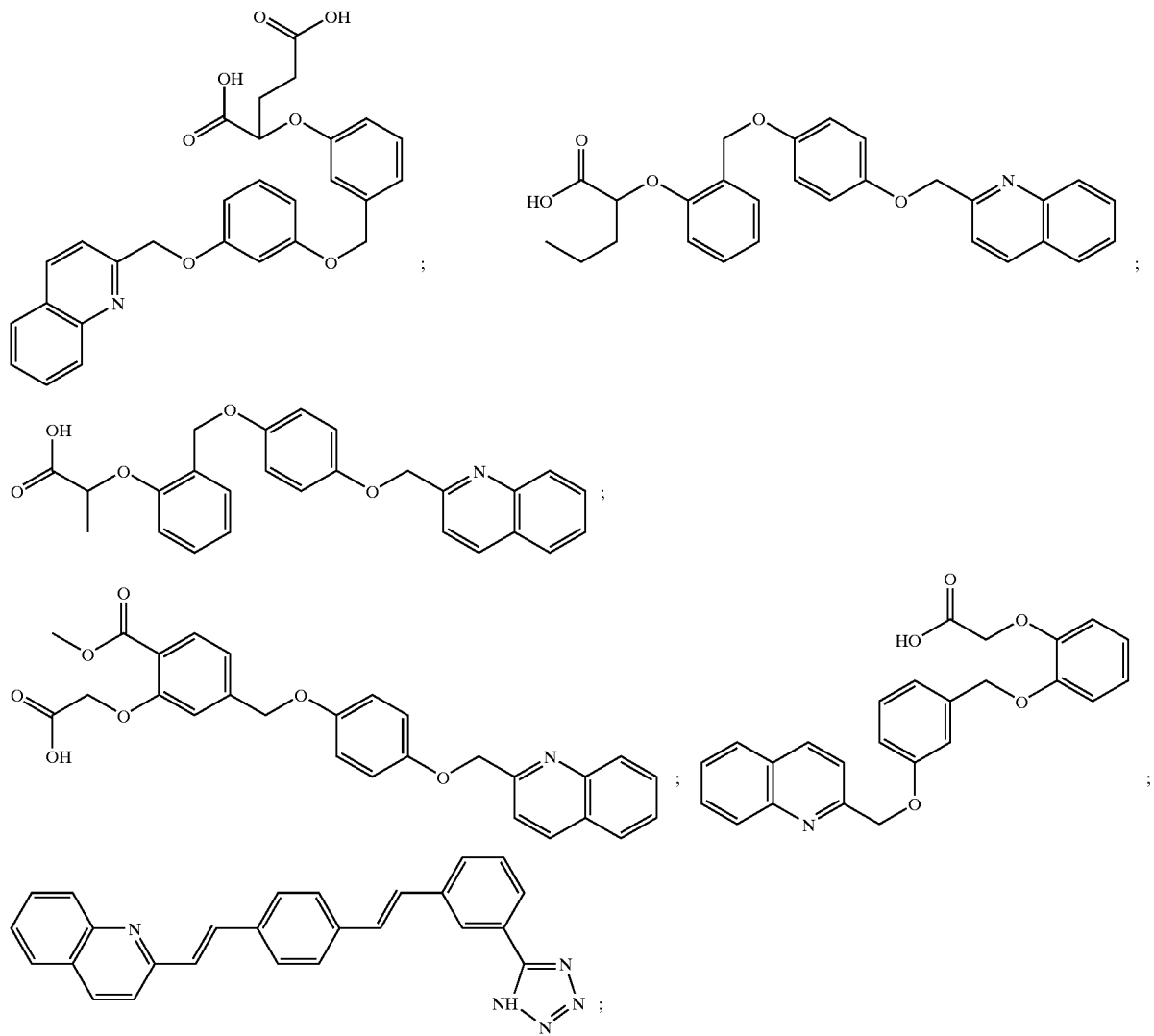
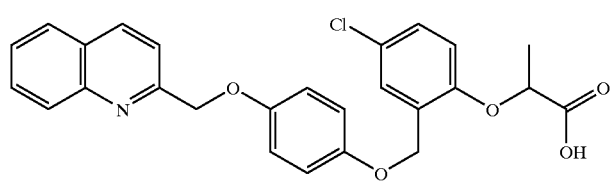

-continued
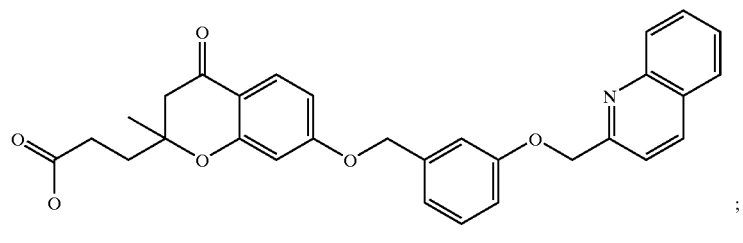
152–154° C.
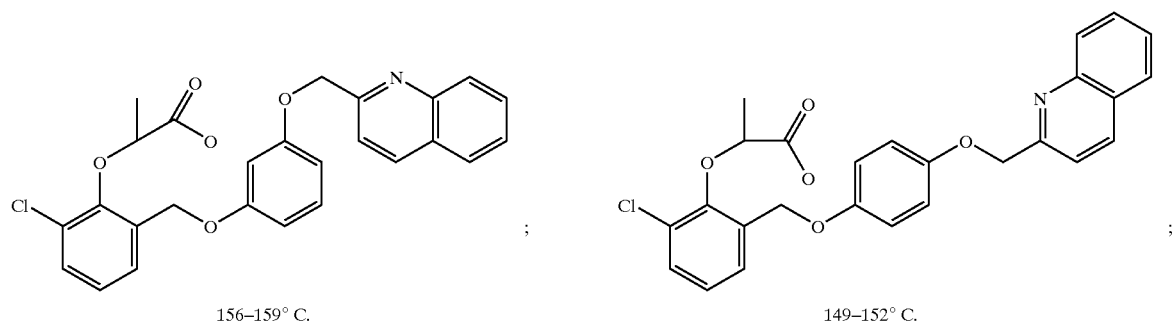
156–159° C. ; 149–152° C. ;
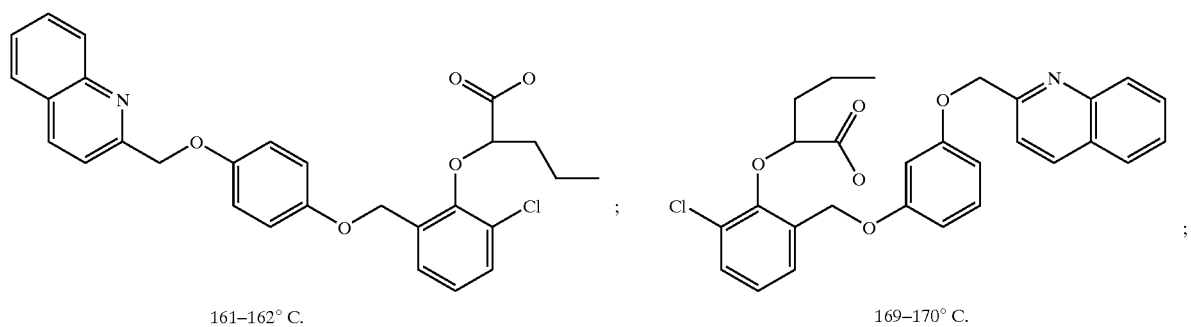
161–162° C. ; 169–170° C. ;
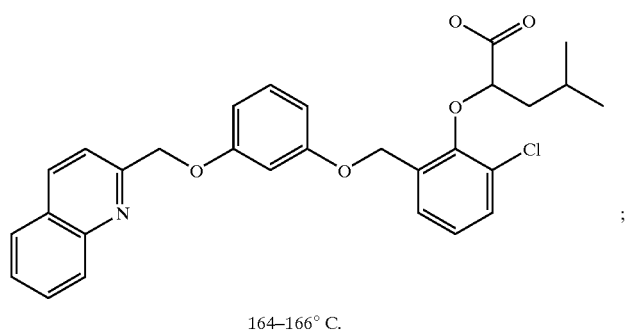
164–166° C.
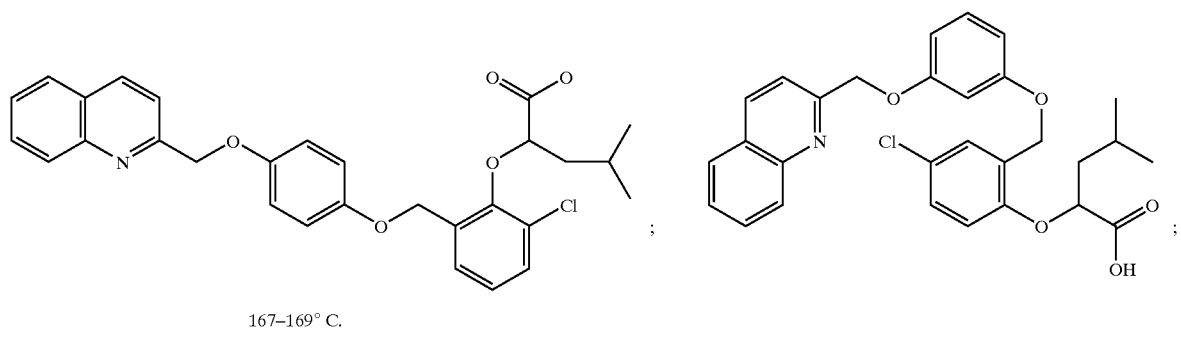
167–169° C. ;

-continued
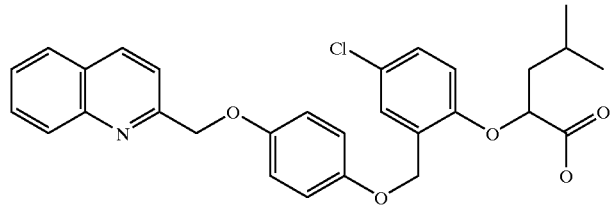
143–147° C.
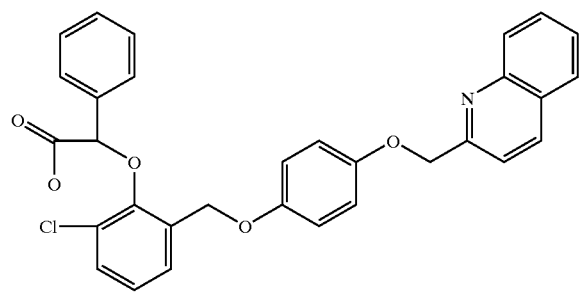
76–87° C.
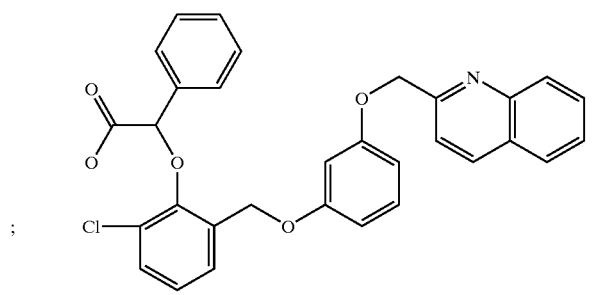
156–157° C.
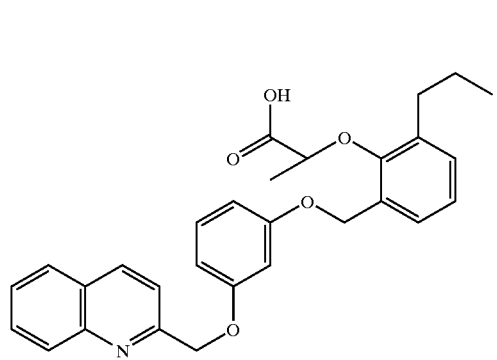
150–157° C.
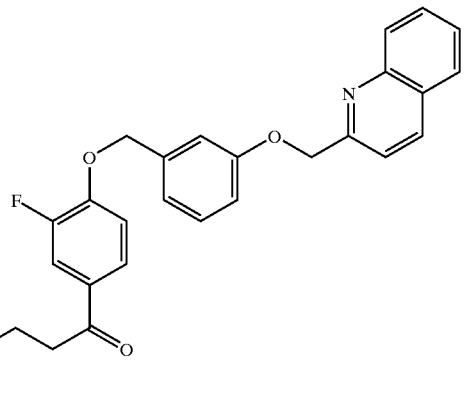
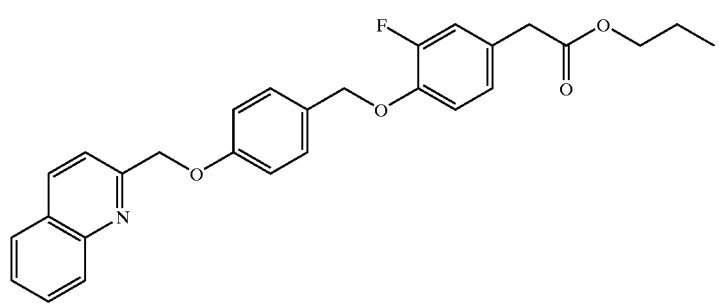
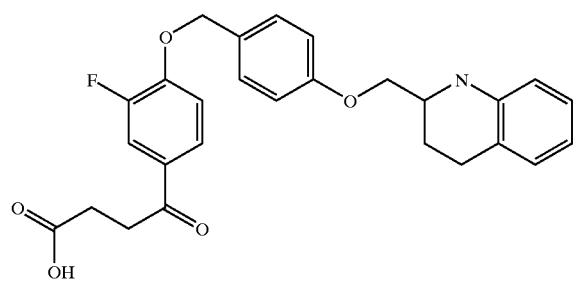

-continued
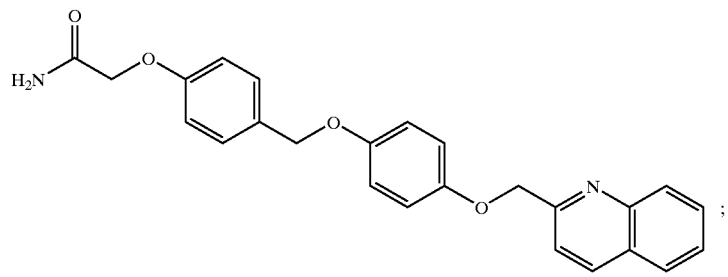
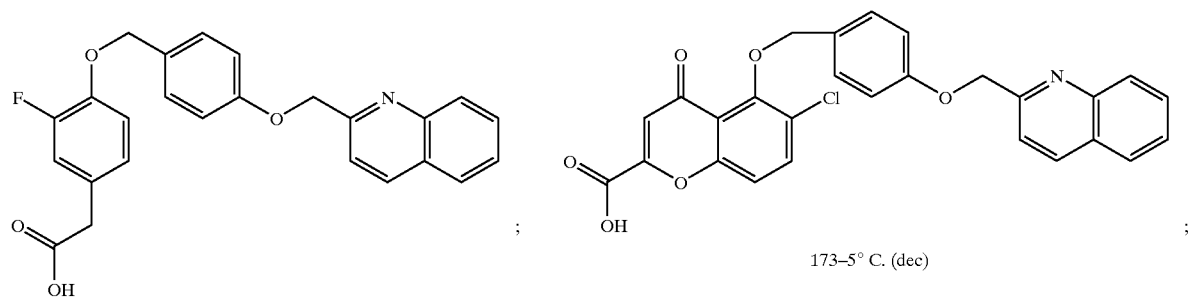
173–5° C. (dec)
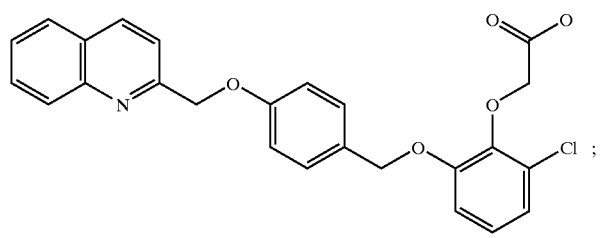
188–191° C.
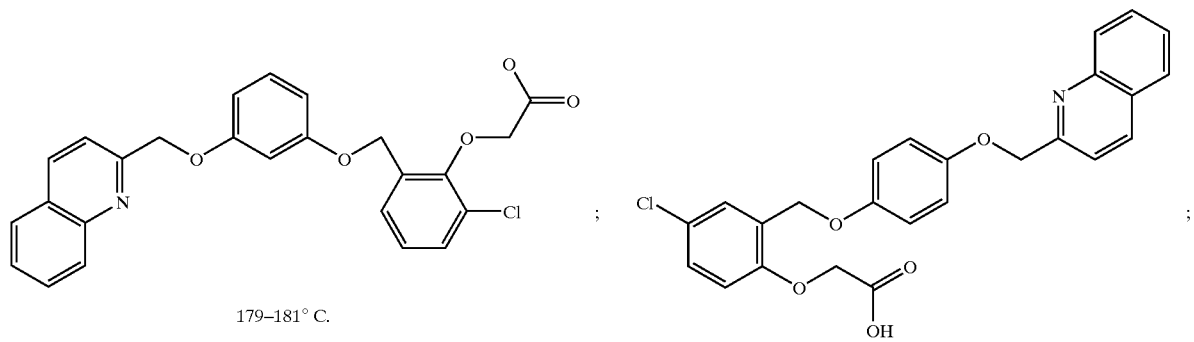
179–181° C.
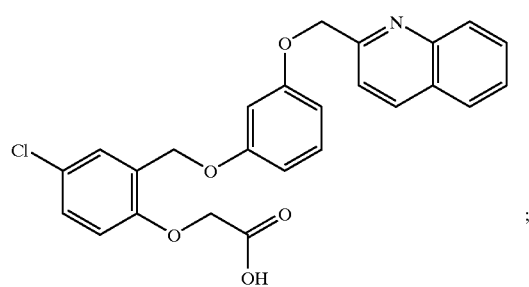

-continued
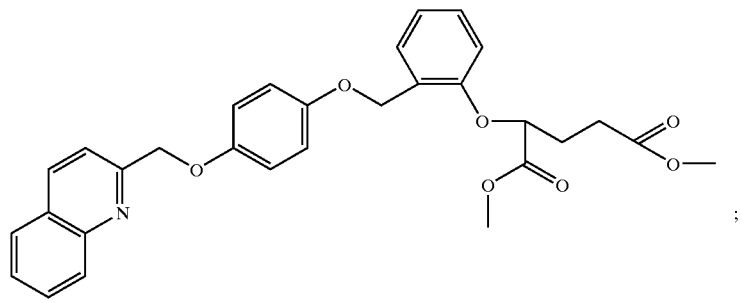
oil: CHN calc.
C30H29NO7+0.5
H2O: C 68.69, H
5.76, N 2.67; found
C 68.68, H 5.71, N
2.86
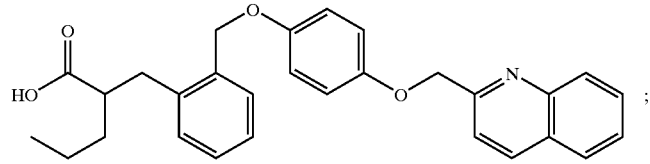
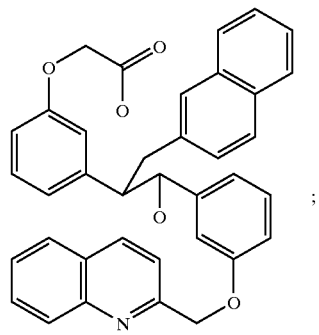
104–106° C.
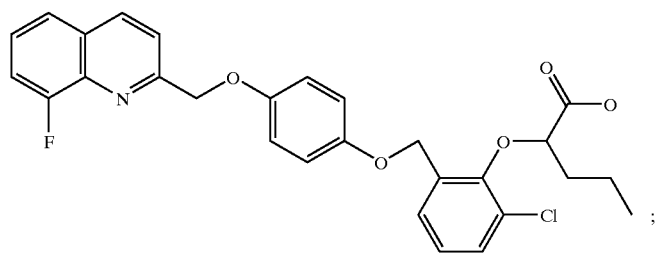
173–177° C.
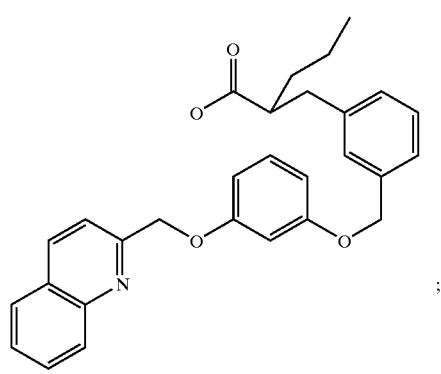
CHN calc.
C29H29NO +
0.75 H2O:
C 74.26, H 6.55,
N 2.99;
found C 73.97,
H 6.31, N 2.89
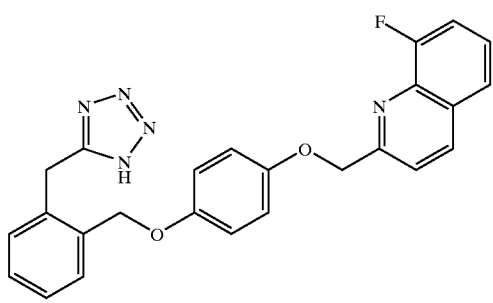

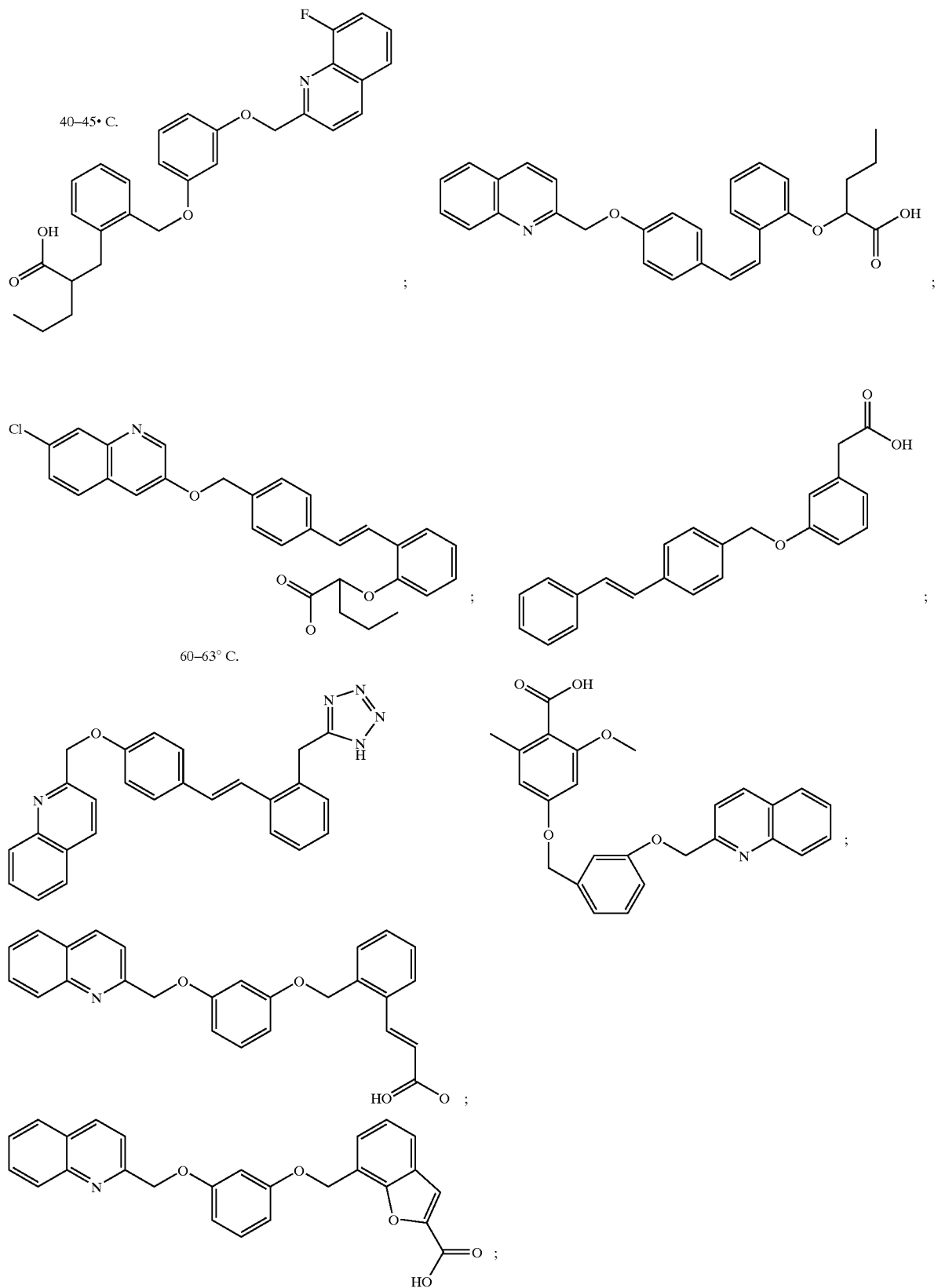

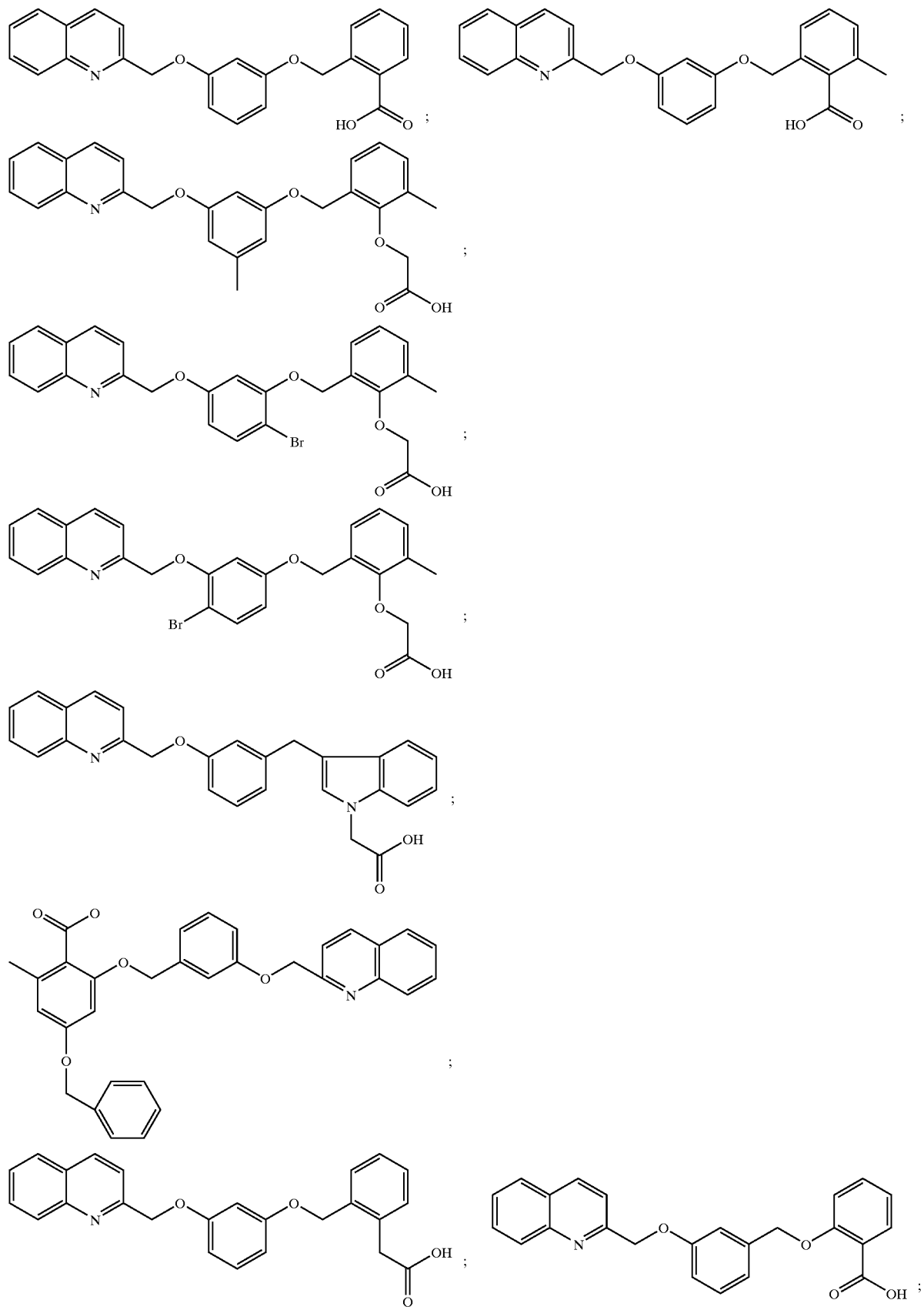

-continued
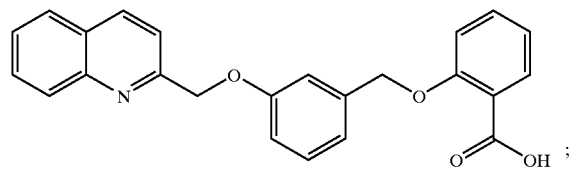
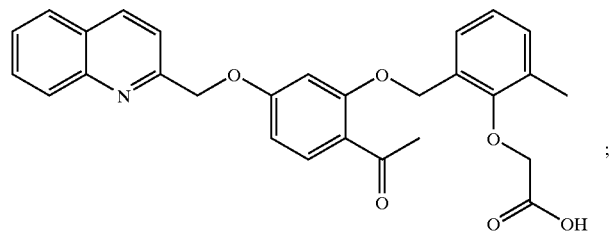
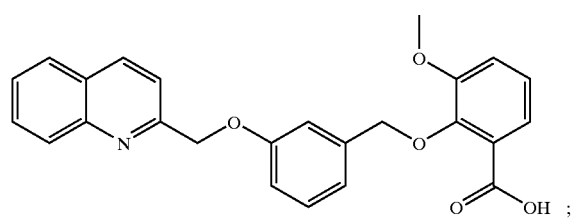
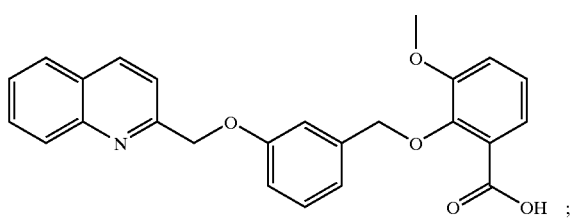
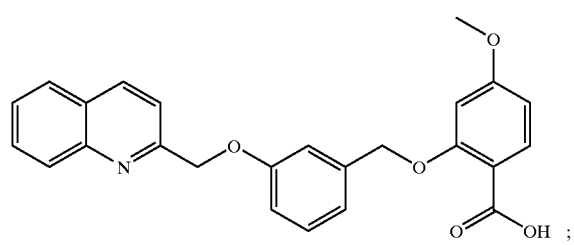
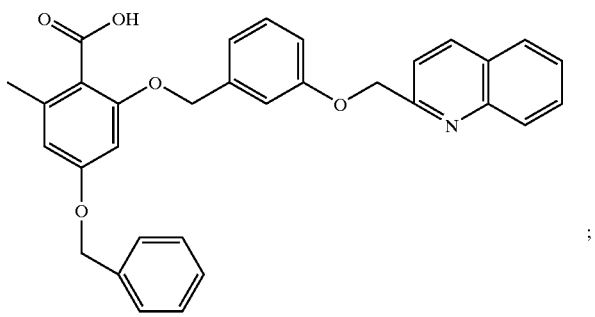
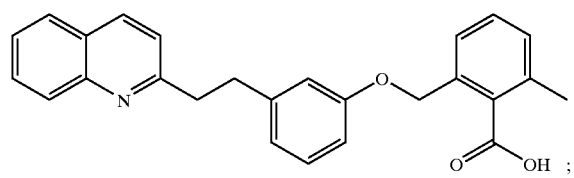
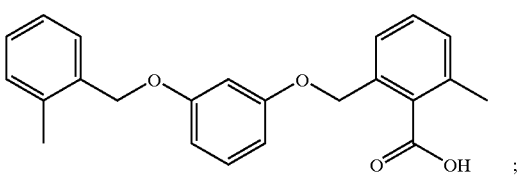
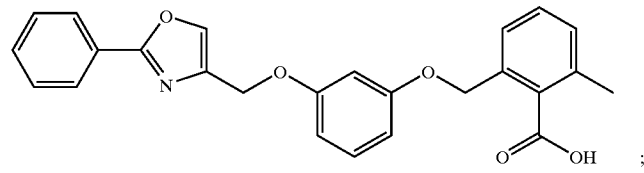
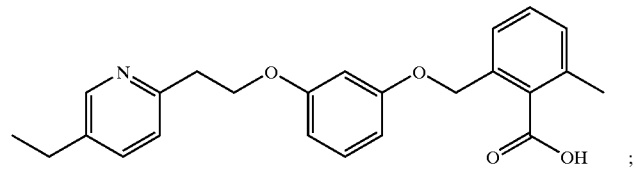

-continued
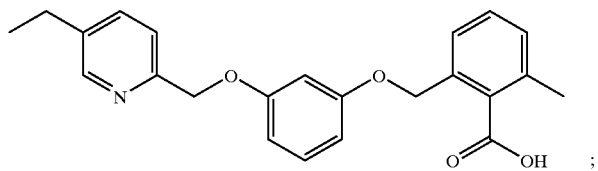
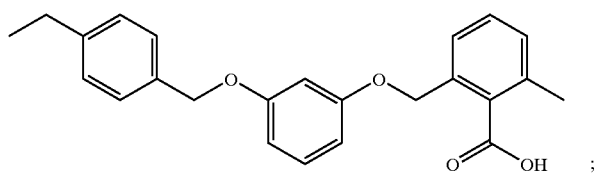
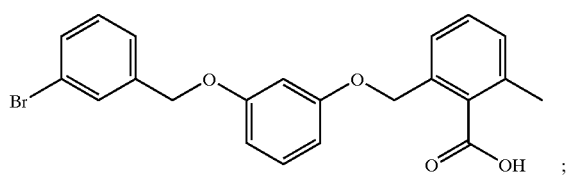
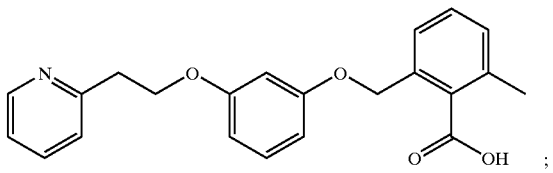
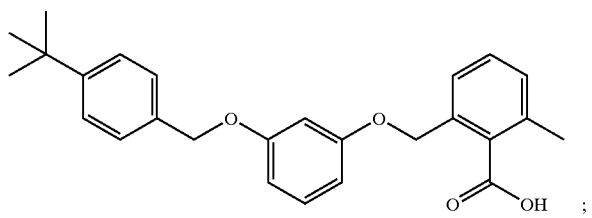
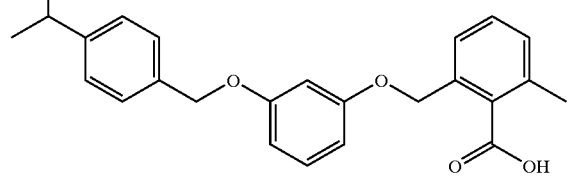
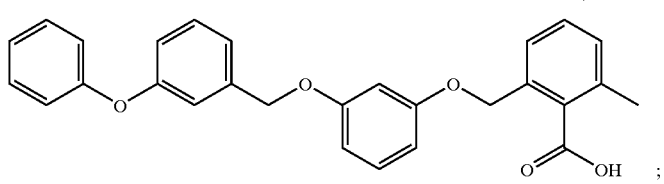
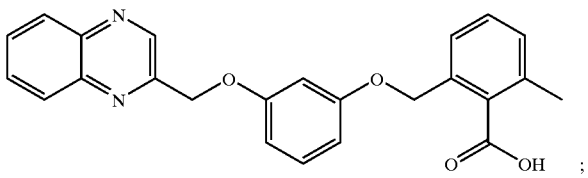
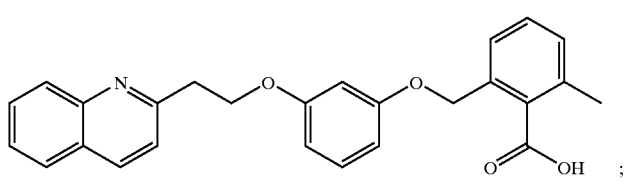

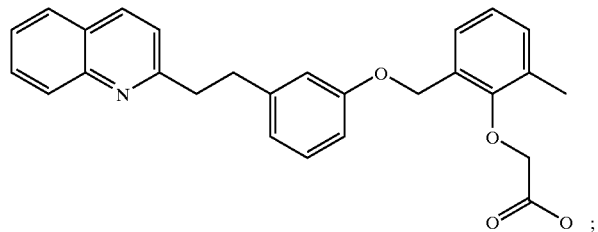
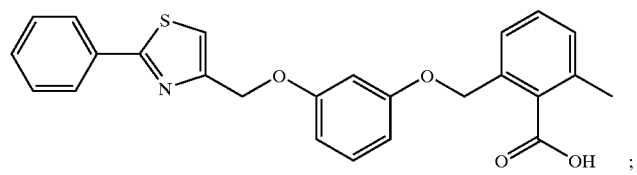
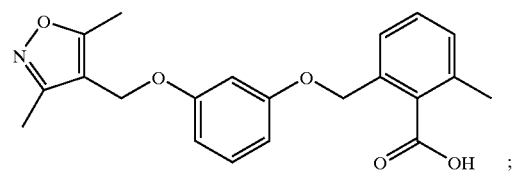
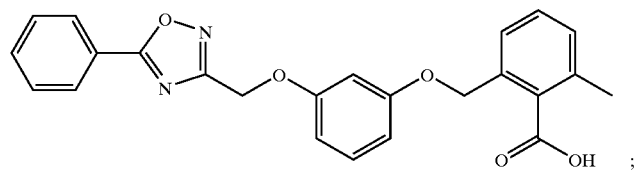
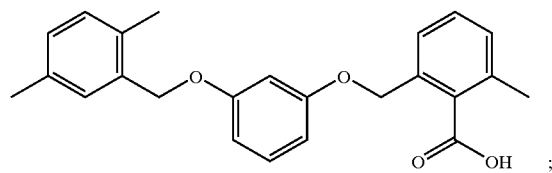
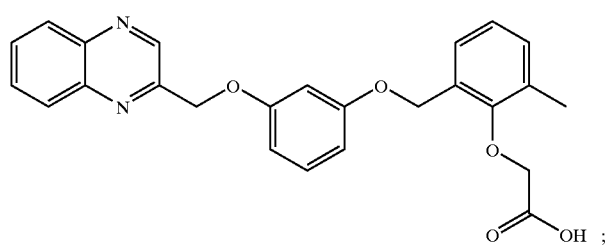
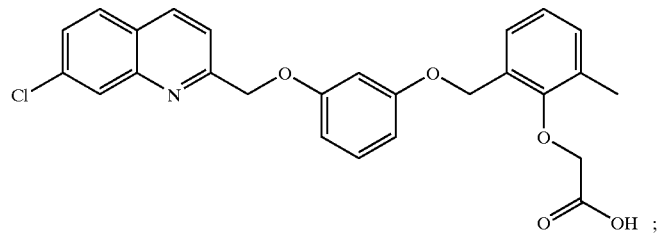
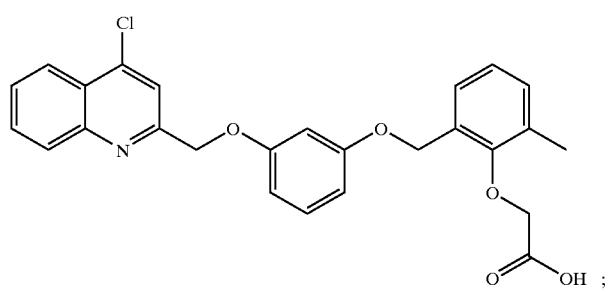

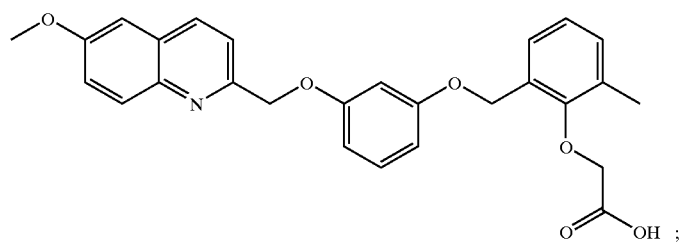
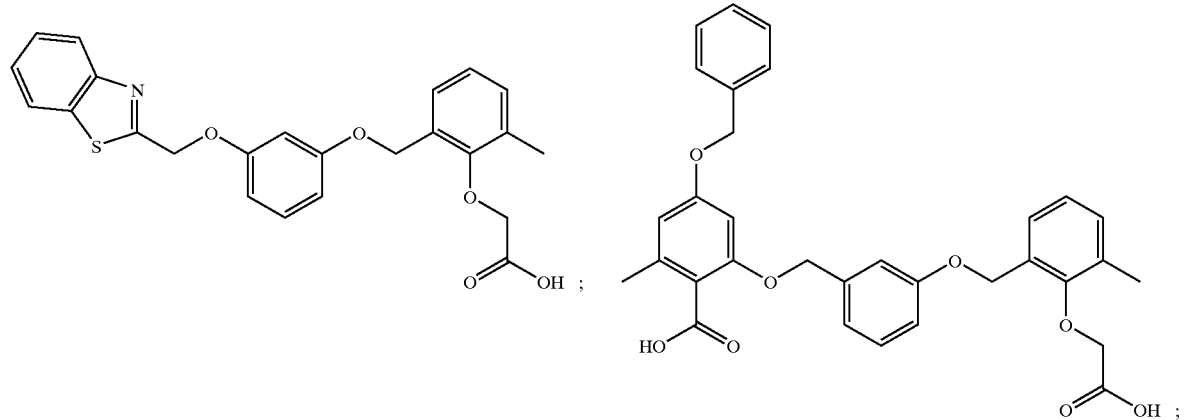
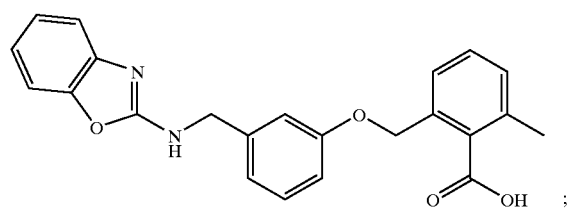
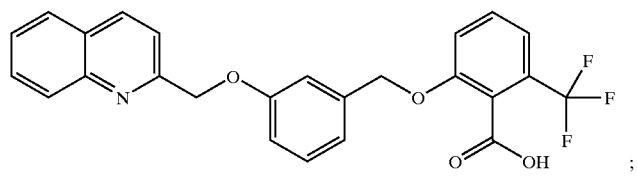
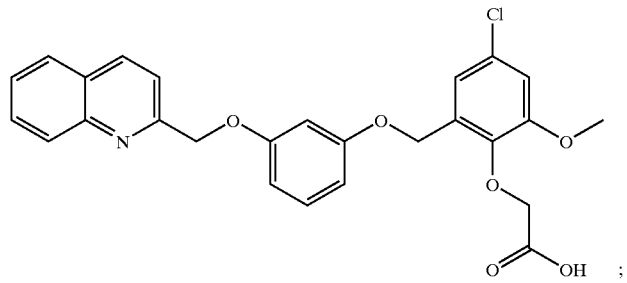
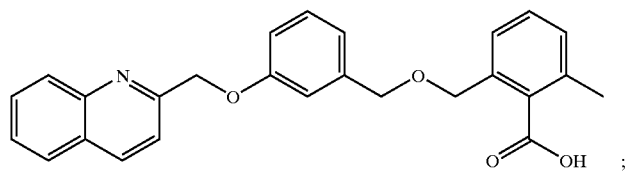
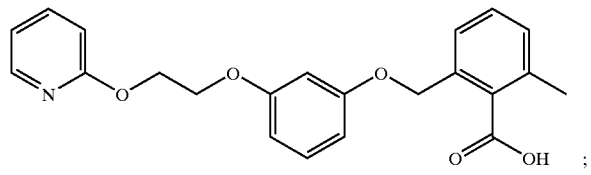

-continued
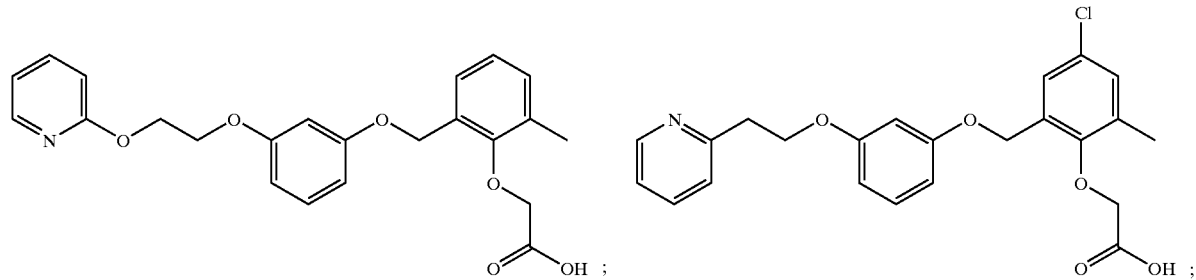
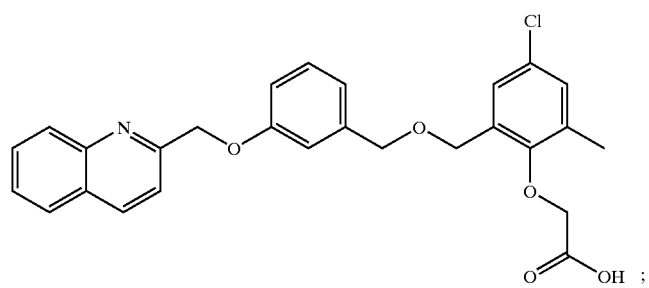
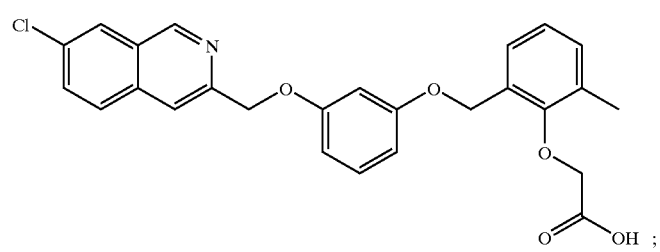
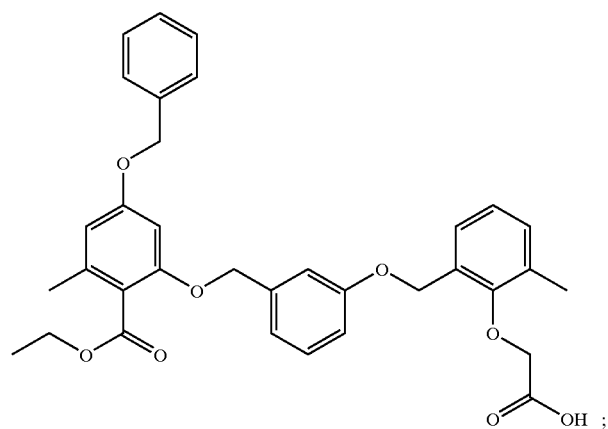
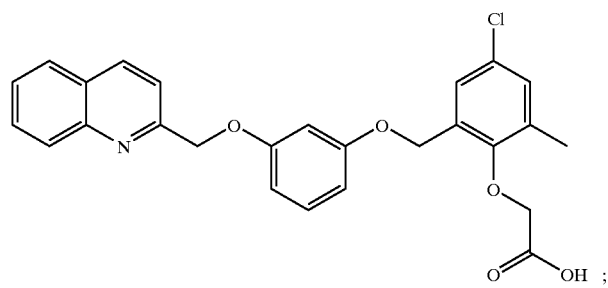

-continued
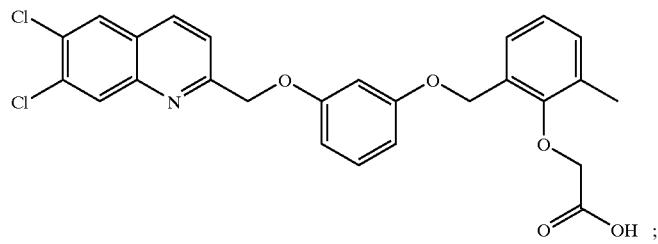
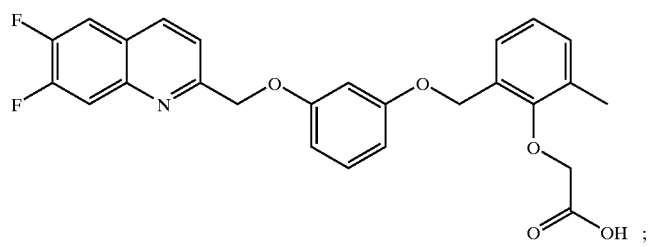
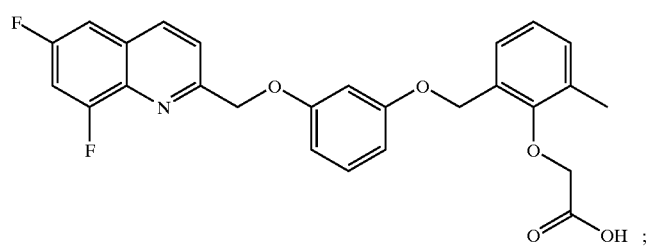
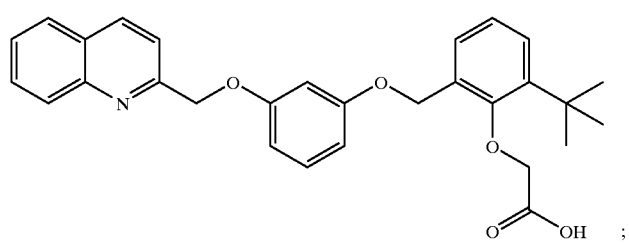
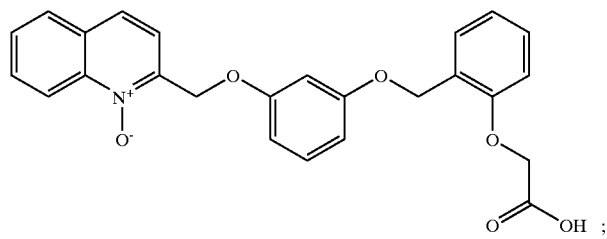
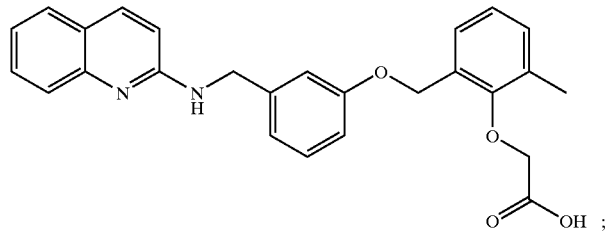
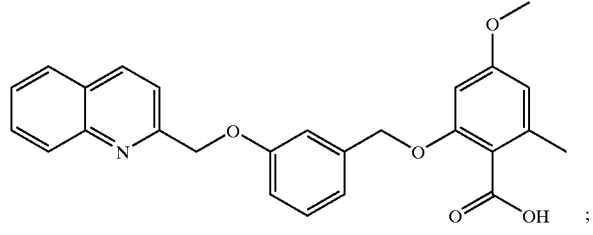

-continued
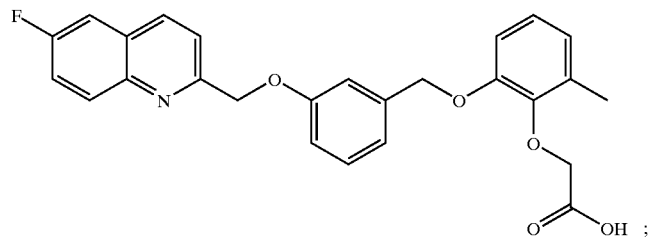
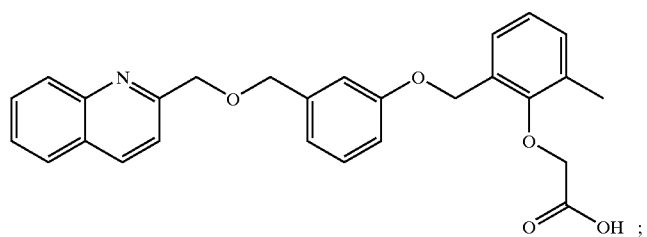
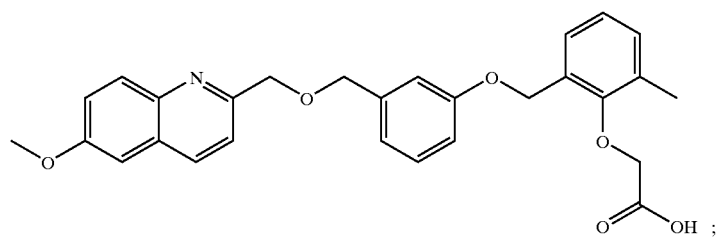
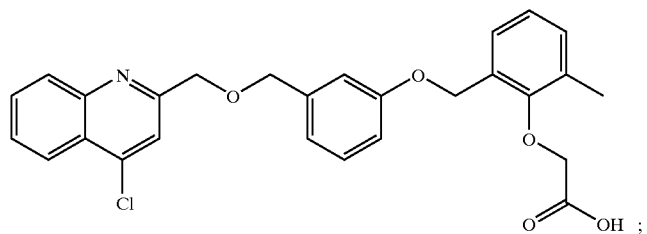
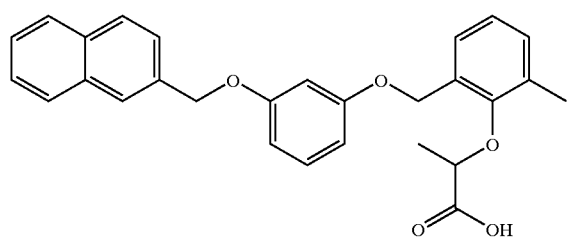
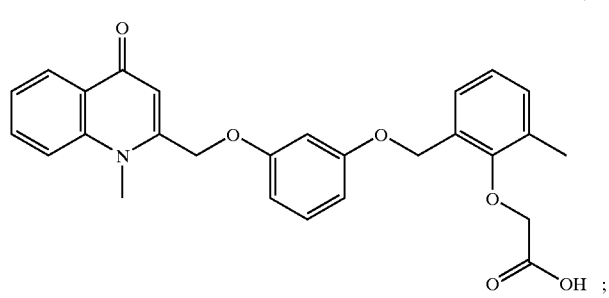

-continued
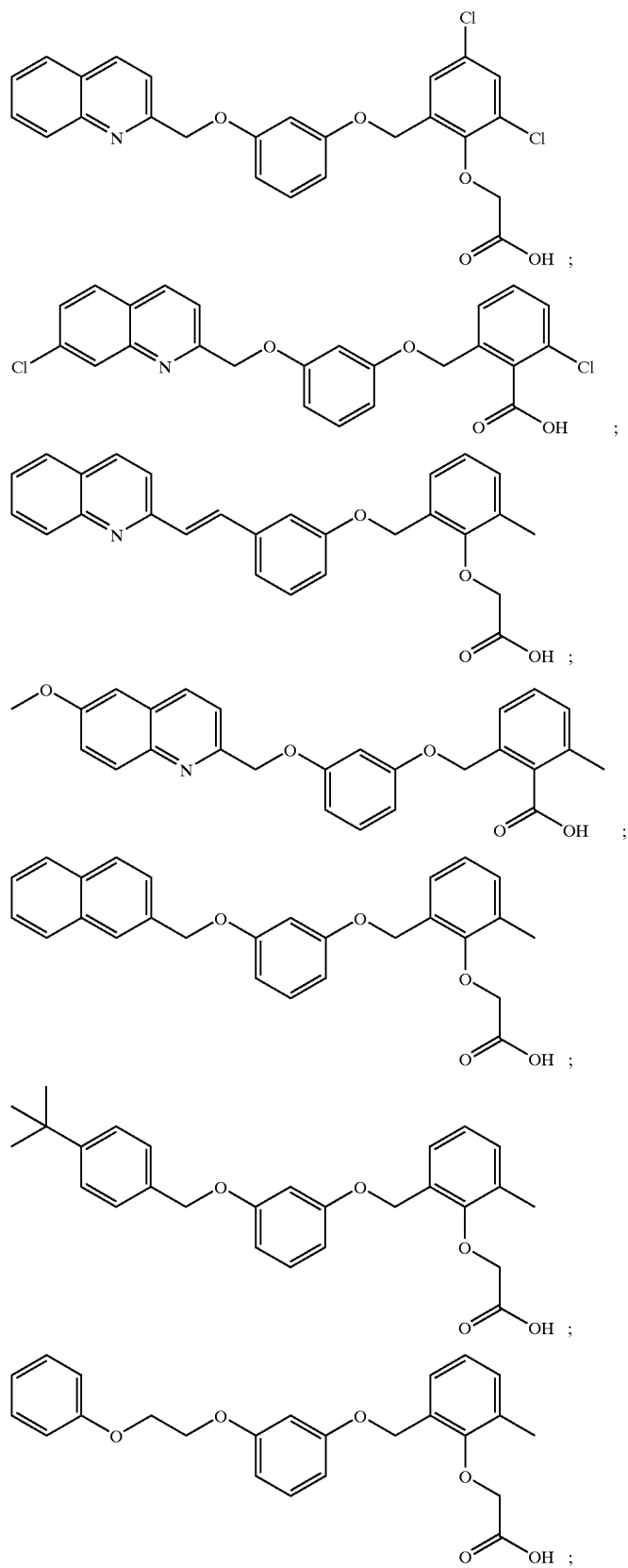

-continued
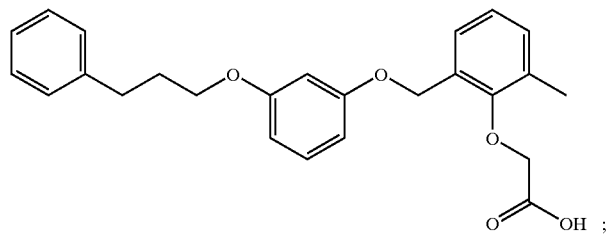
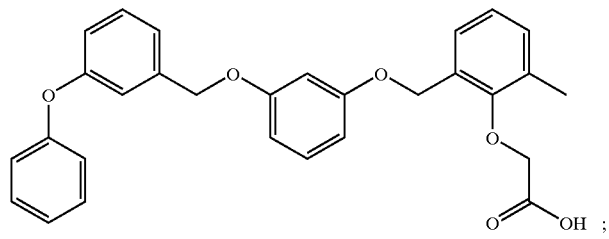
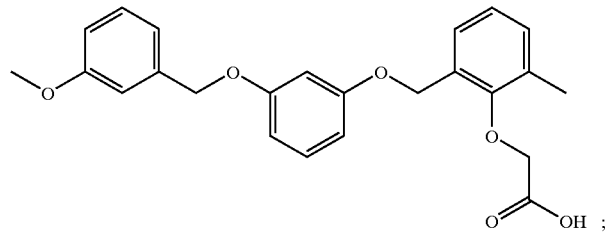
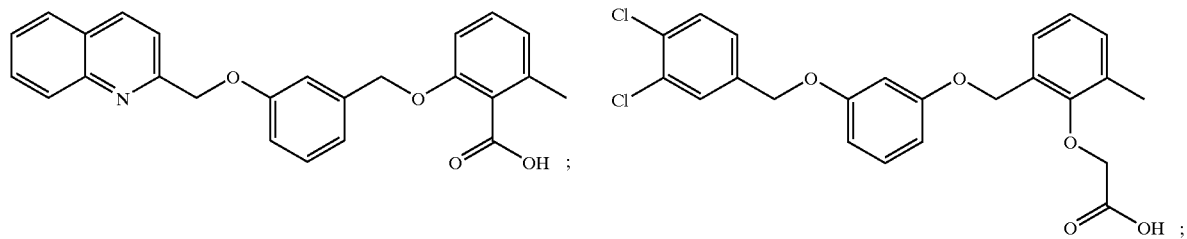
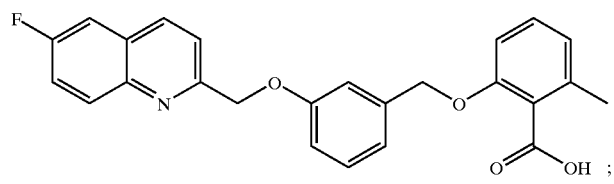
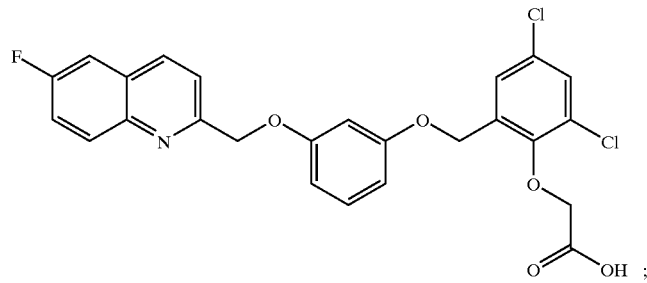
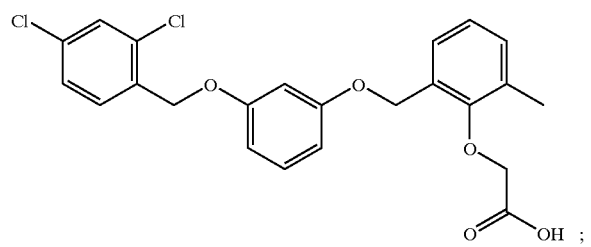

-continued
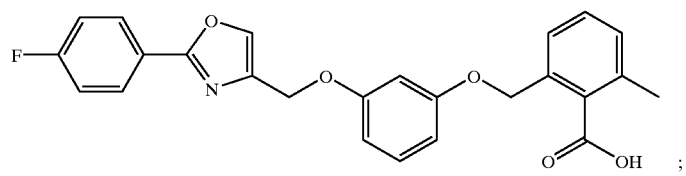
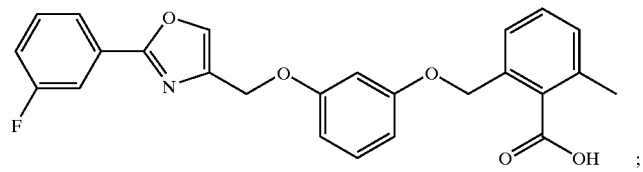
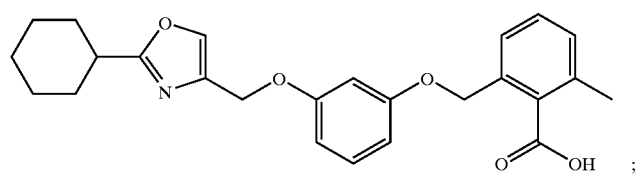
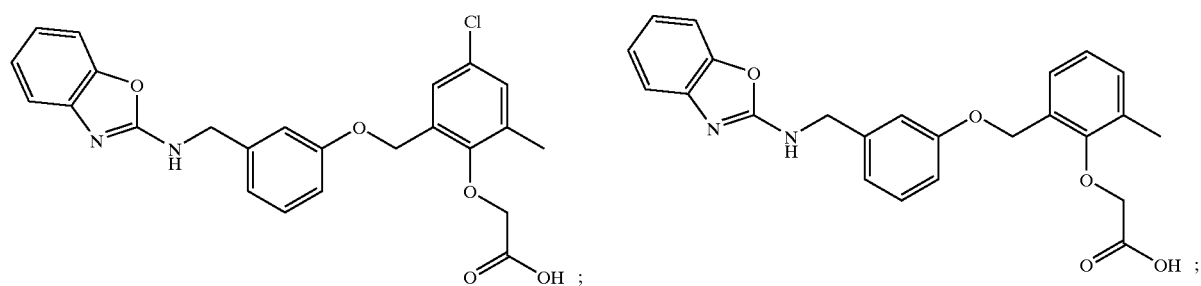
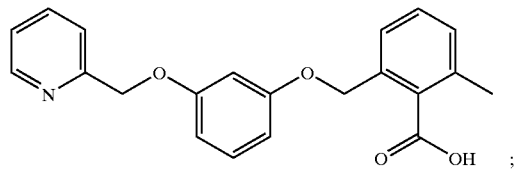
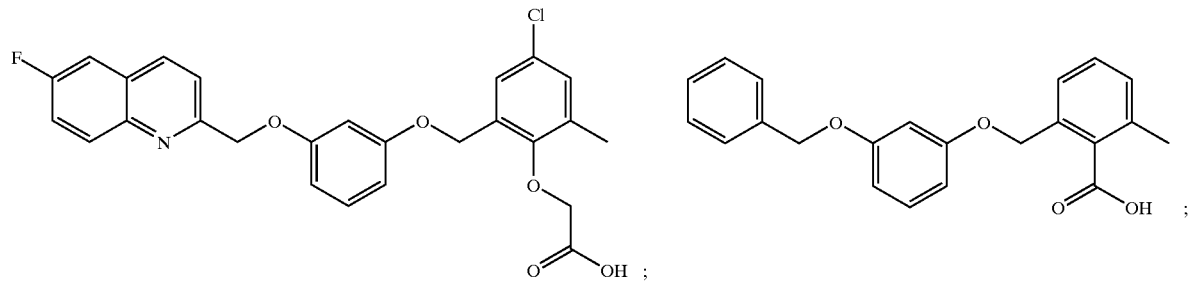
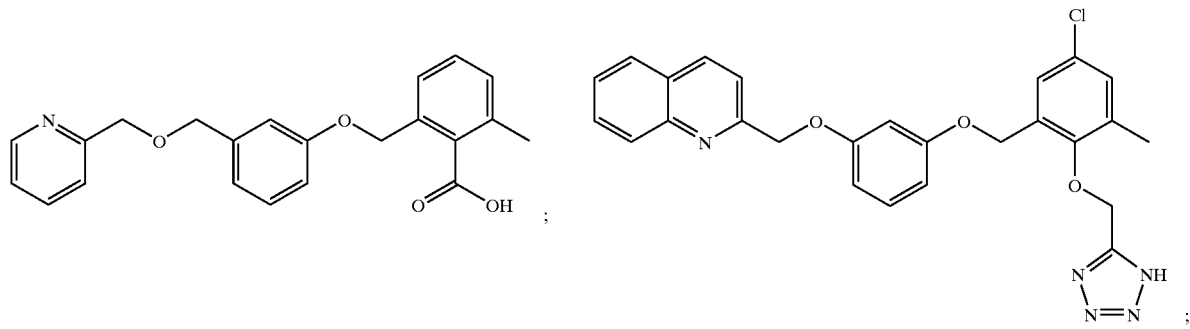

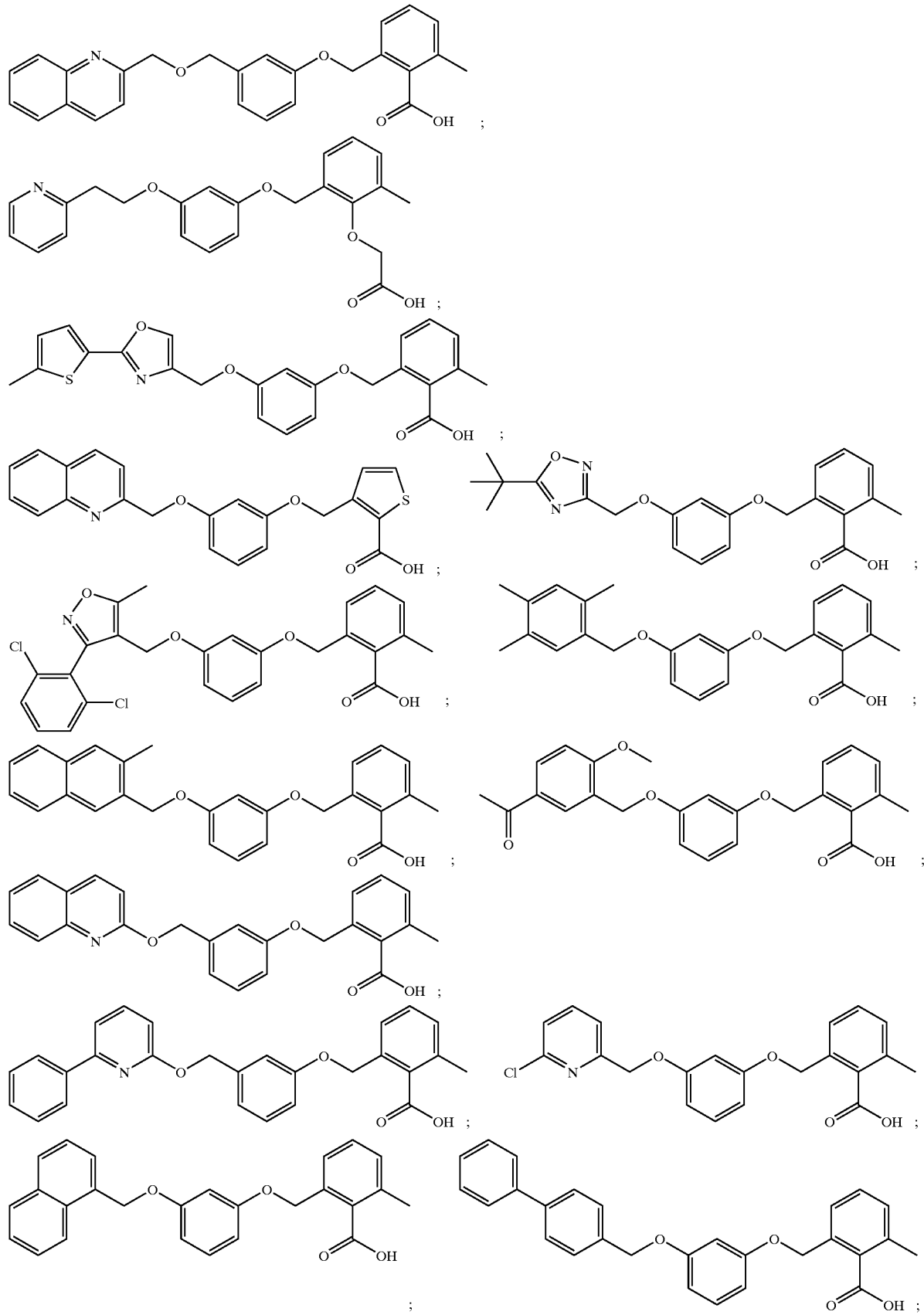

-continued
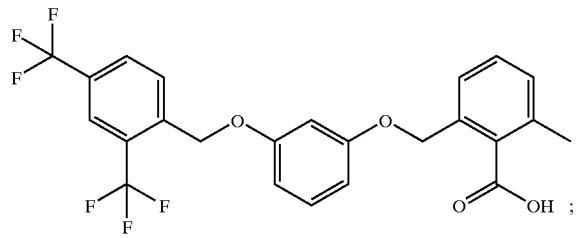
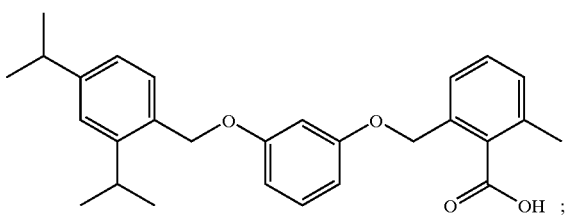
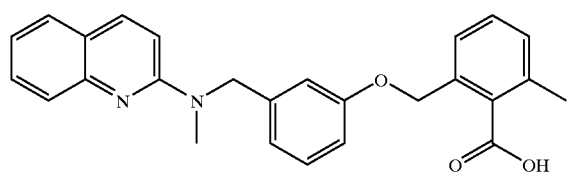
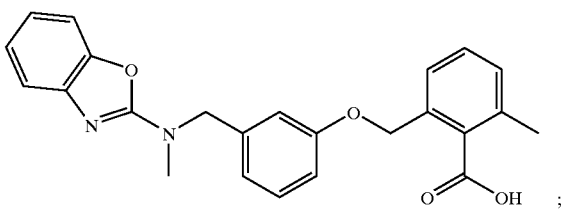
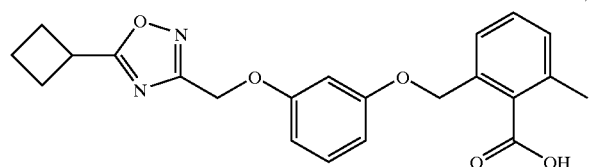
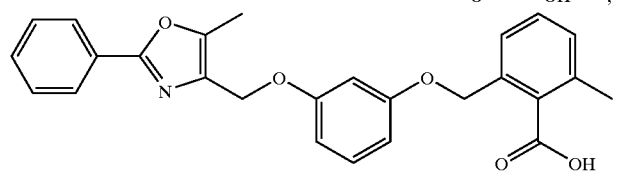
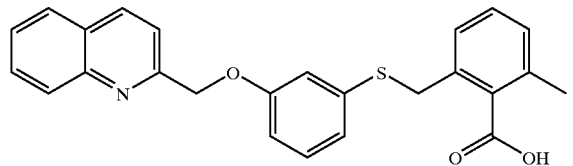
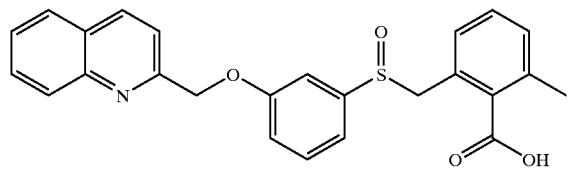
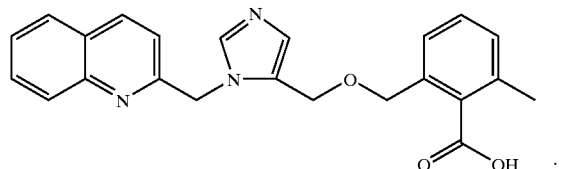
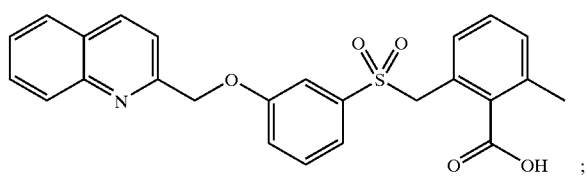
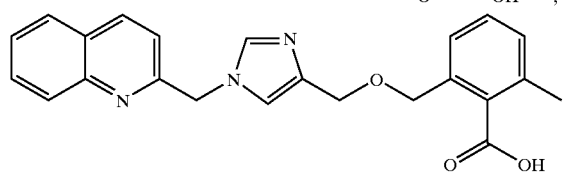
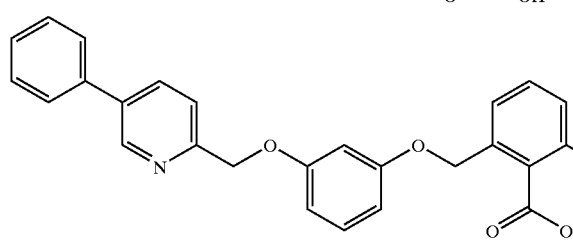
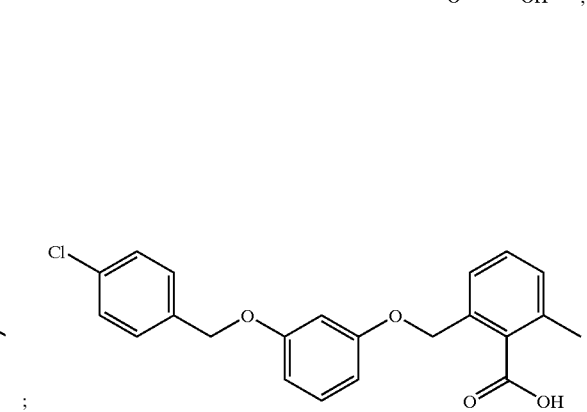

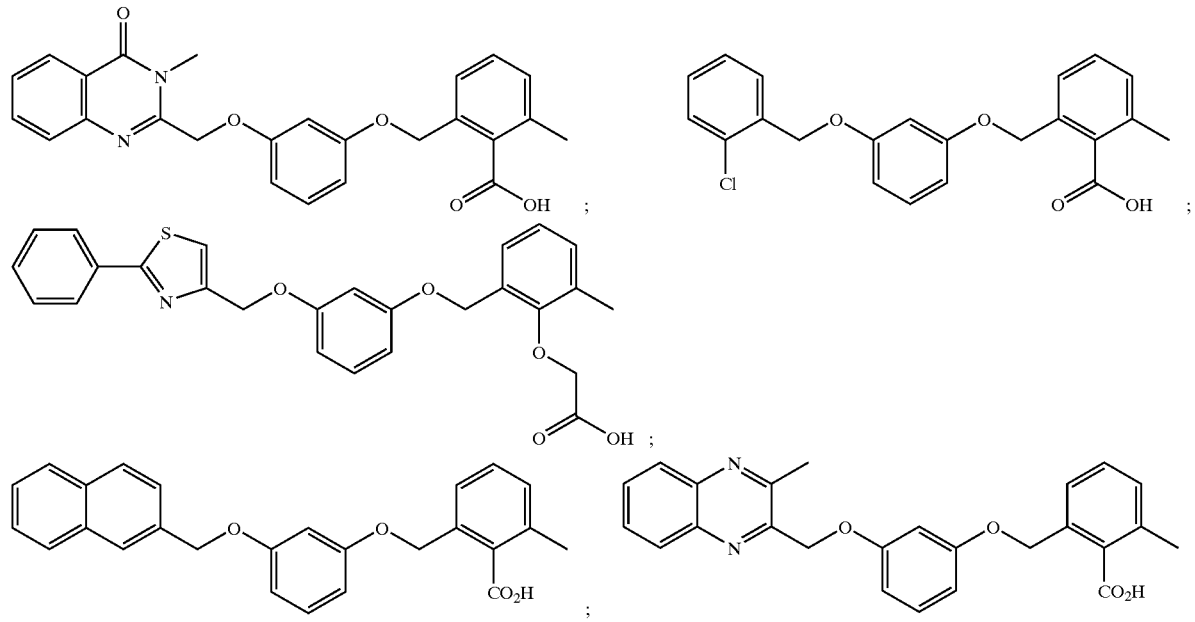
A preferred compound according to the invention is selected from the group consisting of
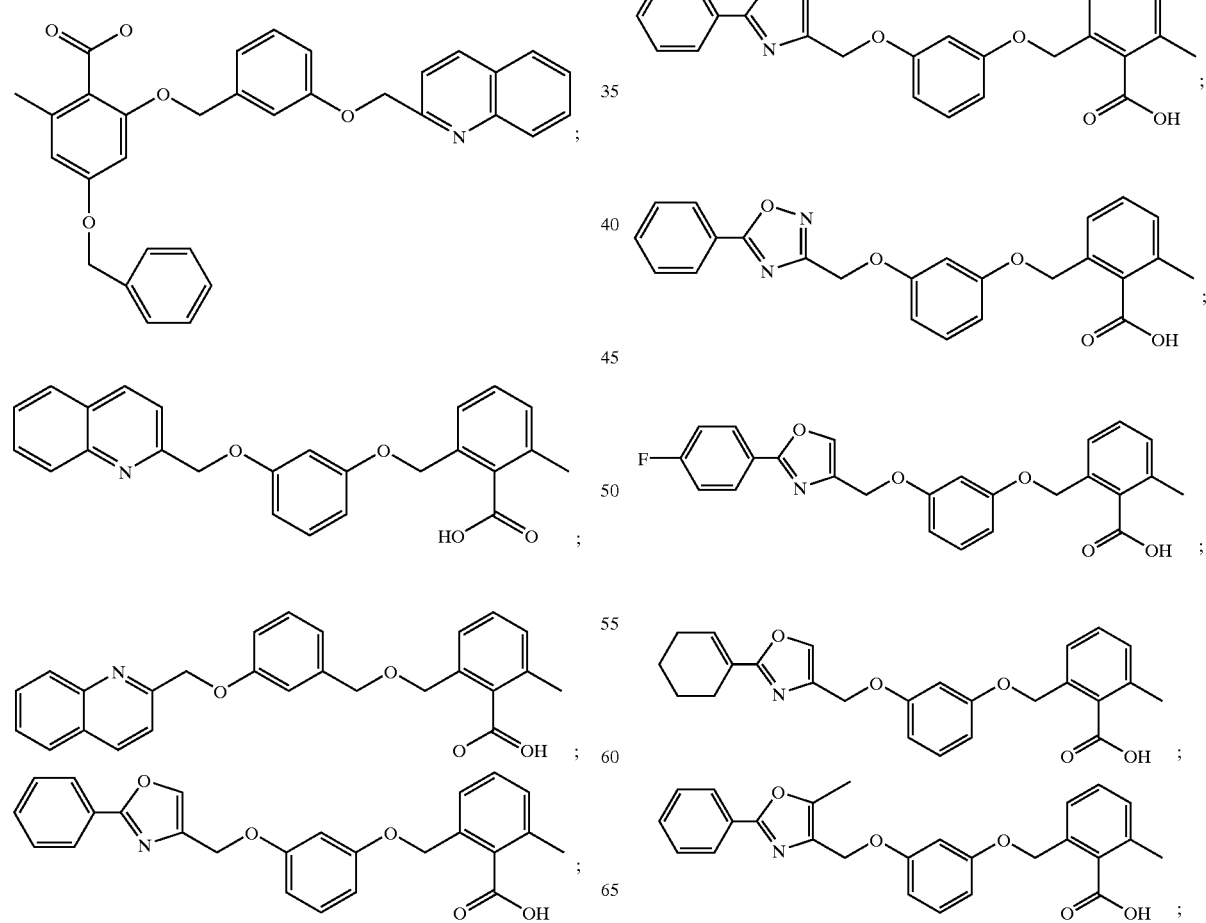

-continued
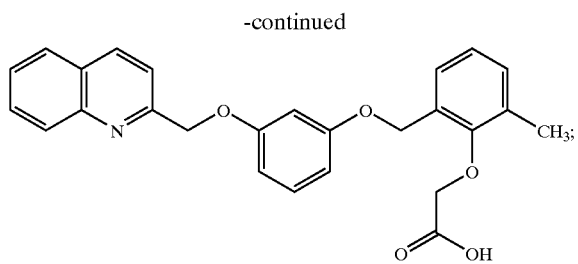
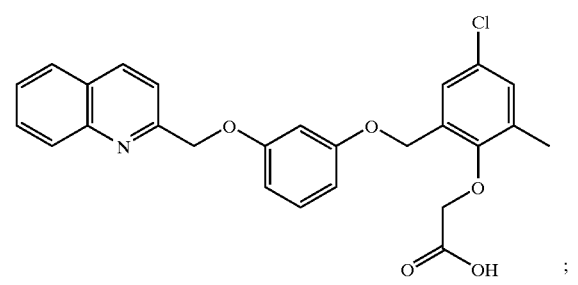
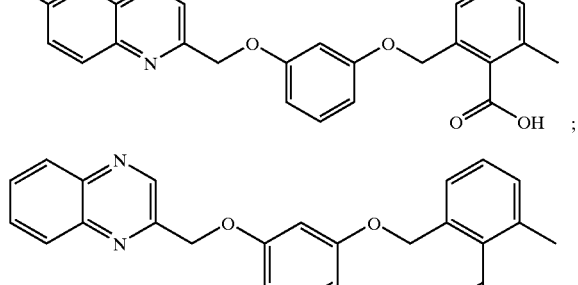
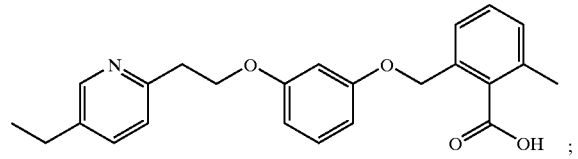
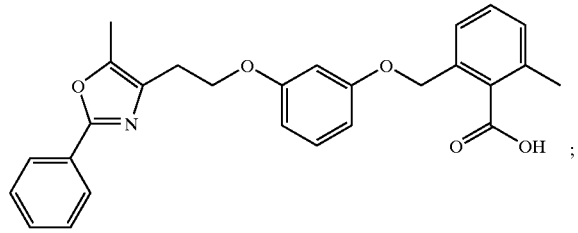
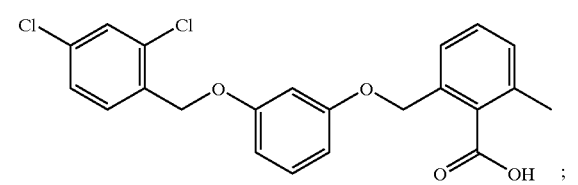
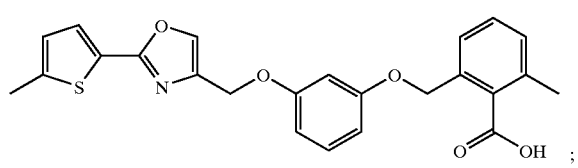
-continued
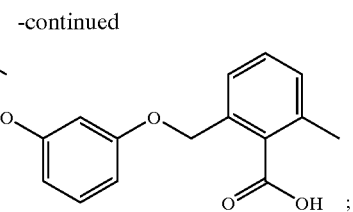
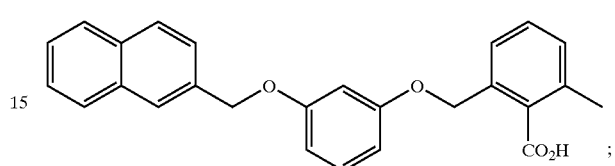
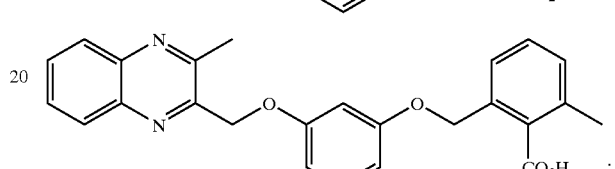
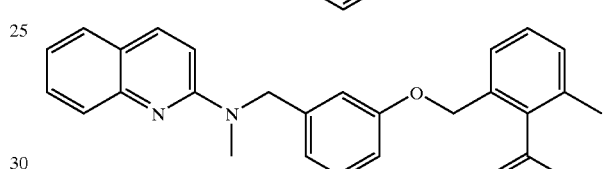
and
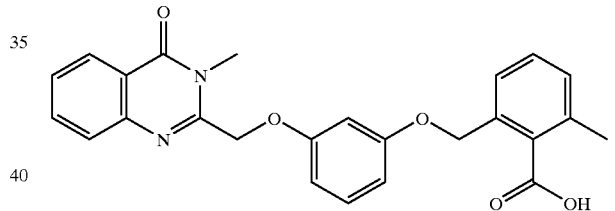
A more preferred compound according to the invention is selected from the group consisting
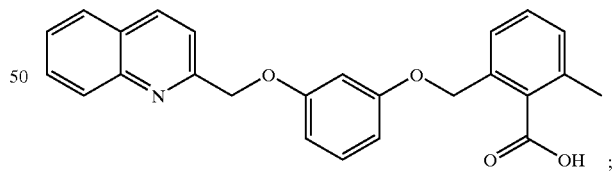
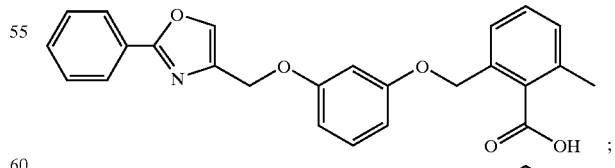
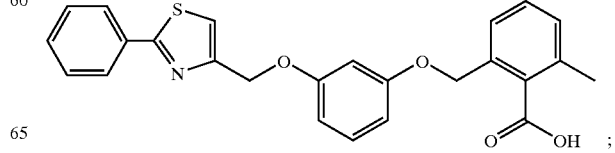

-continued
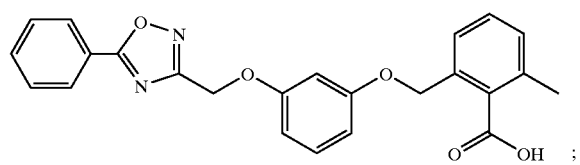
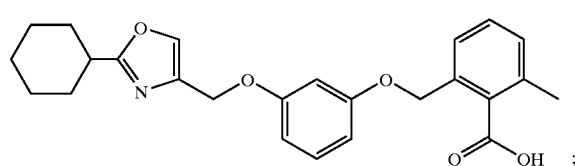
and
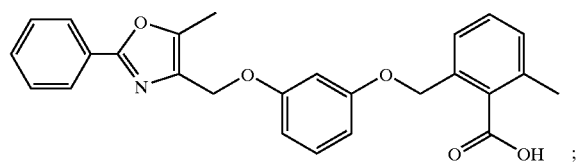
A preferred compound according to the invention having PPARα and PPARγ activity is of the formula:
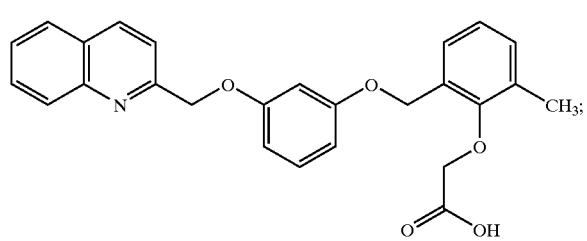
A preferred compound according to the invention that is selective for PPARα is selected from the group consisting of
-continued
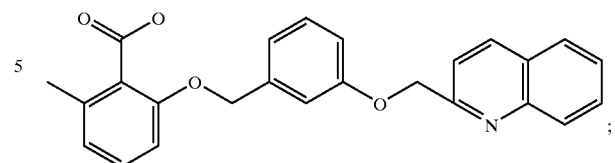
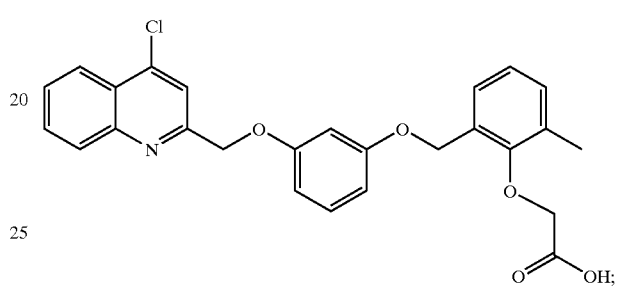
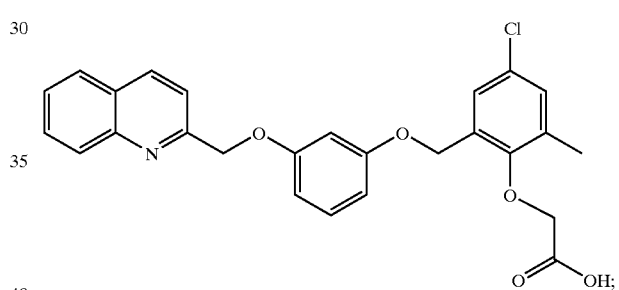
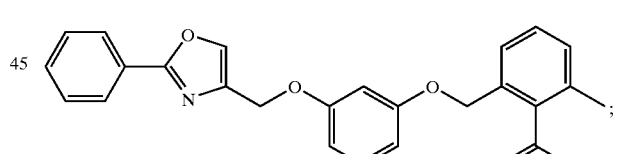
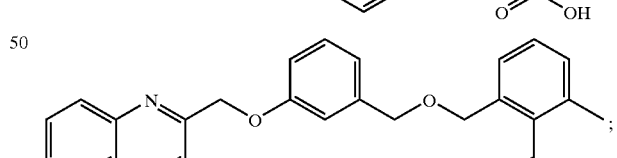
and
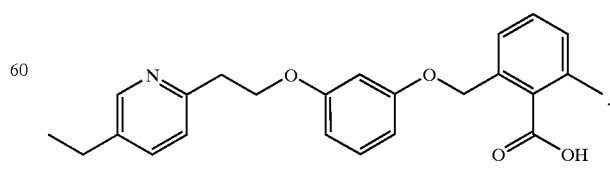
A preferred compound according to the invention that is selective for PPARδ is of the formula:

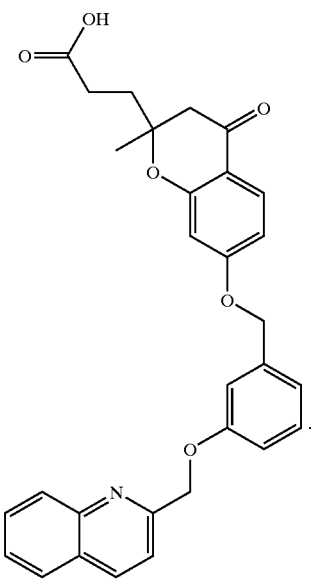

A preferred compound according to the invention that is selective for PPARδ and PPARγ is selected from the group consisting of:

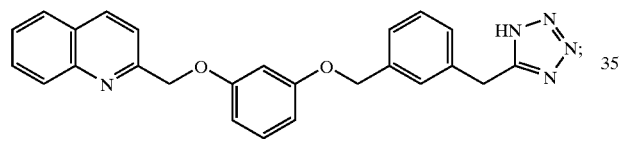

and

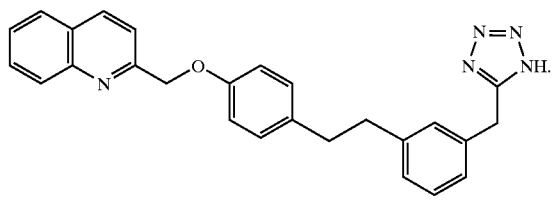

A preferred compound according to the invention that is selective for PPARα and PPARδ is selected from the group consisting of:

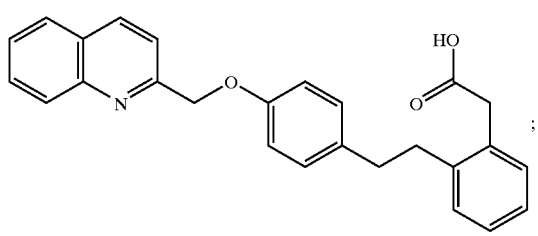

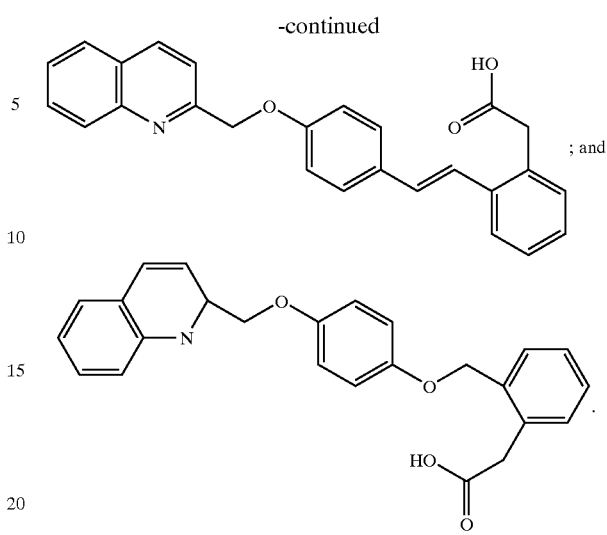

More preferred compounds of the invention having PPARγ activity have the formula:

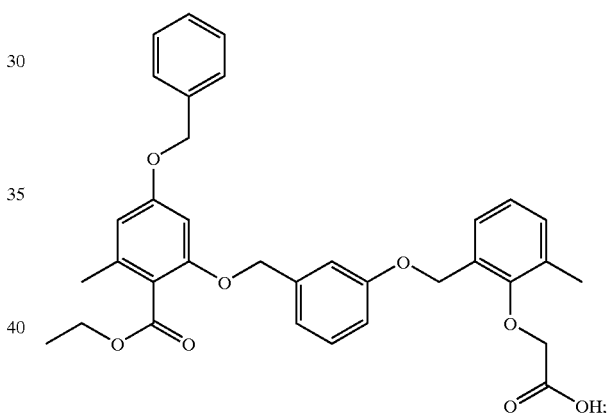

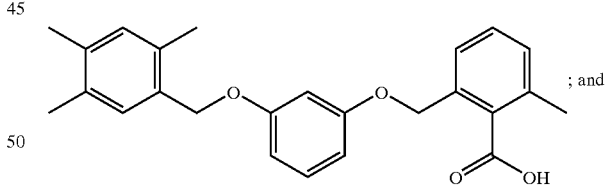

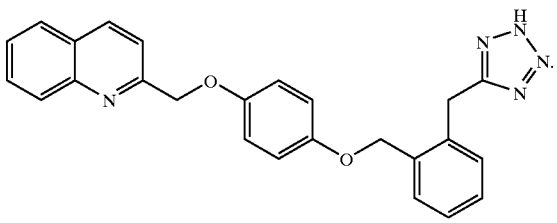

This invention also encompasses all combinations of preferred aspects of the invention noted herein.

Compounds useful according to this invention can be prepared in segments as is common to a long chain molecule. Thus it is convenient to synthesize these molecules by employing condensation reactions at the A, B and D sites of the molecule. Compounds of Formula I can be prepared by the application or adaptation of known methods, by which is meant methods used heretofore or described in the literature. Compounds of Formula I are preparable by recognized procedures from known compounds or readily preparable intermediates. Thus, in order to prepare a compound of the below formula, where Z is generally CN or $CO_2R$

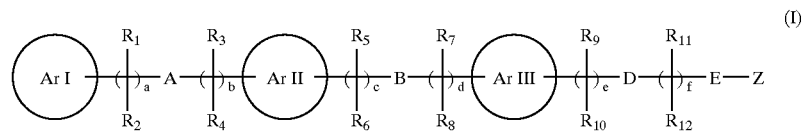

(I)

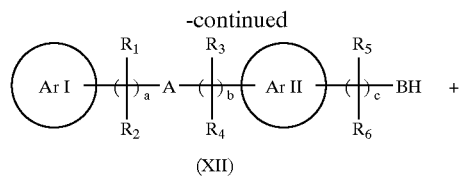

(XII)

The following reactions or combinations of reactions are employable:

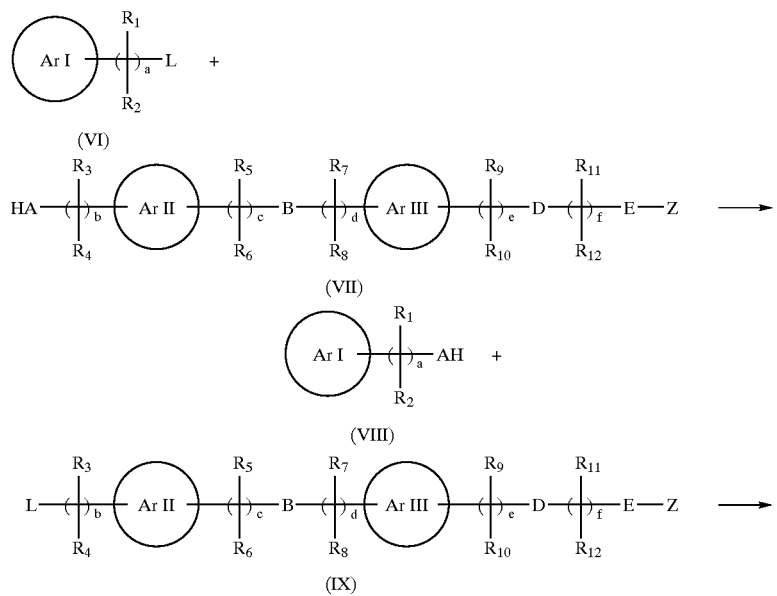

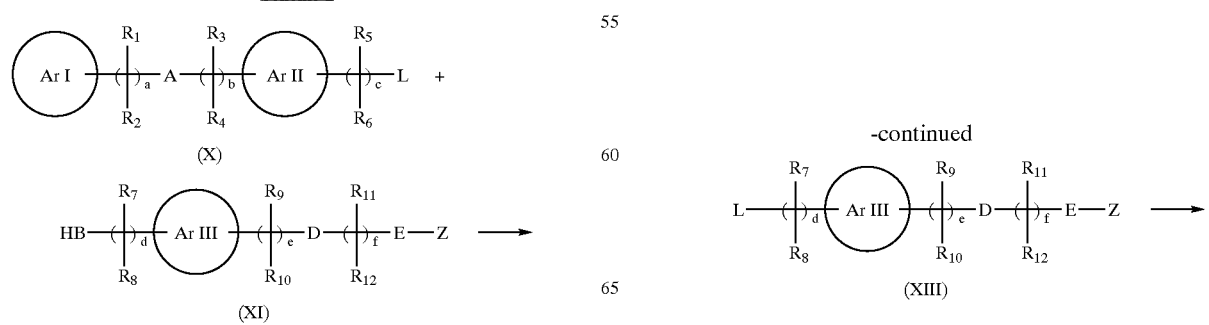

Scheme 3

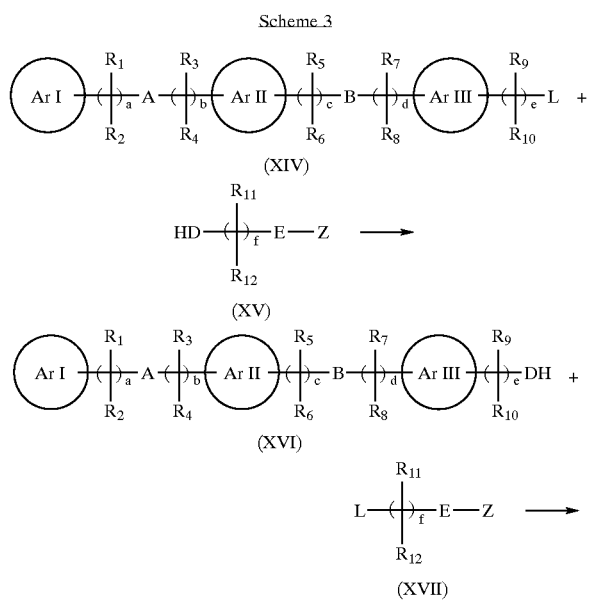

In the above schemes (1–3) a displacement reaction can be used when A, B and D are O, S or NR, and L is a leaving group such as halo, toslyate or mesylate. A base such as sodium hydride, sodium hydroxide, potassium carbonate or triethylamine may be used when A, B or D is O or S.

An alternative coupling reaction is the Mitsunobu reaction (diethylazodicarboxylate/triphenylphosphine see *Synthesis*, 1981, 1). This chemistry can be used to condense fragments when the functionality is amenable to this reaction. An example of this would be the coupling of compounds of scheme 1 where formula VI (L=OH, a>0) and formula VII (A=O, b=0).

Reaction temperatures are in the range of about −78° C. to 80° C. and reaction times vary from about 1 to 48 hours. The reactions are usually carried out in an inert solvent that will dissolve the reactants. Solvents include, but are not limited to N,N-dimethylformamide, acetone, acetonitrile, tetrahydrofuran.

Alternatively, the reactions shown in Schemes 1–3 can be accomplished using a fragment of the described Formula. For example, as shown in Scheme 4, a compound of Formula VI (Scheme 1) may be combined with a compound of Formula VII, where Formula VII optionally contains Ar III and Z. This notation used for Formula VII in Scheme 4 is used throughout this document and is used to generalize the described reaction. Therefore, all of the reactions of Schemes 1–3 may be accomplished as shown or by using a fragment of the described formula. In some instances, the use of a protecting group may be required when a fragment of a formula is used.

Scheme 4

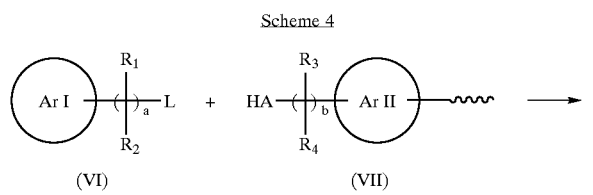

One method for the preparation of compounds where Z=tetrazole is the reaction of an intermediate where Z=CN with sodium azide and ammonium chloride at an elevated temperature.

One method for the preparation of compounds where Z=CO$_2$H, is the hydrolysis of an intermediate where Z is CN or CO$_2$R. This can be accomplished under acidic or basic conditions, with the preferred method generally being sodium or potassium hydroxide in a protic solvent such as aqueous ethanol at a temperature of about 20° C. to 100° C.

An alternative method for the conversion of a nitrile to a carboxylic acid is to reduce the nitrile to the corresponding aldehyde using a reducing agent such as diisobutylaluminum hydride, followed by oxidation of the aldehyde to the carboxylic acid using a reagent such as sodium chlorite, sodium dihydrogen phosphate, isobutene (See, JACS 1980, 45, 1176) or other standard conditions.

Another alternative method for the preparation of compounds where Z=CO$_2$H is the oxidation of a primary alcohol using an appropriate oxidant such as PDC in DMF, RuCl$_3$/NaIO$_4$ in 3:2:2 water acetonitrile:CCl$_4$ or the Swern system (to produce the intermediate aldehyde then oxidation of this functionality to the carboxylic acid as described above).

Some other methods for the preparation of compounds where Z=CO$_2$H are shown in Scheme 5. A carboxylic acid (2) can be generated directly by halogen-metal exchange of the corresponding aromatic halide (1) with an alkyl lithium reagent such as n-butyllithium, followed by quenching the resulting anion with carbon dioxide. Alternatively, alkoxycarbonylation of an aromatic bromide, iodide or triflate can be accomplished in a carbon monoxide atmosphere in the presence of a suitable alcohol (usually methanol) using a catalyst such as Pd(PPh$_3$)$_2$Cl$_2$/Et$_2$NH, Pd(Ph$_2$P(CH$_2$)$_3$PPh$_2$)$_2$/Et$_3$N or alternatively cobalt, ie. Co(OAc)$_2$, plus a base (NaH or K$_2$CO$_3$). The resulting benzoate (3) is then converted to the benzoic acid by hydrolysis as described above.

Scheme 5

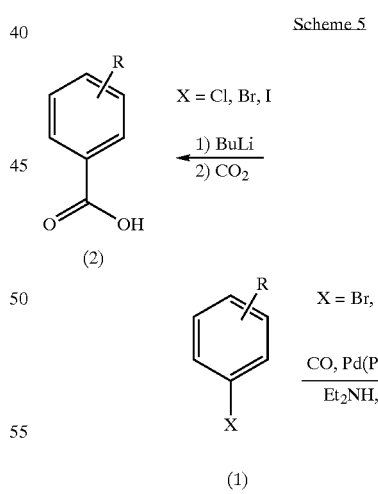

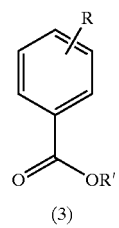

Preparation of phenylacetic acid derivatives can be accomplished from an appropriate aryl halide or triflate as illustrated in Scheme 6. Stille coupling of this type of compound with a vinyl stannane using a palladium catalyst such as Pd(OAc)$_2$, P(o-tolyl)$_3$ provides an olefin, (5). Hydroboration of this vinylbenzene derivative, followed by oxidation of the resulting primary alcohol with an oxidant, such as Jones' reagent, provides the phenylacetic acid (6).

cyclic Chemistry, Vol. 5; Pergamon Press (1984); Katritzky, A. R.; Rees, C. W.; Scriven, E. F. V. Eds. Comprehensive Heterocyclic Chemstry II, Vols 3 & 4, Pergamon Press (1996)). More specifically, oxazoles, imidazoles and thiazoles can be prepared by fusion of an amide, amidine or a thioamide, respectively, with an α-halo-ketone at temperatures ranging from about 40° C. to 150° C. (Scheme 7).

Scheme 6

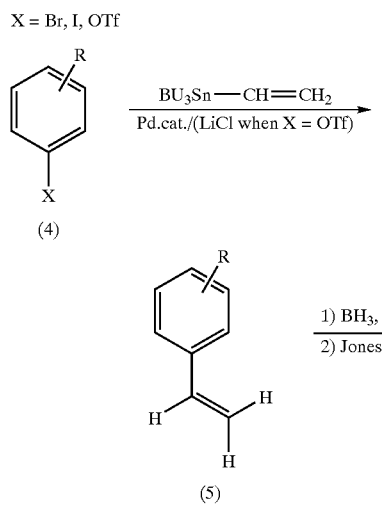

Scheme 7

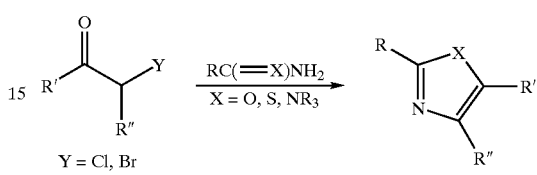

These reactions may be carried out neat, or in a solvent such as toluene, dichlorobenzene, or ethanol. Substituted oxazoles can also be prepared from a diazoketone and a nitrile using BF$_3$ etherate (Scheme 8), Ibata,T; Isogami, Y. Bull. Chem. Soc. Jpn. 1989, 62, 618).

Scheme 8

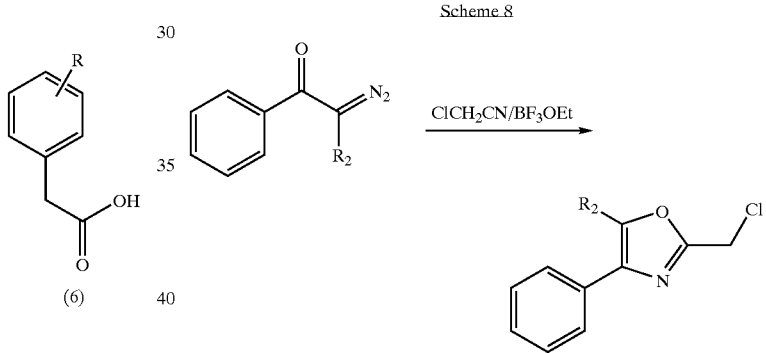

In one embodiment of the current invention, ArI can be a five membered ring heterocycle thus generating astructures of the general form shown in FIG. 1.

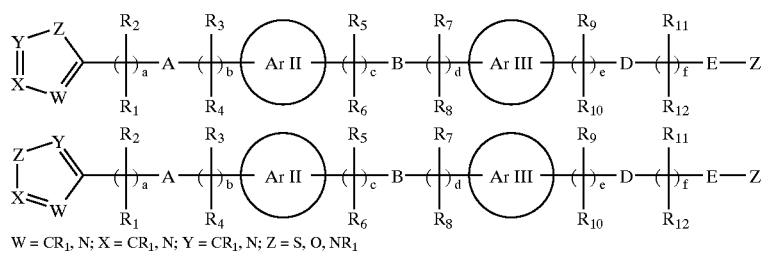

W = CR$_1$, N; X = CR$_1$, N; Y = CR$_1$, N; Z = S, O, NR$_1$

FIG. 1

In particular, the heterocycle can be a substituted thiazole, oxazole, oxadiazole, imidazole, isoxazole, pyrazole, thiadiazole or triazole. These systems can be prepared using methods known in the chemical literature (for reviews see Katritzky, A. R.; Rees, C. W. Eds. Comprehensive Hetero- 1,2,4-oxadiazsoles can be prepared by reaction of a nitrile with hydroxylamine followed by condensation of the resulting hydroxy-amidine with an acid chloride in the presence of a base and heating the adduct in a solvent such as toluene or dichlorobenzene to effect ring closure. (Scheme 9, Banavara, L. M.; Beyer, T. A.; Scott, P. J.; Aldinger, C. F.; Dee, M. F.; siegel, T. W.; Zembrowsky, W. J. J. Med. Chem., 1992, 35, 457).

Scheme 9

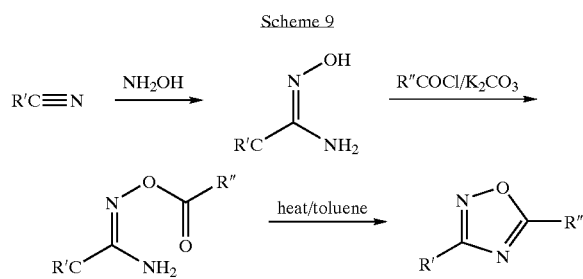

1,3,4-oxadiazsoles are prepared (Scheme 10) by condensation of an acylhydrazide with an acid synthon (such as an ester, acid chloride acyl azide) then cyclization of the resulting diacyl-hydrazide by heating in a solvent such as benzene or ethanol with or without an acid catalyst such as sulphuric acid (for examples see Weidinger, H.; Kranz, *J. Chem. Ber.*, 1963, 96, 1049 and Vakula, T. R.; Srinivarsan, V. R. *Indian J. Chem.*, 1973, 11, 732).

Scheme 10

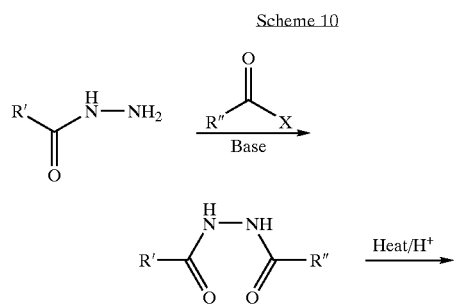

Substituted 1,2,4-thiadiazoles can be prepared by condensation of a thioamide with an N,N-dimethylamide dimethyl acetal derivative in a solvent such as benzene (Scheme 11, MacLeod, A.; Baker, R.; Freedman, S. F.; Patel, S.; Merchant, K. J.; Roe, M. Saunders, J. *J. Med. Chem.*, 1990, 33, 2052. also Patzel, M. Liebscher, J.; Siegfried, A. Schmitz, E. *Synthesis*, 1990, 1071) followed by reaction with an electrophilic aminating agent such as mesitylsulphonyloxyamine in methanol or dialkyloxaziridine in a solvent such as toluene.

Scheme 11

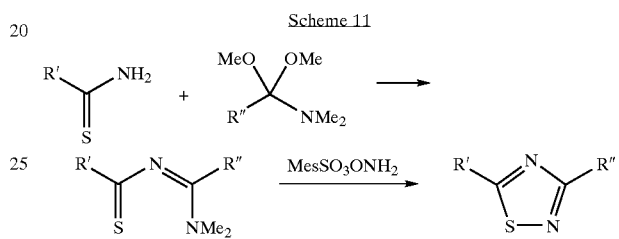

In another embodiment of this invention ArI can be a 1,3,4-thiadiazole. This system is assembled by condensation of a dithioester with an imidate ester salt in a solvent such as ethanol at a temperature between room temperature and reflux (Scheme 12. Stillings, M. R.; Welbourn, A. P.; Walter, D. S. *J. Med. Chem.*, 1986, 29, 2280). The dithioester precursor is obtained from the corresponding Grignard reagent and carbon disulphide/MeI. The imidate ester is prepared from the corresponding nitrile by reaction with HCl gas in the presence of an appropriate alcohol.

Scheme 12

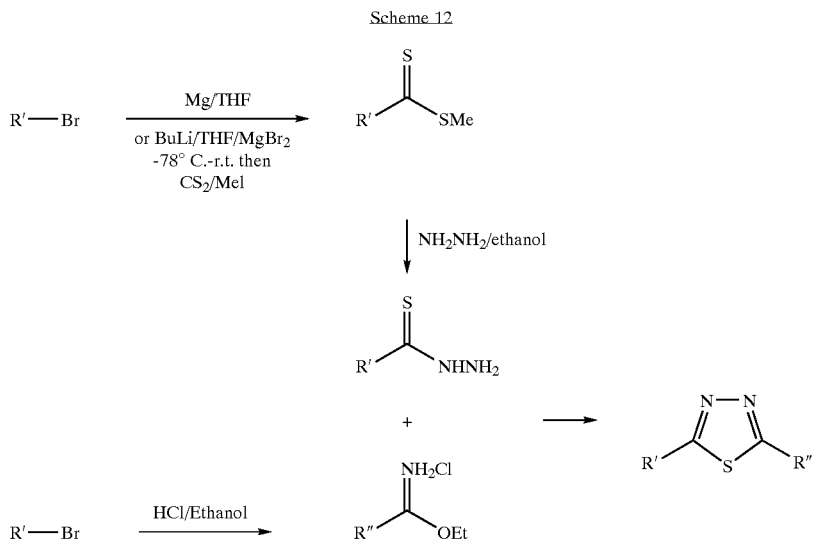

Pyrazoles can be prepared by condensation of a 1,3-diketone (Scheme 13) or a synthetic equivalent with a substituted hydrazine (for example, a β-aminoenone. Alberola, A.; Calvo, L.; Ortega, A. G.; Sadaba, M. L.; Sanudo, M. C.; Granda, S. G.; Rodriguez, E. G., *Heterocycles*, 1999, 51, 2675).

Scheme 13

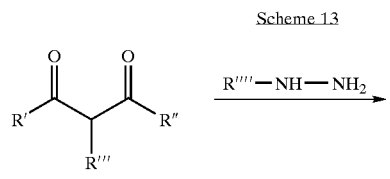

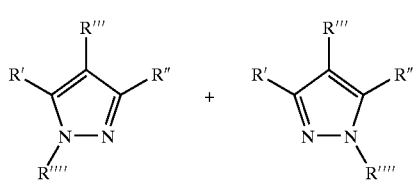

Similarly, isoxazoles can be prepared by reaction of a 1,3 dicarbonyl compound with hydroxylamine (Scheme 14. Pei, Y.; Wickham, B. O. S.; *Tetrahedron Letts*, 1993, 34, 7509) in a solvent such as ethanol at a temperature between 20° C. to reflux temperature.

Scheme 14

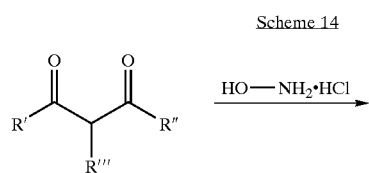

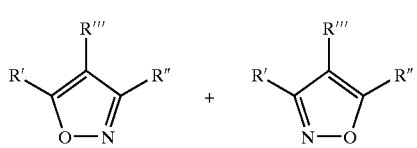

Alternatively, isoxazoles can be prepared by condensation of a hydroxamyl chloride with an alkyne (Scheme 15, Kano, H.; Adachi, I.; Kido, R.; Hirose, K. *J. Med. Chem.* 1967, 10, 411) in the presence of a base such as triethylamine. The hydroxamyl chloride unit can, in turn, be prepared from the corresponding oxime by oxidation with chlorine gas at low temperature (such as −60° C.) in a solvent such as ether (Casanti, G. Ricca, A. *Tetrahedron Lett.*, 1967, 4, 327).

Scheme 15

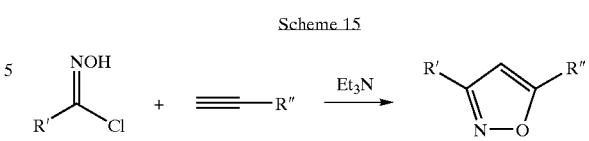

Triazoles are prepared by the Einhorn-Brunner reaction or a variant thereof (Scheme 16)

Scheme 16

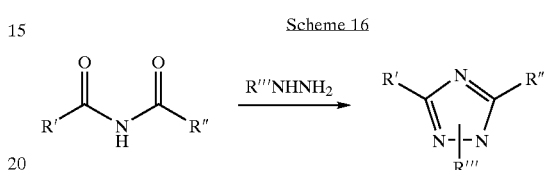

In addition, 5-hydroxymethyl substituted 1,2,4-triazoles can be prepared by condensation of an imidate ester with an 2-hydroxy-acetohydrazide unit (Scheme 17. Browne, E. J.; Nunn, E. E.; Polya, J. B. *J. Chem. Soc., C* 1970, 1515).

Scheme 17

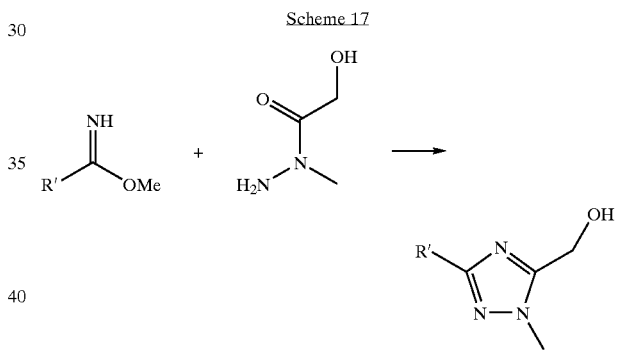

The five membered heterocycles, so formed, can, in certain cases, be coupled directly with a fragment containing ArII using standard methodology detailed elsewhere in the description of this invention (Schemes 1–4). These methods include alkylation of metal alkoxide containing ArII with a chloromethyl substituted heterocycle, or conversely, alkylation of a hydroxyl appended heterocycle (in the presence of a base) with a chloromethyl reagent containing ArII.

In another approach to fragment condensation, the substituents on the preformed heterocycle are first modified to incorporate suitable reactive functionality then this system is coupled to a fragment containing ArII. For example (Scheme 18), treatment of a 1,4-disubstituted imidazole with a base such as n-butyl lithium at a temperature of around −78° C. followed by alkylation of the resulting anion with an electrophile such as ethylene oxide provides the hydroxyethyl-substituted imidazole (other useful electrophiles are DMF or formaldehyde. For example see Manoharan, T. S.; Brown, R. S. *J. Org. Chem.*, 1989, 54, 1439). This intermediate can then be coupled to an ArII fragment containing an aromatic alcohol via a Mitsunobu reaction.

Scheme 18

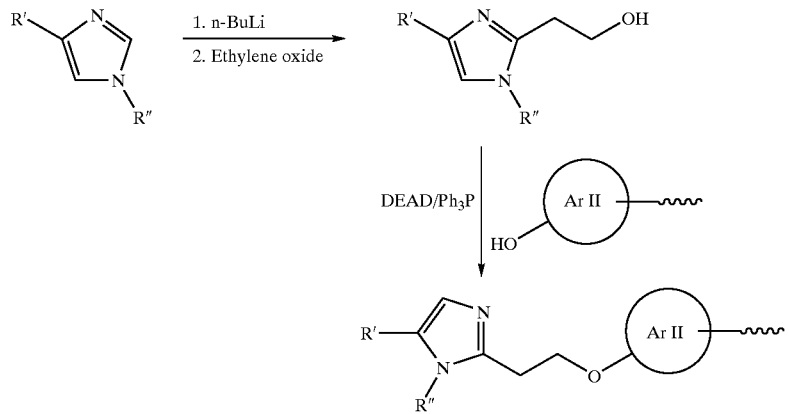

Another example of this general approach is shown in Scheme 19. A ring substituent such as an ester can be reduced to the corresponding alcohol using a reagent such as lithium aluminum hydride or lithium borohydride in a solvent such as THF or ether. Followed by halogenation of the resulting alcohol with a reagent system such as NCS/Ph₃P, Ph₃, Ph₃P/Br₂ or PBr₃ (Pei, Y.; Wickham, B. O. S.; *Tetrahedron Lett.*, 1993, 34, 7509): The alkyl halide produced in this manner can be coupled with a nucleophilic substituent attached to ArII, using a base such as $K_2CO_3$ in the case of an aromatic alcohol, (thiol) or NaH in the case of an aliphatic alcohol (thiol).

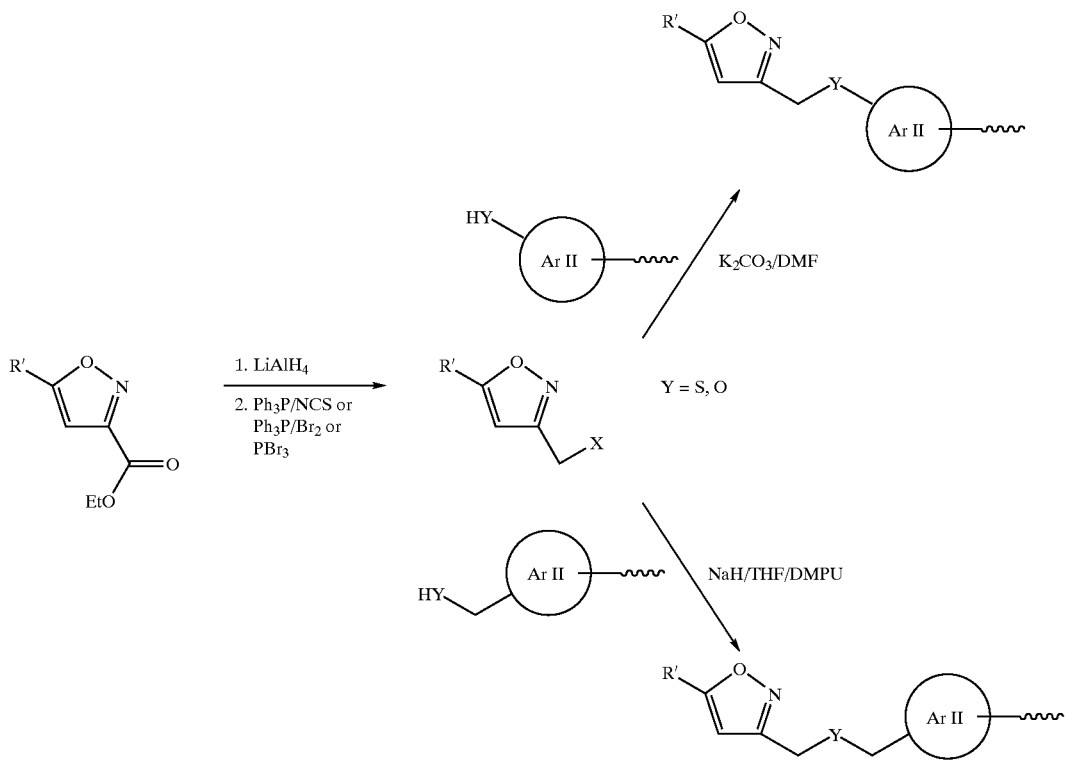

Scheme 19

In a third general approach to fragment condensation, Ar II can be incorporated into, a precursor of the five membered heterocycle. For example (Scheme 20), amination of the 3-aryl-propionate and thionation of the resulting amide provides a suitable functionalized system for thiazole ring synthesis. Similarly formation of the thio-urea from the arylmethyl amine (path B) provides a suitable precursor for fusion with an ?-haloketone leading to a 2-amino-substituted thiazole (Collins, J. L.; Blanchard, S. G.; Boswell, G. E.; Charifson, P. S.; Cobb, J. E.; Henke, B. R.; Hull-Ryde, E. A.; Kazmierski, W. M.; Lake, D. H.; Leesnitzer, L. M.; Lehmann, J.; Lenhard, J. M.; Orband-Miller L. A.; Gray-Nunez, Y.; Parks, D. J.; Plunkett, K. D.; Tong, Wei-Qin. *J. Med. Chem.* 1998, 41, 5037).

Provided that when A=O, N, or S then "a" is >1

FIG. 2

In particular, this heterocycle can be a pyrazole, an imidazole or a triazole. These systems can be prepared by

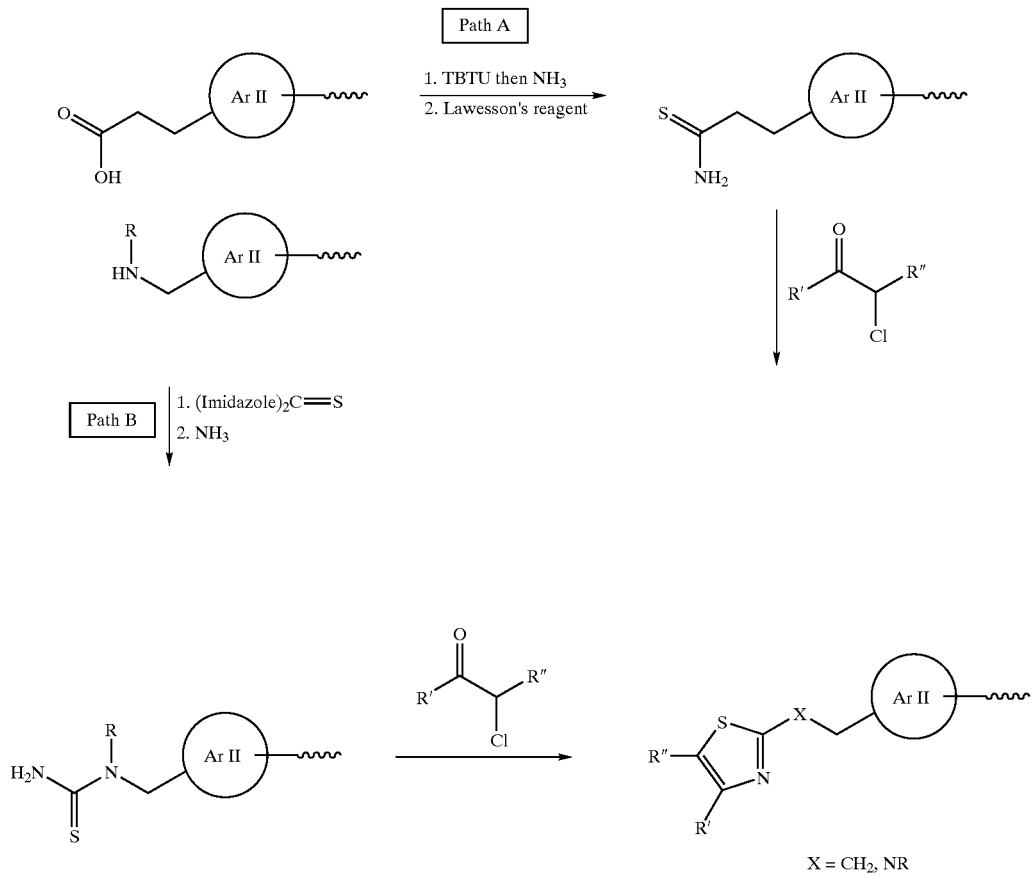

In another embodiment of this invention, ArI is a five membered heterocycle of general formula shown in FIG. 2.

alkylation of an N-unsubstituted heterocycle using a base such as sodium hydride, in a solvent such as DMF, THF,

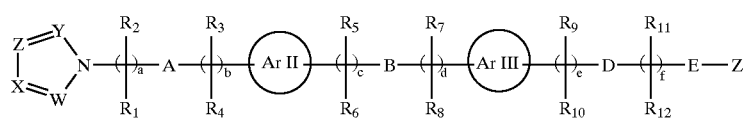

$W = CR_1, N; X = CR_1, N; Y = CR_1, N; Z = CR_1N$

DMPU or a combination of these solvents, at or around 0° C. and an electrophile such as an alkyl halide, cyclic carbonate or an epoxide (Scheme 21).

Scheme 21

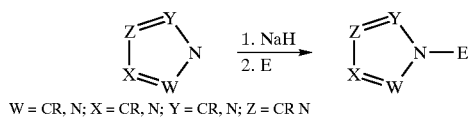

W = CR, N; X = CR, N; Y = CR, N; Z = CR N

These electrophiles can incorporate ArII or the alkylation products can be further modified and coupled to a fragment containing Aril in a subsequent step as described above. For example (Scheme 22), The 3,5-disubstituted pyrazole is prepared by reacting an aldehyde with a β-tosylhydrazino-phosphonate, using the literature procedure (Almirante, N.; Benicchio, A.; Cerri, A.; Fedrizzi, G.; Marazzi, G.; Santagostino, M. *Synlett* 1999, 299). This intermediate can then be alkylated with sodium hydride/ethylene carbonate in DMF (for a specific example see Collins, J. L.; Blanchard, S. G.; Boswell, G. E.; Charifson, P. S.; Cobb, J. E.; Henke, B. R.; Hull-Ryde, E. A.; Kazmierski, W. M.; Lake, D. H.; Leesnitzer, L. M.; Lehmann, J.; Lenhard, J. M.; Orband-Miller L. A.; Gray-Nunez, Y.; Parks, D. J.; Plunkett, K. D.; Tong, Wei-Qin. *J. Med. Chem.* 1998, 41, 5037). This intermediate can in turn be coupled to a fragment containing ArII by a Mitsunobu reaction as described above.

FIG. 3

More specifically (Scheme 23), treatment of the known 5-bromo-2-methyl-pyridine (Graf. *J. Prakt. Chem.*, 1932, 133, 19.) with LDA then formaldehyde in THF at low temperature (typically around −78° C.) followed by Mitsunobu coupling of the resulting alcohol to an aromatic alcohol containing ArII gives the bromo-pyridine derivative which can be further modified to give various alkyl and aryl substituted pyridines by cross coupling with an appropriate alkyl or aryl organometallic under palladium or nickel catalysis (For general reviews see Knight, D. W. and Billington, D. C in *Comprehensive Organic Synthesis* Vol. 3, p 413 and 481, Trost, B. M. and Fleming, I; Eds. Pergamon Press 1993).

Scheme 22

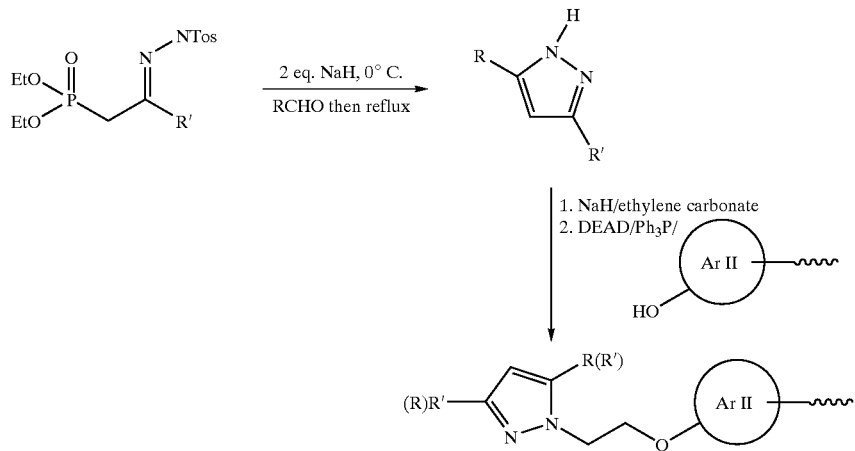

In another embodiment of this invention ArI is a substituted benzene, pyridine, pyrimidine, pyrazine or pyridazine (FIG. 3). These systems can be prepared by applying several of the general synthetic methods detailed elsewhere in the description of this invention.

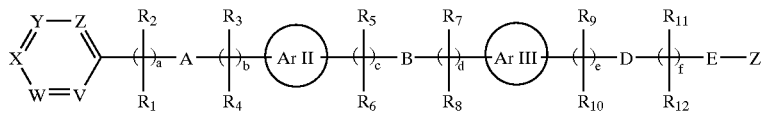

W = CR$_1$, N; X = CR$_1$, N; Y = CR$_1$, N; Z = CR$_1$N

Scheme 23

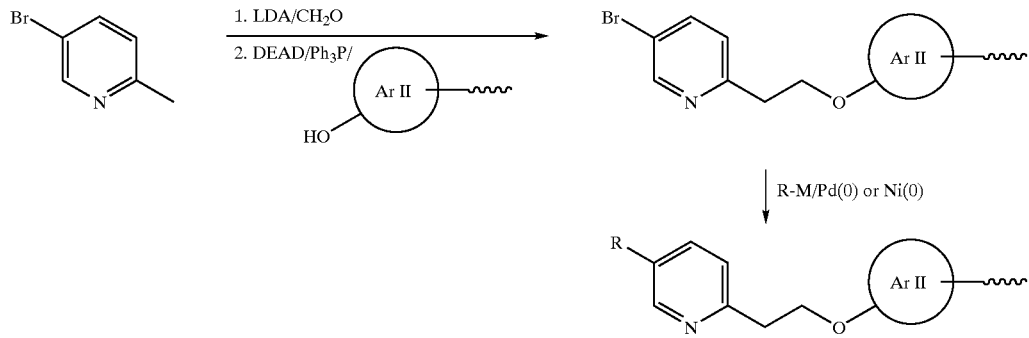

Similar procedures using the appropriate 5-bromo-2-methyl-pyrimidine (Kosolapoff, G. M.; Roy, C. H. *J. Org. Chem.*, 1961, 26, 1895), 2-iodo-5-methyl-pyrazine (Hirshberg, A.; Spoerr, P. E.; .*J. Org. Chem.*, 1961, 26, 1907) and 3-bromo-6-methyl-pyridazine (Counotte-Potman, A.; van der Plas, H. C.; *J. Heterocyclic Chem.*, 1983, 20, 1259) provide access to the corresponding pyrimidines, pyrazines and pyridazines respectively.

In another variant of this general class, ArI is a 3-heteroatom-substituted pyridazine. For example (Scheme 24), treatment of the known 3,6-dibromo-pyridazine with a metal alkoxide (containing ArII and derived from the corresponding alcohol and sodium hydride) in a solvent such as DMSO provides the alkoxy-substituted bromo-pyridazine. The bromide can be converted into a range of substituents as described above for pyridines. In particular, Suzuki coupling with a boronic acid in the presence of a base and a palladium catalyst provides the corresponding aryl substituted pyridazines.

In another embodiment of this invention ArI can be a substituted quinoxaline (FIG. 4). These systems are assembled by condensation of a 1,2-dicarbonyl compound with a 1,2 diamino-benzene (for a review, see Katritzky, A. R.; Rees, C. W.; Scriven, E. F. V. Eds. *Comprehensive Heterocyclic Chemstry* II, Vol 6 Pergamon Press (1996).

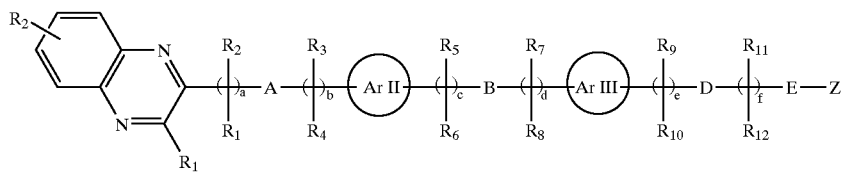

FIG. 4

Functionalization of these systems and coupling to ArII can be effected using procedures described for the related pyrazines. For example (Scheme 25), condensation of 1,2-diamino-benzene with 2,3-butadione provides the 2,3-dimethyl quinoxaline. N-oxidation of this intermediate with a peroxy-carboxylic acid and treatment of the product with acetyl chloride gives the 2-chloromethyl-3-methyl quinoxaline (Ahmed, Y.; Habib, M. S.; Bakhtiari, B. Bakhtiari, Z. *J. Org. Chem.*, 1966, 31, 2613). This intermediate is then coupled to a fragment containing Ar II under standard conditions.

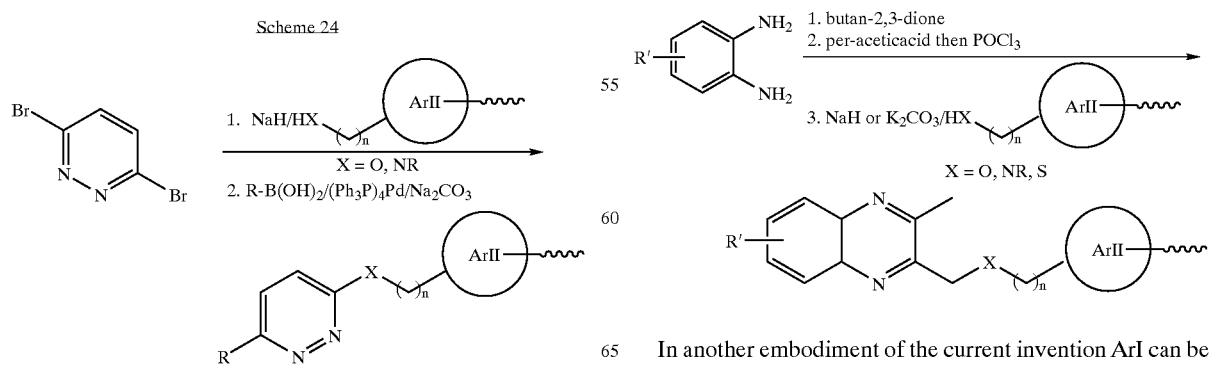

In another embodiment of the current invention ArI can be a quinazoline (Scheme 26). Such systems are commonly prepared by condensation of an o-amino-benzaldehyde or o-amino-aryl-ketone derivative with an acid chloride followed by heating with ammonia. For example, condensation of o-amino-benzaldehyde with chloroacetyl chloride in the presence of pyridine followed by reaction of the product with ethanolic ammonia at room temperature (Armarego, W. L. F.; Smith, J. I. C. *J. Chem. Soc.*, C, 1966, 234) provides a 2-chloromethyl substituted quinazoline which can be coupled to a fragment containing ArII as described above.

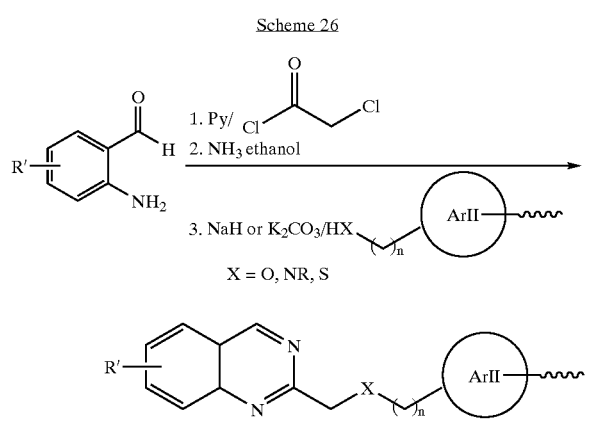

The related quinazolin-4-one ring system (Scheme 27) can be prepared by condensation of an o-aminobenzonitrile and an acid chloride followed by ring closure using a reagent such as urea hydrogen peroxide in the presence of a base such as potassium carbonate (Bavetsias, V. *Synth. Commun.* 1998, 28, 4547). In another variant of the quinazoline system, 4-heteroatom substituted quinazolines can be prepared by condensation of an amino-benzonitrile with chlorocetonitrile in the presence of an acid such as HCl or HBr (Chhabria, M. T.; Shishoo, C. J. *Heterocycles* 1999, 51, 2723.). The resulting system can be coupled to ArII as described above. The 4-halo-substituent can then be modified by nucleophilic displacement by a metal alkoxide in a solvent such as DMSO.

A general reaction for the preparation of reagents such compounds of formulas VI, IX, X, XIII and XIV (schemes 1–3) is shown in Scheme 28. Halogenation of a methyl substituted aromatic with a reagent such as N-bromosuccinimide under free radical conditions provides the halomethyl substituted aromatic reagents.

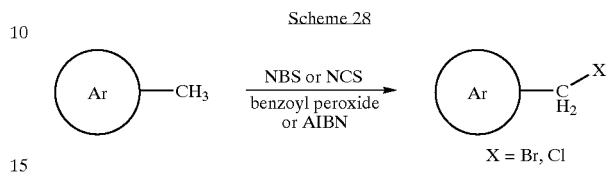

An alternative preparation of certain alkylating reagents is shown in Scheme 29. For example, substituted 2-chloromethyl quinoline derivatives can be prepared using a two step procedure (See, J. Med. Chem. 1991, 34, 3224). Oxidation of the nitrogen to form the N-oxide can be acheived with an oxidant such as m-chloroperbenzoic acid or hydrogen peroxide. Reaction of the N-oxide with a reagent such as toluene sulfonylchloride at elevated temperatures can produce the target chloromethyl derivative. This chemistry can also be extended to 2-picoline derivatives where the 6-position is non-hydrogen.

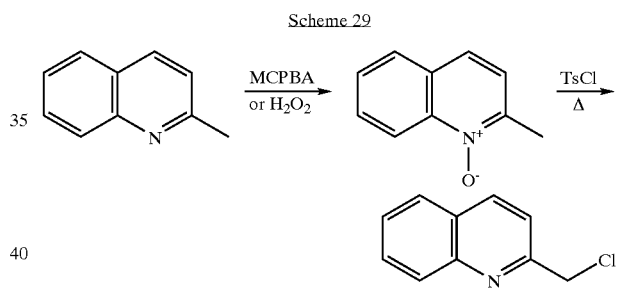

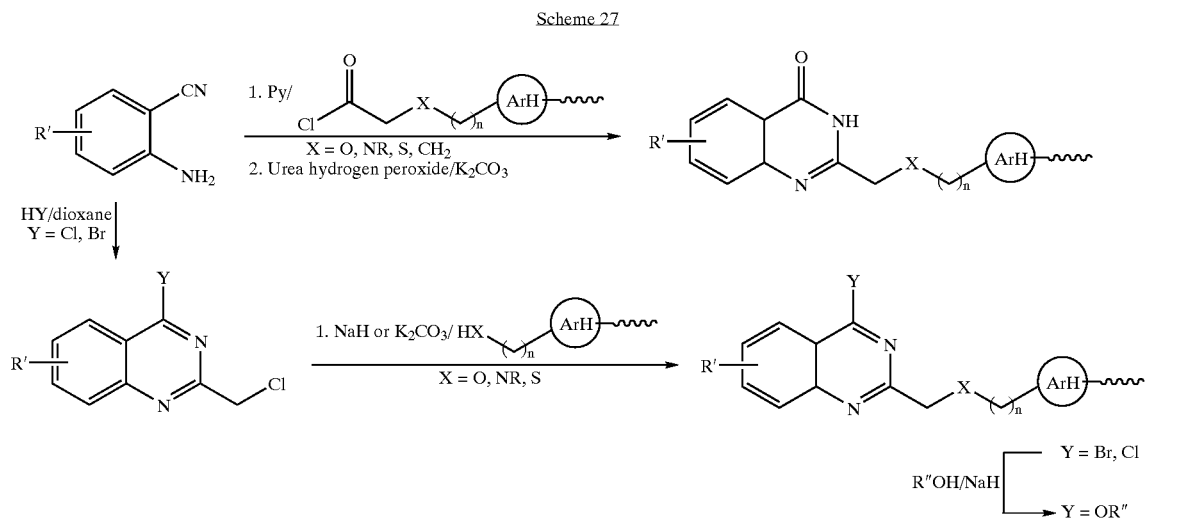

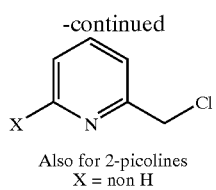

Also for 2-picolines
X = non H

Preparation of reagents which can be used as alkylating agenets of formula VI (scheme 1) are shown in Scheme 30. With the quinoxaline ring system the use of trichloroisocyanuric acid (TCC) can produce the corresponding chloromethyl analog (See, Chem. Ber. 1987, 120, 649).

Scheme 30

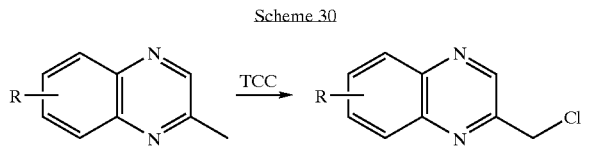

In a particular embodiment of this invention, B of Formula I can be an amide linker of either of the general forms shown in FIG. 5. Compounds of this formula can be prepared from a carboxylic acid fragment and an amine fragment using standard peptide coupling reagents. They can also be prepared by reaction with an activated carboxylic acid derivative such as, but not limited to, an acid chloride or anhydride in combination with an amine fragment in the presence of a suitable base such as triethylamine. It should be clear that essentially the same procedures can be used in the case where group A of Formula I is an amide using the appropriate carboxylic acid and amine fragments.

More specifically, the 2-aminomethyl-6-substituted-benzoic acid system (7) can be prepared using the chemistry shown in Scheme 31. Selective reduction of the substituted phthalic anhydride (9) with a sterically hindered lithium trialklyborohydride, such as L-selectride, provides lactone (10) regioselectively (See Krishnamurthy, Heterocycles, 1982, 18, 4525). Reaction of this lactone with potassium phthalimide provides the protected amine according to the procedure of Bornstein, Org. Syn. Collective Vol IV, 1963, 810. Removal of the phthalimide protecting group using standard deprotection conditions with hydrazine can provide the amino acid (7).

Scheme 31

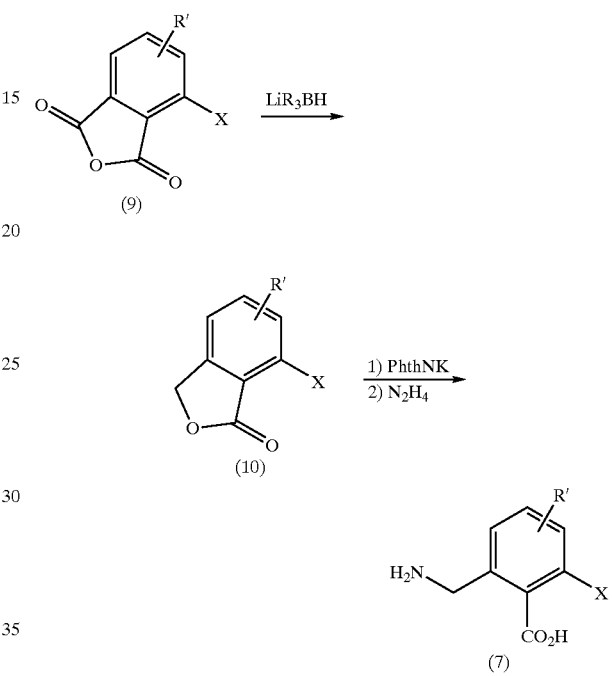

1,2-Carboxylic acid-half esters such as 12 (Scheme 32) are precursors to amide linked structures (FIG. 5) in which the ArIII containing fragment is the acyl doner. These systems can be prepared in several ways: Alcoholysis of the phthalic anhydride (9) can provide selectively isomer (11) plus smaller amounts of isomer (12). Esterification to provide the diester (13) can be accomplished using a variety of conditions, such as Fisher esterification. Hydrolysis of the diester can provide the regioisomer (12) as the major isomer in addition to isomer (11).

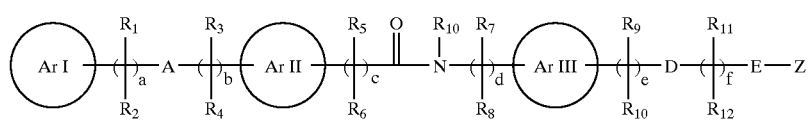

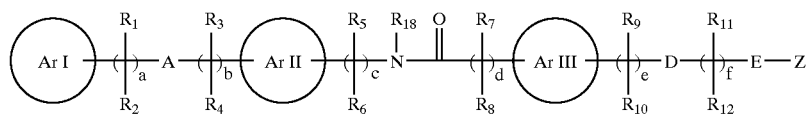

FIG. 5

Scheme 32

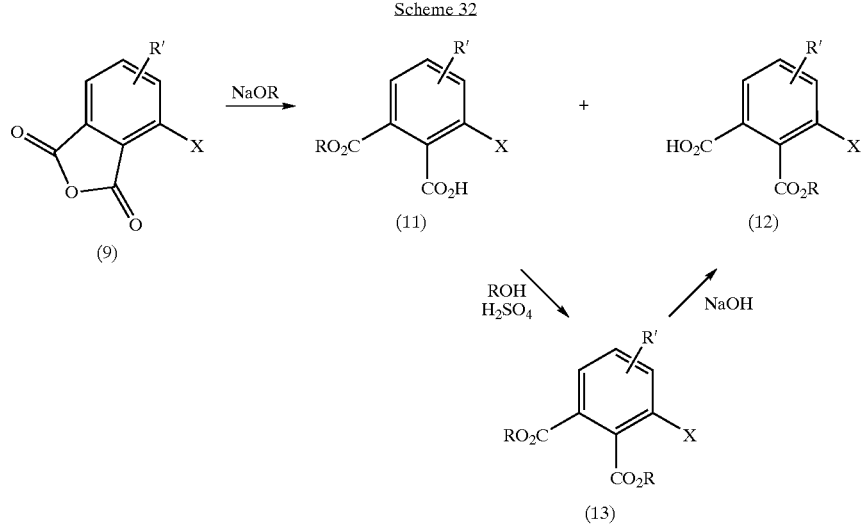

Phthalic anhydride derivatives such as (9) can, in turn, be prepared from the corresponding diacid (14) as shown in Scheme 33 using dehydrating conditions such as, but not limited to, hot acetic anhydride.

Scheme 33

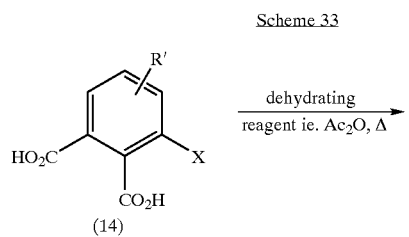

In one embodiment of this invention, ArIII-$(CR_9R_{10})_e$-D-$(CR_{11}R_{12})_f$-E-Z taken together constitutes a substituted benzoic acid. A useful sequence of reactions for constructing this kind of system is shown in Scheme 34. A lactone (obtained as described in Scheme 31) can be heated with hydrobromic acid to provide the bromomethyl carboxylic acid. The carboxylate can be esterified by preparing the acid chloride, followed by reaction with an alcohol to provide an intermediate bromide which can be used as outlined in Scheme 2, Formula XIII.

Scheme 34

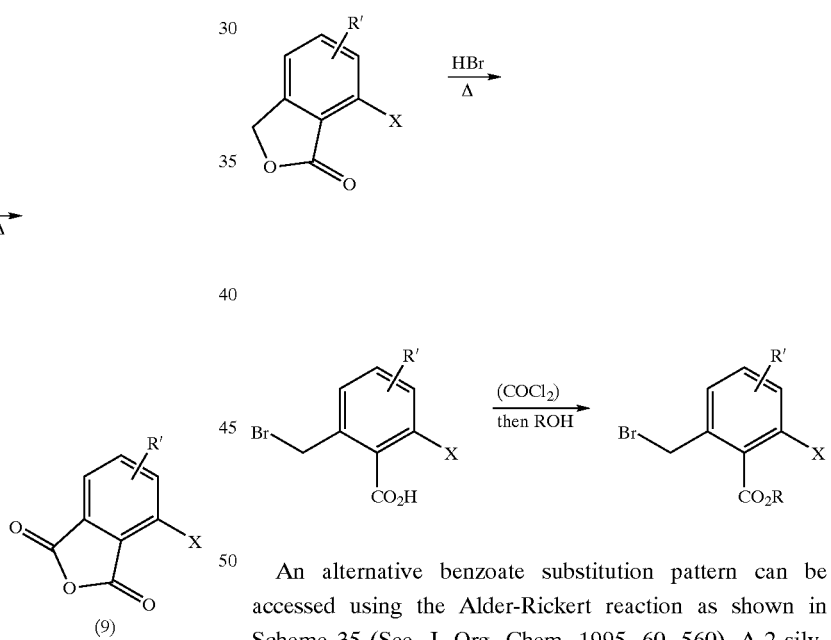

An alternative benzoate substitution pattern can be accessed using the Alder-Rickert reaction as shown in Scheme 35 (See, J. Org. Chem. 1995, 60, 560). A 2-silyloxydiene can be formed from an enone using a strong base such as LDA and trapping the enolate with a silylating reagent. Heating this diene with an acetylenedicarboxylate at elevated temperatures can then yield the Alder-Rickert product. Alkylation of the phenolic hydroxyl under standard conditions (using the alkylating reagent R'-L, where L is a leaving group) followed by saponification of the diester can provide a diacid intermediate which can be manipulated according to the chemistry described in FIGS. 31–34 to provide useful intermediates for the preparation of compounds of Formula I.

Scheme 35

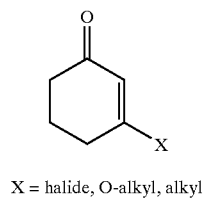

X = halide, O-alkyl, alkyl

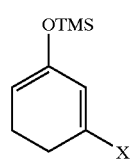

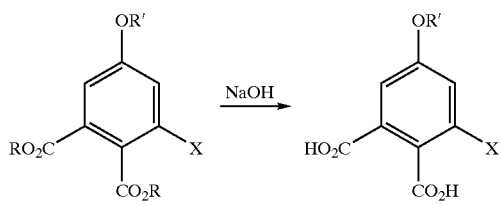

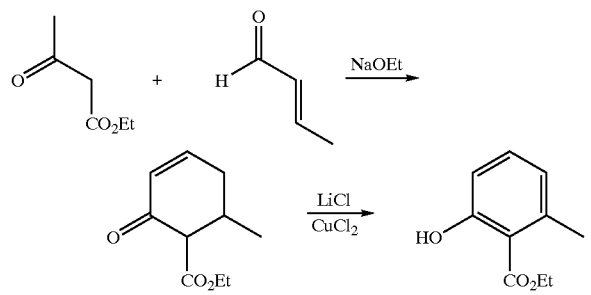

Another particular embodiment of this invention is one in which the substituted benzoic acid moiety described above has a 6-alkyl-2-alkoxy substituent pattern. The preparation of this kind of system is illustrated using the 6-methyl derivative shown in Scheme 36 (See Hamada, Tetrahedron, 1991, 47, 8635). Ethyl acetoacetate and crotonaldehyde can be condensed to form the cyclic β-ketoester. Subsequent lithium chloride/cupric chloride mediated aromatization of this intermediate can be accomplished at elevated temperatures to provide the target salicylate ester. The phenolic hydroxyl of this system can be further derivatized by alkylation as outlined elsewhere in the description of this invention.

Scheme 36

Additional ly, 6-alkyl-2-alkoxy benzoate systems can be prepared by aromatic nucleophilic substitution of a 2-fluorobenzaldehyde, at elevated temperatures, with an alkoxide (Scheme 37) to produce a 2-alkoxy-benzaldehyde. Oxidation of the aldehyde to the acid can then be accomplished using conditions such as sodium chlorite, sodium dihydrogen phosphate, isobutene (See, JACS 1980, 45, 1176).

Scheme 37

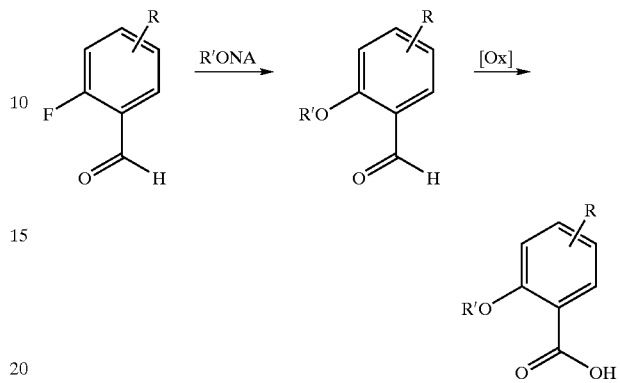

In another embodiment of this invention, B of Formula I can be a sulfur atom forming a thioether linkage (Scheme 2, Formulas (XI and XII). This type of system can be prepared by standard thiol alkylation using a suitable base (such as sodium or potassium carbonate, hydroxide, hydride or an amine such as triethylamine) to form an anion of the thiol and then reaction of this species with an appropriate electrophile such as an alkyl halide or sulphonate ester. Similarly, the groups A and D of Formula I can also be, independently, a sulfur atom. It should be clear that he same transformations described in the Schemes below can be applied to compounds of Formulas (VII, VIII, XI, XII and XVI; schemes 1–3).

Aromatic thiols can be prepared from the corresponding phenols. For example, preparation of a 2-thiobenzoate (10) from the salicylate (7), can be carried out as shown in Scheme 38. (See, Guise *J. Chem Soc.*, Perkin Trans. 1, 1982, 8, 1637). The thionocarbamate (8) can be obtained from the corresponding phenol (7) using a thiocarbamoyl chloride. Pyrolysis of (8) (>300° C.) can yield the rearrangement product (9) which upon hydrolysis can yield the thiol (10).

Scheme 38

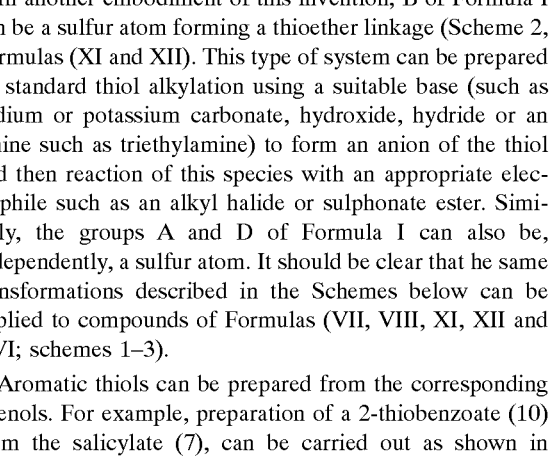

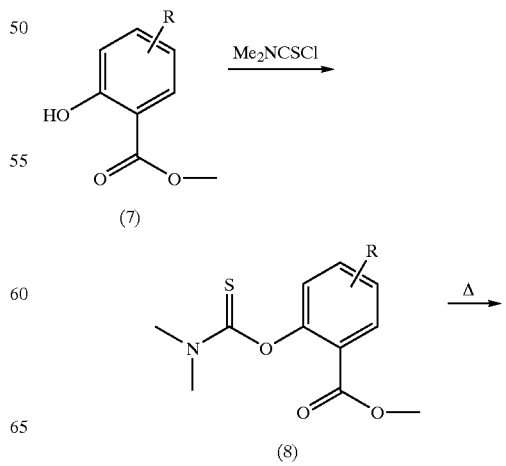

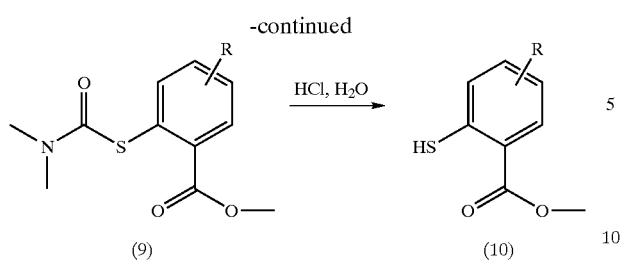

Another useful ring substituent transformation is the conversion of an aniline to an aromatic thiol. As shown in Scheme 39; diazotization of an aniline such as (11) is followed by conversion of the diazonium salt (12) to a disulfide(13) using sodium sulfide. Reduction of the disulfide with zinc/acetic acid can yield the thiol (14) (See, Guise J. Chem Soc., Perkin Trans. 1, 1982, 8, 1637).

Scheme 39

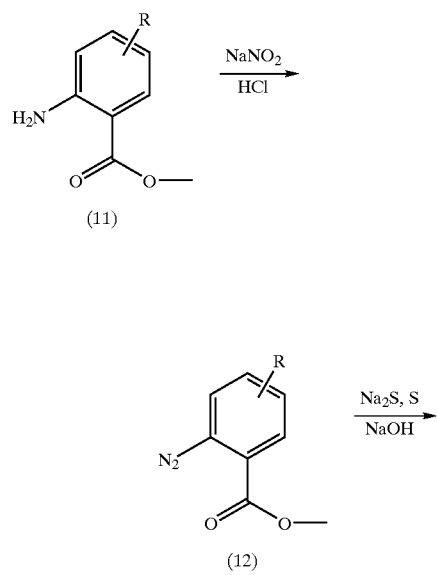

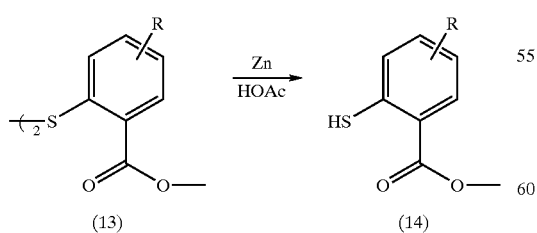

In a particular embodiment of this invention, ArIII can be a halo-substituted aromatic. Synthesis of a particularly relevant system is outlined in scheme 40. Regioselective halogenation of a 2,6-disubstituted-phenol to provide the 4-halophenol system can be accomplished with a halogenating reagent such as sulfuryl chloride (See, J. Het. Chem. 1989, 26, 1547). The phenolic hydroxyl group can be further derivitized as outlined elsewhere in the description of this invention.

Scheme 40

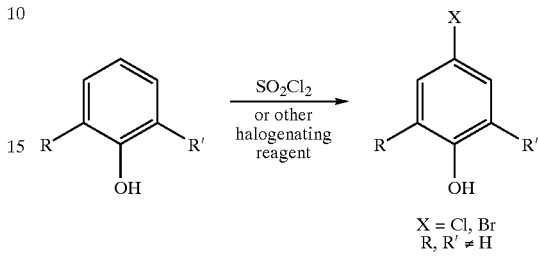

An alternative method for the preparation of a halo (or alkoxy)-substituted benzoate is shown in Scheme 41. An aniline is first converted to its diazonium salt using nitrous acid, followed by transformation to the corresponding nitrile using a reagent such as cuprous cyanide (See Chem. Ber. 1983, 116, 1183). The cyano group is then hydrolyzed to the acid (see, Fuson, JACS 1941, 63, 1679). The acid may then be protected as an ester to allow further derivitization of the system as outlined elsewhere in the description of this invention.

Scheme 41

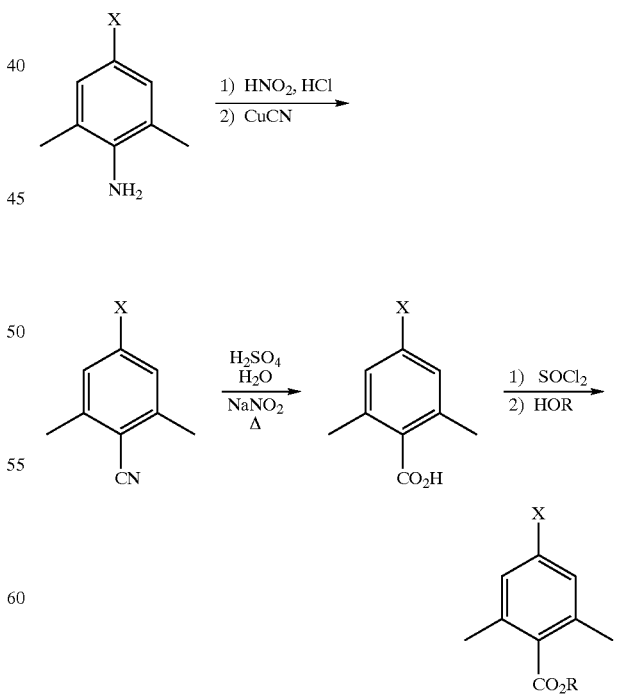

X = halogen or alkoxy

An ortho-halo-benzoate can be prepared similarly, by diazotization of an o-carboxy aniline, followed by reaction with a copper halide (Scheme 42).

Scheme 42

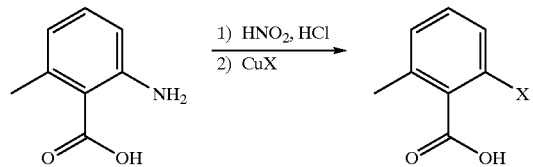

In another embodiment of this invention, ArIII is a benzofuranyl or dihydrobenzofuranyl carboxylic acid as illustrated in FIG. 6.

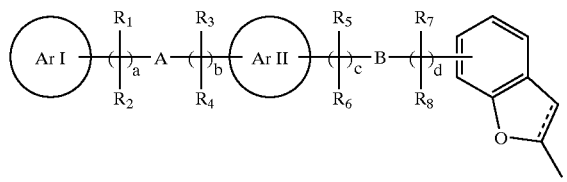

FIG. 6

Benzofuran-2-carboxylate derivatives can be prepared as shown in Scheme 43 by cyclization of the appropriately substituted 2-carbonyl-phenoxyacetate under basic conditions. Reduction of the resulting benzofuran to the corresponding 2,3-dihydro-benzofuran can be accomplished using sodium mercury amalgam under basic conditions. (See, J. Med. Chem. 1984, 27, 570).

Scheme 43

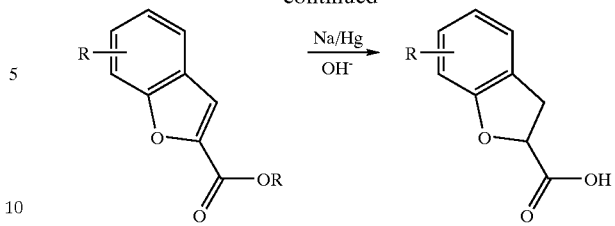

An alternative synthesis of the 2,3-dihydrobenzofuran-2-carboxylate ring system is shown in Scheme 44 (See, J. Med. Chem. 1981, 865). Claisen rearrangement of a substituted allyl-phenyl ether at an elevated temperature such as 250° C. either neat or in a solvent such as dimethylaniline, can provide the o-allyl-phenol Peracid oxidation of this intermediate provides the 2-hydroxymethyl-2,3-dihydrobenzofuran, which can be further oxidized to the carboxylic acid using a variety of oxidizing agents such as Jones' reagent.

Scheme 44

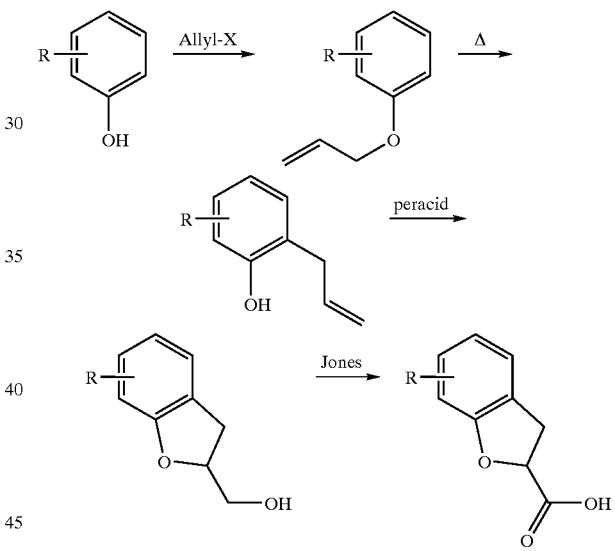

In another embodiment of this invention "A" can be an imidazolidin-2-one, a tetrahydropyrimidin-2-one an imidazoline-2,4-dione, or a tetrahydropyrimidin-2,4-dinone (FIG. 7).

X, Y = $(CR_1R_2)_n$, C = O
n = 1,2

FIG. 7

These systems are prepared from an amine containing ArI by sequential acylation, aminolysis, ring closure and reduction, as illustrated in Scheme 45 (For examples see Kitazaki, T.; asaka, A.; Tamura, N.; Matsushita, Y.; Hosono, H.; Hayashi, R.; Okonogi, K.; Itoh, K. *Chem. Pharm. Bull.*, 1999, 47, 351 and Basha, A.; *Tetrahedron Lett.*, 1988, 29, 2525). Coupling to Aril can be effected by derivitization of the cyclic urea N by treatment with a base such as NaH in THF at around 0° C. then alkylation of the resulting anion with an electrophile such as an alkyl bromide/triflate containing ArII).

Scheme 45

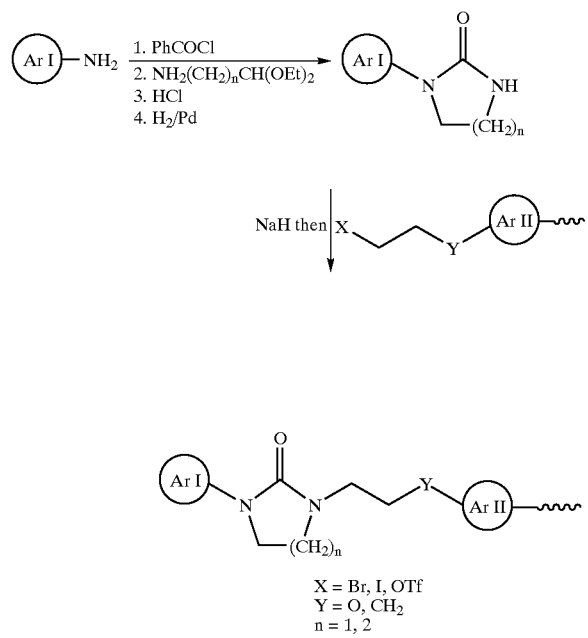

X = Br, I, OTf
Y = O, CH$_2$
n = 1, 2

In another embodiment of this invention ArII is a six membered ring aromatic of general form substituted shown in FIG. 8. In particular, Aril is a substituted benzene, pyridine, pyrimidine, pyridazine or pyrazine.

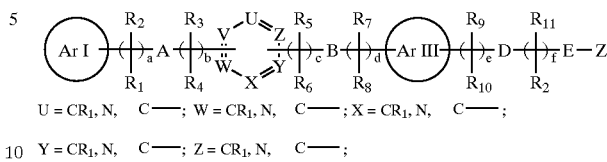

U = CR$_1$, N,   C——;   W = CR$_1$, N,   C——;   X = CR$_1$, N,   C——;
Y = CR$_1$, N,   C——;   Z = CR$_1$, N,   C——;

FIG. 8

In principle, appropriately functionalized ring systems of this kind can be prepared by functionalization of specific precursors followed by ring synthesis or by derivatization of a preformed ring system. There are numerous approaches to the synthesis and functionalization of the aforementioned cyclic frameworks in the chemical literature (for examples, see (a) Katritzky, A. R.; Rees, C. W.; Scriven, E. F. V. Eds. *Comprehensive Heterocyclic Chemstry* II, Vol 5 and Vol 6. Elsevier Science 1996 and references therein). For example, (Scheme 46) alkylation of methyl glycolate with an alkyl halide containing ArI using a base such as sodium hydride in a solvent such as THF or DMSO provides the ester. Claisen condensation of this ester with t-butyl acetate at low temperature (typically below –15° C.) using a base such as LDA in THF provides the keto ester intermediate. This is reacted with formamidine acetate in the presence of a base such as sodium methoxide in methanol to give the pyrimidinone (Butters, M. *J. Heterocyclic Chem.*, 1992, 29, 1369). This type of substituted aromatic system can be further functionalized to incorporate ArI as described elsewhere in the description of this invention.

Scheme 46

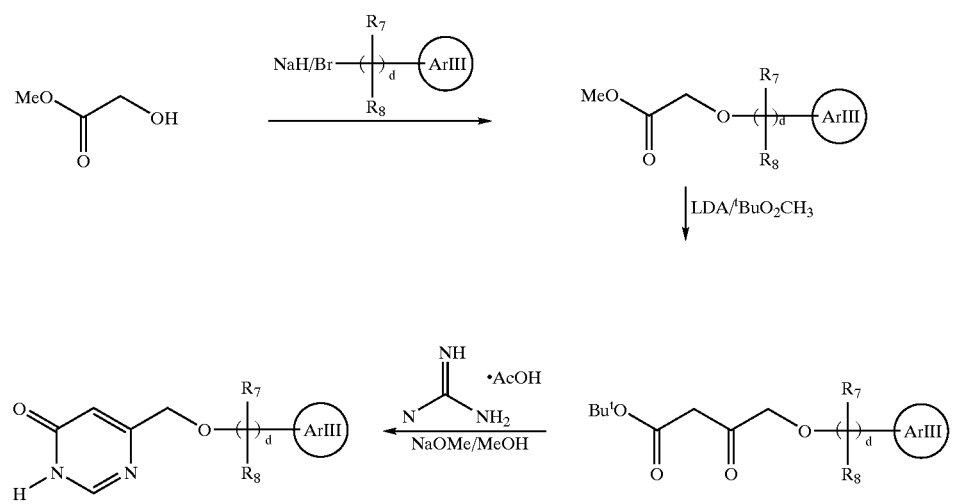

In certain cases, ArII (in FIG. 8) can be assembled by ring transformation of another heterocycle, for example, treatment of the known 4-bromo-2-methoxy-furan (Scheme 47, Marini-Bettolo, R.; Flecker, P.; Tsai, T. Y. R.; Wiesner, K. *Can. J. Chem.* 1981, 59, 1403) with an alkyl lithium at low temperature and reaction of this anion with an electrophile containing ArIII (such as a bromide, aldehyde, epoxide) provides the 4-substituted furan. Oxidative cleavage of this intermediate with dioxirane followed by treatment with hydrazine provides the pyridazinone which can be further modified to incorporate ArI as illustrated elsewhere in the description of this invention.

Scheme 47

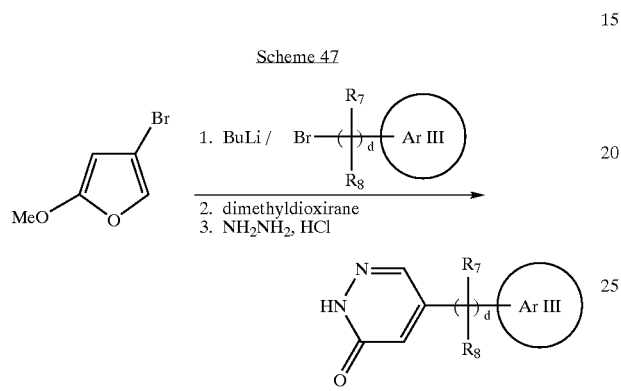

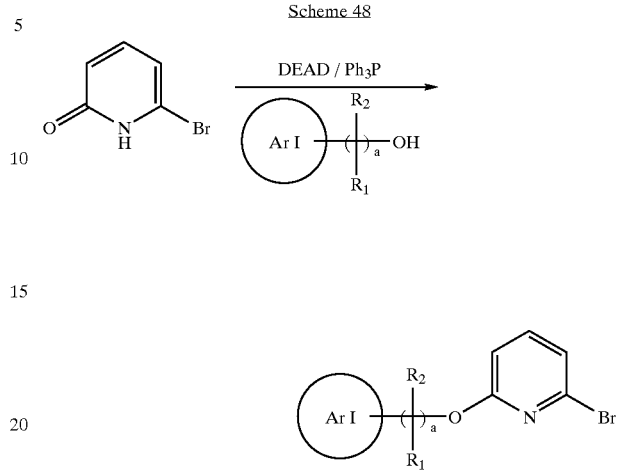

Scheme 48

The heterocyclic bromide, so formed, can be further functionalized in a number of ways. For example, coupling with a vinyl stannane can be effected under palladium (o) catalysis to provide systems with alkenyl linkers (Scheme 49).

Scheme 49

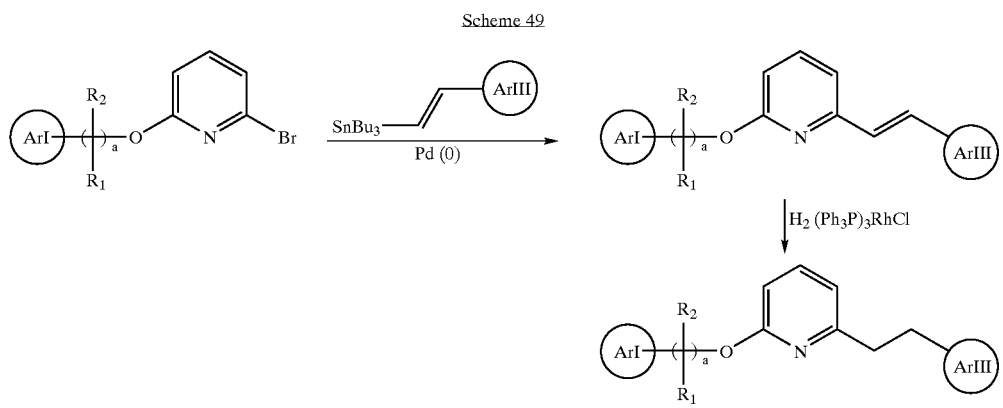

A particularly useful protocol with regard to functionalization of heterocycles involves Mitsunobu etherification of hydroxyl substituted heterocycles (or keto-tautomers) such as outlined in Scheme 48. Treatment of the known 6-bromo-pyridin-2-one (Wibaut, J. P.; Waayman, P. W.; Vandijk, J. *Rec. Trav. Chim. Pays-Bas.* 1940, 59, 202) with an alcohol containing an ArI (or ArIII) under Mitsunobu's conditions provides the corresponding bromo-substituted pyridyl ether. (for typical procedures see Mitsunobu. O., *Synthesis,* 1981, 1).

The choice of catalyst and reaction temperature for this transformation depends on the substrate employed but is most commonly tetrakistriphenylphosphine palladium, bis (triphenylphosphine)palladium chloride, 1,1'-bis(diphenylphosphino)ferrocene/bis-dibenzylideneacetone palladium or 1,2 bis-(diphenylphosphino)ethane/bis(acetonitrile) dichloropalladium at a temperature between 50 and 150° C. Suitable solvents include DMF, DMPU, HMPA, DMSO, toluene, and DME. (for examples see Farina, V. Krishnamurthy, V.; Scott, W. J. *Organic Reactions,* 1997, 50, 1). Reduction of the olefin using, for example, Wilkinson's catalyst in a solvent such as toluene, THF or an alcohol at a temperature between about 20 and 80° C. provides the corresponding alkane linked system.

In certain heterocyclic systems in which a bromide or chloride is situated ortho or para to a ring nitrogen, the halogen can be readily displaced by an alcohol (in the presence of base such as sodium hydride in a solvent such as Toluene, DMSO, THF, DMPU or HMPA) at or above room temperature (For examples see Kelly, T. R. et al. *J. Amer. Chem. Soc.*, 1994, 116, 3657 and Newcome, G. R. et al. *J. Org. Chem.*, 1977, 42, 1500). For example, alcoholysis of a 2,4-dichloro-pyrimidine (Scheme 50) using a controlled stoichiometric amount of an alcohol reagent containing ArI (or ArIII) provides the alkoxy substituted-bromo-pyrimidine. Subsequent reaction of this product (generally above room temperature) with a further equivalent of another alcohol containing ArII (or ArI) provides the unsymmetrically dialkoxy-substituted heterocycle. Since the 4-position of the dichloro-pyrimidine is generally displaced first, the order in which the alkoxy substituents are introduced will dictate their orientation in the product.

Similar procedures using 2,6-dibromo-pyridine or 2,6-dibromo-pyridazine provides the corresponding dialkoxy-substituted pyridines and pyridazines.

A simple alkoxy group positioned ortho to a nitrogen in these heterocyclic systems can be hydrolyzed to the corresponding hydroxy substituent using aqueous hydrochloric acid at a temperature normally between room temperature and reflux. (Scheme 51).

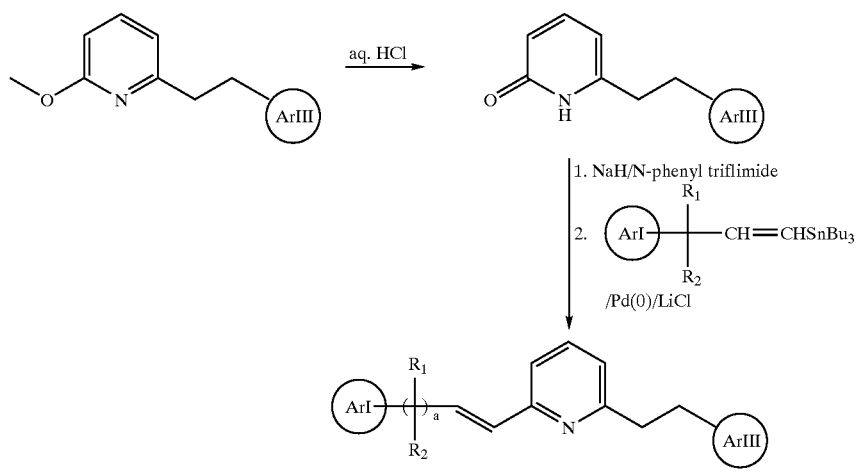

Scheme 51

For example (Scheme 51), treatment of the 2-methoxy-6-alkyl-substituted pyridine derivative with hydrochloric acid provides the 6-alkyl substituted pyridin-2-one. This intermediate, in turn, can be further derivatized to the corresponding 2-alkoxy or 2-alkenyl substituted systems as detailed elsewhere in the description of this invention.

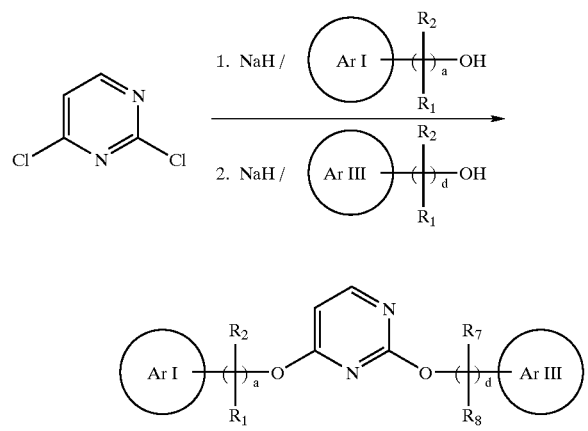

Scheme 50

A methyl, methylene or methine group positioned ortho to a ring nitrogen in these heterocyclic systems can be deprotonated with a base such as an alkyl lithium or LDA in a solvent such as THF, ether or HMPA, generally at low temperature (below 0° C.) and the resulting anion reacted with electrophiles such as aldehydes, epoxides, alkyl halides or α,β-unsaturated carbonyl compounds to provide a variety of functionalized heterocycles.

Scheme 52

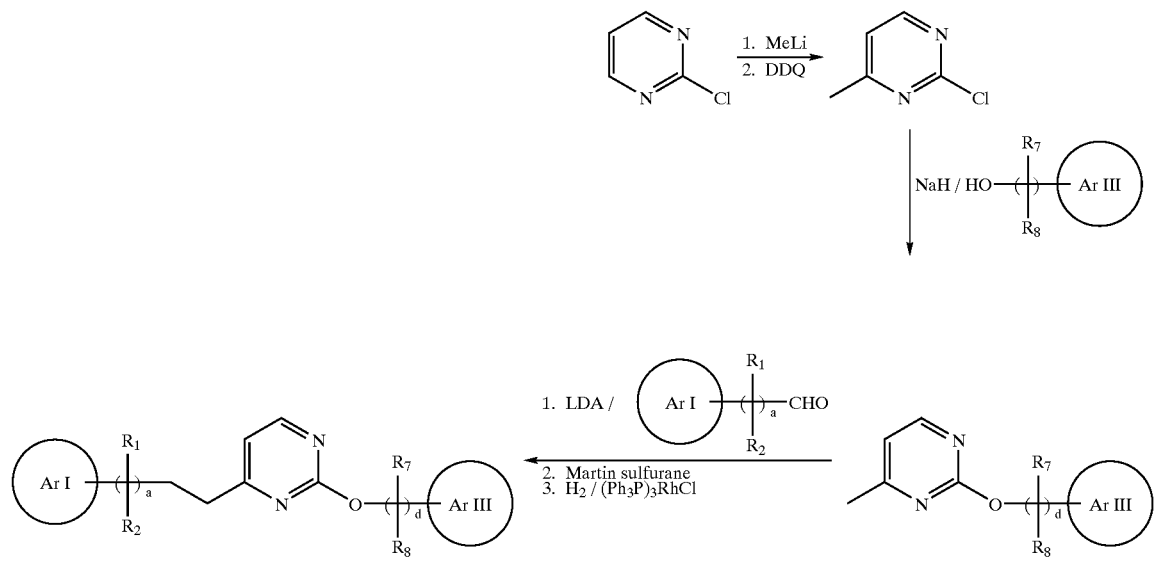

For example (Scheme 52) the 2-alkoxy-4-methyl-pyrimidine is treated, sequentially, with LDA and an aldehyde at −78° C. to give the hydroxy substituted adduct. Subsequent dehydration of this intermediate with martin sulfurane in a solvent such as dichloromethane at ambient temperature followed by hydrogenation of the resulting olefin provides the 4-ArI-containing-alkyl-2-alkoxy-pyrimidine. Similar procedures applied to 2-chloro-6-methyl-pyrazine (Karmas, G.; Spoerri, P. E.; *J. Amer. Chem. Soc.,* 1952, 74, 1580) leads to the corresponding pyrazine.

In another embodiment of this invention, A can be an amide thus generating compounds of the formulas a shown in FIG. 9.

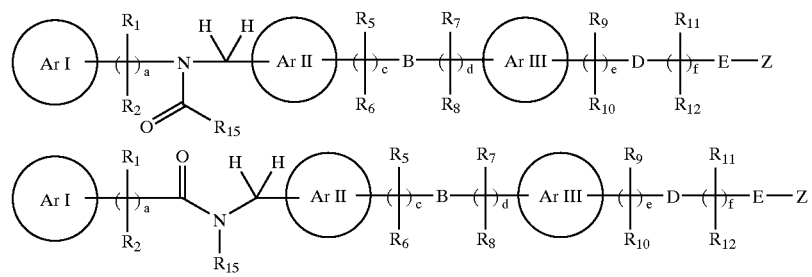

FIG. 9

The preparation of an illustrative example within this series is shown in scheme 53. A hydroxy aldehyde can be reacted with a bromoalkyl-ester to provide an aldehyde-ester intermediate. Reductive amination of the aldehyde followed by acylation can provide the amide.

Scheme 53
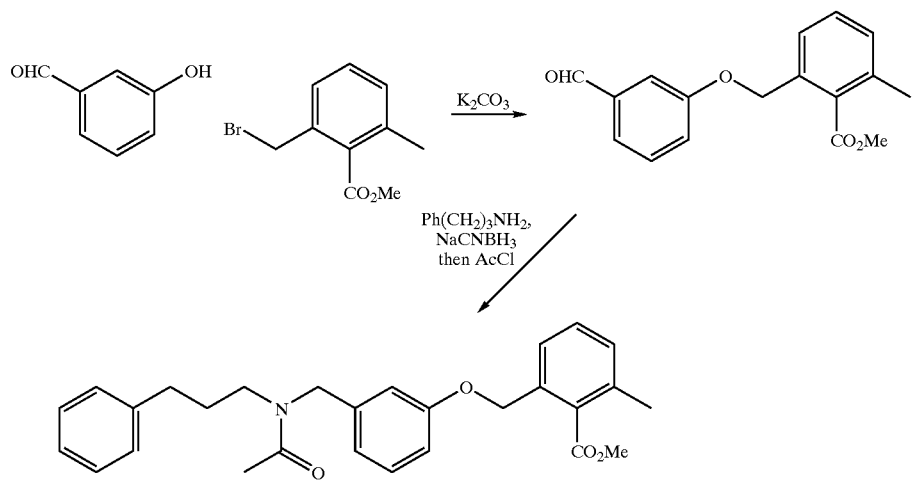
Furthermore, compounds of the invention may be easily synthesized by solid phase methods, as illustrated in Schemes 54 and 55, using inputs (XII)–(XVII) listed in Table 1.
Scheme 54
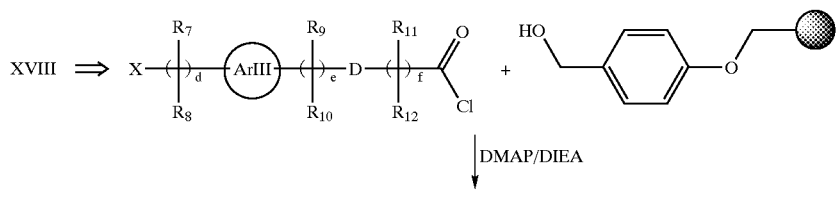
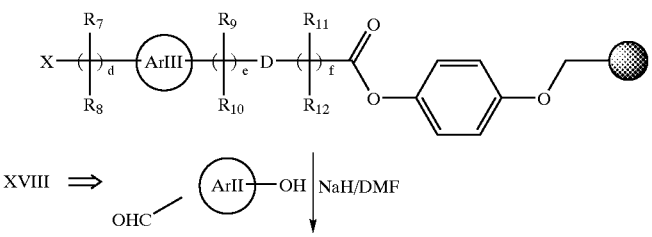
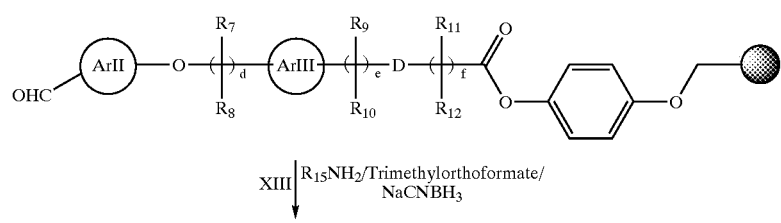

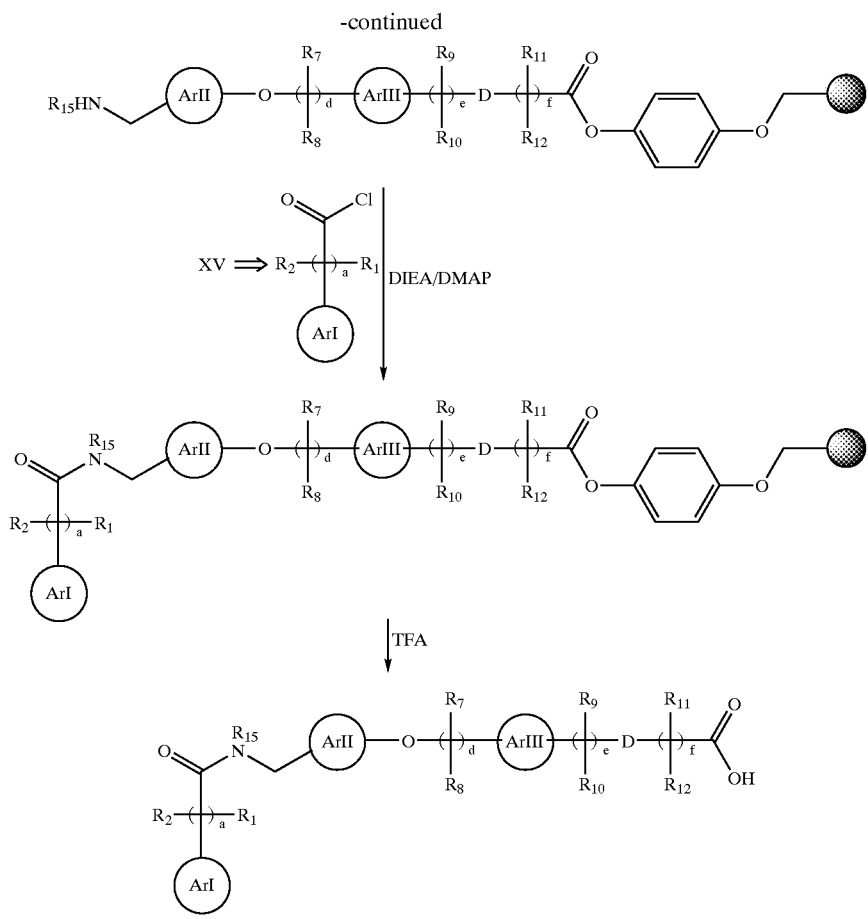
Scheme 55
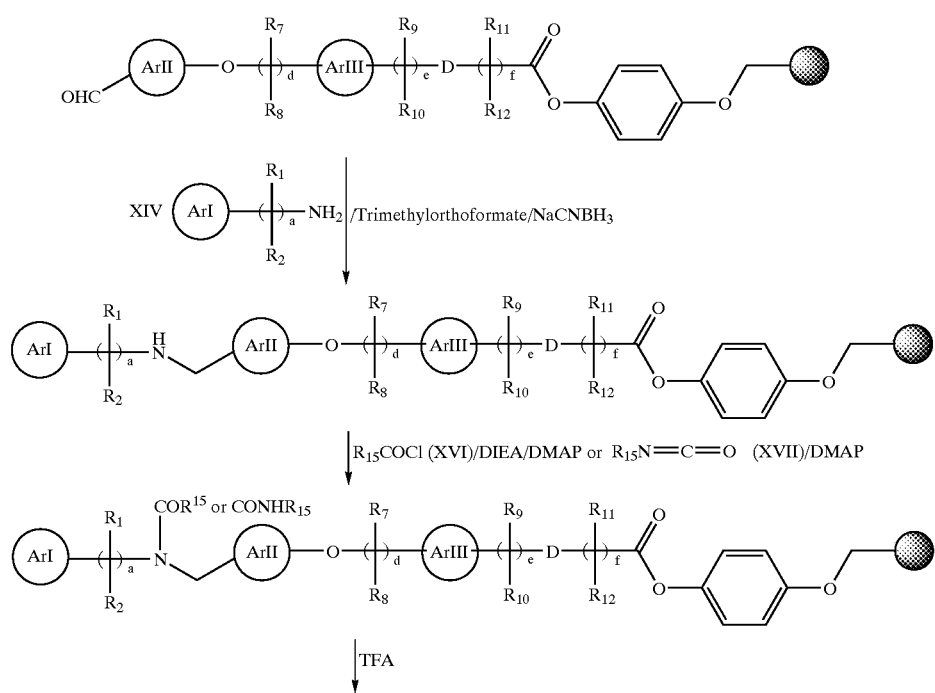

-continued
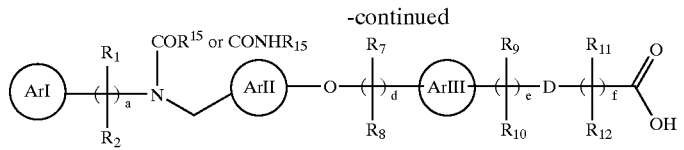

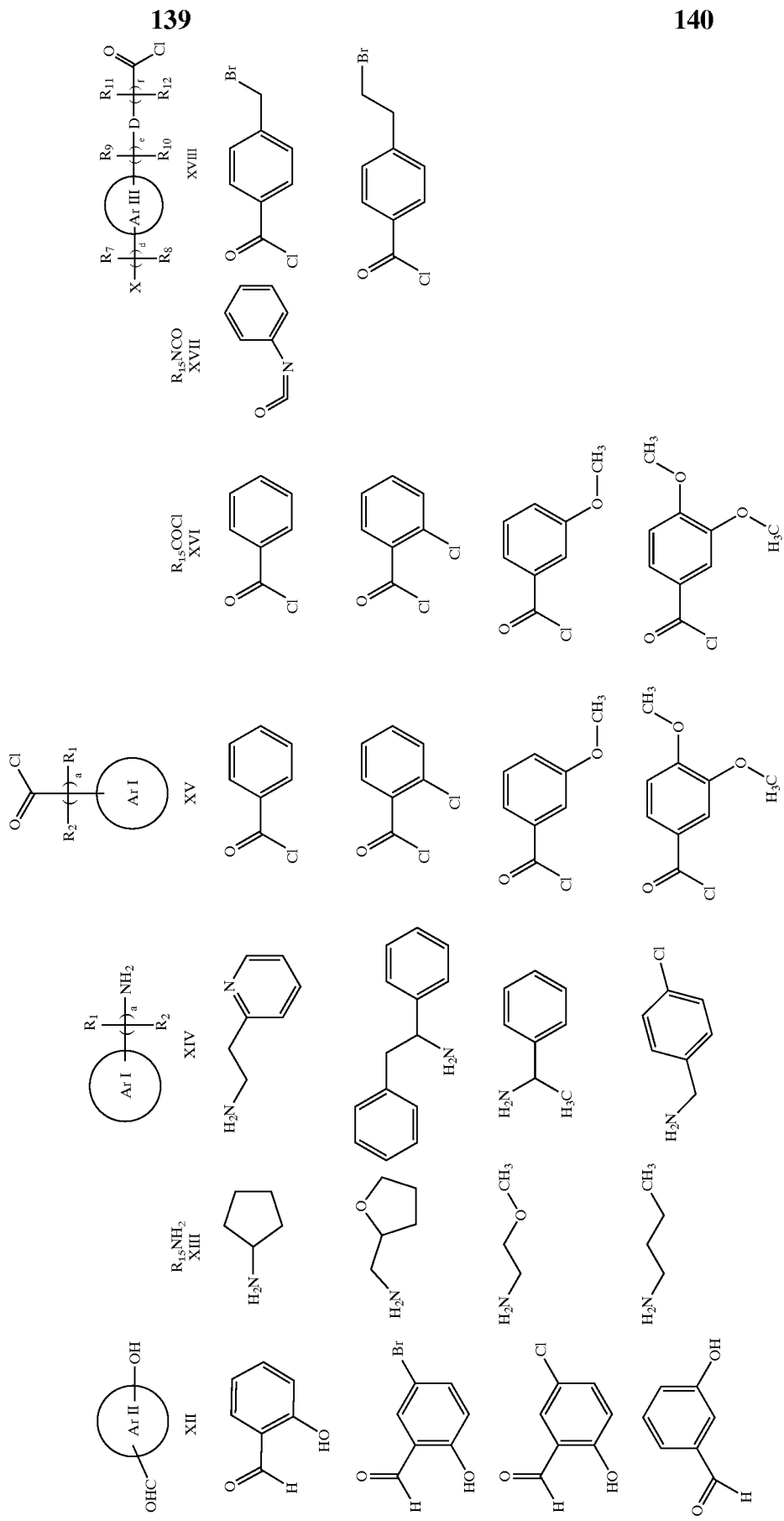
TABLE 1

TABLE 1-continued
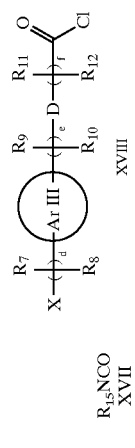
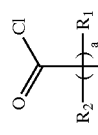
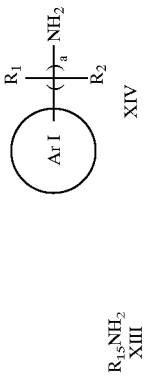
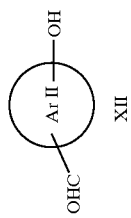
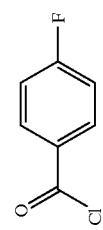
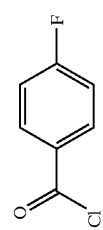
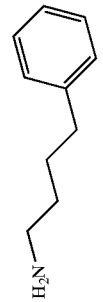
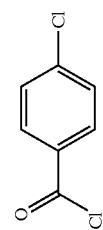
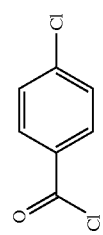
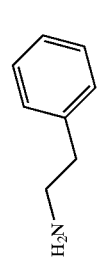
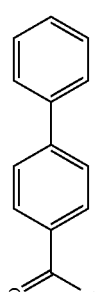
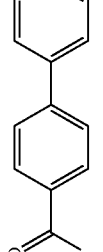
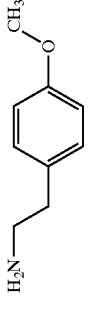
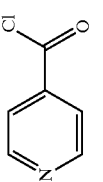
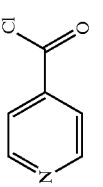
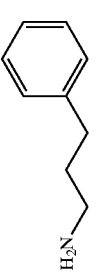
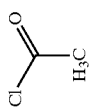
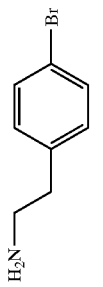
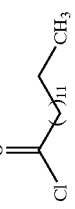

TABLE 1-continued
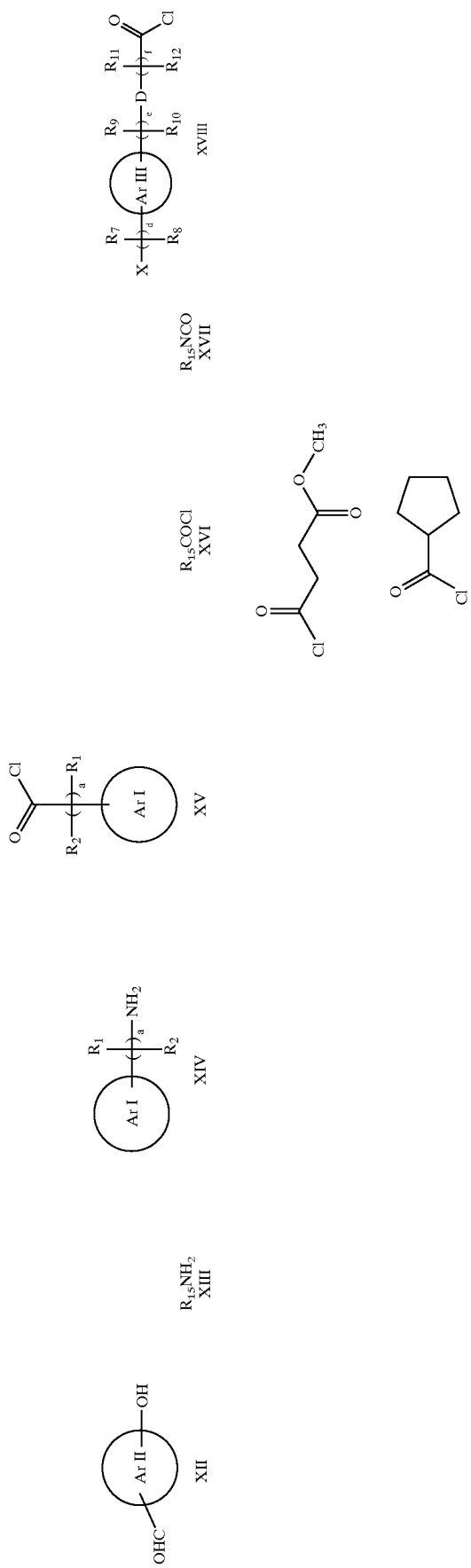

An additional exemplification of the amide linker is shown in Scheme 56. Reaction of an activated carboxylic acid derivative such as, but not limited to, an acid chloride or anhydride with an amine of general formula (15) and a suitable base such as triethylamine provides the amide (16). More explicit exemplification is shown in Scheme 57. Carboxylic acid (17) is activated with oxalyl chloride to provide the acid chloride and then 2-amino-6-methylbenzoic acid (18), is added to provide the amide (19). Alternatively, 2-aminomethyl-6-methylbenzoic acid (20) can be used to provide the amide (21).

the literature, for example those described by R. C. Larock in Comprehensive Organic Transformations, VCH publishers, 1989.

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Green and P. G. M. Wuts in "Protective Groups in

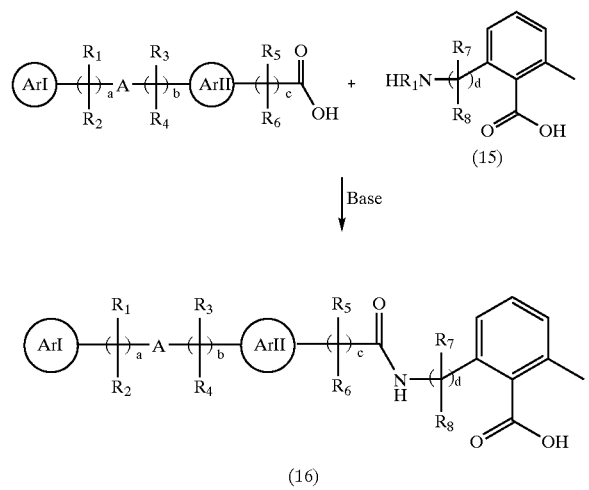

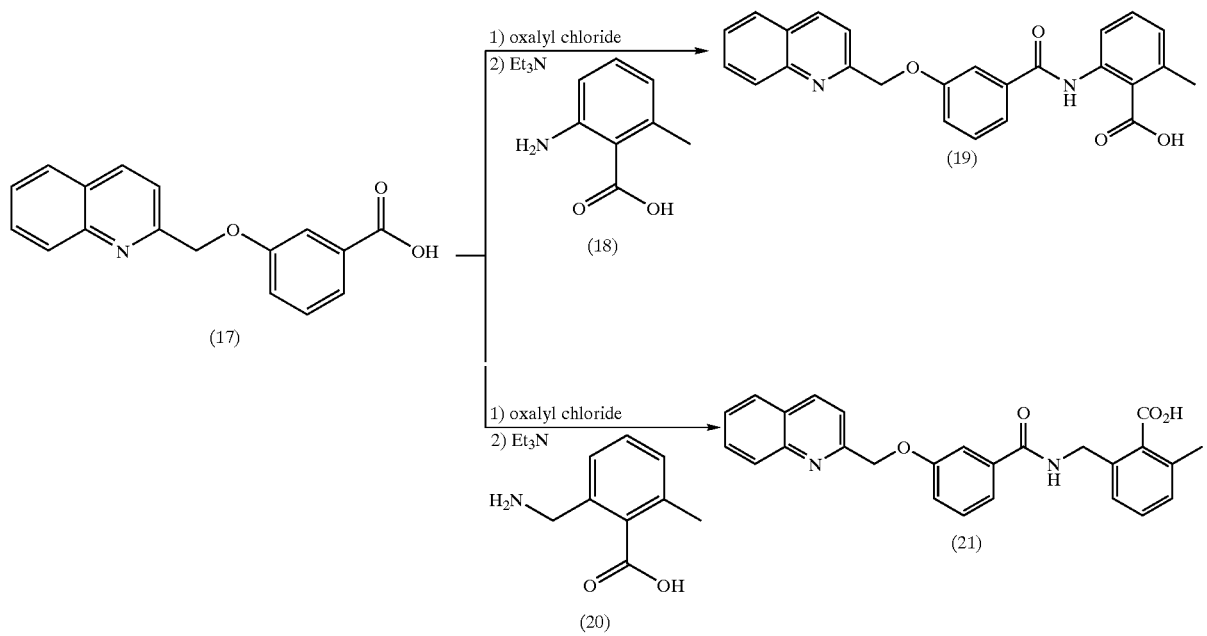

Compounds useful according to the invention may also be prepared by the application or adaptation of known methods, by which is meant methods used heretofore or described in Organic Chemistry" John Wiley and Sons, 1991; J. F. W. McOmie in "Protective Groups in Organic Chemistry" Plenum Press, 1973.

According to a further feature of the present invention, compounds useful according to the invention may be prepared by interconversion of other compounds of the invention.

A compound of the invention including a group containing one or more nitrogen ring atoms, preferably imine (=N—), may be converted to the corresponding compound wherein one or more nitrogen ring atom of the group is oxidized to an N-oxide, preferably by reacting with a peracid, for example peracetic acid in acetic acid or m-chloroperoxybenzoic acid in an inert solvent such as dichloromethane, at a temperature from about room temperature to reflux, preferably at elevated temperature.

The products of this invention may be obtained as racemic mixtures of their dextro and levorotatory isomers since at least one asymmetric carbon atom may be present. When two asymmetric carbon atoms are present, the product may exist as a mixtures of diastereomers based on syn and anti configurations. These diastereomers may be separated by fractional crystallization. Each diastereomer may then be resolved into dextro and levorotatory optical isomers by conventional methods.

It will also be apparent to those skilled in the art that certain compounds of Formula I may exhibit geometrical isomerism. Geometrical isomers include the cis and trans forms of compounds of the invention having an alkenyl moiety. The present invention comprises the individual geometrical isomers and stereoisomers and mixtures thereof.

Such isomers can be separated from their mixtures, by the application or adaptation of known methods, for example chromatographic techniques and recrystallization techniques, or they are separately prepared from the appropriate isomers of their intermediates, for example by the application or adaptation of methods described herein.

Resolution may best be carried out in the intermediate stage where it is convenient to combine the racemic compound with an optically active compound by salt formation, ester formation, or amide formation to form two diastereomeric products. If an acid is added to an optically active base, then two diastereomeric salts are produced which possesses different properties and different solubilities and can be separated by fractional crystallization. When the salts have been completely separated by repeated crystallization, the base is split off by acid hydrolysis and enantiomerically purified acids are obtained.

Compounds useful according to the invention are useful in the form of the free base or acid or in the form of a pharmaceutically acceptable salt thereof. All forms are within the scope of the invention.

Where a compound useful according to the invention is substituted with a basic moiety, acid addition salts are formed and are simply a more convenient form for use; in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial pharmaceutical effects of these compounds in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as an intermediate in preparing a pharmaceutically acceptable salt by ion exchange procedures. Pharmaceutically acceptable salts useful within the scope of the invention are those derived from the following acids: mineral acids such as hydrochloric acid, trifluoroacetic acid, sulfuric acid, phosphoric acid and sulfamic acid; and organic acids such as acetic acid, citric acid, lactic acid, tartaric acid, malonic acid, methanesufonic acid, ethanesulfonic acid, benzenesulfonic acid, p-toluenesulfonic acid, cyclohexylsulfamic acid, quinic acid, and the like. The corresponding acid addition salts comprise the following: hydrohalides, e.g. hydrochloride and hydrobromide, trifluoroacetate, sulfate, phosphate, nitrate, sulfamate, acetate, citrate, lactate, tartarate, malonate, oxalate, salicylate, propionate, succinate, fumarate, maleate, methylene-bis-β-hydroxynaphthoates, gentisates, mesylates, isothionates, di-p-toluoyltartrates, methanesulfonates, ethanesulfonates, benzenesulfonates, p-toluenesulfonates, cyclohexylsulfamate and quinate, respectively.

The acid addition salts of the compounds useful according to the invention are prepared by reaction of the free base with the appropriate acid, by the application or adaptation of known methods. For example, the acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The compounds useful according to the invention may be regenerated from the acid addition salts by the application or adaptation of known methods. For example, parent compounds useful according to the invention can be regenerated from their acid addition salts by treatment with an alkali, e.g., aqueous sodium bicarbonate solution or aqueous ammonia solution.

Where the compound useful according to the invention is substituted with an acidic moiety, base addition salts may be formed and are simply a more convenient form for use; in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the animal organism in pharmaceutical doses of the salts, so that the beneficial pharmaceutical effects on the activity of the compounds of the present invention in the free acid are not vitiated by side effects ascribable to the cations. Pharmaceutically acceptable salts useful according to the invention, include for example alkali and alkaline earth metal salts, including those derived from the following bases: sodium hydride, sodium hydroxide, potassium hydroxide, calcium hydroxide, aluminum hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, diethylamine, N-benzylphenethylamine, piperazine, tris(hydroxymethyl)aminomethane, tetramethylammonium hydroxide, and the like.

Metal salts of compounds useful according to the present invention may be obtained by contacting a hydride, hydroxide, carbonate or similar reactive compound of the chosen metal in an aqueous or organic solvent with the free acid form of the compound. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds useful according to the present invention may be obtained by contacting an amine in an aqueous or organic solvent with the free acid form of the compound. Suitable aqueous solvents include water and mixtures of water with alcohols such as methanol or ethanol, ethers such as tetrahydrofuran, nitriles such as acetonitrile, or ketones such as acetone. Amino acid salts may be similarly prepared.

The base addition salts of the compounds useful according to the invention can be regenerated from the salts by the application or adaptation of known methods. For example, parent compounds useful according to the invention can be regenerated from their base addition salts by treatment with an acid, e.g. hydrochloric acid.

Salt forms useful according to the invention also include compounds having a quarternarized nitrogen. The quarternarized salts are formed by methods such as by alkylation of $sp^3$ or $sp^2$ hybridized nitrogen in the compounds.

As will be self-evident to those skilled in the art, some of the compounds useful according to the invention do not form stable salts. However, acid addition salts are most likely to be formed by compounds useful according to the invention having a nitrogen-containing heteroaryl group and/or wherein the compounds contain an amino group as a substituent. Preferable acid addition salts of the compounds useful according to the invention are those wherein there is not an acid labile group.

As well as being useful in themselves as active compounds, the salts of the compounds useful according to the invention are useful for the purposes of purification of the compounds, for example by exploitation of the solubility differences between the salts and the parent compounds, side products and/or starting materials by techniques well known to those skilled in the art.

Various substituents on the compounds useful according to the invention, e.g., as defined in R, $R_1$ and $R_2$ can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups known in the art may be employed. Examples of many of these possible groups may be found in "Protective Groups in Organic Synthesis" by T. W. Green, John Wiley and Sons, 1981. For example, nitro groups can be added to the aromatic ring by nitration, and the nitro group then converted to other groups, such as amino, by reduction, and halo, by diazotization of the amino group and replacement of the diazo group. Acyl groups can be substituted onto the aryl groups by Friedel-Crafts acylation. The acyl groups then can be transformed to the corresponding alkyl groups by various methods, including the Wolff-Kishner reduction and Clemmenson reduction. Amino groups can be alkylated to form mono and dialkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product.

The starting materials, intermediates and some compounds of the invention are prepared by the application or adaptation of known methods, for example methods as described in U.S. Pat. Nos. 4,920,132; 4,920,131; and 5,059,610; publications Huang, Fu Chih et al, J. Med. Chem. (1991), 34(5), 1704–7; and Huang, Fu Chih et al, J. Med. Chem. (1990), 33(4), 1194–200; and the Reference Examples or their obvious chemical equivalents.

The present invention is further exemplified but not limited by the following examples, which illustrate the preparation of the compounds according to the invention.

EXAMPLE 1

Methyl 2,6-dimethyl-benzoate

To a cooled (0° C.) solution of 2,6-dimethylbenzoic acid (20.2 g, 134 mmol) in dichloromethane (200 mL) is added DMF (1 mL) followed by oxalyl chloride (14 mL, 162 mmol). On completion of addition, the cold bath is removed and stirring continued for 3 h. The resulting solution is concentrated under vacuum and the residue added slowly to a cooled (0° C.) solution comprising methanol (200 mL) and triethylamine (40 mL). On completion of addition, the reaction mixture is stirred for 30 min. then poured into hydrochloric acid solution (400 mL, 2N) which is then extracted with ether. The ether extract is washed with hydrochloric acid solution (1N), sodium bicarbonate solution and brine then dried over $MgSO_4$ and concentrated to give the title compound which is used without further purification. MS (EI) 164 $(M)^+$.

EXAMPLE 2

Methyl 2-bromomethyl-6-methyl-benzoate

To a solution of methyl 2,6-dimethyl-benzoate (22.0 g, 134 mmol, example 1) in $CCl_4$ (250 mL) is added N-bromosuccinimide (19 g, 107 mmol) followed by benzoyl peroxide (1.0 g, 4.0 p mmol). The resulting solution is warmed to reflux and stirred at this temperature for 20 min. The reaction mixture is then allowed to cool before being diluted with ether (200 mL), filtered and concentrated. The residue is purified by flash chromatography (silica, 4% acetone in hexanes) to give the title compound. This product (approx. 85% purity, remainder is methyl 2,6dimethyl benzoate) is used without further purification. MS (EI) 242, 244 ($M^+$, Br pattern).

EXAMPLE 3

3-(Quinolin-2-ylmethoxy)-phenol

2-Chloromethylquinoline hydrochloride (25.0 g, 117 mmol) and resorcinol monobenzoate (37.5 g, 175 mmol) are suspended in dimethylsulfoxide (180 mL) and are mixed with the aid of an overhead stirrer. The mixture is cooled to 15° C. and a 50% solution of sodium hydroxide (25 mL) is added slowly over 10 min with a slight exotherm. The reaction is allowed to come to room temperature and is allowed to stir overnight. The reaction is then heated to 95° C. and a 50% solution of sodium hydroxide (25 mL) is added over 10 min. After 20 min. hot water (300 mL) is added to the reaction and stirred 15 min. The reaction is hot filtered and the filtrate is cooled to provide a brick red solid which is dried in vacuo to provide the sodium salt pentahydrate. A portion of the salt (15.6 g, 43.0 mmol) is neutralized by heating in water (30 mL) with 1N HCl (43 mL) followed by cooling to provide a brown solid. The solid is dissolved in dichloromethane (550 mL) and methanol (14 mL), dried over magnesium sulfate, filtered and concentrated in vacuo to yield the title compound as a tan solid. A portion is recrystallized from ethyl acetate to provide an analytically pure sample; m.p. 152–153° C., MS (ESI) 252 (M+H)$^+$.

EXAMPLE 4

Methyl 2-methyl-6-[3-(quinolin-2-ylmethoxy)-phenoxymethyl]-benzoate 13-(Quinolin-2-ylmethoxy)-phenol (5.2 g, 21 mmol, example 3), methyl 2-bromomethyl-6-methyl-benzoate (example 2) (5.0 g, 21 mmol) and potassium carbonate (4.4 g, 32 mmol) are combined in DMF (50 mL) and heated at 85° C. for 3 h. The reaction is poured into ethyl acetate (500 mL) and washed with water (4×120 mL) and brine (100 mL). The solution is dried over magnesium sulfate, filtered and concentrated in vacuo to provide a residue which is purified by column chromatography (silica, 10 to 20% ethyl acetate in hexane) to provide the title compound. MS (ESI) 414 (M+H)$^+$.

The following compounds are prepared using essentially the same procedure used in example 4 except using the cited phenol in place of 3-(quinolin-2-ylmethoxy)-phenol with either the methyl or isobutyl benzoate (example 2).

EXAMPLE 4a

Methyl {2-methyl-6-[3-(2-quinolin-2-yl-vinyl)-phenoxymethyl]}-benzoate.

MS (ESI) 410 (M+H)$^+$. Prepared from 3-(2-quinolin-2-yl-vinyl)-phenol (example 15).

EXAMPLE 4b

Methyl (2-Methyl-6-{3-[2-(pyridin-2-yloxy)-ethoxy]-phenoxymethyl})-benzoate $^1$H NMR (300 MHz, CDCl$_3$) δ 8.15 (m, 1H), 7.60 (t, 1H), 7.1–7.38 (m, 4H), 6.89 (dd, 1H), 6.81 (d, 1H), 6.56 (m, 3H), 5.08 (s, 2H), 4.70 (t, 2H), 4.32 (t, 2H), 3.85 (s, 3H), 2.36 (s, 3H). Prepared from 3-[2-(pyridin-2-yloxy)-ethoxy]-phenol (example 15a).

EXAMPLE 4c

Methyl 2-{3-[(Benzoxazol-2-yl-methyl-amino)-methyl]-phenoxymethyl}-6-methyl-benzoate MS (ESI) 417 (M+H)$^+$. Prepared from 3-[(N-benzoxazol-2-yl-N-methyl-amino)-methyl]-phenol (example 10a).

EXAMPLE 4d

Methyl 2-methyl-6-{3-[(methyl-quinolin-2-yl-amino)-methyl]-phenoxymethyl}-benzoate MS (ESI) 427 (M+H)$^+$. Prepared from 3-[(N-methyl-N-quinolin-2-yl-amino)-methyl]-phenol (example 10b).

EXAMPLE 4e

Isobutyl 2-methyl-6-[3-(quinolin-2-yloxymethyl)-phenoxymethyl]-benzoate

MS (ESI) 456 (M+H)$^+$. Prepared from 3-(quinolin-2-yloxymethyl)-phenol (example 15b).

EXAMPLE 4f

Methyl 2-{3-[2-(5-ethyl-pyridin-2-yl)-ethoxy]-phenoxymethyl}-6-methyl-benzoate $^1$H NMR (300 MHz, CDCl$_3$) δ 8.39 (bs, 1H), 7.46 (d, 1H), 7.28 (m, 2H), 7.16 (m, 3H), 6.52 (m, 3H), 5.06 (s, 2H), 4.31 (t, 2H), 3.82 (s, 3H), 3.22 (t, 2H), 2.63 (q, 2H), 2.38 (s, 3H), 1.24 (t, 3H). MS (ESI) 406 (M+H)$^+$. Prepared from 3-[2-(5-ethyl-pyridin-2-yl)-ethoxy]-phenol (example 71).

EXAMPLE 4g

Methyl 2-methyl-6-[3-(2-pyridin-2-yl-ethoxy)-phenoxymethyl]-benzoate $^1$H NMR (300 MHz, CDCl$_3$) δ 8.56 (d, 1H), 7.62 (m, 1H), 7.28 (m, 2H), 7.16 (m, 3H), 6.52 (m, 4H), 5.06 (s, 2H), 4.34 (t, 2H), 3.82 (s, 3H), 3.25 (t, 2H), 2.38 (s, 3H). MS (ESI) 378 (M+H)$^+$. Prepared from 3-(2-pyridin-2-yl-ethoxy)-phenol (example 71a).

EXAMPLE 4h

Methyl 2-[3-(Benzooxazol-2-ylaminomethyl)-phenoxymethyl]-6-methyl-benzoate $^1$H NMR (300 MHz, CDCl$_3$) δ 7.54 (m, 1H), 7.38 (d, 1H), 7.26 (m, 3H), 7.18 (m, 2H), 7.05 (m, 1H), 6.98 (m, 2H), 6.88 (dd, 1H), 5.10 (s, 2H), 4.64 (bs, 2H), 3.80 (s, 3H), 2.37 (s, 3H). MS (ESI) 403 (M+H)$^+$. Prepared from 3-(benzooxazol-2-ylaminomethyl)-phenol (example 10c).

EXAMPLE 4i

Methyl 2-methyl-6-[3-(pyridin-2-ylmethoxymethyl)-phenoxymethyl]-benzoate $^1$H NMR (300 MHz, CDCl$_3$) δ 8.56 (d, 1H), 7.71 (m, 1H), 7.48 (d, 1H), 7.25 (m, 5H), 6.99 (m, 2H), 6.87 (dd, 1H), 5.11 (s, 2H), 4.69 (s, 2H), 4.63 (s, 2H), 3.82 (s, 3H), 2.38 (s, 3H). MS (ESI) 378 (M+H)$^+$. Prepared from 3-(pyridin-2-ylmethoxymethyl)-phenol (example 74).

EXAMPLE 4j

Methyl 2-methyl-6-[3-(quinolin-2-ylmethoxymethyl)-phenoxymethyl]-benzoate $^1$H NMR (300 MHz, CDCl$_3$) δ 8.19 (d, 1H), 8.06 (d, 1H), 7.82 (d, 1H), 7.69 (m, 2H), 7.53 (m, 2H), 7.24 (m, 4H), 7.01 (m, 2H), 6.88 (dd, 1H), 5.12 (s, 2H), 4.86 (s, 2H), 4.66 (s, 2H), 3.82 (s, 3H), 2.38 (s, 3H). MS (ESI) 428 (M+H)$^+$. Prepared from 3-(quinolin-2-ylmethoxymethyl)phenol (example 74a).

EXAMPLE 5

Methyl 2-methyl-6-[(3-hydroxy-phenoxy)-methyl]-benzoate

To a solution of 3-hydroxy-phenol (1.5 g, 13.6 mmol) in acetonitrile (50 mL) is added methyl 2-(bromomethyl)-6-methyl-benzoate (0.82 g, 3.4 mmol, example 2) followed by $K_2CO_3$ (3.76 g, 27.2 mmol). The resulting mixture is heated to 50° C. and stirred at this temperature for 90 min. then cooled, filtered and the filtrate concentrated under vacuum. The residue is purified by flash chromatography (silica, 5% ethyl acetate in dichloromethane) to give the title compound as a white solid. MS (EI) 272 ($M^+$).

EXAMPLE 6

Methyl 2-methyl-6-[3-(2-phenyl-oxazol-4-yl-methoxy)-phenoxymethyl]-benzoate

To a solution of 4-chloromethyl-2-phenyl-oxazole (100 mg, 0.5 mmol, example 19) in DMF (2 mL) is added methyl 2-methyl-6-[(3-hydroxy-phenoxy)-methyl]-benzoate (136 mg, 0.5 mmol, example 5) followed by $K_2CO_3$ (75 mg, 0.54 mmol). The resulting mixture is heated to 60° C. and stirred at this temperature for 8 h. This mixture is then cooled to room temperature, diluted with ether, washed with water and brine, dried over $MgSO_4$ and concentrated. The residue is purified by flash chromatography (silica, 20% ethyl acetate in hexanes) to give the title compound. MS (ESI) 429 $(M+H)^+$.

The following compounds are prepared using essentially the same procedure used in Example 6 except using the cited alkyl halide in place of 4-chloromethyl-2-phenyl-oxazole with either methyl (ethyl or isobutyl) 2-methyl-6-[(3-hydroxy-phenoxy)-methyl]-benzoate (example 5).

EXAMPLE 6a

Methyl 2-methyl-6-[3-(2-phenyl-thiazol-4-yl-methoxy)-phenoxymethyl]-benzoate MS (ESI) 446 $(M+H)^+$. Prepared from 4-chloromethyl-2-phenyl-thiazole (example 20).

EXAMPLE 6b

Methyl 2-[3-(3,5-dimethyl-isoxazol-4-ylmethoxy)-phenoxymethyl]-6-methyl-benzoate MS (ESI) 382 $(M+H)^+$. Prepared from 3,5-dimethyl-isoxazol-4-ylmethyl chloride.

EXAMPLE 6c

Methyl 2-methyl-6-[3-(5-phenyl-[1,2,4]oxadiazol-3-ylmethoxy)-phenoxymethyl]-benzoate MS (ESI) 431 $(M+H)^+$. Prepared from 5-phenyl-[1,2,4]oxadiazol-3-ylmethyl chloride.

EXAMPLE 6d

Methyl 2-[3-(2,5-dimethyl-benzyloxy)-phenoxymethyl]-6-methyl-benzoate

MS (ESI) 391 $(M+H)^+$. Prepared from 2,5-dimethyl-benzyl chloride.

EXAMPLE 6e

Methyl 2-[3-(2,4-dichloro-benzyloxy)-phenoxymethyl]-6-methyl-benzoate

MS (ESI) 431 (M+H, $Cl_2$ pattern)$^+$. Prepared from 2,4-dichloro-benzyl chloride.

EXAMPLE 6f

Methyl 2-[3-(5-tert-butyl-[1,2,4]oxadiazol-3-ylmethoxy)-phenoxymethyl]-6-methyl-benzoate MS (ESI) 411 $(M+H)^+$. Prepared from 5-tert-butyl-[1,2,4]oxadiazol-3-ylmethyl chloride.

EXAMPLE 6g

Methyl 2-{3-[3-(2,6-dichloro-phenyl)-5-methyl-isoxazol-4-ylmethoxy]-phenoxymethyl}-6-methyl-benzoate MS (ESI) 512 $(M+H)^+$. Prepared from (3-(2,6-dichloro-phenyl)-5-methyl-isoxazol-4-yl)-methyl chloride.

EXAMPLE 6h

Methyl 2-methyl-6-[3-(2,4,5-trimethyl-benzyloxy)-phenoxymethyl]-benzoate

MS (ESI) 405 $(M+H)^+$. Prepared from 2,4,5-trimethyl-benzyl chloride.

EXAMPLE 6i

Methyl 2-methyl-6-[3-(3-methyl-naphthalen-2-yl-methoxy)-phenoxymethyl]-benzoate MS (ESI) 427 $(M+H)^+$. Prepared from (3-methyl-naphthalen-2-yl)-methyl bromide.

EXAMPLE 6j

Methyl 2-[3-(5-acetyl-2-methoxy-benzyloxy)-phenoxymethyl]-6-methyl-benzoate

MS (ESI) 435 $(M+H)^+$. Prepared from 5-acetyl-2-methoxy-benzyl chloride.

EXAMPLE 6k

Methyl 2-[3-(6-fluoroquinolin-2-ylmethoxy)phenoxymethyl]-6-methylbenzoate

MS (ESI) 432 $(M+H)^+$. Prepared from 6-fluoroquinolin-2-ylmethyl bromide (example 27b).

EXAMPLE 6l

Methyl 2-[3-(4-tert-butylbenzyloxy)phenoxymethyl]-6-methylbenzoate

MS (ESI) 419 (M+H)$^+$. Prepared from 4-(tert-butyl)benzyl bromide.

EXAMPLE 6m

Methyl 2-[3-(4-isopropylbenzyloxy)phenoxymethyl]-6-methylbenzoate

MS (ESI) 405 (M+H)$^+$. Prepared from 4-isopropylbenzyl chloride.

EXAMPLE 6n

Methyl 2-methyl-6-[3-(3-phenoxybenzyloxy)phenoxymethyl]benzoate

MS (ESI) 455 (M+H)$^+$. Prepared from 3-phenoxybenzyl chloride.

EXAMPLE 6o

Methyl 2-[3-(4-tert-butylcyclohexylmethoxy)phenoxymethyl]-6-methylbenzoate

MS 425 (M+H)$^+$. Prepared from 4-tert-butylcyclohexylmethyl bromide (example 29a).

EXAMPLE 6p

Methyl 2-methyl-6-[3-(quinoxalin-2-ylmethoxy)phenoxymethyl]benzoate

MS 415 (M+H)$^+$. Prepared from quinoxalin-2-ylmethyl chloride (See *Chem. Ber.* 1987, 120, 649–651).

EXAMPLE 6q

Methyl 2-methyl-6-[3-(2-methylbenzyloxy)phenoxymethyl]benzoate

MS 377 (M+H)$^+$. Prepared from α-bromo-o-xylene.

EXAMPLE 6r

Methyl 2-methyl-6-{3-[2-(5-methylthiophen-2-yl)-oxazol-4-ylmethoxy]phenoxymethyl}benzoate MS (ESI) 450 (M+H)$^+$. Prepared from 2-(5-methylthiophen-2-yl)oxazol-4-ylmethyl chloride (example 19a).

EXAMPLE 6s

Methyl 2-[3-(2-cyclohexyloxazol-4-ylmethoxy)phenoxymethyl]-6-methylbenzoate

MS (ESI) 436 (M+H)$^+$. Prepared from 2-cyclohexyloxazol-4-ylmethyl chloride (example 19b).

EXAMPLE 6t

Methyl 2-{3-[2-(3-fluorophenyl)oxazol-4-ylmethoxy]phenoxymethyl}-6-methylbenzoate MS (ESI) 448 (M+H)$^+$. Prepared from 2-(3-fluorophenyl)oxazol-4-ylmethyl chloride (example 19c).

EXAMPLE 6u

Methyl 2-{3-[2-(4-fluorophenyl)oxazol-4-ylmethoxy]phenoxymethyl}-6-methylbenzoate MS (ESI) 448 (M+H)$^+$. Prepared from 2-(4-fluorophenyl)oxazol-4-ylmethyl chloride (example 19d).

EXAMPLE 6v

Ethyl 2-[3-(6-chloropyridin-2-ylmethoxy)phenoxymethyl]-6-methylbenzoate

MS (ESI) 412, 414 (M+H)$^+$, Cl pattern. Prepared from 2-chloromethyl-6-chloropyridine (example 27c).

EXAMPLE 6w

Ethyl 2-methyl-6-[3-(5-methyl-2-phenyloxazol-4-ylmethoxy)phenoxymethyl]benzoate

MS (ESI) 458 (M+H)$^+$. Prepared from 4-chloromethyl-5-methyl-2-phenyloxazole.

EXAMPLE 6x

Methyl 2-(3-benzyloxy-phenoxymethyl)-6-methyl-benzoate

MS (EI) 362 (M)$^+$. Prepared from benzyl bromide.

EXAMPLE 6y

Methyl 2-methyl-6-[3-(pyridin-2-ylmethoxy)-phenoxymethyl]-benzoate

Prepared from 2-chloromethyl-pyridine.

EXAMPLE 6z

Methyl 2-[3-(7-chloroquinolin-2-ylmethoxy)phenoxymethyl]-6-methylbenzoate

MS (ESI) 447 (M+H)$^+$, Cl pattern. Prepared from 7-chloroquinolin-2-ylmethyl bromide (example 46a).

EXAMPLE 6aa

Methyl 2-[3-(6-methoxyquinolin-2-ylmethoxy)phenoxymethyl]-6-methylbenzoate

MS (ESI) 443 (M+H)$^+$. Prepared from 6-methoxyquinolin-2-ylmethyl bromide (example 46b).

EXAMPLE 6ab

Ethyl 2-[3-(2,4-diisopropyl-5-methyl-benzyloxy)-phenoxymethyl]-6-methyl-benzoate $^1$H NMR (300 MHz, CDCl$_3$) δ 7.14 (m, 6H), 6.62 (m, 3H), 5.10(s, 2H), 5.00 (s, 2H), 4.32 (m, 2H), 3.20 (m, 1H), 2.86 (m, 1H), 2.40 (bs, 6H), 1.28 (m, 15H). MS (EI) 484 (M)$^+$. Prepared from 1-chloromethyl-2,4-diisopropyl-5-methyl-benzene.

EXAMPLE 6ac

Ethyl 2-[3-(2,4-bis-trifluoromethyl-benzyloxy)-phenoxymethyl]-6-methyl-benzoate $^1$H NMR (300 MHz, CDCl$_3$) δ 7.92 (m, 2H), 7.82 (m, 1H), 7.30 (m, 2H), 7.18 (m, 2H), 6.57 (m, 3H), 5.29 (s, 2H), 5.10 (s, 2H), 4.31 (q, 2H), 2.39 (s, 3H), 1.29 (t, 3H). MS (EI) 512 (M)$^+$. Prepared from 2,4-bis(trifluoromethyl)benzyl bromide.

EXAMPLE 6ad

Ethyl 2-[3-(biphenyl-4-ylmethoxy)-phenoxymethyl]-6-methyl-benzoate $^1$H NMR (300 MHz, CDCl$_3$) δ 7.60 (m, 4H), 7.40 (m, 7H), 7.18 (m, 2H), 6.58 (m, 3H), 5.09 (s, 2H), 5.07 (s, 2H), 4.30 (q, 2H), 2.39 (s, 3H), 1.28 (t, 3H). MS (EI) 452 (M)$^+$. Prepared from 4-phenylbenzyl chloride.

EXAMPLE 6ae

Ethyl 2-methyl-6-[3-(naphthalen-1-ylmethoxy)-phenoxymethyl]-benzoate $^1$H NMR (300 MHz, CDCl$_3$) δ 8.04 (m, 1H), 7.88 (m, 2H), 7.52 (m, 4H), 7.24 (m, 4H), 6.67 (m, 2H), 6.59 (m, 1H), 5.46 (s, 2H), 5.10 (s, 2H), 4.30 (q, 2H), 2.39 (s, 3H), 1.28 (t, 3H). MS (EI) 426 (M)$^+$. Prepared from 1-chloromethyl-naphthalene.

EXAMPLE 6af

Methyl 2-[3-(5-ethyl-pyridin-2-ylmethoxy)-phenoxymethyl]-6-methyl-benzoate $^1$H NMR (300 MHz, CDCl$_3$) δ 8.44 (bs, 1H), 7.54 (dd, 1H), 7.42 (d, 1H), 7.32 (m, 2H), 7.17 (m, 2H), 6.58 (m, 2H), 5.15 (s, 2H), 5.08 (s, 2H), 3.82 (s, 3H), 2.67 (q, 2H), 2.38 (s, 3H), 1.26 (t, 3H). MS (ESI) 392 (M+H)$^+$. Prepared from 5-ethyl-2-chloromethylpyridine (example 68).

EXAMPLE 6ag

Methyl 2-[3-(4-ethyl-benzyloxy)-phenoxymethyl]-6-methyl-benzoate $^1$H NMR (300 MHz, CDCl$_3$) δ 7.28 (m, 8H), 6.58 (m, 3H), 5.08 (d, 2H), 5.00 (d, 2H), 3.81 (d, 3H), 2.68 (m, 2H), 2.38 (s, 3H), 1.24 (m, 3H). MS (EI) 390 (M)$^+$. Prepared from 1-chloromethyl-4-ethyl-benzene.

EXAMPLE 6ah

Methyl 2-[3-(3-bromo-benzyloxy)-phenoxymethyl]-6-methyl-benzoate $^1$H NMR (300 MHz, CDCl$_3$) δ 7.58 (s, 1H), 7.44 (d, 1H), 7.25 (m, 6H), 6.57 (m, 3H), 5.08 (s, 2H), 5.00 (s, 2H), 3.81 (s, 3H), 2.38 (s, 3H). MS (EI) 440 (M)$^+$. Prepared from 3-bromobenzyl bromide.

EXAMPLE 6ai

Ethyl-2-methyl-6-[3-(qiunolin-2-ylmethoxy)-phenylethynyl]-benzoate

The title compound is prepared using essentially the same procedure used in Example 6 except using ethyl 2-(3-hydroxy-phenylethynyl)-6-methyl-benzoate (example 15c) in place of methyl 2-methyl-6-[(3-hydroxy-phenoxy)-methyl]-benzoate and 2-chloromethylquinoline in place of 41!, chloromethyl-2-phenyl-oxazole. MS (ESI) 422 (M+H)$^+$.

EXAMPLE 6aj

Methyl 2-methyl-6-[3-(5-phenylpyridin-2-ylmethoxy) phenoxymethyl]benzoate

MS(ESI) 440 (M+H)$^+$. Prepared from 5-phenylpyridin-2-ylmethyl chloride (example 27 g).

EXAMPLE 6ak

Methyl 2-[3-(2-chloro-benzyloxy)-phenoxymethyl]-6-methyl-benzoate $^1$H NMR (300 MHz, CDCl$_3$) δ 7.55 (m, 1H), 7.40 (m, 1H), 7.30 (m, 4H), 7.20 (m, 2H), 6.60 (m, 3H), 5.14 (s, 2H), 5.09 (s, 2H), 3.82 (s, 3H), 2.38 (s, 3H). MS (EI) 396 (M$^+$.), Cl pattern. Prepared from 2-chlorobenzyl chloride.

EXAMPLE 6al

Methyl 2-[3-(4-chloro-benzyloxy)-phenoxymethyl]-6-methyl-benzoate $^1$H NMR (300 MHz, CDCl$_3$) δ 7.32 (m, 6H), 7.18 (m, 2H), 6.56 (m, 3H), 5.08 (s, 2H), 5.00 (s, 2H), 3.81 (s, 3H), 2.38 (s, 3H). MS (EI) 396 (M+.), Cl pattern. Prepared from 4-chlorobenzyl chloride.

EXAMPLE 6 am

2-Methyl-6-[3-(3-methyl-quinoxalin-2-ylmethoxy)-phenoxymethyl]-benzoic acid methyl ester MS (ESI) 429 (M+H)$^+$. Prepared from 2-methyl-3-chloromethylquinoxaline (See Chem. Ber. 1987, 120, 649).

EXAMPLE 6an

2-Methyl-6-[3-(naphthalen-2-ylmethoxy)-phenoxymethyl]-benzoic acid methyl ester

MS (EI) 412 (M$^+$).

EXAMPLE 7

2-Methyl-6-[3-(quinolin-2-ylmethoxy)-phenoxymethyl]-benzoic acid

A solution of methyl 2-methyl-6-[3-(quinolin-2-ylmethoxy)-phenoxymethyl]-benzoate (1.6 g, 3.8 mmol, example 4) in ethanol (25 mL) is heated with a 10N sodium hydroxide solution (4.0 mL, 40 mmol) at 70° C. for 14 h. The reaction is cooled, neutralized with a 2N HCl solution (20 mL) and concentrated to remove the ethanol. Ethyl acetate is added and washed with water. The aqueous layer is saturated with sodium chloride and back extracted with ethyl acetate. The organic layers are combined, dried over magnesium sulfate, filtered and concentrated to yield a crude solid. The solid is purified by column chromatography (silica, 5 to 10% methanol in dichloromethane) to provide the title compound. An analytically pure sample is prepared by recystallization from methanol: m.p. 167–168° C., $^1$H NMR (300 MHz, CDCl$_3$)δ0.15 (d, 2H), 7.80 (d, 1H), 7.71 (t, 1H), 7.61–7.51 (m, 2H), 7.26–7.10 (m, 3H), 7.00 (t, 1H), 6.66 (s, 1H), 6.52 (d, 1H), 6.46 (d, 1H), 5.26 (s, 2H), 5.15 (s, 2H), 2.44 (s, 3H); MS (ESI) 400 (M+H)$^+$.

An alternate set of conditions that can be used for the hydrolysis of a benzoate ester is to heat a 0.1 M solution of the ester in THF/methanol (1:1) with 10 equivalents of a sodium hydroxide solution (10 N) at 60° C. for 3 h or until starting material disappears, as monitered by TLC analysis.

The following compounds are prepared using essentially the same procedure used in example 7 except using the cited ester in place of methyl 2-methyl-6-[3-(quinolin-2-ylmethoxy)-phenoxymethyl]-benzoate.

EXAMPLE 7a

2-Methyl-6-[3-(2-quinolin-2-yl-vinyl)-phenoxymethyl]-benzoic acid $^1$H NMR (300 MHz, DMSO) d 8.87 (bd, 1H), 8.14–8.36 (m, 4H), 8.00 (t, 1H), 7.81 (d, 1H), 7.71 (m, 1H), 7.34–7.48 (m, 5H), 7.29 (bd, 1H), 7.08, (m, 1H), 5.22 (s, 2H), 2.35 (s, 3H). MS (ESI) 396 (M+H)$^+$. Prepared from methyl {2-methyl-6-[3-(2-quinolin-2-yl-vinyl)-phenoxymethyl]benzoate (example 4a).

EXAMPLE 7b

2-Methyl-6-{3-[2-(pyridin-2-yloxy)-ethoxy]-phenoxymethyl}-benzoic acid $^1$H NMR (300 MHz, DMSO) d 8.17 (d, 1H), 7.71 (m, 1H), 7.22 (d, 1H), 7.04–7.19 (m, 3H), 6.99 (dd, 1H), 6.86 (d, 1H), 6.55 (m, 3H), 5.13 (s, 2H), 4.53 (bs, 2H), 4.28 (bs, 2H), 2.25 (bs, 3H). MS (ESI) 380 (M+H)$^+$. Prepared from methyl (2-methyl-6-{3-[2-(pyridin-2-yloxy)-ethoxy]-phenoxymethyl})-benzoate (example 4b).

EXAMPLE 7c

2-{3-[(Benzoxazol-2-yl-methyl-amino)-methyl]-phenoxymethyl}-6-methyl-benzoic acid $^1$H NMR (300 MHz, CDCl$_3$) δ 7.27 (bd, 1H), 7.07–7.3 (m, 5H), 7.03 (t, 1H), 6.80 (m, 3H), 5.10 (bs, 2H), 4.61 (bs, 2H), 3.03 (s, 3H), 2.38 (bs, 3H). MS (ESI) 403 (M+H)$^+$. Prepared from methyl 2-{3-[(benzoxazol-2-yl-methyl-amino)-methyl]-phenoxymethyl}-6-methyl-benzoate (example 4c).

EXAMPLE 7d

2-Methyl-6-{3-[(methyl-quinolin-2-yl-amino)-methyl]-phenoxymethyl}-benzoic acid $^1$H NMR (300 MHz, CDCl$_3$) δ 8.09 (d, 1H), 7.74 (d, 1H), 7.50 (m, 3H), 7.20 (m, 4H), 6.85 (m, 3H), 6.65 (d, 1H), 5.20 (s, 2H), 4.75 (s, 2H), 3.29 (s, 3H), 2.05 (s, 3H). MS (ESI) 413 (M+H)$^+$.

Prepared from methyl 2-methyl-6-{3-[(methyl-quinolin-2-yl-amino)-methyl]-phenoxymethyl}-benzoate (example 4d).

EXAMPLE 7e

2-Methyl-6-[3-(2-phenyl-oxazol-4-ylmethoxy)-phenoxymethyl]-benzoic acid $^1$H NMR (300 MHz, DMSO) d 8.30 (s, 1H), 8.00 (m, 2H), 7.55 (m, 3H), 7.30 (m, 2H), 7.22 (m, 2H), 6.66 (m, 2H), 6.60 (d, 1H), 5.10 (s, 2H), 5.06 (s, 2H), 2.34 (s, 3H). MS (ESI) 416 (M+H)$^+$. Prepared from methyl 2-methyl-6-[3-(2-phenyl-oxazol-4-ylmethoxy)-phenoxymethyl]-benzoate (example 6).

EXAMPLE 7f

2-Methyl-6-[3-(2-phenyl-thiazol-4-ylmethoxy)-phenoxymethyl]-benzoic acid $^1$H NMR (300 MHz, CDCl$_3$) δ 7.95 (m, 2H), 7.43 (m, 3H), 7.32 (m, 2H), 7.24 (d, 1H), 7.20 (m, 1H), 7.14 (t, 1H), 6.66 (m, 1H), 6.56 (m, 1H), 5.20 (s, 2H), 5.15 (s, 2H), 2.41 (s, 3H). MS (ESI) 432 (M+H)$^+$. Prepared from methyl 2-methyl-6-[3-(2-phenyl-thiazol-4-ylmethoxy)-phenoxymethyl]-benzoate (example 6a).

EXAMPLE 7g

2-[3-(3,5-Dimethyl-isoxazol-4-ylmethoxy)-phenoxymethyl]-6-methyl-benzoic acid $^1$H NMR (300 MHz, CDCl$_3$) δ 7.34 (m, 2H), 7.20 (m, 1H), 7.15 (t, 1H), 6.56 (m, 3H), 5.19 (s, 2H), 4.71 (s, 2H), 2.43 (s, 3H), 2.34 (s, 3H), 2.22 (s, 3H). MS (ESI) 368 (M+H)$^+$. Prepared from methyl 2-[3-(3,5-dimethyl-isoxazol-4-ylmethoxy)-phenoxymethyl]-6-methyl-benzoate (example 6b).

EXAMPLE 7h

2-Methyl-6-[3-(5-phenyl-[1,2,4]oxadiazol-3-yl-methoxy)-phenoxymethyl]-benzoic acid $^1$H NMR (300 MHz, CDCl$_3$) δ8.15 (m, 2H), 7.59 (m, 1H), 7.50 (m, 2H), 7.33 (m, 2H), 7.20 (m, 1H), 7.14 (t, 1H), 6.70 (m, 1H), 6.61 (m, 2H), 5.19 (s, 2H), 2.44 (s, 3H). MS (ESI) 417 (M+H)$^+$.
Prepared from methyl 2-methyl-6-[3-(5-phenyl-[1,2,4]oxadiazol-3-ylmethoxy)-phenoxymethyl]-benzoate (example 6c).

EXAMPLE 7i

2-[3-(2,5-Dimethyl-benzyloxy)-phenoxymethyl]-6-methyl-benzoic acid $^1$H NMR (300 MHz, CDCl$_3$) δ 7.35 (m, 2H), 7.13–7.24 (m, 3H), 7.09 (d, 1H), 7.04 (d, 1H), 6.60 (m, 3H), 5.17 (s, 2H), 4.90 (s, 2H), 2.44 (s, 3H), 2.30 (s, 3H), 2.26 (s, 3H). MS (ESI) 375 (M–H)$^-$. Prepared from methyl 2-[3-(2,5-dimethyl-benzyloxy)-phenoxymethyl]-6-methyl-benzoate (example 6d).

EXAMPLE 7j

2-[3-(2,4-Dichloro-benzyloxy)-phenoxymethyl]-6-methyl-benzoic acid $^1$H NMR (300 MHz, CDCl$_3$) δ 7.40 (m, 2H), 7.34 (m, 2H), 7.24 (m, 2H), 7.17 (t, 1H), 6.59 (m, 3H), 5.19 (s, 2H), 5.03 (s, 2H), 2.45 (s, 3H). MS (ESI) 415 (M–H, Cl$_2$ pattern). Prepared from methyl 2-[3-(2,4-dichloro-benzyloxy)-phenoxymethyl]-6-methyl-benzoate (example 6e).

EXAMPLE 7k

2-[3-(5-tert-Butyl-[1,2,4]oxadiazol-3-ylmethoxy)-phenoxymethyl]-6-methyl-benzoic acid $^1$H NMR (300 MHz, CDCl$_3$) δ 7.32 (m, 2H), 7.19 (m, 1H), 7.15 (t, 1H), 6.66 (d, 1H), 6.60 (d, 1H), 6.59 (d, 1H), 5.17 (s, 2H), 5.10 (s, 2H), 1.45 (s, 9H). MS (ESI) 395 (M–H)$^-$. Prepared from methyl 2-[3-(5-tert-butyl-[1,2,4]oxadiazol-3-ylmethoxy)-phenoxymethyl]-6-methyl-benzoate (example 6f).

EXAMPLE 7l

2-{3-[3-(2,6-Dichloro-phenyl)-5-methyl-isoxazol-4-ylmethoxy]-phenoxymethyl}-6-methyl-benzoic acid $^1$H NMR (300 MHz, CDCl$_3$) δ 7.24–7.41 (m, 5H), 7.21 (m, 1H), 7.08 (t, 1H), 6.53 (m, 1H), 6.40 (m, 2H), 5.11 (s, 2H), 4.65 (s, 2H), 2.48 (s, 3H), 2.41 (s, 3H). MS (ESI) 496 (M–H)$^-$. Prepared from methyl 2-{3-[3-(2,6-dichloro-phenyl)-5-methyl-isoxazol-4-ylmethoxy]-phenoxymethyl}-6-methyl-benzoate (example 6 g).

EXAMPLE 7m

2-Methyl-6-[3-(2,4,5-trimethyl-benzyloxy)-phenoxymethyl]-benzoic acid $^1$H NMR (300 MHz, CDCl$_3$) δ 7.35 (m, 2H), 7.20 (m, 1H), 7.15 (t, 1H), 7.10 (s, 1H), 6.97 (s, 1H), 6.60 (m, 3H), 5.16 (s, 2H), 4.87 (s, 2H), 2.42 (s, 3H), 2.25 (s, 3H), 2.21 (s, 3H), 2.20 (s, 3H). MS (ESI) 389 (M–H)—. Prepared from methyl 2-methyl-6-[3-(2,4,5-trimethyl-benzyloxy)phenoxymethyl]-benzoate (example 6 h).

EXAMPLE 7n

2-Methyl-6-[3-(3-methyl-naphthalen-2-ylmethoxy)-phenoxymethyl]-benzoic acid $^1$H NMR (300 MHz, CDCl$_3$) δ 7.77 (m, 3H), 7.64 (s, 1H), 7.41 (m, 2H), 7.33 (m, 2H), 7.19 (m, 2H), 6.61 (m, 3H), 5.17 (s, 2H), 5.09 (s, 2H), 2.47 (s, 3H), 2.43 (s, 3H). MS (ESI) 411 (M–H)$^-$. Prepared from methyl 2-methyl-6-[3-(3-methyl-naphthalen-2-ylmethoxy)-phenoxymethyl]-benzoate (example 6i).

EXAMPLE 7o

2-[3-(5-Acetyl-2-methoxy-benzyloxy)-phenoxymethyl]-6-methyl-benzoic acid $^1$H NMR (300 MHz, CDCl$_3$) δ 8.05 (bs, 1H), 7.93 (bd, 1H), 7.33 (m, 2H), 7.20 (m, 1H), 7.13. (t, 1H), 6.91 (d, 1H), 6.60 (m, 3H), 5.16 (s, 2H), 5.03 (s, 2H), 3.89 (s, 3H), 2.53 (s, 3H), 2.43 (s, 3H). MS (ESI) 419 (M–H)$^-$. Prepared from methyl 2-[3-(5-acetyl-2-methoxy-benzyloxy)phenoxymethyl]-6-methyl-benzoate (example 6j).

EXAMPLE 7p

2-[3-(6-Fluoroquinolin-2-ylmethoxy)phenoxymethyl]-6-methylbenzoic acid m.p. 153–154° C. $^1$H NMR (300 MHz, CDCl$_3$): δ 8.12 (m, 2H), δ 7.61 (d, 1H), 7.43 (m, 2H), 7.28 (m, 2H), 7.17 (m, 1H), 7.05 (m, 1H), 6.66 (s, 1H), 6.51 (m, 2H), 5.26 (s, 2H), 5.14 (s, 2H), 2.45 (s, 3H). MS (ESI) 418 (M+H)$^+$. Prepared from methyl 2-[3-(6-fluoroquinolin-2ylmethoxy)phenoxymethyl]-6-methylbenzoate (example 6k).

EXAMPLE 7q

2-[3-(4-tert-Butylbenzyloxy)phenoxymethyl]-6-methylbenzoic acid m.p. 122–123° C. $^1$H NMR (300 MHz, CDCl$_3$): δ 7.41–7.28 (m, 5H), 7.23–7.12 (m, 3H), 6.61–6.55 (m, 3H), 5.16 (s, 2H), 4.95 (s, 2H), 2.45 (s, 3H), 1.32 (s, 9H). MS (ESI) 405 (M+H)$^+$. Prepared from methyl 2-[3-(4-tert-butylbenzyloxy)phenoxymethyl]-6-methylbenzoate (example 6l).

EXAMPLE 7r

2-[3-(4-Isopropylbenzyloxy)phenoxymethyl]-6-methylbenzoic acid m.p. 132–133° C. $^1$H NMR (300 MHz, CDCl$_3$): δ 7.35. (m, 5H), 7.22 (m, 2H), 7.17 (m, 1H), 6.58 (m, 3H), 5.15(s, 2H), 4.97 (s, 2H), 2.92 (m, 1H), 2.46 (s, 3H), 1.25 (d, 6H). MS (ESI) 391 (M+H)$^+$. Prepared from methyl 2-[3-(4-isopropylbenzyloxy)phenoxymethyl]-6-methylbenzoate (example 6m).

EXAMPLE 7s

2-Methyl-6-[3-(3-phenoxybenzyloxy)phenoxymethyl]benzoic acid $^1$H NMR (300 MHz, CDCl$_3$): δ 7.31 (m, 5H), 7.15 (m, 1H), 7.12–6.98 (m, 6H), 6.93 (m, 1H), 6.54 (m, 3H), 5.13 (s, 2H), 4.94 (s, 2H), 2.43 (s, 3H). MS (ESI) 441 (M+H)$^+$. Prepared from methyl 2-methyl-6-[3-(3-phenoxybenzyloxy)phenoxymethyl]benzoate (example 6n).

EXAMPLE 7t

2-[3-(4-tert-Butylcyclohexylmethoxy)phenoxymethyl]-6-methylbenzoic acid $^1$H NMR (300 MHz, CDCl$_3$): δ 7.34 (m, 2H), 7.21 (m, 1H), 7.12 (m, 1H), 6.50 (m, 3H), 5.16 (s, 2H), 3.67 (d, 2H), 2.45 (s, 3H), 1.92–1.75 (m, 4H), 1.64 (m, 2H), 0.98 (m, 4H), 0.84 (s, 9H). MS 411 (M+H)$^+$. Prepared from methyl 2-[3-(4-tert-butylcyclohexylmethoxy)phenoxymethyl]-6-methylbenzoate (example 6o).

EXAMPLE 7u

2-Methyl-6-[3-(quinoxalin-2-ylmethoxy)phenoxymethyl]benzoic acid m.p. 57–60° C. $^1$H NMR (300 MHz, CDCl$_3$): δ 8.96 (s, 1H), 8.08 (m, 2H), 7.74 (m, 2H), 7.24 (m, 2H), 7.12 (m, 1H), 7.00 (m, 1H), 6.64 (s, 1H), 6.49 (m, 2H), 5.24 (s, 2H), 5.14 (s, 2H), 2.39 (s, 3H). MS 401 (M+H)$^+$. Prepared from methyl 2-methyl-6-[3-(quinoxalin-2-ylmethoxy)phenoxymethyl]benzoate (example 6p).

EXAMPLE 7v

2-Methyl-6-[3-(2-methylbenzyloxy)phenoxymethyl]benzoic acid $^1$H NMR (300 MHz, CDCl$_3$): δ 7.35 (m, 3H), 7.20 (m, 5H), 6.59 (m, 3H), 5.17 (s, 2H), 4.95 (s, 2H), 2.44 (s, 3H), 2.32 (s, 3H). MS(APcI) 385 (M+H+Na)$^+$. Prepared from methyl 2-methyl-6-[3-(2-methylbenzyloxy)-phenoxymethyl]benzoate (example 6q).

EXAMPLE 7w

2-Methyl-6-{3-[2-(5-methylthiophen-2-yl)-oxazol-4-ylmethoxy]phenoxymethyl}benzoic acid m.p. 129–130° C. $^1$H NMR (300 MHz, CDCl$_3$): δ 7.54 (s, 1H), 7.48 (d, 1H), 7.27 (m, 2H), 7.11 (m, 2H), 6.74 (m, 1H), 6.66 (s, 1H), 6.53 (m, 2H), 5.12 (s, 2H), 4.95 (s, 2H), 2.51 (s, 3H), 2.39 (s, 3H). MS (ESI) 436 (M+H)$^+$. Prepared from methyl 2-methyl-6-{3-[2-(5-methylthiophen-2-yl)-oxazol-4-ylmethoxy]phenoxymethyl}benzoate (example 6r).

EXAMPLE 7x

2-[3-(2-Cyclohexyloxazol-4-ylmethoxy)phenoxymethyl]-6-methylbenzoic acid m.p. 158–159° C. $^1$H NMR (300 MHz, CDCl$_3$): δ 7.57 (s, 1H), 7.30 (m, 2H), 7.20 (m, 1H), 7.12 (m, 1H), 6.72 (m, 1H), 6.53 (m, 2H), 5.13 (s, 2H), 4.95 (s, 2H), 2.84 (m, 1H), 2.45 (s, 3H), 2.06 (m, 2H), 1.81 (m, 2H), 1.73–1.20 (m, 6H). Prepared from methyl 2-[3-(2-cyclohexyloxazol-4-ylmethoxy)-phenoxymethyl]-6-methylbenzoate 6s).

EXAMPLE 7y

2-{3-[2-(3-Fluorophenyl)oxazol-4-ylmethoxy]phenoxymethyl}-6-methylbenzoic acid m.p. 152–154° C. $^1$H NMR (300 MHz, 5:1 CDCl$_3$:CD$_3$OD): δ 7.84 (d, 1H), 7.80 (s, 1H), 7.74 (d, 1H), 7.46 (m, 1H), 7.31 (m, 2H), 7.19 (m, 3H), 6.64 (m, 3H), 5.17 (s, 2H), 5.04 (s, 2H), 2.44 (s, 3H). MS (ESI) 434 (M+H)$^+$. Prepared from methyl 2-{3-[2-(3-fluorophenyl)oxazol-4-ylmethoxy]phenoxymethyl}-6-methylbenzoate (example 6t).

EXAMPLE 7z

2-{3-[2-(4-Fluorophenyl)oxazol-4-ylmethoxy]phenoxymethyl}-6-methylbenzoic acid m.p. 159–160° C. $^1$H NMR (300 MHz, CDCl$_3$): δ 8.03 (m, 2H), 7.70 (s, 1H), 7.32 (d, 2H), 7.16 (m, 3H), 6.93 (m, 1H), 6.69 (m, 1H), 6.55 (m, 2H), 5.16 (s, 2H), 5.03 (s, 2H), 2.44 (s, 3H). MS (ESI) 434 (M+H)$^+$. Prepared from methyl 2-{3-[2-(4-fluorophenyl)oxazol-4-ylmethoxy]phenoxymethyl}-6-methylbenzoate (example 6u).

EXAMPLE 7aa

2-[3-(6-Chloropyridin-2-ylmethoxy)phenoxymethyl]-6-methylbenzoic acid m.p. 97–98° C. $^1$H NMR (300 MHz, 5:1 CDCl$_3$:CD$_3$OD): δ 7.73 (m, 1H), 7.47 (m, 1H), 7.28 (m, 3H), 7.16 (m, 2H), 6.60 (m, 3H), 5.16 (s, 2H), 5.12 (s, 2H), 2.42 (s, 3H). MS (ESI) 384, 386 (M+H)$^+$, Cl pattern. Prepared from ethyl 2-[3-(6-chloropyridin-2-ylmethoxy)phenoxymethyl]-6-methylbenzoate (example 6v).

EXAMPLE 7ab

2-Methyl-6-[3-(5-methyl-2-phenyloxazol-4-ylmethoxy)phenoxymethyl]benzoic acid m.p. 144–145° C. $^1$H NMR (300 MHz, 3:1 CDCl$_3$:CD$_3$OD): δ 7.99 (m, 2H), 7.42 (m, 3H), 7.30 (m, 2H), 7.19 (m, 2H), 6.63 (m, 3H), 5.17 (s, 2H), 4.95 (s, 2H), 2.45 (s, 3H), 2.43 (s, 3H). MS (ESI) 430 (M+H)$^+$. Prepared from ethyl 2-methyl-6-[3-(5-methyl-2-phenyloxazol-4-ylmethoxy)phenoxymethyl]benzoate (example 6w).

EXAMPLE 7ac 2-(3-Benzyloxy-phenoxymethyl)-6-methyl-benzoic acid $^1$H NMR (300 MHz, CD$_3$OD) d 7.40–7.19 (m, 8H), 7.14 (t, 1H), 6.61–6.51 (m, 3H), 5.07 (s, 2H), 5.03 (s, 2H), 2.40 (s, 3H); MS (EI) 348 (M)$^+$. Prepared from methyl 2-(3-benzyloxy-phenoxymethyl)-6-methyl-benzoate (example 6x).

EXAMPLE 7ad

2-Methyl-6-[3-(pyridin-2-ylmethoxy)-phenoxymethyl]-benzoic acid $^1$H NMR (300 MHz, CD$_3$OD) d 8.53 (d, 1H), 7.87 (t, 1H), 7.60 (d, 1H), 7.37–7.13 (m, 5H), 6.64–6.59 (m, 3H), 5.15 (d, 4H), 2.40 (s, 3H); MS (ESI) 350 (M+H)$^+$. Prepared from methyl 2-methyl-6-[3-(pyridin-2-ylmethoxy)-phenoxymethyl]-benzoate (example 6y).

EXAMPLE 7ae

2-[3-(7-Chloroquinolin-2-ylmethoxy)phenoxymethyl]-6-methyl-benzoic acid m.p. 188–193° C.; $^1$H NMR (300 MHz, DMSO-d$_6$) d 8.47 (d, 1H), 8.09 (s, 1H), 8.08 (d, 1H), 7.69 (dd, 2H), 7.29–7.14 (m, 4H), 6.68–6.56 (m, 3H), 5.34 (s, 2H), 5.10 (s, 2H), 2.31 (s, 3H); MS (ESI) 434, 436 (M+H;Cl)$^+$. Prepared from methyl 2-[3-(7-chloroquinolin-2-ylmethoxy)phenoxymethyl]-6-methylbenzoate (example 4bc).

EXAMPLE 7af

2-[3-(6-Methoxyquinolin-2-ylmethoxy)phenoxymethyl]-6-methylbenzoic acid m.p. 176–179° C.; $^1$H NMR (300 MHz, DMSO-d$_6$) d 8.29 (d, 1H), 7.91 (d, 1H), 7.60 (d, 1H), 7.42–7.39 (m, 2H), 7.28–7.14 (m, 4H), 6.67–6.55 (m, 3H), 5.27 (s, 2H), 5.09 (s, 2H), 3.90 (s, 3H), 2.31 (s, 3H); MS (ESI) 430 (M+H)$^+$. Prepared from methyl 2-[3-(6-methoxyquinolin-2-ylmethoxy)phenoxymethyl]-6-methylbenzoate (example 6aa).

EXAMPLE 7ag

2-Methyl-6-[3-(quinolin-2-yloxymethyl)-phenoxymethyl]-benzoic acid m.p. 68–72° C.; $^1$H NMR (300 MHz, DMSO-d$_6$) d 8.25 (d, 1H), 7.88 (d, 1H), 7.78 (d, 1H), 7.67 (dd, 1H), 7.43 (dd, 1H), 7.30–7.05 (m, 7H), 6.89 (d, 1H), 5.45 (s, 2H), 5.11 (s, 2H), 2.30 (s, 3H); MS (ESI) 400 (M+H)$^+$. Prepared from isobutyl 2-methyl-6-[3-(quinolin-2-yloxymethyl)-phenoxymethyl]-benzoate (example 4e).

EXAMPLE 7ah 2-methyl-6-[3-(quinolin-2-ylmethoxy)-benzyloxymethyl]-benzoic Acid m.p. 39–65° C.; $^1$H NMR (300 MHz, CDCl$_3$) δ8.44 (d, 1H), 8.26 (d, 1H), 7.85–7.75 (m, 3H), 7.59 (dd, 1H), 7.38 (s, 1H), 7.23 (obs, 2H), 7.15–7.10 (m, 2H), 6.88 (dd, 1H), 6.71 (d, 1H), 5.59 (s, 2H), 4.67 (s, 2H), 4.44 (s, 2H), 2.64 (s, 3H); MS (ESI) 414 (M+H)$^+$. Prepared from methyl 2-methyl-6-[3-(quinolin-2-ylmethoxy)-benzyloxymethyl]-benzoate (example 53).

EXAMPLE 7ai

2-[3-(Quinolin-2-ylmethoxy)-benzyloxy]-benzoic acid m.p. 149–154° C.; $^1$H NMR (300 MHz, CDCl$_3$) δ 8.19 (d, 1H), 8.15 (dd, 1H), 8.11 (d, 1H), 7.83 (dd, 1H), 7.77–7.71 (m, 1H), 7.66 (d, 1H), 7.58–7.53 (m, 1H), 7.52–7.46 (m, 1H), 7.33 (t, 1H), 7.18–7.17 (m, 1H), 7.11 (t, 1H), 7.07–7.00 (m, 3H), 5.41 (s, 2H), 5.24 (s, 2H); MS (ESI) 386 (M+H)$^+$. Prepared from methyl 2-[3-(quinolin-2-ylmethoxy)-benzyloxy]-benzoate (example 60).

EXAMPLE 7aj

3-Methoxy-2-[3-(quinolin-2-ylmethoxy)-benzyloxy]-benzoic acid $^1$H NMR (300 MHz, CDCl$_3$) δ8.20 (d, 1H), 8.10 (d, 1H), 7.84 (d, 1H), 7.74 (t, 1H), 7.69–7.65 (m, 2H), 7.56 (t, 1H), 7.30 (t, 1H), 7.20–7.12 (m, 3H), 7.02 (d, 1H), 5.41 (s, 2H), 5.22 (s, 2H), 3.93 (s, 3H); MS (ESI) 416 (M+H)$^+$. Prepared from methyl 3-methoxy-2-[3-(quinolin-2-ylmethoxy)-benzyloxy]-benzoate (example 60a).

EXAMPLE 7ak

4-Methoxy-2-[3-(quinolin-2-ylmethoxy)-benzyloxy]-benzoic acid m.p. 117–118° C.; $^1$H NMR (300 MHz, CDCl$_3$) δ8.20 (d, 1H), 8.14 (d, 1H), 8.09 (d, 1H), 7.83 (d, 1H), 7.74 (ddd, 1H), 7.65 (d, 1H), 7.56 (ddd, 1H), 7.34 (t, 1H), 7.14–7.13 (m, 1H), 7.06–7.01 (m, 2H), 6.64 (dd, 1H), 6.56 (d, 1H), 5.41 (s, 2H), 5.21 (s, 2H), 3.84 (s, 3H); MS (ESI) 416 (M+H)$^+$. Prepared from methyl 4-methoxy-2-[3-(quinolin-2-ylmethoxy)-benzyloxy]-benzoate (example 60b).

EXAMPLE 7al

5-Methoxy-2-[3-(quinolin-2-ylmethoxy)-benzyloxy]-benzoic acid m.p. 248–249° C.; $^1$H NMR (300 MHz, DMSO-d$_6$) d 8.40 (d, 1H), 8.01 (t, 2H), 7.78 (t, 1H), 7.68 (d, 1H), 7.61 (t, 1H), 7.28–7.21 (m, 2H), 7.04 (d, 1H), 6.94 (dd, 1H), 6.78–6.71 (m, 2H), 6.56 (dd, 1H), 5.36 (s, 2H), 4.98 (s, 2H), 3.64 (s, 3H); MS (ESI) 416 (M+H)$^+$. Prepared from methyl 5-methoxy-2-[3-(quinolin-2-ylmethoxy)-benzyloxy]-benzoate (example 60c).

EXAMPLE 7am

2-Methoxy-6-[3-(quinolin-2-ylmethoxy)-benzyloxy]-benzoic acid m.p. 149–152° C.; $^1$H NMR (300 MHz, CDCl$_3$) δ8.34 (d, 1H), 8.16 (d, 1H), 7.80 (d, 1H), 7.75 (ddd, 1H), 7.69 (d, 1H), 7.55 (t, 1H), 7.40 (s, 1H), 7.27 (t, 1H), 7.18 (t, 1H), 6.91–87 (m, 2H), 6.60 (d, 2H), 5.45 (s, 2H), 5.08 (s, 2H), 3.89 (s, 3H); MS (ESI) 416 (M+H)$^+$. Prepared from methyl 2-methoxy-6-[3-(quinolin-2-ylmethoxy)-benzyloxy]-benzoate (example 60d).

EXAMPLE 7an

2-Methyl-6-[3-(quinolin-2-ylmethoxy)-benzyloxy]-benzoic acid m.p. 154–156° C., $^1$H NMR (300 MHz, CD$_3$OD) d 8.37 (d, 1H), 8.05 (d, 1H), 7.95-(d, 1H), 7.81–7.71 (m, 2H), 7.63–7.59 (t, 1H), 7.31–7.15 (m, 3H), 7.06–6.97 (m, 2H), 6.87 (d, 1H), 6.82 (d, 1H), 5.35 (s,2H), 5.12 (s, 2H), 2.31 (s, 3H); MS (ESI) 400 (M+H)⁺. Prepared from ethyl-2-methyl-6-[3-(quinolin-2-ylmethoxy)-benzyloxy]-benzoate (example 60e).

EXAMPLE 7ao

5-[3-(Quinolin-2-ylmethoxy)-benzyloxy]-nicotinic acid $^1$H NMR (300 MHz, CDCl$_3$) δ8.90 (s, 1H), 8.52 (s, 1H), 8.19 (d, 1H), 8.12 (d, 1H), 7.87–7.70 (m, 4H), 7.55 (t, 1H), 7.30 (t, 1H), 7.13 (s, 1H), 7.01 (t, 2H), 5.44 (s, 2H), 5.10 (s, 2H); MS (ESI) 387 (M+H)⁺. Prepared from methyl 5-[3-(quinolin-2-ylmethoxy)-benzyloxy]-nicotinate (example 62).

EXAMPLE 7ap

2-[3-(2,4-Diisopropyl-5-methyl-benzyloxy)-phenoxymethyl]-6-methyl-benzoic acid $^1$H NMR (300 MHz, CDCl$_3$) δ 7.35 (m, 2H); 7.08 (m, 4H); 6.60 (m, 3H); 5.18 (s, 2H); 4.98 (s, 2H); 3.19 (m, 1H); 2.86 (m, 1H); 2.44 (s, 3H); 2.35 (s, 3H); 1.22 (m, 12H). MS (EI) 484 (M)⁺. Prepared from ethyl 2-[3-(2,4-diisopropyl-5-methyl-benzyloxy)-phenoxymethyl]-6-methyl-benzoate (example 6ab).

EXAMPLE 7aq

2-[3-(2,4-Bis-trifluoromethyl-benzyloxy)-phenoxymethyl]-6-methyl-benzoic acid $^1$H NMR (300 MHz, CDCl$_3$) δ 7.91 (s, 1H), 7.80 (m, 2H), 7.33 (d, 2H), 7.18 (m, 2H), 6.60 (m, 2H), 6.52 (dd, 1H), 5.24 (s, 2H), 5.17 (s, 2H), 2.45 (s, 3H). MS (EI) 484 (M)⁺. Prepared from ethyl 2-[3-(2,4-bis-trifluoromethyl-benzyloxy)-phenoxymethyl]-6-methyl-benzoate (example 6ac).

EXAMPLE 7ar

2-[3-(Biphenyl-4-ylmethoxy)-phenoxymethyl]-6-methyl-benzoic acid $^1$H NMR (300 MHz, CDCl$_3$) δ 7.58 (m, 4H), 7.44 (m, 4H), 7.35 (m, 3H), 7.18 (m, 2H), 6.60 (m, 3H), 5.17 (s, 2H), 5.02 (s, 2H), 2.44 (s, 3H). MS (EI) 424 (M)⁺. Prepared from ethyl 2-[3-(biphenyl-4-ylmethoxy)-phenoxymethyl]-6-methyl-benzoate (example 6ad).

EXAMPLE 7as

2-Methyl-6-[3-(naphthalen-1-ylmethoxy)-phenoxymethyl]-benzoic acid $^1$H NMR (300 MHz, CDCl$_3$) δ 8.00 (m, 1H), 7.85 (m, 2H), 7.47 (m, 4H), 7.34 (m, 2H), 7.17 (m, 2H), 6.62 (m, 3H), 5.40 (s, 2H), 5.16 (s, 2H), 2.43 (s, 3H). MS (EI) 398 (M)⁺. Prepared from ethyl 2-methyl-6-[3-(naphthalen-1-ylmethoxy)-phenoxymethyl]-benzoate (example 6ae).

EXAMPLE 7at

2-[3-(5-Ethyl-pyridin-2-ylmethoxy)-phenoxymethyl]-6-methyl-benzoic acid $^1$H NMR (300 MHz, DMSO) δ 8.42 (bs, 1H), 7.65 (d, 1H), 7.39 (d, 1H), 6.63 (bs, 1H), 6.56 (m, 2H), 2.60 (q, 2H), 2.29 (s, 3H), 1.21 (t, 3H). MS (ESI) 378 (M+H)⁺. Prepared from methyl 2-[3-(5-ethyl-pyridin-2-ylmethoxy)-phenoxymethyl]-6-methyl-benzoate (example 6af).

EXAMPLE 7au

2-[3-(4-Ethyl-benzyloxy)-phenoxymethyl]-6-methyl-benzoic acid $^1$H NMR (300 MHz, DMSO) δ 7.2 (m, 8H), 6.6 (m, 3H), 5.13 (s, 2H), 5.05 (d, 2H), 2.64 (m, 2H), 2.28 (s, 3H), 1.17 (t, 3H). MS (ESI) 375 (M−H)⁻. Prepared from methyl 2-[3-(4-ethyl-benzyloxy)-phenoxymethyl]-6-methyl-benzoate (example 6ag).

EXAMPLE 7av

2-[3-(3-Bromo-benzyloxy)-phenoxymethyl]-6-methyl-benzoic acid $^1$H NMR (300 MHz, DMSO) δ 7.62 (bs, 1H), 7.50 (d, 1H), 7.42 (d, 1H), 7.33 (d, 1H), 7.08 (m, 94H), 6.67 (bs, 1H), 6.54 (m, 2H), 5.13 (s, 2H), 5.08 (s, 2H), 2.28 (s, 3H). MS (ESI) 425 (M−H)⁻. Prepared from methyl 2-[3-(3-bromo-benzyloxy)-phenoxymethyl]-6-methyl-benzoate (example 6ah).

EXAMPLE 7aw

2-{3-[2-(5-Ethyl-pyridin-2-yl)-ethoxy]-phenoxymethyl}-6-methyl-benzoic acid $^1$H NMR (300 MHz, DMSO) δ 8.36 (bs, 1H), 7.56 (d, 1H), 7.14 (m, 5H), 6.49 (m, 3H), 5.11 (bs, 2H), 4.27 (t, 2H), 3.09 (t, 2H), 2.56 (q, 2H), 2.29 (s, 3H), 1.17 (t, 3H). MS (ESI) 392 (M+H)⁺. Prepared from methyl 2-{3-[2-(5-ethyl-pyridin-2-yl)-ethoxy]-phenoxymethyl}-6-methyl-benzoate (example 4f).

EXAMPLE 7ax

2-Methyl-6-[3-(2-quinolin-2-yl-ethoxy)-phenoxymethyl]-benzoic acid $^1$H NMR (300 MHz, CD$_3$OD) δ 8.28 (d, 1H), 7.97 (d, 1H), 7.88 (d, 1H), 7.74 (t, 1H), 7.51 (m, 1H), 7.26 (d, 2H), 7.16 (m, 2H), 7.02 (m, 1H), 6.38 (m, 3H), 5.10 (s, 2H), 3.83 (t, 2H), 3.22 (t, 2H), 2.39 (s, 3H). Prepared from methyl 2-methyl-6-[3-(2-quinolin-2-yl-ethoxy)-phenoxymethyl]-benzoate (example 2 lb).

EXAMPLE 7ay

2-Methyl-6-[3-(2-pyridin-2-yl-ethoxy)-phenoxymethyl]-benzoic acid $^1$H NMR (300 MHz, DMSO) δ 8.49 (d, 1H), 7.69 (m, 1H), 7.26 (m, 3H), 7.04 (m, 2H), 6.38 (m, 4H), 5.03 (s, 2H), 3.67 (t, 2H), 2.94 (t, 2H), 2.31 (s, 3H). MS (ESI) 364 (M+H)⁺.

Prepared from methyl 2-methyl-6-[3-(2-pyridin-2-yl-ethoxy)-phenoxymethyl]-benzoate (example 4 g).

EXAMPLE 7az

2-[3-(Benzooxazol-2-ylaminomethyl)-phenoxymethyl]-6-methyl-benzoic acid $^1$H NMR (300 MHz, DMSO) δ 8.61 (bt, 1H), 7.34 (d, 1H), 7.04 (m, 10H), 5.12 (s, 2H), 4.47 (bd, 2H), 2.29 (3H). MS (ESI) 389 (M+H)$^+$. Prepared from methyl 2-[3-(benzooxazol-2-ylaminomethyl)-phenoxymethyl]-6-methyl-benzoate (example 4 h).

EXAMPLE 7ba

2-Methyl-6-[3-(pyridin-2-ylmethoxymethyl)-phenoxymethyl]-benzoic acid $^1$H NMR (300 MHz, DMSO) δ 8.52 (bd, 1H), 7.81 (m, 1H), 7.47 (d, 1H), 7.20 (m, 5H), 6.94 (m, 3H), 5.12 (s, 2H), 4.59 (s, 2H), 4.56 (s, 2H), 2.30 (s, 3H). MS (ESI) 364 (M+H)$^+$. Prepared from methyl 2-methyl-6-[3-(pyridin-2-ylmethoxymethyl)-phenoxymethyl]-benzoate (example 4i).

EXAMPLE 7bb

2-Methyl-6-[3-(quinolin-2-ylmethoxymethyl)-phenoxymethyl]-benzoic acid $^1$H NMR (300 MHz, DMSO) δ 8.40 (d, 1H), 7.98 (d, 2H), 7.76 (m, 1H), 7.64 (m, 1H), 7.31 (m, 5H), 7.00 (m, 2H), 6.92 (dd, 1H), 5.12 (s, 2H), 4.79 (s, 2H), 4.62 (s, 2H), 2.32 (s, 3H). MS (ESI) 414 (M+H)$^+$. Prepared from methyl 2-methyl-6-[3-(quinolin-2-ylmethoxymethyl)-phenoxymethyl]-benzoate (example 4j).

EXAMPLE 7bc

2-Methyl-6-{3-[2-(5-methyl-2-phenyloxazol-4-yl)ethoxy]phenoxymethyl}benzoic acid $^1$H NMR (300 MHz, CDCl$_3$): δ 8.03 (m, 2H), 7.43 (m, 3H), 7.26 (m, 2H), 7.17 (m, 1H), 7.10 (m, 1H), 6.68 (s, 1H), 6.51 (m, 2H), 5.18 (s, 2H), 4.22 (m, 2H), 2.96 (m, 2H), 2.41 (s, 3H), 2.36 (s, 3H). MS (ESI) 444 (M+H)$^+$. Prepared from methyl 2-methyl-6-{3-[2-(5-methyl-2-phenyloxazol-4-yl)ethoxy]phenoxymethyl}benzoate (example 21 a).

EXAMPLE 7bd

2-Methyl-6-[3-(6-phenylpyridin-2-ylmethoxy)phenoxymethyl]benzoic acid $^1$H NMR (300 MHz, CDCl$_3$): δ 7.88 (m, 2H), 7.63 (m, 1H), 7.52 (m, 1H), 7.37 (m, 4H), 7.18 (m, 2H), 6.99 (m, 2H), 6.60–6.36 (m, 3H), 5.14 (s, 2H), 5.00 (s, 2H), 2.23 (s, 3H). MS (ESI) 426 (M+H)$^+$. Prepared from ethyl 2-methyl-6-[3-(6-phenylpyridin-2-ylmethoxy)phenoxymethyl]benzoate (example 33).

EXAMPLE 7be

2-Methyl-6-[3-(quinolin-2-ylmethoxy)-phenylsulfanylmethyl]-benzoic acid $^1$H NMR (300 MHz, DMSO-d$_6$) d 8.40 (d, 1H), 7.99 (t, 2H), 7.78 (t, 1H), 7.65–7.57 (m, 2H), 7.20–7.01 (m, 6H), 6.85 (t, 1H), 5.33 (s, 2H), 4.25 (s, 2H), 2.26 (s, 3H); MS (ESI) 415 (M+H)$^+$. Prepared from isobutyl 2-methyl-6-[3-(quinolin-2-ylmethoxy)-phenylsulfanylmethyl]-benzoate (example 84).

EXAMPLE 7bf

2-Methyl-6-[3-(quinolin-2-ylmethoxy)-phenylsulfinylmethyl]-benzoic acid $^1$H NMR (300 MHz, DMSO-d$_6$) d 8.43 (d, 1H), 8.01 (t, 2H), 7.78 (t, 1H), 7.68 (d, 1H), 7.62 (t, 1H), 7.48 (t, 1H), 7.25–7.22 (m, 4H), 7.10 (d, 1H), 6.94 (t, 1H), 5.41 (s, 2H), 4.22 (d, 1H), 4.11 (d, 1H), 2.33 (s, 3H); MS (ESI) 432 (M+H)$^+$. Prepared from isobutyl 2-methyl-6-[3-(quinolin-2-ylmethoxy)-phenylsulfinylmethyl]-benzoate (example 85).

EXAMPLE 7bg

2-Methyl-6-[3-(quinolin-2-ylmethoxy)-phenylsulfonylmethyl]-benzoic acid $^1$H NMR (300 MHz, DMSO-d$_6$) d 8.43 (d, 1H), 8.05–7.98 (m, 2H), 7.77 (t, 1H), 7.67 (d, 1H), 7.60 (t, 1H), 7.51 (t, 1H), 7.43–7.35 (m, 2H), 7.26–7.20 (m, 3H), 6.95–6.92 (m, 1H), 5.42 (s, 2H), 4.81 (s, 2H), 2.32 (s, 3H); MS (ESI) 448 (M+H)$^+$. Prepared from isobutyl 2-methyl-6-[3-(quinolin-2-ylmethoxy)-phenylsulfonylmethyl]-benzoate (example 86).

EXAMPLE 7bh

2-Methyl-6-[3-(qiunolin-2-ylmethoxy)-phenylethynyl]-benzoic acid $^1$H NMR (300 MHz, CDCl$_3$) d 8.19 (d, 1H), 8.04 (d, 1H), 7.89 (d, 1H), 7.82 (d, 1H), 7.73 (dt, 2H), 7.64 (t, 2H), 7,54 (t, 1H), 7.26 (t, 1H), 6.94 (dd, 1H), 6.81–6.85 (m,2H), 5.34 (s, 2H), 2.76 (s, 3H);MS (ESI) 394 (M+H)$^+$. Prepared from ethyl-2-methyl-6-[3-(qiunolin-2-ylmethoxy)-phenylethynyl]-benzoate (example 6ai).

EXAMPLE 7bi

2-Methyl-6-[3-(5-phenylpyridin-2-ylmethoxy)phenoxymethyl]benzoic acid.

mpt 80–83° C. $^1$H NMR (300 mHz, 5:1 CDCl$_3$:CD$_3$OD): δ 8.76 (s, 1H), 7.97 (d, 1H), 7.62 (m, 3H), 7.48 (m, 3H), 7.30 (m, 2H), 7.19 (m, 2H), 6.68 (s, 1H), 6.62 (d, 2H), 5.21 (s, 2H), 5.17 (s, 2H), 2.44 (s, 3H). MS(ESI) 426 (M+H)$^+$. Prepared from methyl 2-methyl-6-[3-(5-phenylpyridin-2-ylmethoxy)phenoxymethyl]benzoate (example 6aj).

EXAMPLE 7bj

2-[3-(2-Chloro-benzyloxy)-phenoxymethyl]-6-methyl-benzoic acid $^1$H NMR (300 MHz, DMSO) δ 7.56 (m, 1H), 7.50 (m, 1H), 7.38 (m, 2H), 7.14 (m, 2H), 7.06 (m, 2H), 6.67 (s, 1H), 6.58 (m, 2H), 5.13 (bd, 4H), 2.28 (s, 3H). MS (EI) 382 (M+), Cl pattern. Prepared from 2-[3-(2-chloro-benzyloxy)-phenoxymethyl]-6-methyl-benzoate (example 6ak).

EXAMPLE 7bk

2-[3-(4-Chloro-benzyloxy)-phenoxymethyl]-6-methyl-benzoic acid $^1$H NMR (300 MHz, DMSO) δ 7.42 (m, 3H), 7.08 (m, 5H), 6.66 (s, 1H), 6.54 (m, 2H), 5.13 (s, 2H), 5.07 (s, 2H), 2.28 (s, 3H). MS (EI) 382 (M+.), Cl pattern. Prepared from 2-[3-(4-chloro-benzyloxy)-phenoxymethyl]-6-methyl-benzoate (example 6al).

EXAMPLE 7bl

2-Methyl-6-[3-(3-methyl-quinoxalin-2-ylmethoxy)-phenoxymethyl]-benzoic acid $^1$H NMR (300 MHz, DMSO) δ 8.05 (m, 2H), 7.82 (m, 2H), 7.14 (m, 4H), 6.75 (s, 1H), 6.61 (m, 2H), 5.41 (s, 2H), 5.11 (s, 2H), 2.76 (s, 3H), 2.27 (s, 3H). MS (ESI) 415 (M+H)+. Prepared from 2-Methyl-6-[3-(3-methyl-quinoxalin-2-ylmethoxy)-phenoxymethyl]-benzoic acid methyl ester (example 6 am).

EXAMPLE 7bm

2-Methyl-6-[3-(naphthalen-2-ylmethoxy)-phenoxymethyl]-benzoic acid $^1$H NMR (300 MHz, DMSO) δ 7.94 (m, 4H), 7.54 (m, 3H), 7.16 (m, 4H), 6.69 (s, 1H), 6.58 (m, 2H), 5.24 (s, 2H), 5.11 (s, 2H), 2.29 (s, 3H). Prepared from 2-Methyl-6-[3-(naphthalen-2-ylmethoxy)-phenoxymethyl]-benzoic acid methyl ester (example 6an).

EXAMPLE 8

3-[(2-Methoxyethoxy)-methoxy-benzonitrile

To a cooled (0° C.) suspension of sodium hydride (840 mg, 60% dispersion in mineral oil, 21 mmol) in THF (20 mL) is added a solution comprising 3-hydroxy-benzonitrile (2.4 g, 20 mmol), MEM Chloride (2.25 mL, 20 mmol) and DMPU (2 mL) in THF (20 mL). On complete addition, the cold bath is removed and stirring continued for 3 h. The reaction mixture is then diluted with ether, washed with water and brine, dried over MgSO$_4$ and concentrated. The residue is purified by flash chromatography (silica, 30% ethyl acetate 10% dichloromethane in hexane) to give the title compound as an oil. MS (ESI) 207 (M+H)+.

EXAMPLE 8a

3-[(2-Methoxyethoxy)-methoxy]-benzaldehyde

The title compound is prepared using essentially the same preocedure used in example 8 except using using 3-hydroxy-benzaldehyde in place of 3-hydroxy-benzonitrile. MS (EI) 210 (M)+.

EXAMPLE 9

3-[(2-Methoxyethoxy)-methoxy]-benzylamine

To a cooled (0° C.) solution of 3-[(2-methoxyethoxy)-methoxy]-benzonitrile (3.9 g, 18.8 mmol, example 8) in THF (40 mL) is added LAH (40 mL, 1M in THF). The resulting solution is stirred for 10 min. then the cold bath removed and stirring continued for 2 h. The resulting mixture is cooled to 0° C. then water (1.5 mL) added dropwise followed by NaOH solution (1.5 mL, SM) and water (1.5 mL). The resulting suspension is diluted with ether then filtered through celite. The filtrate is concentrated to give the title compound which is used without further purification. MS (ESI) 211 (M+H)+.

EXAMPLE 10

3-(Quinolin-2-ylaminomethyl)-phenol

To a solution of 3-[(2-methoxyethoxy)-methoxy]-benzylamine (422 mg, 2 mmol, example 9) in DMSO (4 mL) is added 2-chloroquinoline (328 mg, 2 mmol). The resulting solution is warmed to 140° C. and stirred at this temperature for 3 h. The resulting mixture is cooled, diluted with water, then extracted with ethyl acetate. The organic extract is washed with brine, dried over MgSO$_4$ and concentrated. The residue is taken up in methanol (10 mL) then p-toluene sulphonic acid monohydrate (190 mg, 1 mmol) is added. This mixture is warmed to 60° C. and stirred at this temperature for 2 h. The reaction mixture is then cooled, concentrated under reduced pressure and the residue purified by flash chromatography (silica, 30% ethyl acetate in dichloromethane) to give the title compound. MS (ESI) 251 (M+H)+.

The following compounds are prepared using essentially the same procedure used in example 10 except using the cited chloride and amine in place of 2-chloro-quinoline and 3-[(2-methoxyethoxy)-methoxy]-benzylamine.

EXAMPLE 10a

3-[(N-Benzoxazol-2-yl-N-methyl-amino)-methyl]-phenol

MS (ESI) 255 (M+H)+. Prepared from 3-[(methylamino)-methyl]-(2-methoxyethoxy-methoxy)benzene (example 28) and 2-chloro-benzoxazole. Also, omit heating to 140° C. Reaction stirred at room temperature.

EXAMPLE 10b

3-[(N-Methyl-N-quinolin-2-yl-amino)-methyl]-phenol

MS (ESI) 265 (M+H)+. Prepared from 3-[(methylamino)-methyl]-(2-methoxyethoxy-methoxy)benzene (example 28) and 2-chloro-quinoline.

EXAMPLE 10c 3-(Benzooxazol-2-ylaminomethyl)-phenol

The title compound is prepared using essentially the same procedure used in example 10 except 2-chloro-benzoxazole is used in place of 2-chloro-quinoline. Also, omit heating to 140° C. Reaction stirred at room temperature. MS (ESI) 241 (M+H)+.

EXAMPLE 11

2-(3-([2-Methoxyethoxy]-methoxy)-phenoxy])-ethanol

To a cooled (0° C.) solution of t-butyl (3-([2-methoxyethoxy]-methoxy)-phenoxy])-acetate (1.2 g, 3.8 mmol, example 12) in THF (10 mL) is added a solution of lithium aluminum hydride (5 mL, 1M in THF). The resulting solution is stirred for 10 min. then water (0.2 mL) is added dropwise, followed by NaOH solution (0.2 mL, 5M) and water (0.2 mL). The resulting mixture is diluted with ether, filtered through celite and the filtrate concentrated to give the title compound as an oil which is used without further purification. MS (EI) 242 (M)$^+$.

EXAMPLE 11a 2-(5-Methyl-2-phenyloxazol-4-yl)ethanol

The title compound is prepared using essentially the same procedure used in Example 11 except using methyl 2-(5-methyl-2-phenyloxazol-4-yl)acetate (example 32) in place of t-butyl (3-([2-methoxyethoxy]-methoxy)-phenoxy])-acetate. MS (ESI) 204 (M+H)$^+$.

EXAMPLE 12 t-Butyl (3-([2-methoxyethoxy]-methoxy)-phenoxy])-acetate

The title compound is prepared using essentially the same procedure used in Example 4 except using 3-([2-methoxyethoxy]-methoxy)-phenol (example 13) in place of 3-(quinolin-2-ylmethoxy)-phenol and and t-butyl bromoacetate in place of methyl 2-bromomethyl-6-methyl-benzoate. MS (EI) 312 (M)$^+$.

EXAMPLE 13

3-[(2-Methoxyethoxy)-methoxy]-phenol

To a cooled (0° C.) suspension of NaH (440 mg, 60% dispersion in oil, 11 mmol) in THF (10 mL) is slowly added a solution comprising 3-benzoyl-phenol (2.14 g, 10 mmol), MEM chloride (1.28 mL, 10.5 mmol) and DMPU (3 mL) in THF (20 mL). On complete addition, the cold bath is removed and stirring continued for 2.5 h. Sat. NH$_4$Cl solution is added and the mixture diluted with ether, washed with water and brine, dried over MgSO$_4$ and concentrated. The residue is taken up in methanol (10 mL) and THF (10 mL) then sodium hydroxide solution (10 mL, 2N) added. This mixture is stirred for 20 min. then hydrochloric acid (10 mL, 2N) added. The mixture is then diluted with ether, washed with sat. NaHCO$_3$ solution and brine, dried over MgSO$_4$ and concentrated. The residue is purified by flash chromatography (silica, 30% ethyl acetate in hexanes) to give the title compound as an oil. $^1$H NMR (300 MHz, CDCl$_3$) δ 7.00 (t, 1H), 6.52 (bd, 1H), 6.48 (bs, 1H), 6.38 (bd, 1H), 5.14 (s, 2H), 3.71 (m, 2H), 3.47 (m, 2H), 3.30 (s, 3H).

EXAMPLE 14

[(2-Methoxyethoxy)-methoxy]-3-[2-(pyridin-2-yloxy)-ethoxy]-benzene

To a solution of 2-(3-([2-methoxyethoxy]-methoxy)-phenoxy])-ethanol (242 mg, 1 mmol, example 11) in DMSO (1.5 mL) is added sodium hydride (44 mg, 60% dispersion in mineral oil, 1.1 mmol) followed by 2-fluoro-pyridine (176 mL, 2 mmol). The resulting solution is warmed to 60° C. and stirred at this temperature for 3 h. cooled, diluted with ether, washed with water and brine, dried over MgSO$_4$ and concentrated. The residue is purified by flash chromatography (silica, 30% ethyl acetate in hexanes) to give the title compound. MS (ESI) 320 (M+H)$^+$.

EXAMPLE 15

3-(2-quinolin-2-yl-vinyl)-phenol

To a solution of 1-(2-methoxyethoxy)-methoxy-3-(2-quinolin-2-yl-vinyl)-benzene (120 mg, 0.35 mmol, example 16) is added p-toluene sulphonic acid monohydrate. (74 mg, 0.39 mmol). The resulting solution is heated to 60° C. and stirred at this temperature for 4 h. The reaction mixture is then cooled, concentrated and the residue taken up in dichloromethane. This solution is washed with sat. NaHCO$_3$ solution, dried over MgSO$_4$ then concentrated to give the title compound as a solid. MS (ESI) 248 (M+H)$^+$.

The following compounds are prepared using essentially the same procedure used in example 15 except using the cited MEM ether in place of 1-(2-methoxyethoxy)-methoxy-3-(2-quinolin-2-yl-vinyl)-benzene.

EXAMPLE 15A

3-[2-(pyridin-2-yloxy)-ethoxy]-phenol

MS (ESI) 232 (M+H)$^+$. Prepared from [(2-methoxyethoxy)-methoxy]-3-[2-(pyridin-2-yloxy)ethoxy]-benzene (example 14).

EXAMPLE 15b 3-(Quinolin-2-yloxymethyl)-phenol

MS (ESI) 252 (M+H)$^+$. Prepared from 2-[3-(2-methoxyethoxymethoxy)-benzyloxy]-quinoline (example 81).

EXAMPLE 15c

Ethyl 2-(3-hydroxy-phenylethynyl)-6-methyl-benzoate

MS (EI) 280 (M)$^+$. Prepared from ethyl-2-[3-(2-methoxyethoxymethoxy)-phenylethynyl]-6-methyl-benzoate (example 98).

EXAMPLE 16

1-(2-Methoxyethoxy)-methoxy-3-(2-quinolin-2-yl-vinyl)-benzene

To a cooled (−78° C.) suspension of triphenyl-(quinolin-2-yl-methyl)-phosphonium chloride (1.76 g, 4 mmol, example 17) in THF (24 mL) is added, dropwise, n-butyl lithium solution (1.7 mL, 2.5 M in hexanes). The resulting mixture is stirred for 30 min. then a solution of 3-[(2-methoxyethoxy)-methoxy]-benzaldehyde (756 mg, 3.6 mmol, example 8a) in THF (3 mL) is added. This mixture is stirred for 30 min then the cold bath removed and stirring continued for 2 h. The reaction mixture is then diluted with ethyl acetate, washed with sat. ammonium acetate solution and brine, dried over MgSO$_4$ and concentrated. The residue is purified by flash chromatography (silica, 40% ethyl acetate in hexanes) to give the title compound as an oil. MS (ESI) 336 (M+H)+.

EXAMPLE 17

Triphenyl-(quinolin-2-yl-methyl)-phosphonium chloride

To a solution of 2-chloromethyl-quinoline (2.9 g, 20 mmol) in acetonitrile (32 mL) is added triphenylphosphine (4.49 g, 17 mmol). The resulting mixture is warmed to 60° C. and stirred at this temperature for 15 h. This mixture is cooled, diluted with ether, then filtered. The solid is washed with ether, then dried under high vacuum to give the title compound as a solid. $^1$H NMR (300 MHz, CDCl$_3$) δ 8.20 (d, 1H), 8.06 (d, 1H), 7.95 (m, 6H), 7.42–7.8 (m, 13H), 6.10 (d, 2H).

EXAMPLE 18

{2-Methyl-6-[3-(2-quinolin-2-yl-ethyl)-phenoxymethyl]-phenoxy}-acetic acid

To a solution of {2-methyl-6-[3-(2-quinolin-2-yl-vinyl)-phenoxymethyl]-phenoxy}-acetic acid (94 mg, 0.23 mmol, example 41a) in DMF (1.5 mL) is added tristriphenylphosphine rhodium chloride (25 mg, 0.027 mmol). The resulting solution is placed under an atmosphere of hydrogen, heated to 60° C. and stirred at this temperature for 5 h. The reaction mixture is cooled to room temperature and the system is then flushed with nitrogen and concentrated under vacuum. The residue is purified by reverse phase HPLC to give the title compound as a trifluoroacetate salt. $^1$H NMR (300 MHz, CDCl$_3$) δ 8.57 (d, 1H), 8.40 (d, 1H), 8.0 (m, 2H), 7.80 (t, 1H), 7.52 (d, 1H), 7.24 (bd, 1H), 7.14 (m, 2H), 7.04 (t, 1H), 6.93 (bs, 1H), 6.83 (d, 1H), 6.74 (d, 1H), 5.11 (s, 2H), 4.50 (s, 2H), 3.68 (t, 2H), 3.20 (t, 2H), 2.28 (s, 3H). MS (ESI) 428 (M+H)+.

The following compound is prepared using essentially the same procedure used in example 18 except using the cited acid in place of {2-methyl-6-[3-(2-quinolin-2-yl-vinyl)-phenoxymethyl]phenoxy}-acetic acid.

EXAMPLE 18a

2-Methyl-6-[3-(2-quinolin-2-yl-ethyl)-phenoxymethyl]-benzoic acid $^1$H NMR (300 MHz, CDCl$_3$) δ 8.62 (d, 1H), 8.44 (d, 1H), 8.0 (m, 2H), 7.80 (t, 1H), 7.61 (d, 1H), 7.21 (d, 1H), 7.11 (d, 1H), 7.07 (t, 1H), 6.94 (bs, 1H), 6.76 (bd, 1H), 6.68 (d, 1H), 5.09 (s, 2H), 3.70 (t, 2H), 3.18 (t, 2H), 2.40 (s, 3H). MS (ESI) 398 (M+H)+. Prepared from {2-methyl-6-[3-(2-quinolin-2-yl-vinyl)-phenoxymethyl]-benzoic acid (example 4a).

EXAMPLE 19

4-Chloromethyl-2-phenyl-oxazole

Benzamide (1.21 g, 10 mmol) is mixed with 1,3-dichloroacetone (1.26 g, 10 mmol) and the mixture heated to 130° C. and stirred at this temperature for 1 h. The resulting mixture is then cooled, diluted with ethyl acetate, washed with K$_2$CO$_3$ solution (sat.), then brine, dried over MgSO$_4$ and concentrated to give the title compound as a solid, which is used without further purification. MS (ESI) 194 (M+H, Cl pattern)+.

The following compounds are prepared using essentially the same procedure used in Example 19 except using the cited amide in place of benzamide.

EXAMPLE 19a 2-(5-Methylthiophen-2-yl)oxazol-4-ylmethyl chloride

MS (ESI) 214, 216 (M+H)+, Cl pattern. Prepared from 5-methylthiophene-2-carboxamide.

EXAMPLE 19b

2-Cyclohexyloxazol-4-ylmethyl chloride

MS (ESI) 200, 202 (M+H)+, Cl pattern. Prepared from cyclohexanecarboxamide.

EXAMPLE 19c 2-(3-Fluorophenyl)oxazol-4-ylmethyl chloride

MS (ESI) 212, 214 (M+H)+, Cl pattern. Prepared from 3-fluorobenzamide.

EXAMPLE 19d 2-(4-Fluorophenyl)oxazol-4-ylmethyl chloride

MS (ESI) 212, 214 (M+H)+, Cl pattern. Prepared from 4-fluorobenzamide

EXAMPLE 20

4-Chloromethyl-2-phenyl-thiazole

A solution of thiobenzamide (1.37 g, 10 mmol) and 1,3-dichloro-acetone (1.27 g, 10 mmol) in ethanol (25 mL) is warmed to 75° C. and stirred at this temperature for 1 h. The resulting solution is cooled, poured into ice then brought to pH 8 with K$_2$CO$_3$ solution (sat.). This mixture is extracted with ethyl acetate, dried over MgSO$_4$ and concentrated to give the title compound. This product is used without further purification. MS (ESI) 210 (M+H)+.

EXAMPLE 21

{2-Methyl-6-[3-(2-pyridin-2-yl-ethoxy)-phenoxymethyl]-phenoxy-acetonitrile

To a solution of [2-methyl-6-(3-hydroxy-phenoxymethyl)-phenoxy]-acetonitrile (135 mg, 0.5 mmol, example 25) and 2-(pyridin-2-yl)-ethanol (126 mL, 0.94 mmol) in THF (2 mL) is added triphenylphosphine (262 mg, 1 mmol) followed by DEAD (118 mL, 0.75 mmol). The resulting solution is stirred for 2 h, then concentrated and the residue purified by flash chromatography (silica, 50% ethyl acetate in hexanes) to give the title compound as an oil. MS (ESI) 375 (M+H)+.

The following compound is prepared using essentially the same procedure used in Example 21 except using the cited alcohol and phenol in place of 2-(pyridin-2-yl)-ethanol and [2-methyl-6(3-hydroxy-phenoxymethyl)-phenoxy]-acetonitrile respectively.

EXAMPLE 21a

Methyl 2-methyl-6-{3-[2-(5-methyl-2-phenyloxazol-4-yl)ethoxy]phenoxymethyl}benzoate MS (ESI) 458 (M+H)$^+$. Prepared from 2-(5-methyl-2-phenyloxazol-4-yl)ethanol (example 11a) and methyl 2-(3-hydroxyphenoxymethyl)-6-methylbenzoate (example 5).

EXAMPLE 21B

Methyl 2-methyl-6-[3-(2-quinolin-2-yl-ethoxy)-phenoxymethyl]-benzoate $^1$H NMR (300 MHz, CDCl$_3$) δ 8.08 (m, 2H), 7.80 (d, 1H), 7.70 (t, 1H), 7.51 (t, 1H), 7.42 (d, 1H), 7.29 (m, 2H), 7.16 (m, 2H), 6.53 (m, 3H), 5.06 (s, 2H), 4.46 (t, 2H), 3.81 (s, 3H), 3.45 (t, 2H), 2.37 (s, 3H). MS (ESI) 428 (M+H)$^+$. Prepared from 2-quinolin-2-yl-ethanol (example 69a) and 2-(3-hydroxy-phenoxymethyl)-6-methyl-benzoate (example 5).

EXAMPLE 22

2-Cyanomethoxy-3-methylbenzaldehyde

A mixture of 2-hydroxy-3-methylbenzaldehyde (10.2 g, 75.0 mmoles, Aldrich), bromoacetonitrile (5.70 mL, 82.5 mmoles), and potassium carbonate (11.4 g, 82.5 mmoles) in DMF (150 mL) is heated to 55° C. for 3 hours, cooled, then diluted with ether. The mixture is washed with distilled water, saturated NaCl solution, then the organic layer dried over MgSO$_4$ and concentrated to give the title compound as a yellow solid. $^1$H NMR (300 MHz, CDCl$_3$): δ10.20 (s, 1H), 7.70 (d, 1H), 7.53 (d, 1H), 7.29 (m, 1H), 4.81 (s, 2H), 2.42 (s, 3H).

The following compounds are prepared using essentially the same procedure used in example 22 except using the cited phenol in place of 2-hydroxy-3-methylbenzaldehyde.

EXAMPLE 22a

2-Cyanomethoxy-3,5-dichloro-benzaldehyde

MS (EI) 229, 231 (M)$^+$. Prepared from 3,5-dichlorosalicylaldehyde.

EXAMPLE 22b

2-Cyanomethoxy-5-chloro-3-methoxy-benzaldehyde

MS (EI) 225. (M)$^+$. Prepared from 5-chloro-2-hydroxy-3-methoxy-benzaldehyde (example 44).

EXAMPLE 22c

Methyl 2-(2-formyl-6-methyl-phenoxy)-propionate

The title compound is prepared using essentially the same procedure used in example 22 except using methyl 2-bromopropionate in place of bromoacetonitrile.

EXAMPLE 23

(2-Hydroxymethyl-6-methyl-phenoxy)-acetonitrile

A 2M triglyme solution of sodium borohydride (16.0 mL, 32.1 mmoles) is slowly added to a cooled (−78° C.) solution of 2-cyanomethoxy-3-methylbenzaldehyde (11.25 g, 64.2 mmoles, example 22) in THF (180 mL). After stirring for one hour, the reaction is warmed to 0° C. for two hours, then quenched with 2N HCl (16.8 mL) and diluted with ether. The organic layer is isolated and washed with twice with distilled water and brine, then dried over MgSO$_4$. The organic solution is concentrated to give the title compound as a yellow oil.

The following compounds are prepared using essentially the same procedure used in example 23 except using the cited aldehyde in place of 2-cyanomethoxy-3-methylbenzaldehyde.

EXAMPLE 23a (2,4-Dichloro-6-hydroxymethyl-phenoxy)-acetonitrile

Prepared using 2-cyanomethoxy-3,5-dichloro-benzaldehyde (example 22a)

EXAMPLE 23b (4-Chloro-2-hydroxymethyl-6-methoxy-phenoxy)-acetonitrile

MS (EI) 227 (M)$^+$. Prepared using 2-cyanomethoxy-5-chloro-3-methoxy-benzaldehyde (example 22b).

EXAMPLE 23c 2-(2-Hydroxymethyl-6-methyl-phenoxy)-propionic acid methyl ester MS (EI) 194 (M)$^+$. Prepared using methyl 2-(2-formyl-6-methyl-phenoxy)-propionate (example 22c).

EXAMPLE 24

(2-Bromomethyl-6-methyl-phenoxy)-acetonitrile

Triphenylphosphine (15.2 g, 57.8 mmoles) is added to 2-cyanomethoxy-3-methylbenzylalcohol (9.3 g, 52.5 mmoles, example 23) in THF (175 mL). The mixture is stirred until homogeneous and cooled to 0° C., followed by addition, in three portions, of N-bromosuccinimide (10.3 g, 57.8 mmoles). After 90 minutes the reaction is concentrated and the residue purified by column chromatography (silica, 5:1 hex: EtOAc) to yield the title compound as a pale yellow crystalline solid. MS (EI) 239, 241 (M)$^+$, Br pattern.

The following compounds are prepared using essentially the same procedure used in example 24 except using the cited alcohol in place of 2-cyanomethoxy-3-methylbenzylalcohol.

EXAMPLE 24a (2-Bromomethyl-4,6-dichloro-phenoxy)-acetonitrile

MS (EI) 277 (M−16)$^+$. Prepared from (2,4-dichloro-6-hydroxymethyl-phenoxy)-acetonitrile (example 23a).

EXAMPLE 24b (2-Bromomethyl-4-chloro-6-methoxy-phenoxy)-acetonitrile

MS (EI) 289 (M)$^+$. Prepared from (4-chloro-2-hydroxymethyl-6-methoxy-phenoxy)-acetonitrile (example 23b).

EXAMPLE 24c

Methyl 2-(2-bromomethyl-6-methyl-phenoxy)-propionate

MS (EI) 286 (M)$^+$, bromine pattern. Prepared from methyl 2-(2-hydroxymethyl-6-methyl-phenoxy)-propionate (example 23c).

EXAMPLE 25

(2-[3-Hydroxyphenoxymethyl]-6-methylphenoxy) acetonitrile

Heated (60° C.) a mixture of 2-cyanomethoxy-3-methylbenzyl bromide (10.2 g, 42.7 mmoles, example 24), resorcinol (18.8 g, 171 mmoles), and potassium carbonate (47.2 g, 342 mmoles) in acetonitrile (140 mL) for two hours. The reaction is diluted with ether and washed three times with distilled water, once with brine, and dried over MgSO$_4$. The organic layer is isolated and concentrated, and the resulting residue is purified by column chromatography (silica, 5% EtOAc/CH$_2$Cl$_2$) to yield the title compound as a white crystalline solid. MS(EI) 269 (M)$^+$.

The following compounds are prepared using essentially the same procedure used in example 25 except using the cited bromide in place of 2-cyanomethoxy-3-methylbenzyl bromide.

EXAMPLE 25a

[4-Chloro-2-(3-hydroxy-phenoxymethyl)-6-methyl-phenoxy]-acetonitrile

Prepared from (2-bromomethyl-4-chloro-6-methyl-phenoxy)-acetonitrile (example 43).

EXAMPLE 25b

[4,6-Dichloro-2-(3-hydroxy-phenoxymethyl)-phenoxy]-acetonitrile

Prepared from (2-bromomethyl-4,6-dichloro-phenoxy)-acetonitrile (example 24a).

EXAMPLE 26

2-Methyl-6,7-difluoroquinoline

To a refluxing solution of 3,4-difluoroaniline (2.30 ml, 23.2 mmoles), tetrachloro-1,4-benzoquinone (5.70 g, 23.2 mmoles), and concentrated hydrochloric acid (6 ml) in 2-butanol (40 ml) is added crotonaldehyde (1.92 ml, 23.2 mmoles). After 2.5 hours the reaction mixture is concentrated and the resulting residue is stirred in warm (50° C.) THF (15 ml). This mixture is cooled (0° C.) and the solid collected by filtration and washed with cold THF. The solid is stirred in distilled water (200 ml), and the resulting solution made basic with K$_2$CO$_3$ and extracted with EtOAc (3×100 ml). The organic extracts are combined and dried over sodium sulfate, and then concentrated to give the title compound. MS (ESI) 180 (M+H)$^+$.

The following compounds are prepared using essentially the same procedure used in example 26 except using the cited aniline in place of 3,4-difluoro-aniline.

EXAMPLE 26a

2-Methyl-6,8-difluoroquinoline

MS (ESI) 180 (M+H)$^+$. Prepared using 2,4-difluoro-aniline.

EXAMPLE 27

6,8-Difluoroquinolin-2-ylmethyl bromide

A solution of 2-methyl-6,8-difluoroquinoline (0.147 g, 0.820 mmoles, Example 26a), benzoyl peroxide (9.93 mg, 0.0410 mmoles), and N-bromosuccinamide (0.168 g, 0.943 mmoles) in carbon tetrachloride (20 mL) is heated to reflux for 18 hours. The reaction is concentrated and the resulting residue purified by column chromatography (silica, 3:1 CH$_2$Cl$_2$:hexane, then CH$_2$Cl$_2$) to yield the title compound as a white solid. MS (ESI) 258, 260 (M+H)$^+$, Br pattern.

The following compounds are prepared using essentially the same procedure used in example 27 except using the cited methyl compound in place of 6,8-difluoro-2-methyl quinoline.

EXAMPLE 27a 6,7-Difluoroquinolin-2-ylmethyl chloride

MS (ESI) 214, 216 (M+H)$^+$, Cl pattern. Prepared from 6,7-difluoro-quinoline (example 26) and NCS in place of NBS.

EXAMPLE 27b

6-Fluoroquinolin-2-ylmethyl bromide

MS (ESI) 240, 242 (M+H)$^+$, Br pattern. Prepared from 6-fluoro-2-methylquinoline.

EXAMPLE 27c

2-Chloromethyl-6-chloropyridine

MS (ESI) 162, 164, 166 (M+H)$^+$, Cl$_2$ pattern. Prepared from 6-chloro-2-picoline and NCS in place of NBS.

EXAMPLE 27c

2-Bromomethyl-benzonitrile

MS (EI) 195 (M)$^+$, Br pattern. Prepared from o-tolunitrile.

EXAMPLE 27e

Methyl 3-bromomethyl-thiophene-2-carboxylate

MS (EI) 234 (M)$^+$, Br pattern. Prepared from methyl 3-methyl-thiophene-2-carboxylate.

EXAMPLE 27f

6,7-Dichloro-2-chloromethyl-quinoline

MS (ESI) 246 (M+H)+. Prepared from 6,7-dichloro-quinaldine and NCS in place of NBS.

EXAMPLE 27g

5-Phenylpyridin-2-ylmethyl chloride

MS(ESI) 204, 206 (M+H)+, Cl pattern. Prepared from 5-phenyl-2-methylpyridine (example 104) and NCS in place of NBS.

EXAMPLE 28

3-[(Methylamino)-methyl]-(2-methoxyethoxy-methoxy)-benzene

To a solution of 3-(2-methoxyethoxy-methoxy)-benzaldehyde (2.10 g, 10 mmol, example 8a) in THF (60 mL) is added methylamine (20 mL, 2M in THF) followed by palladium on carbon (210 mg, 10% Pd). The resulting mixture is stirred for 24 h under an atmosphere of hydrogen gas, then purged with nitrogen, filtered through celite and the filtrate concentrated. The residue is purified by flash chromatography (silica, 10% methanol in dichloromethane) to give the title compound as an oil.

EXAMPLE 29

1-Methyl-4-oxo-1,4-dihydroquinolin-2-ylmethyl bromide

A solution of 1-methyl-4-oxo-1,4-dihydroquinolin-2-ylmethanol (112 mg, 0.592 mmoles, Coppola, G. M. *J. Heterocyclic Chem.*, 1986, 23, 1717) and phosphorous tribromide (56.2 uL, 0.592 mmoles) in 3:1 $CH_2Cl_2$: DMF (20 mL) is stirred 18 hours and another portion (20 mL) of phosphorous tribromide is added. After 24 hours distilled water (10 mL) is added and extracted with EtOAc. The organic layer is concentrated and the resulting residue purified by column chromatography (silica, 20:1 $CH_2Cl_2$:MeOH) to yield the title compound as a white solid. MS (ESI) 252, 254 (M+H)+, Br pattern.

The following compound is prepared using essentially the same procedure used in example 29 except using the cited alcohol in place of 1-methyl-4-oxo-1,4-dihydroquinolin-2-ylmethanol.

EXAMPLE 29a

4-tert-Butylcyclohexylmethyl bromide $^1$H NMR (300 MHz, $CDCl_3$): δ 3.27 (d, 2H), 1.93 (m, 2H), 1.81 (m, 2H), 1.54 (m, 2H), 0.98 (m, 4H), 0.84 (s, 9H). Prepared from 4-tert-butylcyclohexylmethanol (example 30).

EXAMPLE 30

4-tert-Butylcyclohexylmethanol

To a cooled (0° C.) solution of 4-tert-butylcyclohexanecarboxylic acid (3.00 g, 16.3 mmoles) in THF (30 mL) is slowly added a THF solution of borane-THF complex (1.0M, 21.2 mL, 21.2 mmoles). The solution is stirred at room temperature for 18 hours, then quenched with 2N HCl solution (30 mL), and extracted with EtOAc. The organic layer is isolated, washed with 1N NaOH, dried over sodium sulfate, and concentrated to yield the title compound as a clear oil. $^1$H NMR (300 MHz, $CDCl_3$): δ 2.06 (d, 2H), 1.82 (m, 4H), 1.52 (m, 2H), 0.88 (m, 4H), 0.83 (s, 9H).

EXAMPLE 31

Methyl 4-bromo-3-oxopentanoate

To a cooled (0° C.) solution of methyl 3-oxopentanoate (9.62 mL, 76.8 mmoles, Acros) in carbon tetrachloride (60 mL) is added dropwise over a period of 45 minutes a solution of bromine (3.96 mL, 76.8 mmoles) in carbon tetrachloride (10 mL). After 30 minutes, let stir at room temperature for one hour. Bubbled $N_2$ through reaction mixture for twenty minutes. Concentrated to yield the title compound as a brown oil. MS (EI) 208, 210 (M)+, Br pattern.

EXAMPLE 32

Methyl 2-(5-methyl-2-phenyloxazol-4-yl)acetate

A solution of benzamide (0.606 g, 5.00 mmoles) and methyl 4-bromo-3-oxopentanoate (1.05 g, 5.00 mmoles, example 31) are heated in toluene (6 ml) to 120° C. for 18 hours. The reaction is then purified by column chromatography (silica, 4:1 hex: EtOAc) to give the title compound as a clear oil. MS (APcI) 232 (M+H)+.

EXAMPLE 33

Ethyl 2-methyl-6-[3-(6-phenylpyridin-2-ylmethoxy)phenoxymethyl]benzoate

A solution of phenylboronic acid (74.0 mg, 0.607 mmoles), ethyl 2-[3-(6-chloropyridin-2-ylmethoxy)-phenoxymethyl]-6-methylbenzoate (250 mg, 0.607 mmoles, example 6v), and sodium carbonate (77.8 mg, 1.21 mmoles) in 1:1$H_2O$:AcCN (8 mL) is stirred under vacuum for five minutes. The reaction is placed under nitrogen, and tetrakis (triphenylphosphine)-palladium(0) (60.7 mg) is added followed by heating to 90° C. After two hours, another portion (15 mg) of phenylboronic acid is added. After another hour heating is stopped. Distilled water (10 mL) is added, followed by extraction with methylene chloride (twice with 20 mL). The organic extracts are combined and concentrated, and the resulting residue is purified by column chromatography (silica, 6:1 hex:EtOAc) to yield the title compound. MS (ESI) 454 (M+H)+.

EXAMPLE 34

1-Oxyquinolin-2-ylmethyl chloride

Partitioned 2-(chloromethyl)quinoline hydrochloride (1.00 g, 4.67 mmoles) between methylene chloride (15 mL) and sodium hydroxide solution (1M, 15 mL) to form the free base. The organic layer is isolated and cooled (0° C.), followed by addition of 3-chloroperbenzoic acid (57–86%, 1.13 g, 4.67 mmoles). After stirring at room temperature 18 hours the reaction mixture is washed with dilute sodium hydroxide. The organic layer is isolated and concentrated. The resulting residue is purified by column chromatography

EXAMPLE 35

{2-[3-(Quinolin-2-ylmethoxy)phenoxymethyl]
-6-methylphenoxy}acetonitrile 3-(Quinolin-2-ylmethoxy)-phenol (1.3 g, 5.4 mmol, example 3), (2-bromomethyl-6-methyl-phenoxy)-acetonitrile (1.56 g, 6.5 mmol, example 24), tetrabutylammonium iodide (99 mg, 0.27 mmol) and potassium carbonate (0.45 g, 3.3 mmol) are refluxed in acetone (20 mL) for 16 h. The reaction is filtered, washed with dichloromethane, concentrated and purified by column chromatography (silica, 1% ether in dichloromethane) to provide the title compound. MS (ESI) 411 (M+H)$^+$.

The following compounds are prepared using essentially the same procedure used in example 35 except using the cited phenol in place of 3-(quinolin-2-ylmethoxy)-phenol.

EXAMPLE 35a

{2-Methyl-6-[3-(quinolin-2-ylaminomethyl)-phenoxymethyl]-phenoxy}-acetonitrile

MS (ESI) 409 (M+H)$^+$. Prepared from 3-(quinolin-2-ylaminomethyl)-phenol (example 10).

EXAMPLE 35b

{2-Methyl-6-[3-(2-quinolin-2-yl-vinyl)-phenoxymethyl]-phenoxy}-acetonitrile

MS (ESI) 407 (M+H)$^+$. Prepared from 3-(2-quinolin-2-yl-vinyl)-phenol (example 15).

EXAMPLE 35c (2-Methyl-6-{3-[2-(pyridin-2-yloxy)-ethoxy]-phenoxymethyl}-phenoxy)-acetonitrile MS (ESI) 391 (M+H)$^+$. Prepared from 3-[2-(pyridin-2-yloxy)-ethoxy]-phenol (example 15a).

EXAMPLE 35d

{2-[3-(Benzooxazol-2-ylaminomethyl)-phenoxymethyl]-6-methyl-phenoxy}-acetonitrile $^1$H NMR (300 MHz, CDCl$_3$) δ 7.15 (m, 11H), 5.36 (bs, 1H), 5.08 (s, 2H), 4.67 (s, 4H), 2.37 (s, 3H). MS (ESI) 400 (M+H)$^+$. Prepared from 3-(benzooxazol-2-ylaminomethyl)-phenol (example 10c).

EXAMPLE 35e

{2-[3-(4-Chloro-quinolin-2-ylmethoxymethyl)-phenoxymethyl]-6-methyl-phenoxy}-acetonitrile $^1$H NMR (300 MHz, CDCl$_3$) δ 8.22 (d, 1H), 8.06 (d, 1H), 7.76 (m, 2H), 7.63 (m, 1H), 7.32 (m, 2H), 7.23 (m, 1H), 7.13 (m, 1H), 7.04 (m, 2H), 6.94 (m, 1H), 5.09 (s, 2H), 4.83 (s, 2H), 4.72 (s, 2H), 4.68 (s, 2H), 2.39 (s, 3H). MS (ESI) 459 (M+H)$^+$. Prepared from 3-(4-chloro-quinolin-2-ylmethoxymethyl)-phenol (example 74b).

EXAMPLE 35f

{2-[3-(6-Methoxy-quinolin-2-ylmethoxymethyl)-phenoxymethyl]-6-methyl-phenoxy}-acetonitrile $^1$H NMR (300 MHz, CDCl$_3$) δ 8.08 (d, 1H), 7.96 (d, 1H), 7.60 (d, 1H), 7.19 (m, 8H), 6.92 (dd, 1H), 5.07 (s, 2H), 4.84 (s, 2H), 4.71 (s, 2H), 4.66 (s, 2H), 3.93 (s, 3H), 2.39 (s, 3H). MS (ESI) 455 (M+H)$^+$. Prepared from 3-(6-methoxy-quinolin-2-ylmethoxymethyl)-phenol (example 74c).

EXAMPLE 35g

{2-Methyl-6-[3-(quinolin-2-ylmethoxymethyl)-phenoxymethyl]-phenoxy}-acetonitrile Prepared from 3-(quinolin-2-ylmethoxymethyl)-phenol (example 74a).

The following compounds are prepared using essentially the same procedure used in example 35 except using the cited bromide in place of (2-bromomethyl-6-methyl-phenoxy)-acetonitrile.

EXAMPLE 36a

2-{2-Methyl-6-[3-(quinolin-2-ylmethoxy)-phenoxymethyl]-phenoxy}-propionic acid methyl ester MS (ESI) 457 (M+H)$^+$. Prepared using methyl 2-(2-bromomethyl-6-methyl-phenoxy)-propionate (example 24c).

EXAMPLE 36b

{2,4-Dichloro-6-[3-(quinolin-2-ylmethoxy)-phenoxymethyl]-phenoxy}-acetonitrile

MS (ESI) 465 (M+H)$^+$,Cl$_2$ pattern. Prepared from (2-bromomethyl-4,6-dichloro-phenoxy)-acetonitrile (example 24a).

EXAMPLE 36c

{4-Chloro-2-methyl-6-[3-(quinolin-2-ylmethoxy)-phenoxymethyl]-phenoxy}acetonitrile MS (ESI) 445 (M+H)$^+$. Prepared from (2-bromomethyl-4-chloro-6-methyl-phenoxy)-acetonitrile (example 43).

EXAMPLE 36d

{2-tert-Butyl-6-[3-(quinolin-2-ylmethoxy)-phenoxymethyl]-phenoxy}-acetonitrile

MS (ESI) 453 (M+H)$^+$. Prepared from (2-bromomethyl-6-tert-butyl-phenoxy)-acetonitrile (example 43a).

EXAMPLE 36e

{4-Chloro-2-methoxy-6-[3-(quinolin-2-ylmethoxy)-phenoxymethyl]-phenoxy}-acetonitrile MS (ESI) 461 (M+H)$^+$, Cl pattern. Prepared from (2-bromomethyl-4-chloro-6-methoxy-phenoxy)-acetonitrile (example 24b).

EXAMPLE 36f

2-[3-(Quinolin-2-ylmethoxy)-phenoxymethyl]
-benzonitrile

MS (ESI) 386 (M+H)$^+$. Prepared from 2-bromomethyl-benzonitrile (example 27d).

EXAMPLE 36g

Methyl
2-[3-(Quinolin-2-ylmethoxy)-phenoxymethyl]
-thiophene-2-carboxylate

MS (ESI) 406 (M+H)$^+$. Prepared from methyl 3-bromomethyl-thiophene-2-carboxylate (example 27e).

EXAMPLE 36h

Ethyl {2-methyl-6-[3-(quinolin-2-ylmethoxy)-phenoxymethyl]-phenoxy}-acetate

MS (ESI) 457 (M+H)$^+$. Prepared from ethyl (2-bromomethyl-6-methyl-phenoxy)-acetate (example 43b).

EXAMPLE 36i

Ethyl 7-[3-(quinolin-2-ylmethoxy)-phenoxymethyl]
-benzofuran-2-carboxylate

MS (ESI) 354 (M+H)$^+$. Prepared from ethyl 7-bromomethyl-benzofuran-2-carboxylate (example 94).

EXAMPLE 36j

Ethyl {2-methyl-6-[3-methyl-5-(quinolin-2-ylmethoxy)-phenoxymethyl]-phenoxy}-acetate The title compound is prepared using essentially the same procedure used in example 35 except using 3-methyl-5-(quinolin-2-ylmethoxy)-phenol (example 55) in place of 3-(quinolin-2-ylmethoxy)-phenol and ethyl (2-bromomethyl-6-methyl-phenoxy)-acetate (example 43b) in place of (2-bromomethyl-6-methyl-phenoxy)-acetonitrile.

The following compounds are prepared using essentially the same procedure used in example 35 except using the cited phenol in place of 3-(quinolin-2-ylmethoxy)-phenol and (2-bromomethyl-4-chloro-6-methyl-phenoxy)-acetonitrile (example 43) in place of (2-bromomethyl-6-methyl-phenoxy)-acetonitrile.

EXAMPLE 36k

{4-Chloro-2-methyl-6-[3-(2-pyridin-2-yl-ethoxy)-phenoxymethyl]-phenoxy}-acetonitrile $^1$H NMR (300 MHz, CDCl$_3$) δ 8.56 (d, 1H), 7.62 (m, 1H), 7.30 (m, 1H), 7.18 (m, 3H), 6.57 (m, 4H), 4.99 (s, 2H), 4.67 (s, 2H), 4.36 (t, 2H), 3.27 (t, 2H), 2.36 (s, 3H). MS (ESI) 409 (M+H)$^+$. Prepared from 3-(2-pyridin-2-yl-ethoxy)-phenol (example 71a).

EXAMPLE 36l

{2-[3-(Benzooxazol-2-ylaminomethyl)-phenoxymethyl]-4-chloro-6-methyl-phenoxy}-acetonitrile $^1$H NMR (300 MHz, CDCl$_3$) δ 7.14 (m, 10H), 5.35. (bs, 1H), 5.04 (s, 2H), 4.67 (d, 2H), 4.63 (s, 2H), 2.34 (s, 3H). MS (ESI) 434 (M+H)$^+$. Prepared from 3-(benzooxazol-2-ylaminomethyl)-phenol (example 10c).

EXAMPLE 37

2-[3-(2-Chloromethyl-benzyloxy)-phenoxymethyl]
-quinoline

The title compound is prepared using essentially the same procedure used in example 35 except using excess 1,2-bis-chloromethyl-benzene in place of (2-bromomethyl-6-methyl-phenoxy)-acetonitrile and without using tetrabutylammonium iodide. MS (ESI) 390 (M+H)$^+$, Cl pattern.

EXAMPLE 38

{2-[3-(Quinolin-2-ylmethoxy)-phenoxymethyl]
-phenyl}-acetonitrile

Sodium cyanide (14 mg, 0.28 mmol) is added to a solution of 2-[3-(2-chloromethyl-benzyloxy)-phenoxymethyl]-quinoline (110 mg, 0.28 mmol, example 37) in DMSO (5 mL) and the reaction is stirred 5 h. The reaction is partitioned between water and ethyl acetate, the organic phase is washed with water, dried and concentrated to provide the title compound which is used without further purification. MS (ESI) 381 (M+H)$^+$.

EXAMPLE 39

{2-[3-(Quinoxalin-2-ylmethoxy)]phenoxymethyl]
-6-methylphenoxy}acetonitrile

A solution of (2-[3-hydroxyphenoxymethyl]-6-methylphenoxy)acetonitrile (100 mg, 0.37 mmol, example 25), quinoxalin-2-ylmethyl chloride [72 mg, 0.40 mmol (See *Chem. Ber.* 1987, 120, 649–651)] in DMF (1 mL) is heated with potassium carbonate (105 mg, 0.75 mmol) at 60° C. for 16 h. The reaction is filtered and partioned between ethyl acetate and water. The organic phase is washed with water, dried over magnesium sulfate, concentrated and purified by column chromatography (silica, 30% ethyl acetate in hexanes) to provide the title compound. MS (ESI) 412 (M+H)$^+$.

The following compounds are prepared using essentially the same procedure used in example 39 except using the cited halide in place of quinoxalin-2-ylmethyl chloride.

EXAMPLE 39a

{2-[3-(7-Chloro-isoquinolin-3-ylmethoxy)-phenoxymethyl]-6-methyl-phenoxy}-acetonitrile MS (ESI) 445 (M+H, Cl pattern)$^+$. Prepared from {2-methyl-6-[(3-hydroxy-phenoxy)-methyl]-phenoxy}-acetonitrile (example 25) and (7-chloro-isoquinolin-3-yl) methyl bromide (see Ewing, William R.; Becker, Michael R.; Choi-Sledeski, Yong Mi; Pauls, Heinz W.; He, Wei; Condon, Stephen M.; Davis, Roderick S.; Hanney, Barbara A.; Spada, Alfred P.; Burns, Christopher J.; Jiang, John Z.; Li, Aiwen; Myers, Michael R.; Lau, Wan F.; Poli, Gregory B; *Substi-*

*tuted piperazinone derivatives and other oxoazaheterocyclyl compounds useful as factor Xa inhibitors*. PCT Int. Appl., (1999), WO 9937304.

EXAMPLE 39b

{2-Methyl-6-[3-(naphthalen-2-ylmethoxy)-phenoxymethyl]-phenoxy}-acetonitrile

MS (ESI) 410 (M+H)$^+$. Prepared from napthalen-2-ylmethyl chloride.

EXAMPLE 39c

{2-[3-(4-tert-Butyl-benzyloxy)-phenoxymethyl]-6-methyl-phenoxy}-acetonitrile

MS (ESI) 416 (M+H)$^+$. Prepared from 4-tert-butylbenzyl chloride.

EXAMPLE 39d

{2-Methyl-6-[3-(2-phenoxy-ethoxy)-phenoxymethyl]-phenoxy}-acetonitrile

MS (ESI) 390 (M+H)$^+$. Prepared from 2-phenoxy-ethyl-bromide.

EXAMPLE 39e

2-Methyl-6-[3-(3-phenyl-propoxy)-phenoxymethyl]-phenoxy}-acetonitrile

MS (ESI) 388 (M+H)$^+$. Prepared from 3-phenyl-propyl bromide.

EXAMPLE 39f

{2-Methyl-6-[3-(3-phenoxy-benzyloxy)-phenoxymethyl]-phenoxy}-acetonitrile

MS (ESI) 452 (M+H)$^+$. Prepared from 3-phenoxy-benzyl chloride.

EXAMPLE 39g

{2-[3-(3-Methoxy-benzyloxy)-phenoxymethyl]-6-methyl-phenoxy}-acetonitrile

MS (ESI) 390 (M+H)$^+$. Prepared from 3-methoxy-benzyl chloride.

EXAMPLE 39h

{2-[3-(3,4-Dichloro-benzyloxy)-phenoxymethyl]-6-methyl-phenoxy}-acetonitrile

MS (ESI) 428 (M+H)$^+$. Prepared from 3,4-dichloro-benzyl chloride.

EXAMPLE 39i

{2-[3-(6,7-Difluoroquinolin-2-ylmethoxy)phenoxymethyl]-6-methyl-phenoxy}acetonitrile MS (ESI) 446 (M+H)$^+$. Prepared from 6,7-difluoroquinolin-2-ylmethyl chloride (example 27).

EXAMPLE 39j

{2-[3-(6,8-Difluoroquinolin-2-ylmethoxy)phenoxymethyl]-6-methylphenoxy}acetonitrile MS (ESI) 446 (M+H)$^+$. Prepared from 6,8-difluoroquinolin-2-ylmethyl bromide (example 27a).

EXAMPLE 39k

{2-Methyl-6-[3-(1-oxyquinolin-2-ylmethoxy)phenoxymethyl]phenoxy}acetonitrile

MS (ESI) 427 (M+H)$^+$. Prepared from 1-oxyquinolin-2-ylmethyl chloride (example 34).

EXAMPLE 39l

2-[3-(6-Fluoroquinolin-2-ylmethoxy)phenoxymethyl]-6-methylphenoxy}acetonitrile

MS (ESI) 429 (M+H)$^+$. Prepared from 6-fluoroquinolin-2-ylmethyl bromide (example 27b).

EXAMPLE 39m

{2-Methyl-6-[3-(1-methyl-4-oxo-1,4-dihydroquinolin-2-ylmethoxy)phenoxymethyl]-phenoxy}acetonitrile MS (ESI) 441 (M+H)$^+$. Prepared from 1-methyl-4-oxo-1,4-dihydroquinolin-2-ylmethyl bromide (example 29).

EXAMPLE 39n

{2-[3-(4-Chloroquinolin-2-ylmethoxy)phenoxymethyl]-6-methylphenoxy}acetonitrile

MS (ESI) 445 (M+H)$^+$. Prepared from 4-chloroquinolin-2-ylmethyl chloride (example 46).

EXAMPLE 39o

{2-[3-(7-Chloroquinolin-2-ylmethoxy)phenoxymethyl]-6-methylphenoxy}acetonitrile

MS (ESI) 445 (M+H)$^+$. Prepared from 7-chloroquinolin-2-ylmethyl chloride (example 46a).

EXAMPLE 39p

{2-[3-(6-Methoxyquinolin-2-ylmethoxy)phenoxymethyl]-6-methylphenoxy}acetonitrile MS (ESI) 441 (M+H)$^+$. Prepared from 6-methoxyquinolin-2-ylmethyl chloride (example 46b).

EXAMPLE 39q

{2-Methyl-6-[3-(pyridin-4-ylmethoxy)-phenoxymethyl]-phenoxy}-acetonitrile $^1$H NMR (300 MHz, CDCl$_3$) δ 8.62 (bd, 2H), 7.24 (m, 6H), 6.62 (m, 3H), 5.08 (s, 2H), 5.06 (s, 2H), 4.70 (s, 2H), 2.39 (s, 3H). MS (ESI) 361 (M+H)$^+$. Prepared from 4-chloromethyl-pyridine hydrochloride.

EXAMPLE 39r

{2-Methyl-6-[3-(pyridin-2-ylmethoxy)-phenoxymethyl]-phenoxy}-acetonitrile $^1$H NMR (300 MHz, CDCl$_3$) δ 8.60 (d, 1H), 7.72 (m, 1H), 7.52 (d, 1H), 7.21 (m, 5H), 6.63 (m, 3H), 5.20 (s, 2H), 5.04 (s, 2H), 4.69 (s, 2H), 2.39 (s, 3H). MS (ESI) 361 (M+H)$^+$. Prepared from 2-chloromethyl-pyridine hydrochloride.

EXAMPLE 39s

{2-Methyl-6-[3-(pyridin-3-ylmethoxy)-phenoxymethyl]-phenoxy}-acetonitrile $^1$H NMR (300 MHz, CDCl$_3$) δ 8.68 (bs, 1H), 8.59 (bd, 1H), 7.78 (m, 1H), 7.24 (m, 5H), 6.63 (m, 3H), 5.07 (s, 2H), 5.06 (s, 2H), 4.70 (s, 2H), 2.39 (s, 3H). MS (ESI) 361 (M+H)$^+$. Prepared from 3-chloromethyl-pyridine hydrochloride.

EXAMPLE 39t

{2-[3-(6,7-Dichloro-quinolin-2-ylmethoxy)-phenoxymethyl]-6-methyl-phenoxy}-acetonitrile $^1$H NMR (300 MHz, CDCl$_3$) δ 8.20 (s, 1H), 8.10 (d, 1H), 7.94 (s, 1H), 7.70 (d, 1H), 7.20 (m, 4H), 6.65 (m, 3H), 5.34 (s, 2H), 5.05 (s, 2H), 4.69 (s, 2H), 2.38 (s, 3H). MS (ESI) 479 (M+H)$^+$.

Prepared from 6,7-dichloro-2-chloromethyl-quinoline (example 27f).

EXAMPLE 39u

{2-Methyl-6-[3-(2-phenyl-thiazol-4-ylmethoxy)-phenoxymethyl]-phenoxy}-acetonitrile MS (ESI) 443 (M+H)$^+$. Prepared from 4-chloromethyl-2-phenyl-thiazole (example 20).

The following compounds are prepared using essentially the same procedure used in example 39 except using the cited phenol in place of (2-[3-hydroxyphenoxymethyl]-6-methylphenoxy)acetonitrile and 6-fluoroquinolin-2-ylmethyl bromide (example 27b) in place of quinoxalin-2-ylmethyl chloride.

EXAMPLE 40a

{4-Chloro-2-[3-(6-fluoroquinolin-2-ylmethoxy)phenoxymethyl]-6-methylphenoxy}acetonitrile MS (ESI) 463, 465 (M+H)$^+$, Cl pattern. Prepared from (2-[3-hydroxyphenoxymethyl]-4-chloro-6-methylphenoxy) acetonitrile (example 25a).

EXAMPLE 40b

{2,4-Dichloro-6-[3-(6-fluoroquinolin-2-ylmethoxy)phenoxymethyl]phenoxy}acetonitrile MS (EST) 483, 485, 487 (M+H)$^+$, Cl$_2$ pattern. Prepared from [4,6-dichloro-2-(3-hydroxy-phenoxymethyl)-phenoxy]-acetonitrile (example 25b).

EXAMPLE 41

{2-Methyl-6-[3-(quinolin-2-ylaminomethyl)-phenoxymethyl]-phenoxy}-acetic acid

To a solution of {2-methyl-6-[3-(quinolin-2-ylaminomethyl)-phenoxymethyl]-phenoxy}-acetonitrile (134 mg, 0.31 mmol, example 35a) in methanol (1 mL) is added THF (1 mL) followed by sodium hydroxide solution (0.2 mL, 10 N). The resulting mixture is warmed to 60° C. and stirred at this temperature for 3 h. The reaction mixture is then cooled to room temperature and acidified to ca. pH 5 with hydrochloric acid (1 mL, 2N), then extracted with ethyl acetate, washed with brine, dried over MgSO$_4$ and concentrated. The residue is purified by flash chromatography (silica, 10% methanol in dichloromethane) to give the title compound. $^1$H NMR (300 MHz, CDCl$_3$) δ 8.10 (d, 1H), 7.80 (d, 1H), 7.68 (t, 2H), 7.40 (t, 1H), 7.25 (m, 2H), 7.04 (m, 3H), 6.90 (m, 3H), 6.6 (bs, 0.1H), 5.15 (s, 2H), 4.60 (d, 2H), 4.50 (s, 2H), 2.27 (s, 3H). MS (ESI) 429 (M+H)$^+$.

The following compounds are prepared using essentially the same procedure used in example 41 except using the cited nitrile or ester in place of {2-methyl-6-[3-(quinolin-2-ylaminomethyl)-phenoxymethyl]-phenoxy}-acetonitrile.

EXAMPLE 41a

{2-Methyl-6-[3-(2-quinolin-2-yl-vinyl)-phenoxymethyl]-phenoxy}-acetic acid $^1$H NMR (300 MHz, DMSO) d 8.38 (d, 1H), 8.01 (d, 1H), 7.97 (d, 1H), 7.89 (d, 1H), 7.83 (d, 1H), 7.78 (dt, 1H), 7.59 (dt, 1H), 7.53 (d, 1H), 7.44 (bd, 1H), 7.36 (m, 3H), 7.25 (bd, 1H), 7.11 (t, 1H), 7.02 (dt, 1H), 5.25 (s, 2H), 4.54 (s, 2H), 2.32 (s, 3H). MS (ESI) 426 (M+H)$^+$. Prepared from {2-methyl-6-[3-(2-quinolin-2-yl-vinyl)-phenoxymethyl]-phenoxy}-acetonitrile (example 35b).

EXAMPLE 41b (2-Methyl-6-{3-[2-(pyridin-2-yloxy)-ethoxy]-phenoxymethyl}-phenoxy)-acetic acid $^1$H NMR (300 MHz, DMSO) d 8.17 (dd, 1H), 7.72 (m, 1H), 7.29 (dd, 1H), 7.20 (m, 2H), 7.07 (t, 1H), 6.99 (m, 1H), 6.85 (d, 1H), 6.60 (m, 3H), 5.13 (s, 2H), 4.57 (t, 2H), 4.49 (s, 2H), 4.30 (t, 2H), 2.28 (s, 3H). MS (ESI) 410 (M+H)$^+$. Prepared from (2-methyl-6-{3-[2-(pyridin-2-yloxy)-ethoxy]-phenoxymethyl}-phenoxy)-acetonitrile (example 35c).

EXAMPLE 41c

{2-[3-(7-Chloro-isoquinolin-3-ylmethoxy)-phenoxymethyl]-6-methyl-phenoxy}-acetic acid $^1$H NMR (300 MHz, CDCl$_3$) δ 9.13 (d, 1H), 7.96 (s, 1H), 7.79 (s, 1H), 7.74 (d, 1H), 7.65 (d, 1H), 7.30 (d, 1H), 7.20 (d, 1H), 7.10 (m, 2H), 6.81 (s, 1H), 6.62 (d, 1H), 6.49 (d, 1H), 5.25 (s, 2H), 5.16 (s, 2H), 4.59 (s, 2H), 2.37 (s, 3H). MS (ESI) 464 (M+H, Cl pattern)$^+$. Prepared from {2-[3-(7-chloro-isoquinolin-3-ylmethoxy)-phenoxymethyl]-6-methyl-phenoxy}-acetonitrile (example 39a).

EXAMPLE 41d

{2-Methyl-6-[3-(naphthalen-2-ylmethoxy)-phenoxymethyl]-phenoxy}-acetic acid $^1$H NMR (300 MHz, CDCl$_3$) δ 8.00 (m, 3H), 7.48 (dd, 1H), 7.43 (m, 2H), 7.23 (m, 2H), 7.16 (m, 2H), 7.05 (t, 1H), 6.62 (m, 1H), 6.55. (m, 2H). MS (ESI) 429 (M+H)$^+$. Prepared from {2-methyl-6-[3-(naphthalen-2-ylmethoxy)-phenoxymethyl]-phenoxy}-acetonitrile (example 39b).

EXAMPLE 41e

{2-[3-(4-tert-Butyl-benzyloxy)-phenoxymethyl]-6-methyl-phenoxy}-acetic acid $^1$H NMR (300 MHz, CDCl$_3$) δ 7.38 (m, 3H), 7.27 (m, 2H), 7.24 (d, 1H), 7.17 (d, 1H), 7.10 (d, 1H), 6.59 (m, 3H), 5.07 (s, 2H), 4.98 (s, 2H), 4.57 (s, 2H), 2.33 (s, 3H), 1.33 (s, 9H). MS (ESI) 435 (M+H)$^+$. Prepared from {2-[3-(4-tert-butyl-benzyloxy)-phenoxymethyl]-6-methyl-phenoxy}-acetonitrile (example 39c).

EXAMPLE 41f

{2-Methyl-6-[3-(2-phenoxy-ethoxy)-phenoxymethyl]-phenoxy}-acetic acid $^1$H NMR (300 MHz, CDCl$_3$) δ 7.03–7.33 (m, 6H), 6.95 (m, 3H), 6.57 (m, 3H), 5.07 (s, 2H), 4.55 (s, 2H), 4.29 (m, 4H), 2.33 (s, 3H). MS (ESI) 409 (M+H)$^+$. Prepared from {2-methyl-6-[3-(2-phenoxy-ethoxy)-phenoxymethyl]-phenoxy}-acetonitrile (example 39d).

EXAMPLE 41g

{2-Methyl-6-[3-(3-phenyl-propoxy)-phenoxymethyl]-phenoxy}-acetic acid $^1$H NMR (300 MHz, CDCl$_3$) δ 7.07–7.41 (m, 9H), 6.54 (m, 3H), 5.08 (s, 2H), 4.58 (s, 2H), 3.94 (t, 2H), 2.80 (t, 2H), 2.34 (s, 3H), 2.09 (qn, 2H). MS (ESI) 407 (M+H)$^+$. Prepared from {2-methyl-6-[3-(3-phenyl-propoxy)-phenoxymethyl]-phenoxy}-acetonitrile (example 39e).

EXAMPLE 41h

{2-Methyl-6-[3-(3-phenoxy-benzyloxy)-phenoxymethyl]-phenoxy}-acetic acid $^1$H NMR (300 MHz, CDCl$_3$) δ 7.31 (m, 4H), 7.06–7.25 (m, 6H), 7.01 (m, 2H), 6.94 (m, 1H), 6.57 (m, 3H), 5.06 (s, 2H), 4.99 (s, 2H), 4.56 (s, 2H), 2.33 (s, 3H). MS (ESI) 471 (M+H)$^+$. Prepared from {2-methyl-6-[3-(3-phenoxy-benzyloxy)-phenoxymethyl]-phenoxy}-acetonitrile (example 39f).

EXAMPLE 41i

{2-[3-(3-Methoxy-benzyloxy)-phenoxymethyl]-6-methyl-phenoxy}-acetic acid

MS (ESI) 409 (M+H)$^+$. Prepared from {2-[3-(3-methoxy-benzyloxy)-phenoxymethyl]-6-methyl-phenoxy}-acetonitrile (example 39 g).

EXAMPLE 41j

{2-[3-(3,4-Dichloro-benzyloxy)-phenoxymethyl]-6-methyl-phenoxy}-acetic acid $^1$H NMR (300 MHz, CDCl$_3$) δ 7.60 (d, 1H), 7.51 (d, 1H), 7.30–7.38 (m, 2H), 7.28 (d, 1H), 7.23 (d, 1H), 7.17 (d, 1H), 6.66 (m, 3H), 5.16 (s, 2H), 5.05 (s, 2H), 4.65 (s, 2H), 2.42 (s, 3H). MS (ESI) 447 (M+H)$^+$. Prepared from {2-[3-(3,4-dichloro-benzyloxy)-phenoxymethyl]-6-methyl-phenoxy}-acetonitrile (example 39 h.

EXAMPLE 41k

{2-[3-(6,7-Difluoroquinolin-2-ylmethoxy)phenoxymethyl]-6-methylphenoxy}acetic acid m.p. 94–95° C. $^1$H NMR (300 MHz, CDCl$_3$): δ 8.10 (d, 1H), 7.73 (m, 1H), 7.56 (d, 1H), 7.44 (d, 1H), 7.29 (s, 1H), 7.18 (m, 1H), 7.08 (m, 2H), 6.79 (s, 1H), 6.61 (d, 1H), 6.51 (m, 1H), 5.31 (s, 2H), 5.15 (s, 2H), 4.61 (s, 2H), 2.35 (s, 3H). MS (ESI) 466 (M+H)$^+$. Prepared from {2-[3-(6,7-difluoro-quinolin-2-ylmethoxy)phenoxymethyl]-6-methylphenoxy}acetonitrile (example 39i).

EXAMPLE 41l

{2-[3-(6,8-Difluoroquinolin-2-ylmethoxy)phenoxymethyl]-6-methylphenoxy}acetic acid m.p. 137–141° C. $^1$H NMR (300 MHz, CDCl$_3$): δ 8.16 (d, 1H), 7.79 (d, 1H), 7.29–7.05 (m, 6H), 6.71 (s, 1H), 6.61 (m, 2H), 5.53 (s, 2H), 5.10 (s, 2H), 4.57 (s, 2H), 2.33 (s, 3H). MS (ESI) 466 (M+H)$^+$. Prepared from {2-[3-(6,8-difluoroquinolin-2-ylmethoxy)phenoxymethyl]-6methylphenoxy}acetonitrile (example 39j).

EXAMPLE 41m

{2-Methyl-6-[3-(1-oxyquinolin-2-ylmethoxy)phenoxymethyl]phenoxy}acetic acid m.p. 146–147° C. $^1$H NMR (300 MHz, CDCl$_3$): δ 8.73 (d, 1H), 8.01 (m, 1H), 7.93 (m, 1H), 7.89 (m, 1H), 7.70 (m, 1H), 7.55 (d, 1H), 7.26 (m, 2H), 7.01 (m, 2H), 6.75 (m, 3H), 5.69 (s, 2H), 5.26 (s, 2H), 4.47 (s, 2H), 2.24 (s, 3H). MS (ESI) 446 (M+H)$^+$. Prepared from {2-methyl-6-[3-(1-oxyquinolin-2-ylmethoxy)phenoxymethyl]phenoxy}-acetonitrile (example 39k).

EXAMPLE 41n

{2-[3-(6-Fluoroquinolin-2-ylmethoxy)phenoxymethyl]-6-methylphenoxy}acetic acid m.p. 160–161° C. $^1$H NMR (300 MHz, CDCl$_3$): δ 8.17 (m, 2H), 7.72 (d, 1H), 7.48 (m, 2H), 7.27 (m, 1H), 7.19 (d, 1H), 7.08 (m, 2H), 6.63 (s, 1H), 6.62 (d, 1H), 6.53 (d, 1H), 5.35 (s, 2H), 5.14 (s, 2H), 4.61 (s, 2H), 2.34 (s, 3H). MS (ESI) 448 (M+H)$^+$. Prepared from {2-[3-(6-fluoroquinolin-2-ylmethoxy)phenoxymethyl]-6-methylphenoxy}acetonitrile (example 39l).

EXAMPLE 41o

{2-Methyl-6-[3-(1-methyl-4-oxo-1,4-dihydroquinolin-2-ylmethoxy)phenoxymethyl]-phenoxy}acetic acid m.p. 192–194° C. $^1$H NMR (300 MHz, 1:1 CDCl$_3$: CD$_3$OD): δ 8.29 (m, 1H), 7.76 (m, 2H), 7.41 (m, 1H), 7.25–6.92 (m, 4H), 6.81–6.41 (m, 4H), 5.11 (m, 4H), 4.39 (s, 2H), 3.88 (s, 3H), 2.27 (s, 3H). MS (ESI) 460 (M+H)$^+$. Prepared from {2-methyl-6-[3-(1-methyl-4-oxo-1,4dihydroquinolin-2-ylmethoxy)phenoxymethyl]phenoxy}acetonitrile (example 39m).

EXAMPLE 41p

{4-Chloro-2-[3-(6-fluoroquinolin-2-ylmethoxy)phenoxymethyl]-6-methylphenoxy}acetic acid m.p. 140–141° C. $^1$H NMR (300 MHz, 5:1 CDCl$_3$: CD$_3$OD): δ 8.20 (d, 1H), 8.07 (m, 1H), 7.69 (d, 1H), 7.50 (m, 2H), 7.25 (s, 1H), 7.16 (m, 1H), 7.11 (s, 1H), 6.67 (s, 1H), 6.60 (m, 2H), 5.30 (s, 2H), 5.07 (s, 2H), 4.24 (s, 2H), 2.25 (s, 3H). MS (ESI) 482, 484 (M+H)$^+$, Cl pattern. Prepared from {4-chloro-2-[3-(6-fluoroquinolin-2-ylmethoxy)phenoxymethyl]-6-methylphenoxy}acetonitrile (example 40a).

EXAMPLE 41q

{2,4-Dichloro-6-[3-(6-fluoroquinolin-2-ylmethoxy)phenoxymethyl]phenoxy}acetic acid m.p. 189–190° C. $^1$HNMR(300 MHz, 5:1 CDCl$_3$: CD$_3$OD): δ 8.22 (d, 1H), 8.07 (m, 1H), 7.73 (d, 1H), 7.52 (m, 2H), 7.35 (m, 2H), 7.21 (m, 1H), 6.72 (s, 1H), 6.65 (m, 2H), 5.34 (s, 2H), 5.22 (s, 2H), 4.68 (s, 2H). MS (ESI) 502, 504, 506 (M+H)$^+$, Cl$_2$ pattern. Prepared from {2,4-dichloro-6-[3-(6-fluoroquinolin-2-ylmethoxy)phenoxymethyl]phenoxy}acetonitrile (example 40b).

EXAMPLE 41r

{2-Methyl-6-[3-(2-pyridin-2-yl-ethoxy)-phenoxymethyl]-phenoxy}-acetic acid $^1$H NMR (300 MHz, DMSO) d 8.50 (d, 1H), 7.73 (dt, 1H), 7.36 (d, 1H), 7.20 (m, 4H), 7.04 (m, 1H), 6.58 (m, 2H), 6.50 (d, 1H), 5.77 (s, 2H), 5.15 (s, 2H), 4.35 (m, 4H), 3.20 (t, 2H), 2.25 (s, 3H). MS (ESI) 394 (M+H)$^+$. Prepared from {2-methyl-6-[3-(2-pyridin-2-yl-ethoxy)phenoxymethyl]-phenoxy}-acetonitrile (example 21).

EXAMPLE 41s

{2-[3-(Quinolin-2-ylmethoxy)phenoxymethyl]-6-methylphenoxy}-acetic acid m.p. 154–157° C.; $^1$H NMR (300 MHz, CDCl$_3$) δ 8.25 (d, 1H), 8.19 (d, 1H), 7.81 (d, 1H), 7.77–7.70 (m, 2H), 7.60–7.55 (m, 1H), 7.27 (dd, 1H), 7.18 (d, 1H), 7.13–7.04 (m, 2H), 6.85 (t, 1H), 6.61 (dd, 1H), 6.53 (dd, 1H), 5.40 (s, 2H), 5.18 (s, 2H), 4.62 (s, 2H), 2.35 (s, 3H); MS (ESI) 430 (M+H)$^+$. Prepared from {2-[3-(quinolin-2-ylmethoxy)phenoxymethyl]-6-methylphenoxy}acetonitrile (example 35).

EXAMPLE 41t

{2-Methyl-6-[3-(quinoxalin-2-ylmethoxy)-phenoxymethyl]-phenoxy}-acetic acid $^1$H NMR (300 MHz, DMSO-d$_6$) δ 9.07 (s, 1H), 8.14–8.05 (m, 2H), 7.87–7.82 (m, 2H), 7.19–7.05 (m, 3H), 6.97–6.92 (m, 1H), 6.77 (s, 1H), 6.67–6.57 (m, 2H), 5.41 (s, 2H), 5.19 (s, 2H), 4.10 (s, 2H), 2.21 (s, 3H); MS (ESI) 431 (M+H)$^+$. Prepared from {2-[3-(quinoxalin-2-ylmethoxy)-phenoxymethyl]-6-methylphenoxy}acetonitrile (example 39).

EXAMPLE 41u

2-{2-Methyl-6-[3-(quinolin-2-ylmethoxy)-phenoxymethyl]-phenoxy}-propionic acid $^1$H NMR (300 MHz, DMSO-d$_6$) d 8.40 (d, 1H), 7.99 (dd, 2H), 7.77 (dd, 1H), 7.67–7.58 (m, 2H), 7.22–7.10 (m, 3H), 6.98 (dd, 1H), 6.73 (s, 1H), 6.60 (dd, 2H), 5.33 (s, 2H), 5.19 (dd, 2H), 4.40–4.34 (m, 1H), 2.24 (s, 3H), 1.35 (d, 3H); MS (ESI) 444 (M+H)$^+$. Prepared from methyl 2-{2-methyl-6-[3-(quinolin-2-ylmethoxy)-phenoxymethyl]-phenoxy}-propionate (example 36a).

EXAMPLE 41v 2,4-Dichloro-6-[3-(quinolin-2-ylmethoxy)-phenoxymethyl]-phenoxy}-acetic acid m.p. 201–203° C.; $^1$H NMR (300 MHz, DMSO-d$_6$) d 8.38 (d, 1H), 7.98 (dd, 2H), 7.76 (dd, 1H), 7.66–7.57 (m, 2H), 7.54 (d, 1H), 7.39 (d, 1H), 7.18 (dd, 1H), 6.75 (s, 1H), 6.66–6.61 (m, 2H), 5.33 (s, 2H), 5.28 (s, 2H), 4.48 (s, 2H); MS (ESI) 484, 486 (M+H; Cl$_2$)$^+$. Prepared from {2,4-dichloro-6-[3-(quinolin-2-ylmethoxy)-phenoxymethyl]-phenoxy}-acetonitrile (example 36b).

EXAMPLE 41w

{4-Chloro-2-methyl-6-[3-(quinolin-2-ylmethoxy)-phenoxymethyl]-phenoxy}acetic acid $^1$H NMR (300 MHz, CDCl$_3$) δ 8.37 (d, 1H), 8.02 (d, 1H), 7.93 (d, 1H), 7.78–7.70 (m, 2H), 7.60 (t, 1H), 7.24–7.15 (m, 3H), 6.73 (s, 1H), 6.66–6.61 (m, 2H), 5.34 (s, 2H), 5.14 (s, 2H), 4.27 (s, 2H), 2.29 (s, 3H); MS (ESI) 464 (M+H)$^+$. Prepared from {4-chloro-2-methyl-6-[3-(quinolin-2-ylmethoxy)-phenoxymethyl]-phenoxy}acetonitrile (example 36c).

EXAMPLE 41x

{2-tert-Butyl-6-[3-(quinolin-2-ylmethoxy)-phenoxymethyl]-phenoxy}-acetic acid $^1$H NMR (300 MHz, CD$_3$OD) d 8.33 (d, 1H), 8.01 (d, 1H), 7.90 (d, 1H), 7.80–7.55 (m, 3H), 7.35–7.28 (m, 2H), 7.15–7.01 (m, 2H), 6.71 (s, 1H), 6.60 (d, 2H), 5.40 (s, 2H), 5.10 (s, 2H), 4.40 (s, 2H), 1.41 (s, 9H); MS (ESI) 472 (M+H)$^+$. Prepared from {2-tert-butyl-6-[3-(quinolin-2-ylmethoxy)-phenoxymethyl]-phenoxy}-acetonitrile (example 36d).

EXAMPLE 41y

{4-Chloro-2-methoxy-6-[3-(quinolin-2-ylmethoxy)-phenoxymethyl]-phenoxy}-acetic acid M.P. 185–190° C., $^1$H NMR (300 MHz, DMSO) d 8.45 (d, 1H), 8.04 (t, 2H), 7.82 (t, 1H), 7.71–7.76 (m, 2H), 7.23 (t, 1H), 7.13 (d, 1H), 7.02 (d, 1H), 6.77 (d, 1H), 6.71–6.67 (m, 2H), 5.38 (s, 2H), 5.28 (s, 2H), 4.62 (s, 2H), 3.86 (s, 3H); MS (ESI) 480 (M+H)$^+$. Prepared from {4-chloro-2-methoxy-6-[3-(quinolin-2-ylmethoxy)-phenoxymethyl]-phenoxy}-acetonitrile (example 36e).

EXAMPLE 41z

2-[3-(Quinolin-2-ylmethoxy)-phenoxymethyl]-benzoic acid $^1$H NMR (300 MHz, CDCl$_3$) δ 8.13 (d, 1 µl), 8.03 (d, 1H), 7.79 (d, 1H), 7.70–7.41 (m, 5H), 7.10 (t, 1H), 6.67 (s, 1H), 6.58 (d, 2H), 5.51 (s, 2H), 5.36 (s, 2H); MS (ESI) 386 (M+H)$^+$. Prepared from 2-[3-(quinolin-2-ylmethoxy)-phenoxymethyl]-benzonitrile (example 36f).

EXAMPLE 41aa

2-[3-(Quinolin-2-ylmethoxy)-phenoxymethyl]-thiophene-2-carboxylic acid $^1$H NMR (300 MHz, CD$_3$OD) d 8.36 (d, 1H), 8.04 (d, 1H), 7.94 (d, 1H), 7.78 (t, 1H), 7.70 (d, 1H), 7.61 (t, 1H), 7.48 (d, 1H), 7.13–7.19 (m, 2H), 6.70 (s, 1H), 6.61 (dt, 2H), 5.46 (s, 2H), 5.32 (s, 2H); MS (ESI) 392 (M+H)$^+$. Prepared from methyl 2-[3-(quinolin-2-ylmethoxy)-phenoxymethyl]-thiophene-2-carboxylate (example 36 g).

EXAMPLE 41ab

{2-[3-(Quinolin-2-ylmethoxy)-phenoxymethyl]-phenyl}-acetic acid $^1$H NMR (300 MHz, CDCl$_3$) δ 8.20–8.11 (m, 2H), 7.83–7.52 (m, 4H), 7.40–7.27 (m, 4H), 7.18–7.10 (m, 1H), 6.67–6.46 (m, 3H), 5.35 (s, 2H), 5.12 (s, 2H), 3.76 (s, 2H); MS 400 (M+H)$^+$. Prepared from {2-[3-(quinolin-2-ylmethoxy)-phenoxymethyl]-phenyl}-acetonitrile (example 38).

EXAMPLE 41ac

{4-Chloro-2-methyl-6-[3-(quinolin-2-ylmethoxy)-benzyloxymethyl]-phenoxy}-acetic acid $^1$H NMR (300 MHz, CDCl$_3$) δ 8.19 (d, 1H), 8.09 (d, 1H), 7.82 (d, 1H), 7.78–7.65 (m, 2H), 7.75 (dd, 1H), 7.31–26 (dd, 1H), 7.18 (dd, 1H), 7.05–6.92 (m, 4H), 5.20 (s, 2H), 4.26 (s, 2H), 4.23 (s, 2H), 4.15 (s, 2H), 2.12 (s, 3H); MS (ESI) 478, 480 (M+H;Cl)$^+$. Prepared from (example 52).

EXAMPLE 41ad

{2-[3-(4-Chloro-quinolin-2-ylmethoxy)-phenoxymethyl]-6-methyl-phenoxy}-acetic acid $^1$H NMR (300 MHz, DMSO) δ 8.20 (dd, 1H), 8.08 (d, 1H), 7.91–7.74 (m, 3H), 7.24–7.15 (m, 3H), 7.01 (t, 1H), 6.74 (t, 1H), 6.66–6.59 (m, 2H), 5.32 (s, 2H), 5.12 (s, 3H), 4.43 (s, 2H), 2.24 (s, 3H); MS (ESI) 464 (M+H)$^+$. Prepared from {2-[3-(4-chloro-quinolin-2-ylmethoxy)-phenoxymethyl]-6-methyl-phenoxy}-acetonitrile (example 39n).

EXAMPLE 41ae

{2-[3-(7-Chloro-quinolin-2-ylmethoxy)-phenoxymethyl]-6-methyl-phenoxy}-acetic acid $^1$H NMR (300 MHz, DMSO) δ 8.42 (d, 1H), 8.03–8.00 (m, 2H), 7.68–7.60 (m, 2H), 7.27–7.07 (m, 3H), 6.94 (t, 1H), 6.70 (d, 1H), 6.59 (dd, 2H), 5.31 (s, 2H), 5.18 (s, 2H), 2.20 (s, 3H); MS (ESI) 464 (M+H)$^+$. Prepared from {2-[3-(7-chloro-quinolin-2-ylmethoxy)-phenoxymethyl]-6-methyl-phenoxy}-acetonitrile (example 39o).

EXAMPLE 41af

{2-[3-(6-Methoxy-quinolin-2-ylmethoxy)-phenoxymethyl]-6-methyl-phenoxy}-acetic acid $^1$H NMR (300 MHz, CDCl$_3$) δ 8.07 (t, 2H), 7.60 (d, 1H), 7.36 (dd, 1H), 7.27–7.24 (m, 1H), 7.15 (d, 1H), 7.05–7.00 (m, 3H), 6.79 (s, 1H), 6.58 (d, 1H), 6.49 (dd, 1H), 5.31 (s, 2H), 5.14 (s, 2H), 4.54 (s, 2H), 3.90 (s, 3H), 2.30 (s, 3H); MS (ESI) 460 (M+H)$^+$. Prepared from {2-[3-(6-methoxy-quinolin-2-ylmethoxy)-phenoxymethyl]-6-methyl-phenoxy}-acetonitrile (example 39p).

EXAMPLE 41ag

{2-[4-Bromo-3-(quinolin-2-ylmethoxy)-phenoxymethyl]-6-methyl-phenoxy}-acetic acid $^1$H NMR (300 MHz, DMSO) δ 8.42 (d, 1H), 8.00–7.97 (m, 2H), 7.79–7.70 (m, 2H), 7.63–7.58 (m, 1H), 7.46 (d, 1H), 7.20–7.13 (m, 2H), 6.99–6.95 (m, 2H), 6.59 (dd, 1H), 5.42 (s, 2H), 5.17 (s, 2H), 4.30 (s, 2H), 2.22 (s, 3H); MS (ion spray) 508 (M+H)$^+$. Prepared from ethyl {2-[4-bromo-3-(quinolin-2-ylmethoxy)-phenoxymethyl]-6-methyl-phenoxy}-acetate (example 54).

EXAMPLE 41ah

{2[2-Bromo-5-(quinolin-2-ylmethoxy)-phenoxymethyl]-6-methyl-phenoxy}-acetic acid $^1$H NMR (300 MHz, CDCl$_3$) δ 8.18–8.15 (m, 2H), 7.81–7.72 (m, 2H), 7.63–7.53 (m, 2H), 7.37 (d, 1H), 7.28 (d, 1H), 7.17–7.13 (m, 1H), 7.09–7.03 (m, 1H), 6.91 (d, 1H), 6.42 (dd, 2H), 5.36 (s, 2H), 5.32 (s, 2H), 4.63 (s, 2H), 2.32 (s, 3H); MS (ion spray) 508 (M+H)$^+$. Prepared from ethyl {2-[2-bromo-5-(quinolin-2-ylmethoxy)-phenoxymethyl]-6-methyl-phenoxy}-acetate (example 54).

EXAMPLE 41ai

{2-Methyl-6-[3-methyl-5-(quinolin-2-ylmethoxy)-phenoxymethyl]-phenoxy}-acetic acid $^1$H NMR (300 MHz, CDCl$_3$) δ 8.21–8.14 (m, 2H), 7.82–7.66 (m, 3H), 7.58 (t, 1H), 7.27–7.24 (m, 1H), 7.17 (d, 1H), 7.04 (t, 1H), 6.60 (s, 1H), 6.43 (s, 1H), 6.37 (s, 1H), 5.24 (s, 2H), 5.13 (s, 2H), 4.60 (s, 2H), 2.32 (s, 3H), 2.19 (s, 3H); MS (ion spray) 444 (M+H)$^+$. Prepared from ethyl {2-methyl-6-[3-methyl-5-(quinolin-2-ylmethoxy)-phenoxymethyl]-phenoxy}-acetate (example 36j).

EXAMPLE 41aj

{2-[2-Acetyl-5-(quinolin-2-ylmethoxy)-phenoxymethyl]-6-methyl-phenoxy}-acetic acid $^1$H NMR (300 MHz, DMSO) δ 8.39 (d, 1H), 8.00–7.96 (m, 2H), 7.76 (t, 1H), 7.67–7.57 (m, 3H), 7.28 (d, 1H), 7.14 (d, 1H), 7.02–7.00 (m, 2H), 6.69 (d, 1H), 5.43 (s, 2H), 5.35 (s, 2H), 4.27 (s, 2H), 2.39 (s, 3H), 2.23 (s, 3H); MS (ion spray) 472 (M+H)$^+$. Prepared from ethyl {2-[2-acetyl-5-(quinolin-2-ylmethoxy)-phenoxymethyl]-6-methyl-phenoxy}-acetate (example 59).

EXAMPLE 41ak

{4-Chloro-2-methyl-6-[3-(2-pyridin-2-yl-ethoxy)-phenoxymethyl]-phenoxy}-acetic acid $^1$H NMR (300 MHz, DMSO) δ 8.52 (d, 1H), 7.73 (m, 1H), 7.26 (m, 5H), 6.56 (m, 3H), 5.12 (s, 2H), 4.48 (s, 2H), 4.34 (t, 2H), 3.17 (t, 2H), 2.26 (s, 3H). MS (ESI) 428 (M+H)$^+$. Prepared from {4-chloro-2-methyl-6-[3-(2-pyridin-2-yl-ethoxy)-phenoxymethyl]-phenoxy}-acetonitrile (example 36k).

EXAMPLE 41al

{2-[3-(Benzooxazol-2-ylaminomethyl)-phenoxymethyl]-6-methyl-phenoxy}-acetic acid $^1$H NMR (300 MHz, DMSO) δ 8.48 (bs, 1H), 7.12 (m, 11H), 5.14 (s, 2H), 4.46 (m, 4H), 2.26 (s, 3H). MS (ESI) 419 (M+H)$^+$. Prepared from {2-[3-(benzooxazol-2-ylaminomethyl)-phenoxymethyl]-6-methyl-phenoxy}-acetonitrile (example 35d).

EXAMPLE 41am

{2-[3-(Benzooxazol-2-ylaminomethyl)-phenoxymethyl]-4-chloro-6-methyl-phenoxy}-acetic acid $^1$H NMR (300 MHz, DMSO) δ 8.47 (bt, 1H), 7.28 (m, 5H), 7.02 (m, 5H), 5.14 (s, 2H), 4.49 (d, 2H), 4.46 (s, 2H), 2.26 (s, 3H). MS (ESI) 453 (M+H)$^+$. Prepared from {2-[3-(benzooxazol-2-ylaminomethyl)-phenoxymethyl]-4-chloro-6-methyl-phenoxy}-acetonitrile (example 36l).

EXAMPLE 41an

{2-[3-[(4-Chloro-quinolin-2-ylmethoxymethyl)-phenoxymethyl]-6-methyl-phenoxy}-acetic acid $^1$H NMR (300 MHz, DMSO) δ 8.20 (d, 1H), 8.05 (d, 1H), 7.81 (m, 3H), 7.25 (m, 2H), 7.12 (m, 1H), 7.00 (m, 4H), 5.21 (s, 2H), 4.77 (s, 2H), 4.62 (s, 2H), 4.15 (s, 2H), 2.24 (s, 3H). MS (ESI) 478 (M+H)$^+$. Prepared from {2-[3-(4-chloro-quinolin-2-ylmethoxymethyl)-phenoxymethyl]-6-methyl-phenoxy}-acetonitrile (example 35e).

EXAMPLE 41ao

{2-[3-(6-Methoxy-quinolin-2-ylmethoxymethyl)-phenoxyethyl]-6-methyl-phenoxy}-acetic acid $^1$H NMR (300 MHz, CDCl$_3$) δ 8.18 (d, 1H), 8.10 (d, 1H), 7.64 (d, 1H), 7.36 (m, 2H), 7.26 (m, 3H), 7.12 (m, 2H), 6.98 (m, 2H), 5.24 (s, 2H), 4.73 (s, 2H), 4.69 (s, 2H), 4.62 (s, 2H), 3.93 (s, 3H), 2.38 (s, 3H). MS (ESI) 474 (M+H)$^+$. Prepared from {2-[3-(6-methoxy-quinolin-2-ylmethoxymethyl)-phenoxymethyl]-6-methyl-phenoxy}-acetonitrile (example 35f).

EXAMPLE 41ap

{2-Methyl-6-[3-(quinolin-2-ylmethoxymethyl)-phenoxymethyl]-phenoxy}-acetic acid $^1$H NMR (300. MHz, CDCl$_3$) δ 8.30 (d, 1H), 8.18 (d, 1H), 7.85 (d, 1H), 7.74 (m, 2H), 7.58 (m, 1H), 7.38 (d, 1H), 7.28 (m, 3H), 7.12 (m, 1H), 6.99 (m, 2H), 5.24 (s, 2H), 4.78 (s, 2H), 4.71 (s, 2H), 4.63 (s, 2H), 2.39 (s, 3H). MS (ESI) 444 (M+H)$^+$. Prepared from {2-methyl-6-[3-(quinolin-2-ylmethoxymethyl)-phenoxymethyl]-phenoxy}-acetonitrile (example 35 g).

EXAMPLE 41aq

{2-Methyl-6-[3-(pyridin-4-ylmethoxy)-phenoxymethyl]-phenoxy}-acetic acid $^1$H NMR (300 MHz, DMSO) δ 8.57 (bs, 2H), 7.44 (m, 2H), 7.22 (m, 3H), 7.07 (m, 1H), 6.69 (m, 1H), 6.61 (m, 2H), 5.15 (s, 2H), 5.13 (s, 2H), 4.47 (s, 2H), 2.27 (s, 3H). MS (ESI) 380 (M+H)$^+$. Prepared from {2-methyl-6-[3-(pyridin-4-ylmethoxy)-phenoxymethyl]-phenoxy}-acetonitrile (example 39q).

EXAMPLE 41ar

{2-Methyl-6-[3-(pyridin-2-ylmethoxy)-phenoxymethyl]-phenoxy}-acetic acid $^1$H NMR (300 MHz, DMSO) δ 8.58 (bd, 1H), 7.83 (m, 1H), 7.50 (d, 1H), 7.34 (m, 1H), 7.21 (m, 3H), 7.05 (m, 1H), 6.64 (m, 3H), 5.14 (s, 4H), 4.38 (s, 2H), 2.26 (s, 3H). MS (ESI) 380 (M+H)$^+$. Prepared from {2-methyl-6-[3-(pyridin-2-ylmethoxy)-phenoxymethyl]-phenoxy}-acetonitrile (example 39r).

EXAMPLE 41as

{2-Methyl-6-[3-(pyridin-3-ylmethoxy)-phenoxymethyl]-phenoxy}-acetic acid $^1$H NMR (300 MHz, DMSO) δ 8.67 (s, 1H), 8.55 (bd, 1H), 7.86 (d, 1H), 7.43 (m, 1H), 7.28 (m, 3H), 7.07 (m, 1H), 6.70 (s, 1H), 6.62 (m, 2H), 5.13 (s, 4H), 4.47 (s, 2H), 2.27 (s, 3H). MS (ESI) 380 (M+H)$^+$. Prepared from {2-methyl-6-[3-(pyridin-3-ylmethoxy)-phenoxymethyl]-phenoxy}-acetonitrile (example 39s).

EXAMPLE 41at

{2-[3-(6,7-Dichloro-quinolin-2-ylmethoxy)-phenoxymethyl]-6-methyl-phenoxy}-acetic acid $^1$H NMR (300 MHz, DMSO) δ 8.44 (m, 2H), 8.30 (s, 1H), 7.76 (d, 1H), 7.22 (m, 3H), 7.04 (m, 1H), 6.72 (m, 1H), 6.63 (m, 2H), 5.35 (s, 2H), 5.13 (s, 2H), 4.46 (s, 2H), 2.26 (s, 3H). MS (ESI) 498 (M+H)$^+$. Prepared from {2-[3-(6,7-dichloro-quinolin-2-ylmethoxy)-phenoxymethyl]-6methyl-phenoxy}-acetonitrile (example 39t).

EXAMPLE 41au

Ethyl 4-benzyloxy-2-[3-(2-carboxymethoxy-3-methyl-benzyloxy)-benzyloxy]-6-methyl; benzoate $^1$H NMR (300 MHz, DMSO) δ 7.31 (m, 8H), 7.06 (m, 2H), 6.96 (m, 2H), 6.65 (d, 1H), 6.54 (d, 1H), 5.12 (d, 6H), 4.48 (s, 2H), 4.22 (q, 2H), 2.28 (s, 3H), 2.19 (s, 3H), 1.21 (t, 3H). MS (ESI) 571 (M+H)$^+$. Prepared from ethyl 4-benzyloxy-2-[3-(2-cyanomethoxy-3-methyl-benzyloxy)-benzyloxy]-6-methyl-benzoate (example 64b).

EXAMPLE 41av

4-Benzyloxy-2-[3-(2-carboxymethoxy-3-methyl-benzyloxy-benzyloxy]-6-methyl-benzoic acid $^1$H NMR (300 MHz, DMSO) δ 7.32 (m, 8H), 7.02 (m, 4H), 6.64 (d, 1H), 6.52 (d, 1H), 5.13 (m, 6H), 4.48 (s, 2H), 2.28 (s, 3H), 2.22 (s, 3H). MS (ESI) 543 (M+H)$^+$. Prepared from ethyl 4-benzyloxy-2-[3-(2-carboxymethoxy-3-methyl-benzyloxy)-benzyloxy]-6-methyl-benzoate (example 41au).

EXAMPLE 41aw

{2-Methyl-6-[3-(1,3,3-trimethyl-2-oxo-2,3-dihydro-1H-indol-6-yloxymethyl)-phenoxymethyl]-phenoxy}-acetic acid $^1$H NMR (300 MHz, DMSO) δ 7.21 (m, 5H), 6.99 (m, 3H), 6.75 (d, 1H), 6.64 (dd, 1H), 5.24 (s, 2H), 5.07 (s, 2H), 4.12 (s, 2H), 3.10 (s, 3H), 2.25 (s, 3H), 1.21 (s, 6H). MS (ESI) 476 (M+H)$^+$. Prepared from {2-methyl-6-[3-(1,3,3-trimethyl-2-oxo-2,3-dihydro-1H-indol-6-yloxymethyl)-phenoxymethyl]-phenoxy}-acetonitrile (example 64c).

EXAMPLE 41ax

7-[3-(quinolin-2-ylmethoxy)-phenoxymethyl]-benzofuran-2-carboxylic acid $^1$H NMR (300 MHz, CD$_3$OD) d 8.36 (dd, 1H), 8.03 (dd, 1H), 7.94 (dd, 1H), 7.61–7.78 (m, 4H), 7.45–7.49 (m, 2H), 7.16–7.29 (m, 2H), 6.77 (s, 1H), 6.67 (dt, 2H), 5.42 (s, 2H), 5.32 (s, 2H); MS (ESI) 426 (M+H)$^+$. Prepared from ethyl 7-[3-(quinolin-2-ylmethoxy)-phenoxymethyl]-benzofuran-2-carboxylate (example 36i).

EXAMPLE 41ay

{2-Methyl-6-[3-(2-phenyl-thiazol-4-ylmethoxy)-phenoxymethyl]-phenoxy}-acetic acid $^1$H NMR (300 MHz, DMSO): δ 7.92 (m, 2H), 7.77 (s, 1H), 7.47 (m, 3H), 7.20 (m, 1H), 7.15 (m, 2H), 6.98 (t, 1H), 6.72 (t, 1H), 6.60 (m, 2H), 5.15 (s, 2H), 5.14 (s, 2H), 4.15 (s, 2H), 2.23 (s, 3H); MS (ESI) 462 (M+H)$^+$. Prepared from {2-methyl-6-[3-(2-phenyl-thiazol-4-ylmethoxy)-phenoxymethyl]-phenoxy}-acetonitrile (example 39u).

EXAMPLE 42

(4-Chloro-2,6-dimethyl-phenoxy)-acetonitrile

4-Chloro-2,6-dimethylphenol (5.0 g, 32 mmol), bromoacetonitrile (2.2 mL, 32 mmol) and potassium carbonate (6.6 g, 48 mmol) are combined with acetone (50 mL) and heated at reflux for 18 h. The reaction is filtered, concentrated and the residue partitioned between dichloromethane and water. The organic phase is washed with 1N HCl and water and is then dried over magnesium sulfate, concentrated and purified by column chromatography (silica, 10% ethyl acetate in hexanes) to provide the title compound. MS (EI) 195 (M)$^+$, Cl pattern.

EXAMPLE 42a (2-tert-Butyl-6-methylphenoxy)-acetonitrile

The title compound is prepared using essentially the same procedure used in example 42 except using 2-tert-butyl-6-methylphenol in place of 4-chloro-2,6-dimethylphenol. MS (EI) 203 (M+)$^+$.

EXAMPLE 42b

Ethyl (2,6-dimethyl-phenoxy)-acetate

The title compound is prepared using essentially the same procedure used in example 42 except using 2,6-dimethylphenol in place of 4-chloro-2,6-dimethylphenol and ethyl bromoacetate in place of bromoacetonitrile.

EXAMPLE 43

(2-Bromomethyl-4-chloro-6-methyl-phenoxy)-acetonitrile (4-Chloro-2,6-dimethyl-phenoxy)-acetonitrile (700 mg, 3.6 mmol, example 42), N-bromosuccinimide (510 mg, 2.9 mmol) and benzoyl peroxide (72 mg, 0.29 mmol) are heated at reflux in carbon tetrachloride (10 mL) for 16 h. The reaction is cooled, filtered and the filtrate is concentrated and purified by column chromatograpy (silica, 5% ethyl acetate in hexanes) to provide the title compound. MS (EI) 273, 275(M)$^+$, Br pattern.

The following compounds are prepared using essentially the same procedure used in example 43 except using the cited methyl analog in place of (4-chloro-2,6-dimethyl-phenoxy)-acetonitrile.

EXAMPLE 43a (2-Bromomethyl-6-tert-butyl phenoxy)-acetonitrile

MS (EI) 281 (M+)$^+$. Prepared from (2-tert-butyl-6-methylphenoxy)-acetonitrile (example 42a).

EXAMPLE 43b

Ethyl (2-bromomethyl-6-methyl-phenoxy)-acetate

Prepared from ethyl (2,6-dimethyl-phenoxy)-acetate (example 42b).

EXAMPLE 44

5-Chloro-2-hydroxy-3-methoxy-benzaldehyde

A solution of sulfuryl chloride (15 mL, 190 mmol) in toluene (20 mL) is added dropwise over 1.5 h to a solution of o-vanillin (25.0 g, 164 mmol) in toluene (90 mL) and the reaction is then stirred 16 h. Water (30 mL) is added over 10 minutes with ice-bath cooling. The solid is filtered, washed with water and dried to provide the title compound. MS (EI) 186 (M)+.

EXAMPLE 45

4-Chloro-2-methyl-1-oxo-quinoline mCPBA 70% pure (6.9 g, 29 mmol) is added to a solution of 4-chloroquinaldine (5.1 g, 29 mmol) in dichloroethane and heated to 50° C. for 4 h. The reaction is concentrated and partitioned between ethyl acetate and aqueous potassium carbonate. The organic phase is washed with additional aqueous potassium carbonate, water and is then dried over magnesium sulfate. The solution is filtered and concentrated to yield the title compound which is used without further purification. MS (ESI) 194 (M+H)+.

The following compounds are prepared using essentially the same procedure used in example 45 except using the cited quinaldine in place of 4-chloroquinaldine.

EXAMPLE 45a

7-Chloro-2-methyl-1-oxo-quinoline

MS (ESI) 194 (M+H)+. Prepared from 7-chloroquinaldine.

EXAMPLE 45b

6-Methoxy-2-methyl-1-oxo-quinoline

MS (ESI) 190 (M+H)+. Prepared from 6-methoxyquinaldine.

EXAMPLE 45c

5-ethyl-2-methyl-pyridine 1-oxide

MS (ESI) 138 (M+H)+. Prepared from 5-ethyl-2-methylpyridine.

EXAMPLE 46

4-Chloroquinolin-2-ylmethyl chloride

4-Chloro-2-methyl-1-oxo-quinoline (4.3 g, 22 mmol) is dissolved in chloroform (200 mL) and p-toluenesulfonyl chloride (3.7 g, 20 mmol) is added and the reaction is heated at 65° C. for 24 h. The reaction is allowed to cool and then concentrated and partitioned between ethyl acetate and 10% aqueous potassium carbonate. The organic phase is dried over magnesium sulfate, concentrated and purified by column chromatography (silica, 60% dichloromethane in hexanes) to provide the title compound. MS (ESI) 212 (M+H)+.

The following compounds are prepared using essentially the same procedure used in example 45 except using the cited quinaldine in place of 4-chloroquinaldine.

EXAMPLE 46a

7-Chloroquinolin-2-ylmethyl chloride

MS (ESI) 212 (M+H)+. Prepared from 7-chloro-2-methyl-1-oxo-quinoline (example 45a).

EXAMPLE 46b

6-Methoxyquinolin-2-ylmethyl chloride

MS (ESI) 208 (M+H)+. Prepared from 6-methoxy-2-methyl-1-oxo-quinoline (example 45b).

EXAMPLE 47

2-{3-[5-Chloro-3-methyl-2-(1H-tetrazol-5-yl-methoxy)-benzyloxy]-phenoxymethyl}-quinoline Sodium azide (395 mg, 6.1 mmol) and ammonium chloride (325 mg, 6.1 mmol) are added to a solution of {4-chloro-2-methyl-6-[3-(quinolin-2-ylmethoxy)-phenoxymethyl]-phenoxy}-acetonitrile (300 mg, 0.68 mmol, example 36c) in DMF (2 mL) and heated at 110° C. for 2 h. The reaction is then cooled and poured into a 1 N sodium hydroxide solution (20 mL) with the formation of a solid. This mixture is then washed with ether (4×) and the ether is discarded. The remaining aqueous solution contains a solid which is filtered. This solid is dissolved in 10% ethanol water (250 mL) and the pH is lowered to about 5 with 2N HCl. A solid precipitates which is filtered to provide the title compound. m.p. 181–184° C.; $^1$H NMR (300 MHz, DMSO-$d_6$) d 8.40 (d, 1H), 8.01–7.97 (m, 2H), 7.77 (dd, 1H), 7.66–7.60 (m, 2H), 7.33 (d, 2H), 7.18 (dd, 1H), 6.72 (dd, 1H), 6.65 (dd, 1H), 6.59 (dd, 1H), 5.33 (s, 2H), 5.27 (s, 2H), 5.07 (s, 2H), 2.24 (s, 3H); MS (EST) 488, 490 (M+H;Cl)+.

EXAMPLE 48

[3-(Quinolin-2-ylmethoxy)-phenyl]-methanol

2-Chloromethylquinoline hydrochloride (11.6 g, 54 mmol), 3-hydroxybenzyl alcohol (6.7 g, 54 mmol) and potassium carbonate (16 g, 116 mmol) are heated in DMF (45 mL) at 50° C. for 14 h. The temperature is increased to 80° C. and heated an additional 24 h. The reaction is cooled and added to water, filtered and the solid is washed with water to yield a semi-pure product. The residue is dissolved in ethyl acetate, dried over magnesium sulfate, filtered and concentrated. The sample is then recrystallized from ethyl acetate and hexanes to provide the title compound. MS (ESI) 266 (M+H)+.

EXAMPLE 49

2-(3-Chloromethyl-phenoxymethyl)-quinoline hydrochloride

Thionyl chloride (0.95 mL, 13 mmol) is added to a solution of [3-(quinolin-2-ylmethoxy)-phenyl]-methanol (2.9 g, 11 mmol, example 48) in dichloromethane (30 mL) and allowed to stir 18 h. The reaction is concentrated in vacuo and azeotroped twice from chloroform to yield the title compound which is used without further purification.

EXAMPLE 50

2-[3-(Quinolin-2-ylmethoxy)-benzyloxy]-6-trifluoromethyl-benzaldehyde

[3-(Quinolin-2-ylmethoxy)-phenyl]-methanol (300 mg, 1.13 mmol, example 48) is dissolved in DMF (6 mL) and sodium hydride (60%, 60 mg, 1.5 mmol) is added and allowed to stir 20 min. 2-Fluoro-6-(trifluoromethyl)benzaldehyde (0.30 mL, 2.2 mmol) is added and the reaction is heated at 90° C. for 5 h. The reaction is partitioned between ethyl acetate (200 mL) and water (200 mL), dried over magnesium sulfate, filtered, concentrated in vacuo and purified by column chromatography (silica, 25% ethyl acetate in hexanes) to provide the title compound; MS (ESI) 438 (M+H)$^+$.

EXAMPLE 51

2-[3-(Quinolin-2-ylmethoxy)-benzyloxy]-6-trifluoromethyl-benzoic acid

A solution of 2-[3-(quinolin-2-ylmethoxy)-benzyloxy]-6-trifluoromethyl-benzaldehyde (46 mg, 0.1 mmol, example 50) in 2-methyl-2-butene (1 mL), t-butanol (2 mL) and water (2 mL) is treated with sodium dihydrogenphosphate dihydrate (153 mg, 1.1 mmol) and sodium chlorite (198 mg, 2.2 mmol). After 45 min. the reaction is partioned between dichloromethane (50 mL) and water (50 mL). The organic layer is dried over magnesium sulfate, filtered and concentrated in vacuo to provide the title compound: m.p. 184–185° C.; $^1$H NMR (300 MHz, CDCl$_3$) δ 8.28 (d, 1H), 8.12 (d, 1H), 7.82–7.75 (m, 2H), 7.66–7.55 (m, 2H), 7.42 (dd, 1H), 7.30–7.27 (m, 2H), 7.16 (d, 1H), 7.07 (dd, 1H), 6.88 (d, 1H), 6.77 (dd, 1H), 5.44 (s, 2H), 5.07 (s, 2H); MS (ESI) 454 (M+H)$^+$.

EXAMPLE 52

4-Chloro-2-methyl-6-[3-(quinolin-2-ylmethoxy)-benzyloxymethyl]-phenoxy}-acetonitrile

[3-(Quinolin-2-ylmethoxy)-phenyl]-methanol (190 mg, 0.72 mmol, example 48) is dissolved in DMF (6 mL) and sodium hydride (60%, 30 mg, 0.75 mmol) is added and allowed to stir for 10 min. (2-Bromomethyl-4-chloro-6-methyl-phenoxy)-acetonitrile (210 mg, 0.78 mmol, example 43) is added and the reaction is allowed to stir 6 h. The reaction is partitioned between ethyl acetate and water and the organic phase is washed with additional water. The organic phase is dried, concentrated and purified by column chromatography (silica, 25% ethyl acetate in hexanes) to provide the title compound. MS (ESI) 458 (M+H)$^+$, Cl pattern.

EXAMPLE 53

Methyl 2-methyl-6-[3-(quinolin-2-ylmethoxy)-benzyloxymethyl]-benzoate

The title compound is prepared using essentially the same procedure used in example 52 except using methyl 2-bromomethyl-6-methyl-benzoate (example 2) in place of (2-bromomethyl-4-chloro-6-methyl-phenoxy)-acetonitrile. MS (ESI) 427 (M+H)$^+$.

EXAMPLE 54

Ethyl {2-[4-bromo-3-(quinolin-2-ylmethoxy)-phenoxymethyl]-6-methyl-phenoxy}-acetate and Ethyl {2-[2-bromo-5-(quinolin-2-ylmethoxy)-phenoxymethyl]-6-methyl-phenoxy}-acetate Ethyl {2-methyl-6-[3-(quinolin-2-ylmethoxy)-phenoxymethyl]-phenoxy}-acetate (350 mg, 0.76 mmol, example 36 h), NBS (150 mg, 0.84 mmol) and benzoyl peroxide (20 mg, 0.08 mmol) are dissolved/suspended in chloroform (7 mL) and heated to reflux for 2 hrs. The reaction is cooled to r.t., filtered, preadsorbed onto silica gel by rotary evaporation. The crude material is purified by flash chromatography (silica, 15% ethyl acetate in hexanes) to give the title compounds in approximately a 1:1 ratio. Regioisomers are determined by NMR NOE data. MS (ion spray) 537 (M+H)$^+$ for both compounds.

EXAMPLE 55

3-Methyl-5-(quinolin-2-ylmethoxy)-phenol 2) 2-(Chloromethyl)-quinoline hydrochloride (1.28 g, 6.0 mmol), orcinol (568 mg, 4.0 mmol), K$_2$CO$_3$ (1.68 g, 12.0 mmol) and a catalytic amount of tetrabutylammonium iodide (~10 mg) are dissolved/suspended in anhyd. DMF (10 mL) and heated at 50° C. overnight. The reaction is cooled to r.t. and partitioned between water (100 mL) and ethyl ether (100 mL). The pH of the aqueous layer is adjusted to ~5 and further extracted with ethyl ether (100 mL). The organic fractions are pooled and washed with brine (2×100 mL), dried over MgSO$_4$, filtered and preadsorbed onto silica gel. The crude preadsorbed material is purified by flash chromatography (silica, 20% ethyl acetate in hexanes) to give the title compound. This product (approx. 80% purity, remainder is 2-methylquinoline) is used without further purification. MS (ESI) 266 (M+H)$^+$.

EXAMPLE 56

2-[3-(Quinolin-2-ylmethoxy)-benzyloxy]-benzaldehyde 2-(3-Chloromethyl-phenoxymethyl)-quinoline (371 mg, 1.3 mmol, example 49) and salicylaldehyde (133 µL, 1.25 mmol) are dissolved in acetone (10 mL). K$_2$CO$_3$ (525 mg, 3.75 mmol) is added and the contents are heated to reflux for 16 hrs. The reaction is cooled to r.t., poured into water (100 mL) and extracted with ethyl ether (3×50 mL). The ether layers are combined and washed with Brine (3×75 mL) and dried over MgSO$_4$. The crude material is preadsorbed onto silica gel and purified by flash chromatography (silica, 20 to 25% ethyl acetate in hexanes) to give the title compound. MS (ion spray) 370 (M+H)$^+$.

EXAMPLE 57

3-{2-[3-(Quinolin-2-ylmethoxy)-benzyloxy]-phenyl}-acrylic acid

2-[3-(Quinolin-2-ylmethoxy)-benzyloxy]-benzaldehyde (110 mg, 0.3 mmol, example 56) is dissolved in pyridine (1 mL). Malonic acid (63 mg, 0.6 mmol) and piperidine (10 µL, 0.1 mmol) are added and the contents are heated to 85° C. for 2 hrs, then at 110° C. for another 2 hrs. The reaction is cooled and placed under a nitrogen stream at 40° C. to remove the pyridine. A small amount of toluene is added and the contents are again placed under a nitrogen stream at 40° C. (repeat). The crude material is purified on silica gel by flash chromatography (silica, 2.5% methanol in dichloromethane) to give the title compound. $^1$H NMR (300 MHz, CDCl$_3$) δ 8.33 (d, 1H), 8.21–8.16 (m, 2H), 7.81–7.70 (m, 3H), 7.56–7.50 (m, 2H), 7.37–7.25 (m, 3H), 7.03–6.93 (m, 4H), 6.50 (d, 1H), 5.48 (s, 2H), 5.14 (s, 2H); MS (ion spray) 412 (M+H)$^+$.

EXAMPLE 58

1-[2-Hydroxy-4-(quinolin-2-ylmethoxy)-phenyl]-ethanone

2',4'-Dihydroxy-acetophenone (912 mg, 6 mmol) and 2-chloromethyl-quinoline hydrochloride (856 mg, 4.0 mmol, example 49) are dissolved in acetonitrile (20 mL). $K_2CO_3$ (1.12 g, 8.0 mmol) is added and the contents are heated to 50° C. for 16 hrs. The reaction is cooled to room temperature, and the solvent is removed by rotary evaporation. The contents are partitioned between ethyl acetate (100 mL) and water (100 mL), the aqueous layer is acidified with 2 N HCl to ~pH 2 and further extracted with ethyl acetate (2×50 mL). All organic fractions are combined and washed with brine (3×150 mL), dried over $MgSO_4$ and concentrated. The crude material is preadsorbed onto silica gel and purified by flash chromatography (silica, 15% ethyl acetate in hexanes) to give the title compound; MS (ion spray) 294 $(M+H)^+$.

EXAMPLE 59

Ethyl {2-[2-acetyl-5-(quinolin-2-ylmethoxy)-phenoxymethyl]-6-methyl-phenoxy}-acetate 1-[2-Hydroxy-4-(quinolin-2-ylmethoxy)-phenyl]-ethanone (185 mg, 0.63 mmol, example 58) is dissolved in 2:1 DMF/acetonitrile (6 mL). Ethyl (2-bromomethyl-6-methyl-phenoxy)-acetate (272 mg, 0.95 mmol, example 43b) and $K_2CO_3$ (177 mg, 1.26 mmol) are added and the contents are heated to 50° C. for 2 days. The reaction is cooled to r.t. and the volume reduced under a nitrogen stream at 40° C. The contents are partitioned between ethyl acetate (50 mL) and water (50 mL). The aqueous layer is further extracted with ethyl acetate (2×50 mL). The organic fractions are combined and washed with brine (3×75 mL), dried over $MgSO_4$ and concentrated. The crude material is dissolved in 1:1 dichloromethane/methanol, preadsorbed onto silica gel, and purified by flash chromatography (silica, 20% ethyl acetate in hexanes) to give the title compound. MS (ion spray) 500 $(M+H)^+$.

EXAMPLE 60

Methyl 2-[3-(quinolin-2-ylmethoxy)-benzyloxy]-benzoate

The free base of 2-(3-chloromethyl-phenoxymethyl)-quinoline hydrochloride (540 mg, 1.7 mmol, example 49) is prepard by partioning the material between ethyl ether and sodium bicarbonate and drying the organic phase with magnesium sulfate. This material is then dissolved with methyl salicylate (260 mg, 1.7 mmol) in DMF (10 mL) at 0° C. and sodium hydride (60%, 65 mg 1.7 mmol) is added. The reaction is brought to room temperature for 15 min. and is then heated at 60° C. for 6 h. The reaction is cooled and partioned between ethyl acetate and a saturated ammonium chloride solution. The organic phase is dried over magnesium sulfate, filtered, concentrated in vacuo and purified by column chromatography (silica, 50 to 80% ether in hexanes) to provide the title compound; MS (ESI) 400 $(M+H)^+$.

The following compounds are prepared using essentially the same procedure used in example 60 except using the cited substituted salicylate in place of methyl salicylate.

EXAMPLE 60a

Methyl 3-methoxy-2-[3-(quinolin-2-ylmethoxy)-benzyloxy]-benzoate

Prepared from methyl 3-methoxysalicylate.

EXAMPLE 60b

Methyl 4-methoxy-2-[3-(quinolin-2-ylmethoxy)-benzyloxy]-benzoate

Prepared from methyl 4-methoxysalicylate.

EXAMPLE 60c

Methyl 5-methoxy-2-[3-(quinolin-2-ylmethoxy)-benzyloxy]-benzoate

Prepared from methyl 5-methoxysalicylate.

EXAMPLE 60d

Methyl 2-methoxy-6-[3-(quinolin-2-ylmethoxy)-benzyloxy]-benzoate

Prepared from methyl 6-methoxysalicylate (example 61).

EXAMPLE 60e

Ethyl 2-methyl-6-[3-(quinolin-2-ylmethoxy)-benzyloxy]-benzoate

MS (ESI) 428 $(M+H)^+$. Prepared from ethyl 6-methylsalicylate (See, Hauser, Frank M., *Synthesis* 1980, 10, 814–15.

EXAMPLE 61

Methyl 6-methoxysalicylate

A mixture of 6-methoxysalicylic acid (10.0 g, 59.5 mmol) in methanol (40 mL) and sulfuric acid (2 mL) is heated at reflux 48 h. Although some acid remains the reaction is concentrated to remove the methanol and partitioned between ethyl acetate and saturated sodium carbonate solution. The organic phase is separated and washed with sodium carbonate until no acid remains by TLC analysis. The organic phase is dried and concentrated to provide the title compound as a low melting solid.

EXAMPLE 62

Methyl 5-[3-(quinolin-2-ylmethoxy)-benzyloxy]-nicotinate

To a solution of 5-hydroxy nicotinic acid methyl ester (200 mg, 1.3 mmol) in DMF (3 mL) is added 60% sodium hydride emulsion (50 mg, 1.2 mmol) and this mixture is stirred 30 minutes. The free base of 2-(3-chloromethyl-phenoxymethyl)-quinoline hydrochloride (350 mg, 1.2 mmol, example 49) is prepard by partioning the material between ethyl ether and sodium bicarbonate and drying the organic phase with magnesium sulfate. A solution of this free base in DMF (2 mL) is added to the alcohol and this mixture is stirred at 25° C. for 16 hours. The solvent is removed in vacuo, dichloromethane (10 mL) and water (5 mL) is added, and this mixture is acidified to pH6 with acetic acid. The organic layer is dried over magnesium sulfate and the solvent removed in vacuo. The residue is purified by flash chromatography (silica, 4% methanol in dichloromethane) to give the title compound. MS (ESI) 401 $(M+H)^+$.

EXAMPLE 63

Ethyl 4-benzyloxy-2-hydroxy-6-methyl-benzoate

To a solution of ethyl-2,4-dihydroxy-6-methyl benzoate (4.22 g, 22 mmol) in acetone (80 mL) is added potassium carbonate (3.0 g, 22 mmol) and benzyl bromide (2.6 mL, 22 mmol) and this mixture is heated under reflux overnight. The cooled reaction is diluted with ethyl acetate (100 mL) and water (100 mL) and the organic layer washed with water (2×80 mL) and brine (2×80 mL). The organic layer is dried over magnesium sulfate and the solvent removed to provide the title compound without further purification. MS (EI) 286 $(M)^+$.

EXAMPLE 63a

Ethyl 2-hydroxy-4methoxy-6-methyl-benzoate

The title compound is prepared using essentially the same procedure used in example 63 except using iodomethane in place of benzyl bromide.

EXAMPLE 64

Ethyl 4-benzyloxy-2-methyl-6-[3-(quinolin-2-yl-methoxy)-benzyloxy]-benzoate

To a solution of ethyl 4-benzyloxy-2-hydroxy-6-methyl-benzoate (5.1 g, 16 mmol, example 63) in DMF (100 mL), with 25° C. water bath cooling, is added 60% sodium hydride emulsion (1.3 g, 32 mmol) over 2 minutes. This mixture is stirred 30 minutes with the cooling bath removed. A solution of 3-(quinolin-2-ylmethoxy)-benzyl chloride hydrochloride (5.1 g, 16 mmol, example 49), in DMF (55 mL) is added and the reaction heated at 60° C. for 6 hours. The solvent is removed in vacuo and the residue purified by flash chromatography (silica, 0.5 to 2% methanol in dichloromethane) to give the title compound. MS (ESI) 534 $(M+H)^+$.

EXAMPLE 64a

Ethyl 4-methoxy-2-methyl-6-[3-(quinolin-2-yl-methoxy)-benzyloxy]-benzoate

The title compound is prepared using essentially the same procedure used in example 64 except using ethyl 2-hydroxy-4methoxy-6-methyl-benzoate (example 63a) in place of ethyl 4-benzyloxy-2-hydroxy-6-methyl-benzoate. MS (ESI) 458 $(M+H)^+$.

EXAMPLE 64b

Ethyl 4-benzyloxy-2-[3-(2-cyanomethoxy-3-methyl-benzyloxy)-benzyloxy]-6-methyl-benzoate The title compound is prepared using essentially the same procedure used in example 64 except using [2-(3-bromomethyl-phenoxymethyl)-6-methyl-phenoxy]-acetonitrile (example 76) in place of 3-(quinolin-2-ylmethoxy)-benzyl chloride hydrochloride. $^1$H NMR (300 MHz, CDCl$_3$) δ 7.30 (m, 8H), 7.12 (m, 1H), 7.06 (bs, 1H), 6.99 (d, 1H), 6.90 (dd, 1H), 6.42 (s, 2H), 5.07 (s, 2H), 5.04 (s, 2H), 5.02 (s, 2H), 4.71 (s, 2H), 4.33 (q, 2H), 2.39 (s, 3H), 2.30 (s, 3H), 1.31 (t, 3H). MS (ESI) 552 $(M+H)^+$.

EXAMPLE 64c

{2-Methyl-6-[3-(1,3,3-trimethyl-2-oxo-2,3-dihydro-1H-indol-6-yloxymethyl)-phenoxymethyl]-phenoxy}-acetonitrile The title compound is prepared using essentially the same procedure used in example 64 except using [2-(3-bromomethyl-phenoxymethyl)-6-methyl-phenoxy]-acetonitrile (example 76) in place of 3-(quinolin-2-ylmethoxy)-benzyl chloride hydrochloride and 6-hydroxy-1,3,3-trimethyl-1,3-dihydro-indol-2-one (example 80) in place of ethyl 4-benzyloxy-2-hydroxy-6-methyl-benzoate. $^1$H NMR (300 MHz, CDCl$_3$) δ 7.32 (dd, 2H), 7.24 (s, 1H), 7.11 (m, 4H), 6.96 (dd, 1H), 6.62 (dd, 1H), 6.54 (d, 1H), 5.10 (s, 2H), 5.06 (s, 2H), 4.72 (s, 2H), 3.18 (s, 3H), 2.39 (s, 3H), 1.34 (s, 6H). MS (ESI) 457 $(M+H)^+$.

EXAMPLE 65

Ethyl 2-hydroxy-6-methyl-4-[3-(quinolin-2-yl-methoxy)-benzyloxy]-benzoate 2,4-Dihydroxy-6-methyl-benzoic acid ethyl ester (315 mg, 1.6 mmol) is combined with 2-(3-chloromethyl-phenoxymethyl)-quinoline hydrochloride (0.51 g, 1.6 mmol, example 49), tetrabutylammonium iodide (55 mg, 0.15 mmol) and potassium carbonate (0.48 g, 3.5 mmol) in acetone (9 mL). The reaction is heated at reflux 48 h. The reaction is partitioned between ethyl acetate and saturated ammonium chloride. The organic phase is washed with brine, dried over magnesium sulfate, filtered and concentrated to yield the crude product. This material is purified by column chromatography (silica, 3% ether in dichloromethane) to the title compound; m.p. 127–128° C., MS (ESI) 444 $(M+H)^+$.

EXAMPLE 66

Ethyl 2-methoxy-6-methyl-4-[3-(quinolin-2-yl-methoxy)-benzyloxy]-benzoate

To a solution of ethyl 2-hydroxy-6-methyl-4-[3-(quinolin-2-ylmethoxy)-benzyloxy]-benzoate (150 mg, 0.34 mmol, example 65) in DMF (5 mL) is added sodium hydride (60%, 14 mg, 0.34 mmol) and the reaction is stirred 20 min. Iodomethane (0.03 mL, 0.5 mmol) is added and the reaction is heated at 50° C. for 7 h. The reaction is concentrated in vacuo and the residue is partioned between dichloromethane and aqueous ammonium chloride. The water layer is back-extracted with dichloromethane, the organic phases are combined, dried over magnesium sulfate, filtered and concentrated to yield crude product. The residue is purified by column chromatography (silica, 10 to 20% ethyl acetate in hexanes to provide the title compound; MS (ESI) 458 (M+H)$^+$.

EXAMPLE 66a

Ethyl 2-benzyloxy-6-methyl-4-[3-(quinolin-2-yl-methoxy)-benzyloxy]-benzoate

The title compound is prepared using essentially the same procedure used in example 66 except using benzyl bromide in place of iodomethane. MS (ESI) 534 (M+H)$^+$.

EXAMPLE 67

4-Benzyloxy-2-methyl-6-[3-(quinolin-2-ylmethoxy)-benzyloxy]-benzoic acid

Ethyl 4-benzyloxy-2-methyl-6-[3-(quinolin-2-yl-methoxy)-benzyloxy]-benzoate (2.4 g, 4.5 mmole, example 64) is added to ethanol (50 ml) and 11N sodium hydroxide (4.4 ml, 44 mmole) and refluxed for 8 hours. The solvent is removed in vacuo and the residue is dissolved in dichloromethane with a small amount of water and is acidified to pH6 with 1N HCl. The organic layer is dried over MgSO$_4$ and the solvent removed in vacuo. The crude product is purified by column chromatography (silica, 1% methanol in dichloromethane) to provide the title compound. m.p. 146–149° C.; $^1$H NMR (300 MHz, CD$_3$OD) d 8.34 (d, 1H), 8.04 (d, 1H), 7.91 (d, 1H), 7.78–7.70 (m, 2H), 7.61 (t, H), 7.37–7.20 (m, 7H), 7.05–6.91 (m, 2H), 6.51 (d, 1H), 6.47 (d, 1H), 5.35 (s, 2H), 5.09 (s, 2H), 5.03 (s, 2H), 2.29 (s, 3H); MS (ESI) 506 (M+H)$^+$.

The following compounds are prepared using essentially the same procedure used in example 67 except using the cited ester in place of ethyl 4-benzyloxy-2-methyl-6-[3-(quinolin-2-ylmethoxy)-benzyloxy]-benzoate.

EXAMPLE 67a

2-Methoxy-6-methyl-4-[3-(quinolin-2-ylmethoxy)-benzyloxy]-benzoic acid $^1$H NMR (300 MHz, CDCl$_3$) δ 8.38 (d, 1H), 8.03 (d, 1H), 7.79 (d, H), 7.70–7.67 (m, 2H), 7.61 (t, H), 7.28 (t, 1H), 7.14 (s, 1H), 7.01 (t, 2H), 6.35 (t, 2H), 5.37 (s, 2H), 5.03 (s, 2H), 3.71 (s, 3H), 2.26 (s, 3H); MS (ESI) 430 (M+H)$^+$. Prepared from ethyl 2-methoxy-6-methyl-4-[3-(quinolin-2-yl-methoxy)-benzyloxy]-benzoate (example 66).

EXAMPLE 67b

2-Benzyloxy-6-methyl-4-[3-(quinolin-2-ylmethoxy)-benzyloxy]-benzoic acid

125–127° C.; $^1$H NMR (300 MHz, CDCl$_3$) δ 8.18 (d, 1H), 7.83 (d, 1H), 7.74–7.55 (m, 3H), 7.40 (s, 5H), 7.39–7.29 (m, 1H), 7.09 (s, 1H), 7.00 (m, 2H), 6.50 (s, 2H), 5.41 (s, 2H), 5.13 (s, 2H), 5.04 (s, 2H), 2.58 (s, 3H); MS (ESI) 506 (M+H)$^+$. Prepared from ethyl 2-benzyloxy-6-methyl-4-[3-(quinolin-2-ylmethoxy)-benzyloxy]-benzoate (example 66a).

EXAMPLE 67c

4-Methoxy-2-methyl-6-[3-(quinolin-2-ylmethoxy)-benzyloxy]-benzoic acid $^1$H NMR (300 MHz, DMSO) δ 8.39 (d, 1H), 8.02–7.96 (m, 2H), 7.79–7.74 (m, 1H), 7.67–7.57 (m, 2H), 7.31–7.25 (m, 1H), 7.16 (s, 1H), 7.02–6.96 (m, 2H), 6.49 (s, 1H), 6.39 (s, 1H), 5.34 (s, 2H), 5.09 (s, 2H), 3.71 (s, 2H), 2.20 (s, 3H); MS (ESI) 429 (M+H)$^+$. Prepared from ethyl 4-methoxy-2-methyl-6-[3-(quinolin-2-ylmethoxy)-benzyloxy]-benzoate (example 64a).

EXAMPLE 68

5-ethyl-2-chloromethyl pyridine

To a solution of 5-ethyl-2-methyl-pyridine-1-oxide (427 mg, 3.11 mmol, example 45c) in CH$_2$Cl$_2$ (2 mL) is added a solution (0.2 mL) of phosphorous (v) trichloride oxide (327 µL) in CH$_2$Cl$_2$ (2 mL). Added simultaneously the remaining phosphorous (v) trichloride oxide solution and a solution of triethylamine (488 µL) in CH$_2$Cl$_2$ (2 mL) at such a rate as to maintain a reflux. After the addition is complete, let reaction mixture cool to 20° C. and diluted with EtOAc. The organic layer is washed with sat. NaHCO$_3$ soln., brine, dried over MgSO$_4$ and concentrated. The residue is purified by flash chromatography (silica, 10% ethyl acetate in dichloromethane) to provide the title compound. MS (ESI) 156 (M+H)$^+$.

EXAMPLE 69

2-(5-Ethyl-pyridin-2-yl)-ethanol

To a cooled solution (−10° C.) of diisopropylamine (2.31 mL, 16.5 mL) in THF (45 mL) is added dropwise (2.5M) n-butyllithium (6.6 mL, 16.5 mmol), let stir 10 min. then cooled to −78° C. To this mixture is added dropwise a solution of 5-ethyl-2-methylpyridine (1.98 mL, 15 mmol) in THF (3 mL) and let stir for 10 min at −78° C. To the reaction mixture is added paraformaldehyde (1.13 g, 37.5 mmol), the cold bath removed and stirring continued for 1 hr. Quenched reaction with H$_2$O, diluted with EtOAc and the organic layer washed with brine, dried over MgSO$_4$ and concentrated. The residue is purified by flash chromatography (silica, 0.5% ammonia/5% methanol/dichloromethane) to give the title compound as a pale yellow oil. MS (EI) 151 (M)$^+$.

EXAMPLE 69a 2-quinolin-2-yl-ethanol

The title compound is prepared using essentially the same procedure used in example 69 except using 2-methyl-quinoline in place of 5-ethyl-2-methylpyridine. MS (ESI) 174 (M+H)$^+$.

EXAMPLE 70

Benzoic acid 3-[2-(5-ethyl-pyridin-2-yl)-ethoxy]-phenyl ester

To a solution of 2-(5-ethyl-pyridin-2-yl)-ethanol (480 mg, 3.17 mmol, example 69) in THF (10 mL) is added resorcinol monobenzoate (630 mg, 2.94 mmol), triphenylphosphine (850 mg, 3.24 mmol) and diethyl azodicarboxylate (510 µL, 3.24 mmol). The resulting mixture is stirred for 1 h then concentrated. The residue is purified by flash chromatography (silica, 35% ethyl acetate in hexane) to give the title compound as a yellow oil. MS (ESI) 348 (M+H)$^+$.

EXAMPLE 70a

Benzoic acid 3-(2-pyridin-2-yl-ethoxy)-phenyl ester

The title compound is prepared using essentially the same procedure used in example 70 except using 2-(2-hydroxyethyl)pyridine in place of 2-(5-ethyl-pyridin-2-yl)-ethanol. MS (ESI) 320 (M+H)$^+$.

EXAMPLE 71

3-[2-(5-ethyl-pyridin-2-yl)-ethoxy]-phenol

To a solution of benzoic acid 3-[2-(5-ethyl-pyridin-2-yl)-ethoxy]-phenyl ester (493 mg, 1.42 mmol, example 70) in 1:1 THF/CH$_3$OH (5 mL) is added 10N NaOH soln. (0.5 mL) and water (50 μL). The reaction mixture is stirred for 15 min then cooled to 5° C., adjusted to pH 7 with 2N HCl soln. and diluted with EtOAc. The organic layer is washed sequentially with brine, sat NaHCO$_3$ soln. then dried over MgSO$_4$ and concentrated. The residue is purified by several triturations with hexane to give the title compound as a crystalline solid. MS (ESI) 244 (M+H)$^+$.

EXAMPLE 71a 3-(2-pyridin-2-yl-ethoxy)-phenol

The title compound is prepared using essentially the same procedure used in example 71 except using benzoic acid 3-(2-pyridin-2-yl-ethoxy)-phenyl ester (example 70a) in place of 3-[2-(5-ethyl-pyridin-2-yl)-ethoxy]-phenyl ester. MS (ESI) 216 (M+H)$^+$.

EXAMPLE 72

[3-(2-Methoxy-ethoxymethoxy)-phenyl]-methanol

To a cooled suspension (0° C.) of 60% NaH (660 mg, 16.5 mmol) in THF (35 mL) is added dropwise a solution of 3-hydroxybenzaldehyde (1.89 g, 15 mmol) in THF (15 mL) and the resulting mixture stirred for 20 min. To the mixture is added 2-methoxyethoxymethyl chloride (1.88 mL, 16.5 mmol) and DMPU (5 mL), the cold bath removed and stirred for 1 hr. The reaction mixture is cooled to 0° C. then slowly added 2M NaBH$_4$ (in triglyme) (3.75 mL, 7.5 mmol) and let stir for 1 hr. Slowly quenched with 2N HCl soln (3.9 mL) and diluted reaction mixture with ether. The organic layer is washed with brine, dried over MgSO$_4$ and concentrated. The residue is purified by flash chromatography (silica, 60% ethyl acetate in hexanes) to give the title compound as a pale yellow oil. MS (EI) 212 (M)$^+$.

EXAMPLE 73

2-[3-(2-Methoxy-ethoxymethoxy)-benzyloxymethyl]-pyridine

To a cooled solution (0° C.) of [3-(2-methoxy-ethoxymethoxy)-phenyl]-methanol (212 mg, 1 mmol, example 72) in THF (3 mL) is added 60% NaH (80 mg, 2 mmol) and the mixture stirred 10 min. Added 2-picolyl chloride hydrochloride (164 mg, 1 mmol) and DMPU (0.8 mL), removed cold bath and let reaction mixture stir for 2 hrs. Quenched reaction with sat NH$_4$Cl soln. and diluted with EtOAc. The organic layer is washed with brine, dried over MgSO$_4$ and concentrated. The residue is purified by flash chromatography (silica, 70% ethyl acetate in hexanes) to give the title compound as a pale yellow oil. MS (ESI) 304 (M+H)$^+$.

The following compounds are prepared using essentially the same procedure used in example 73 except using the cited halide in place of 2-picolyl chloride hydrochloride.

EXAMPLE 73a

2-[3-(2-Methoxy-ethoxymethoxy)-benzyloxymethyl]-quinoline

MS (ESI) 354 (M+H)$^+$. Prepared from 2-(chloromethyl)quinoline hydrochloride.

EXAMPLE 73b

4-Chloro-2-[3-(2-methoxy-ethoxymethoxy)-benzyloxymethyl]-quinoline

MS (ESI) 388 (M+H)$^+$. Prepared from 2-chloromethyl-4-chloroquinoline (example 46).

EXAMPLE 73c

6-Methoxy-2-[3-(2-methoxy-ethoxymethoxy)-benzyloxymethyl]-quinoline

MS (ESI) 384 (M+H)$^+$. Prepared from 2-chloromethyl-6-methoxyquinoline (example 46b).

EXAMPLE 74

3-(Pyridin-2-ylmethoxymethyl)-phenol

To a solution of 2-[3-(2-methoxy-ethoxymethoxy)-benzyloxymethyl]-pyridine (171 mg, 0.56 mmol, example 73) in CH$_3$OH (1.9 mL) is added p-toluenesulfonic acid monohydrate (148 mg, 0.78 mmol). The mixture is heated to 60° C. and stirred for 1.5 hrs, then cooled to room temperature and diluted with EtOAc. The organic layer is washed with sat NaHCO3, brine, then dried over MgSO$_4$ and concentrated to give the title compound as a white crystalline solid. MS (ESI) 216 (M+H)$^+$.

The following compounds are prepared using essentially the same procedure used in example 74 except using the cited MEM ether in place of 2-[3-(2-methoxy-ethoxymethoxy)-benzyloxymethyl]-pyridine.

EXAMPLE 74a 3-(Quinolin-2-ylmethoxymethyl)-phenol

MS (ESI) 266 (M+H)$^+$. Prepared from 2-[3-(2-methoxy-ethoxymethoxy)-benzyloxymethyl]-quinoline (example 73a).

EXAMPLE 74b 3-(4-Chloro-quinolin-2-ylmethoxymethyl)-phenol

MS (ESI) 300 (M+H)$^+$. Prepared from 4-chloro-2-[3-(2-methoxy-ethoxymethoxy)-benzyloxymethyl]-quinoline (example 73b).

EXAMPLE 74c 3-(6-Methoxy-quinolin-2-ylmethoxymethyl)-phenol

MS (ESI) 296 (M+H)$^+$. Prepared from 6-methoxy-2-[3-(2-methoxy-ethoxymethoxy)-benzyloxymethyl]-quinoline (example 73c).

EXAMPLE 75

[2-(3-Hydroxymethyl-phenoxymethyl)-6-methyl-phenoxy]-acetonitrile

To a solution of 3-hydroxybenzyl alcohol (202 mg, 1.63 mmol) in DMF (5.4 mL) is added $K_2CO_3$ (247 mg, 1.79 mmol) and (2-bromomethyl-6-methyl-phenoxy)-acetonitrile (430 mg, 1.79 mmol, example 24). Heated resulting mixture to 60° C. and stirred for 3 hrs then cooled to room temp and diluted with ether. Washed organic layer with water, brine, dried over $MgSO_4$ and concentrated. The residue is purified by flash chromatography (silica, 30% ethyl acetate in hexanes) to give the title compound. MS (EI) 283 (M)$^+$.

EXAMPLE 76

[2-(3-Bromomethyl-phenoxymethyl)-6-methyl-phenoxy]-acetonitrile

To a solution of [2-(3-hydroxymethyl-phenoxymethyl)-6-methyl-phenoxy]-acetonitrile (230 mg, 0.81 mmol, example 75) in THF (3 mL) is added $Ph_3P$ (233 mg, 0.89 mmol) and stirred until homogeneous. Cooled solution to 0° C. then added portionwise NBS (151 mg, 0.85 mmol) and let stir 45 min. Concentrated reaction mixture under reduced pressure. The residue is purified by flash chromatography (silica, 40% $CH_2Cl_2$ in hexanes) to give the title compound as a white crystalline solid. MS (EI) 345, 347 (M)$^+$, Br pattern.

EXAMPLE 77

6-Methoxy-3-methyl-1,3-dihydro-indol-2-one

To a cooled solution (−78° C.) of 6-methoxy-1,3-dihydro-indol-2-one (840 mg, 5.2 mmol, See Quallich, *Synthesis* 1993, 51–53) in THF (20 mL) is added dropwise TMEDA (1.57 mL, 10.4 mL) followed by dropwise addition of 2.5M n-BuLi (4.16 mL, 10.4 mmol). The mixture is allowed to stir for 15 min then warmed to −25° C. Iodomethane (405 μL, 6.5 mmol) is added dropwise and stirred for 20 min. The reaction is quenched with sat $NH_4Cl$ soln, warmed to room temp and diluted with EtOAc. Washed organic layer with sat $NH_4Cl$ soln, brine, dried over $MgSO_4$ and concentrated. The residue is purified by flash chromatography (silica, 45% ethyl acetate in hexanes) to give the title compound. MS (ESI) 178 (M+H)$^+$.

EXAMPLE 78

6-Methoxy-3,3-dimethyl-1,3-dihydro-indol-2-one

To a cooled solution (−78° C.) of 6-methoxy-3-methyl-1,3-dihydro-indol-2-one (679 mg, 3.83 mmol, example 77) in THF (13 mL) is added TMEDA (1.16 mL, 7.66 mmol) followed by dropwise addition of 2.5M n-BuLi (3.06 mL, 7.66 mmol). The mixture is stirred 15 min then warmed to −25° C. Iodomethane (275 μL, 4.40 mmol) is added dropwise and stirred for 30 min. Reaction is quenched with sat $NH_4Cl$ soln, warmed to room temp and diluted with EtOAc. Washed organic layer with sat $NH_4Cl$ soln, brine, dried over $MgSO_4$ and concentrated. The residue is purified by flash chromatography (silica, 35% ethyl acetate in hexanes) to give the title compound as a white crystalline solid. MS (ESI) 192 (M+H)$^+$.

EXAMPLE 79

6-Methoxy-1,3,3-trimethyl-1,3-dihydro-indol-2-one

To a cooled solution (−5°–0° C.) of 6-methoxy-3,3-dimethyl-1,3-dihydro-indol-2-one (600 mg, 3.14 mmol, example 78) in THF (10.5 mL) is added 60% NaH (132 mg, 3.30 mmol) and is stirred for 15 min. Iodomethane (215 μL, 3.45 mmol) is added to the reaction mixture and stirred for 2 hrs. Quenched reaction with sat $NH_4Cl$ soln and diluted with EtOAc. Washed organic layer with sat $NH_4Cl$ soln, brine, dried over $MgSO_4$ and concentrated. The residue is purified by flash chromatography (silica, 30% ethyl acetate in hexanes) to give the title compound as a white crystalline solid. MS (ESI) 206 (M+H)$^+$.

EXAMPLE 80

6-Hydroxy-1,3,3-trimethyl-1,3-dihydro-indol-2-one

To a solution of 6-methoxy-1,3,3-trimethyl-1,3-dihydro-indol-2-one (601 mg, 2.93 mmol, example 79) in acetic acid (880 μL) is added hydrobromic acid (48% in $H_2O$) (8.8 mL). The resulting solution is heated to reflux (105°110° C.), stirred 2 hrs, then cooled to room temp and concentrated under reduced pressure. The residue is dissolved in EtOAc and the organic layer washed with water, brine, dried over $MgSO_4$ and concentrated. The residue is purified by triturating with a small volume of ether to give the title compound as an off white solid. MS (ESI) 192 (M+H)$^+$.

EXAMPLE 81

2-[3-(2-Methoxy-ethoxymethoxy)-benzyloxy]-quinoline

To a suspension of 60% NaH (44 mg, 1.1 mmol) in DMSO (2 mL) is added dropwise a solution of [3-(2-methoxy-ethoxymethoxy)-phenyl]-methanol (212 mg, 1.0 mmol, example 72) in DMSO (1 mL). Let stir 20 min. then added 2-chloroquinoline (180 mg, 1.1 mmol) and heated to 100° C. for 1 hr. Cooled reaction mixture to room temp. and diluted with EtOAc. The organic layer is washed with sat. $NH_4Cl$ soln., brine, dried over $MgSO_4$ and concentrated. The residue is purified by flash chromatography (silica, 25% ethyl acetate in hexanes) to give the title compound as a colorless oil. MS (ESI) 340 (M+H)$^+$.

EXAMPLE 82

Isobutyl 2-[3-(methoxy)-phenylsulfanylmethyl]-6-methyl-benzoate

A 10N solution of sodium hydroxide (0.32 mL, 3.2 mmol) is added slowly to a solution of 3-methoxybenzenethiol (0.42 g, 3.0 mmol) in isobutanol (2 mL) followed by a solution of isobutyl 2-bromomethyl-6-methyl-benzoate (0.96 g, 3.3 mmol, example 2) in isobutanol (2 mL). The reaction is allowed to stir 15 min and is then partitioned between ethyl acetate and dilute aqueous HCl. The organic phase is washed with water, dried over magnesium sulfate, concentrated and purified by column chromatography

EXAMPLE 83

Isobutyl 2-[3-(hydroxy)-phenylsulfanylmethyl]-6-methyl-benzoate

Boron tribromide (1.3 mL, 1.0 M in dichloromethane, 1.3 mmol) is added to a solution of isobutyl 2-[3-(methoxy)-phenylsulfanylmethyl]-6-methyl-benzoate (194 mg, 0.56 mmol, example 82) in dichloromethane (3 mL) at 0° C. and then the reaction is stirred at room temperature 3 h. The reaction is then partitioned between sodium bicarbonate solution and ethyl acetate. The organic phase is dried over magnesium sulfate, concentrated and purified by column chromatography (silica, 15% ethyl acetate in hexanes) to provide the title compound. MS (EI) 330 (M)$^+$.

EXAMPLE 84

Isobutyl 2-methyl-6-[3-(quinolin-2-ylmethoxy)-phenylsulfanylmethyl]-benzoate

The free base of 2-(chloromethyl)quinoline hydrochloride (148 mg, 0.69 mmol) is prepard by partioning the material between ethyl ether and sodium bicarbonate and drying the organic phase with magnesium sulfate. This material is then dissolved with isobutyl 2-[3-(hydroxy)-phenylsulfanylmethyl]-6-methyl-benzoate (220 mg, 0.67 mmol, example 83) in DMF (2 mL) at 0° C. and sodium hydride (60%, 27 mg 0.67 mmol) is added. The reaction is allowed to stir 16 h and is then partitioned between ethyl acetate and water. The organic phase is washed with water (3×), dried over magnesium sulfate, concentrated and purified by column chromatography (silica, 10% ethyl acetate in hexanes) to provide the title compound. $^1$H NMR (300 MHz, CDCl$_3$) δ 8.19 (d, 1H), 8.08 (d, 1H), 7.83 (d, 1H), 7.74 (t, 1H), 7.63 (d, 1H), 7.55 (t, 1H), 7.18–7.07 (m, 4H), 6.99 (d, 1H), 6.89 (d, 1H), 6.82 (dd, 1H), 5.33 (s, 2H), 4.18 (s, 2H), 4.10 (d, 2H), 2.36 (s, 3H), 2.07–2.01 (m, 1H), 0.98 (d, 6H); MS (ESI) 472 (M+H)$^+$.

EXAMPLE 85

Isobutyl 2-methyl-6-[3-(quinolin-2-ylmethoxy)-phenylsulfinylmethyl]-benzoate m-Chloroperbenzoic acid (<86%, 34 mg, 0.17 mmol) is added to a solution of isobutyl 2-methyl-6-[3-(quinolin-2-ylmethoxy)-phenylsulfanylmethyl]-benzoate (80 mg, 0.17 mmol, example 84) in dichloromethane (1 mL) and the reaction is stirred overnight. The reaction is partitioned between ethyl acetate and sodium bicarbonate and the organic phase is washed with additional bicarbonate solution, dried over magnesium sulfate, concentrated and purified by column chromatography (silica, 40% ethyl acetate in hexanes) to provide the title compound. MS (ESD) 488 (M+H)$^+$.

EXAMPLE 86

Isobutyl 2-methyl-6-[3-(quinolin-2-ylmethoxy)-phenylsulfonylmethyl]-benzoate m-Chloroperbenzoic acid (<86%, 62 mg, 0.31 mmol) is added to a solution of isobutyl 2-methyl-6-[3-(quinolin-2-ylmethoxy)-phenylsulfanylmethyl]-benzoate (73 mg, 0.16 mmol, example 85) in dichloromethane (1 mL) and the reaction is stirred overnight. The reaction is partitioned between ethyl acetate and sodium bicarbonate and the organic phase is washed with additional bicarbonate solution, dried over magnesium sulfate, concentrated and purified by column chromatography (silica, 30% ethyl acetate in hexanes) to provide the title compound. MS (ESI) 504 (M+H)$^+$.

EXAMPLE 87

(1-Quinolin-2-ylmethyl-1H-imidazol-4-yl)-methanol and (3-quinolin-2-ylmethyl-3H-imidazol-4-yl)-methanol 2-Chloromethyl-quinoline hydrochloride (2.24 g, 10.5 mmol), 4-(hydroxymethyl)-imidazole hydrochloride (1.35 g, 10 mmol) and K$_2$CO$_3$ (4.2 g, 30 mmol) are dissolved/suspended in anhyd. DMF (20 mL) and heated to 100° C. with rapid stirring overnight. The reaction is cooled to r.t. and poured into water (400 mL) and extracted with chloroform (3×150 mL). The organic fractions are pooled and washed with brine (2×200 mL), dried over MgSO4, filtered and reduced under vacuum to an oil. The crude material is purified by flash chromatography (silica, 5% methanol in dichloromethane) to give (3-quinolin-2-ylmethyl-3H-imidazol-4-yl)-methanol and (1-quinolin-2-ylmethyl-1H-imidazol-4-yl)-methanol in a 2:3 ratio. The identity of each regioisomer was determined by NMR NOE experiments. MS (ESI) 240 (M+H)$^+$ found for both regioisomers.

EXAMPLE 88

Isobutyl 2-methyl-6-(1-quinolin-2-ylmethyl-1H-imidazol-4-ylmethoxymethyl)-benzoate (1-Quinolin-2-ylmethyl-1H-imidazol-4-yl)-methanol (350 mg, 1.46 mmol, example 87) is dissolved in 20% DMPU in THF (5 mL) and cooled to 0° C. Sodium hydride (60%, 60 mg, 1.50 mmol) is added portionwise, and the contents stirred for 15 min. Isobutyl 2-bromomethyl-6-methyl-benzoate (57%, 730 mg, 1.46 mmol, example 2) is added, the reaction is allowed to come to r.t. and stirred overnight. The contents are poured into water (200 mL) and extracted with dichloromethane (3×75 mL). The organic fractions are pooled and washed with brine (3×100 mL), dried over MgSO4, filtered and reduced under vacuum to an oil. The crude material is purified by flash chromatography (silica, 3% methanol in dichloromethane) to give the title compound. MS (ESI) 443 (M+H)$^+$.

EXAMPLE 88a

Isobutyl 2-methyl-6-(3-quinolin-2-ylmethyl-3H-imidazol-4-ylmethoxymethyl)-benzoate The title compound is prepared using essentially the same procedure used in example 88 except using (3-quinolin-2-ylmethyl-3H-imidazol-4-yl)-methanol in place of (1-quinolin-2-ylmethyl-1H-imidazol-4-yl)-methanol. MS (ESI) 443 (M+H)$^+$.

EXAMPLE 89

2-Methyl-6-(1-quinolin-2-ylmethyl-1H-imidazol-4-ylmethoxymethyl)-benzoic acid

Isobutyl 2-methyl-6-(1-quinolin-2-ylmethyl-1H-imidazol-4-ylmethoxymethyl)-benzoate (300 mg, 0.68 mmol, example 88) is dissolved in ethanol (5 mL). 10 N NaOH (680 µL, 6.8 mmol) is added and the contents heated to 90° C. overnight. The reaction is cooled to r.t., 2 N HCl (3.4 mL, 6.8 mmol) is added and the pH adjusted to ~5–7. The contents are poured into water (100 mL) and extracted with chloroform (3×75 mL). The organic fractions are pooled, washed with brine (3×100 mL), dried over MgSO4, filtered and reduced under vacuum to an oil. The crude material is purified by HPLC (C-18, 25–50% acetonitrile in water over 15 min.) to give the title compound as the TFA salt. $^1$H NMR (300 MHz, CDCl$_3$) δ 8.93 (s, 1H), 8.31 (d, 1H), 8.07 (d, 1H), 7.86 (d, 1H), 7.78 (t, 1H), 7.63 (t, 1H), 7.51 (d, 1H), 7.44 (s, 1H), 7.17–7.12 (m, 1H), 7.06–7.01 (m, 2H), 5.64 (s, 2H), 4.66 (s, 2H), 4.48 (s, 2H), 2.29 (s, 3H). MS (ESI) 388 (M+H)$^+$.

EXAMPLE 89a

2-Methyl-6-(3-quinolin-2-ylmethyl-3H-imidazol-4-ylmethoxymethyl]-benzoic acid

The title compound is prepared using essentially the same procedure used in example 89 except using isobutyl 2-methyl-6-(3-quinolin-2-ylmethyl-3H-imidazol-4-ylmethoxymethyl)-benzoate in place of isobutyl 2-methyl-6-(1-quinolin-2-ylmethyl-1H-imidazol-4-ylmethoxymethyl)-benzoate. $^1$H NMR (300 MHz, CDCl$_3$) δ 8.95 (s, 1H), 8.27 (d, 1H), 8.05 (d, 1H), 7.82–7.76 (m, 2H), 7.64–7.59 (m, 1H), 7.46 (s, 1H), 7.38 (d, 1H), 7.10–6.99 (m, 2H), 6.92 (d, 1H), 5.91 (s, 2H), 4.52 (s, 2H), 4.49 (s, 2H), 2.23 (s, 3H). MS (ESI) 388 (M+H)$^+$.

EXAMPLE 90

2-[3-(1H-Indol-3-ylmethyl)-phenoxymethyl]-quinoline

Indole (230 mg, 2.0 mmol) is dissolved in tetrahydrofuran (3 mL) and ethylmagnesium bromide (1 M, 2.0 mL, 2.0 mmol) is added and the reaction is heated for 2 h at 65° C. The free base of 2-(3-chloromethyl-phenoxymethyl)-quinoline hydrochloride (400 mg, 1.2 mmol, example 49) is prepard by partioning the material between ethyl ether and sodium bicarbonate and drying the organic phase with magnesium sulfate. This free base is dissolved in tetrahydrofuran (2 mL) and is added to the cooled indole/Grignard solution, along with catalytic tetrabutylammonium iodide. This mixture is heated 6 h at 65° C. The reaction is then cooled and partitioned between ethyl ether and ammonium chloride. The organic phase is washed with brine, dried over magnesium sulfate, concentrated and purified by column chromatography (silica, dichloromethane) to yield the title compound. MS (ESI) 365 (M+H)$^+$.

EXAMPLE 91

{3-[3-(quinolin-2-ylmethoxy)-benzyl]-indol-1-yl}-acetic acid

Sodium hydride (60%, 22 mg, 0.55 mmol) is added to a solution of 2-[3-(1H-indol-3-ylmethyl)-phenoxymethyl]-quinoline (90 mg, 0.25 mmol, example 90) in DMF (2.5 mL). After stirring 5 minutes ethyl bromoacetate (0.1 mL, 0.9 mmol) is added and the reaction is allowed to stir 2 h. The reaction is partitioned between ethyl acetate and ammonium chloride and the organic phase is washed with water. The organic phase is dried over magnesium sulfate, concentrated and then the solid is titurated with ethyl ether and ethyl acetate to provide the title compound as a solid. m.p. 151–159° C.; $^1$H NMR (300 MHz, CDCl$_3$) δ 8.20 (t, 2H), 7.83–7.80 (m, 1H), 7.77–7.71 (m, 1H), 7.67 (d, 1H), 7.61–7.53 (m, 1H), 7.45–7.42 (m, 1H), 7.29–7.14 (m, 3H), 7.05–6.99 (m, 2H), 6.94 (s, 1H), 6.85 (m, 2H), 5.16 (s, 2H), 4.84(s, 2H), 4.11 (s, 2H); MS (ESI) 423 (M+H)$^+$.

EXAMPLE 92

Ethyl (2-formyl-6-methyl-2-phenoxy)-acetate

Ethyl bromoacetate (4.5 mL, 40 mmol), 2-hydroxy-3-methyl-benzaldehyde (5 g, 37 mmol and potassium carbonate (8.1 g, 59 mmol) are combined in acetone (60 mL) and refluxed overnight. The reaction is filtered and the solvent removed from the filtrate under reduced pressure to give the title compound. MS (GC-MS) 222 (M)$^+$.

EXAMPLE 93

Ethyl 7-methyl-benzofuran-2-carboxylate

Sodium (0.52 g, 23 mmol) is dissolved in ethanol (60 mL) and to this is added ethyl (2-formyl-6-methyl-2-phenoxy)-acetate (5 g, 23 mmol, example 92). This mixture is refluxed for 3 hours and the solvent is removed in vacuo. The residue is dissolved in dichloromethane/water and acidified with 1N HCl. The organic layer is washed with water and brine and then dried over magnesium sulfate and the solvent removed in vacuo. The residue is purified by flash chromatography (silica, 1% methanol in dichloromethane) to give the title compound. MS (GC-EI) 176 (M)$^+$.

EXAMPLE 94

Ethyl 7-bromomethyl-benzofuran-2-carboxylate

Ethyl 7-methyl-benzofuran-2-carboxylate (0.5 g, 2.4 mmol, example 93), N-bromosuccinimde (0.48 g, 2.7 mmol) and benzoyl peroxide (0.06 g, 2.4 mmol) are combined in carbon tetrachloride (10 mL) and heated in an oil bath at 90° C. overnight. The reaction is filtered and the filtrate solvent is removed in vacuo. The residue is purified by flash chromatography (silica, 5% to 10% ethyl acetate in hexanes) to give the title compound. MS (GC-EI) 360, 362 (M$^+$, Br pattern).

EXAMPLE 95

Ethyl 2-methyl-6-trifluoromethanesulfonyloxy benzoate

Ethyl 6-methylsalicylate (2.5 g, 14 mmol, See, Hauser, Frank M., *Synthesis* 1980, 10, 814–15) is dissolved in THF (20 mL) under nitrogen and cooled in an ice bath. Sodium hydride (60%, 0.56 g, 14 mmol) is added and the mixture is stirred 15 minutes. Then DMPU (0.20 mL) and N-phenyl-trifluoromethanesulfonimde (5.0 g, 14 mmol) are added and the reaction is stirred with cooling for 2 hours. The solvent is removed in vacuo and ether is added and the organics are washed with water, then dried over magnesium sulfate and concentrated under reduced pressure. The residue is purified by flash chromatography (silica, dichloromethane) to give the title compound.

EXAMPLE 96

3-(2-methoxy-ethoxymethoxy)-phenyliodide

To a suspension of 60% sodium hydride (1.76 g, 44 mmol) in THF (10 mL), cooled to 0° C., is added 3-iodophenol (8.8 g, 40 mmol) and methoxyethoxymethyl chloride (5 mL, 44 mmol) in THF (50 mL). Then DMPU (10 mL) is added, the cooling bath is removed and the reaction is stirred for an hour. The reaction is diluted with ether, washed with water and brine and the organic layer dried over magnesium sulfate. The solvent is removed in vacuo to give the title compound.

EXAMPLE 97

[3-(2-Methoxy-ethoxymethoxy)-phenylethynyl]-trimethyl silane 3-(2-Methoxy-ethoxymethoxy)-phenyliodide (12.1 g, 39 mmol, 96) and tetrakis(triphenylphosphine)palladium (1.2 g, 1.0 mmol) and cuprous iodide (0.096 g, 0.5 mmol) are dissolved in THF (120 mL) and to this is added piperidine (12 mL) and (trimethylsilyl)acetylene (8 mL, 57 mmol). This mixture is degassed and is then stirred for 2 hours. The reaction is then diluted with ether and washed twice with water and brine and the organic layer dried over magnesium sulfate. The solvent is removed in vacuo to give the title compound. MS (EI) 206 (M)$^+$.

EXAMPLE 98

Ethyl-2-[3-(2-methoxy-ethoxymethoxy)-phenylethynyl]-6-methyl-benzoate

[3-(2-Methoxy-ethoxymethoxy)-phenylethynyl]-trimethyl silane (0.57 g, 2 mmol, example 97) and 1.0 M tetrabutylammonium fluoride (2.1 mL, 2 mmol) are added to THF (10 mL) and acetic acid (0.13 g, 2 mmol) is added and this mixture is stirred at 20° C., under nitrogen. After 15 minutes, the solvent is removed in vacuo and the residue is azeotroped with benzene and purified by flash chromatography (silica, 20% ethyl acetate, 30% dichloromethane in hexanes) to give 1-ethynyl-3-(2-methoxy-ethoxymethoxy)-benzene (0.28 g, 1.4 mmol) which is dissolved in THF (8 mL), cooled to −78° C., under nitrogen and to this solution is added 2.5M n-butyl lithium (0.56 mL, 1.4 mmol) dropwise over 30 seconds. After stirring for 15 minutes, 1.0M zinc chloride in ether (1.4 mL, 1.4 mmol) is added dropwise over 30 seconds and this mixture is stirred for 30 minutes. Bis-(dibenzylideneacetone) palladium (0.04 g, 0.07 mmol) and bis (diphenyl phosphino) ferrocene (0.04 g, 0.07 mmol) is added and to this mixture is added ethyl-2-methyl-6-trifluoromethanesulfonyloxy benzoate (0.44 g, 1.4 mmol, 95) in THF (2 mL). The cooling bath is removed and the reaction allowed to warm to room temperature. Then the reaction mixture is heated in an oil bath at 65° C. overnight. The reaction is then diluted with ethyl acetate (50 mL), washed with saturated ammonium chloride and brine and then dried over magnesium sulfate. The solvent is removed in vacuo and the residue purified by flash chromatography (silica, 10% ethyl acetate, 25% dichloromethane in hexanes) to give the title compound. MS (ESI) 369 (M+H)$^+$.

EXAMPLE 99

(3-Methyl-4-oxo-3,4-dihydro-quinazolin-2-yl)-methyl chloride

To a suspension of isatoic anhydride (1.63 g, 10 mmol) in dioxane (40 mL) is added methylamine solution (5 mL, 2M in THF). The resulting solution is stirred for 1 h then concentrated under vacuum. The residue is taken up in toluene (30 mL) then pyridine (5.5 mL) is added followed by a solution of chloroacetyl chloride (2.7 mL, 34 mmol) in toluene (15 mL). The resulting mixture is stirred for 15 h. The solid product is filtered, washed with water, then dried under vacuum to give 2.1 g of a tan solid. A portion of this product (452 mg, 2 mmol) is suspended in benzene (10 mL) then p-toluene sulphonic acid monohydrate (394 mg, 2 mmol) is added. This mixture is warmed to 70° C. and stirred at this temperature for 10 h. The mixture is then cooled to room temperature and the benzene solution decanted. The residual solid is mixed with sodium bicarbonate solution (sat.) and this mixture is extracted with ethyl acetate/methanol/dichloromethane. The combined extracts are washed with brine, dried over MgSO$_4$ and concentrated to give the title compound as a tan solid. $^1$H NMR (300 MHz, CDCl$_3$): δ 8.28 (d, 1H), 7.75 (t, 1H), 7.67 (d, 1H), 7.51 (t, 1H), 4.62 (s, 3H), 3.76 (s, 3H).

EXAMPLE 100

3-(2-Hydroxymethyl-3-methyl-benzyloxy)-phenol

To a cooled (0° C.) solution of methyl 2-methyl-6-[(3-hydroxy-phenoxy)-methyl]-benzoate (220 mg, 0.76 mmol, example 5) in THF (2 mL) is added lithium aluminum hydride solution (1.5 mL, 1 M in THF). The resulting solution is stirred for 10 min then warmed to room temperature and stirred for 40 min. This solution is then cooled to 0° C. and water (75 mL) added, dropwise, followed by sodium hydroxide solution (75 mL, 5N) and water (75 mL). The resulting suspension is diluted with ether, filtered through celite and the solid washed thoroughly with methanol (until the solid is free of product by TLC analysis). The combined filtrates are concentrated under vacuum to give the title compound as a white solid. MS (EI) 244 (M)$^+$.

EXAMPLE 101

2-[3-(2-Hydroxymethyl-3-methyl-benzyloxy)-phenoxymethyl]-3-methyl-3H-quinazolin-4-one To a solution of 3-(2-hydroxymethyl-3-methyl-benzyloxy)-phenol (87 mg, 0.38 mmol, example 100) and (3-methyl-4-oxo-3,4-dihydro-quinazolin-2-yl)-methyl chloride (94 mg, 0.45 mmol, example 99) in DMF (1 mL) is added powdered K$_2$CO$_3$ (78 mg, 0.5 mmol). The resulting mixture is warmed to 60° C. and stirred at this temperature for 5 h. This mixture is cooled to room temperature, diluted with ethyl acetate, washed with water and brine, dried over MgSO$_4$ and concentrated. The residue is purified by flash chromatography (silica, 40% ethyl acetate/30% dichloromethane in hexanes) to give the title compound as a foam. MS (ESI) 417 (M+H)$^+$.

EXAMPLE 101a

{2-[3-(5-Cyclobutyl-[1, 2,4]oxadiazol-3-yl-methoxy)-phenoxymethyl]-6-methyl-phenyl}-methanol The title compound is prepared using essentially the same procedure used in example 101 except using 3-chloromethyl-5-cyclobutyl-[1,2,4]oxadiazole in place of (3-methyl-4-oxo-3,4-dihydro-quinazolin-2-yl)-methyl chloride. MS (ESI) 381 (M+H)$^+$.

EXAMPLE 102

2-Methyl-6-[3-(3-methyl-4-oxo-3,4-dihydro-quinazolin-2-ylmethoxy)-phenoxymethyl]-benzaldehyde To a cooled (−78° C.) solution of oxalyl chloride (2.5 mL, 1.75 M in CH$_2$Cl$_2$) is added, dropwise, DMSO (80 mL). On complete addition, a solution of 2-[3-(2-hydroxymethyl-3-methyl-1 benzyloxy)-phenoxymethyl]-3-methyl-3H-quinazolin-4-one (120 mg, 0.28 mmol, example 101) in dichloromethane (1 mL) is added dropwise. This solution is stirred for 5 min then triethylamine (276 mL, 2 mmol) is added in one portion. The cold bath is removed and stirring continued for 10 min. The mixture is then diluted with ethyl acetate, washed with water and brine, dried over MgSO$_4$ and concentrated to give the title compound as a solid. MS (ESI) 415 (M+H)$^+$.

EXAMPLE 102a

2-[3-(5-Cyclobutyl-[1,2,4]oxadiazol-3-ylmethoxy)-phenoxymethyl]-6-methyl-benzaldehyde The title compound is prepared using essentially the same procedure used in example 102 except using {2-[3-(5-cyclobutyl-[1,2,4]oxadiazol-3-ylmethoxy)-phenoxymethyl]-6-methyl-phenyl}-methanol (example 101a) in place of 2-[3-(2-hydroxymethyl-3-methyl-benzyloxy)-phenoxymethyl]-3-methyl-3H-quinazolin-4-one. MS (ESI) 379 (M+H)$^+$.

EXAMPLE 103

2-Methyl-6-[3-(3-methyl-4-oxo-3,4-dihydro-quinazolin-2-ylmethoxy)-phenoxymethyl]-benzoic acid To a suspension of 2-methyl-6-[3-(3-methyl-4-oxo-3,4-dihydro-quinazolin-2-ylmethoxy)phenoxymethyl]-benzaldehyde (120 mg, 0.28 mmol, example 102) in t-butanol (1.5 mL) is added iso-butene (0.5 mL) followed by NaClO$_2$ (220 mg, tech grade 1.6 mmol) in water (1.5 mL) and NaH$_2$PO$_4$.H$_2$O (220 mg, 1.6 mmol) in water (1.5 mL). This mixture is stirred for 1 h (during which time the solids dissolve) then diluted with ethyl acetate, washed with water and brine, dried over MgSO$_4$ and concentrated. The residue is purified by flash chromatography (10% methanol in dichloromethane). This product was suspended in chloroform and filtered through celite. The filtrate is concentrated under reduced pressure to give the title compound as an amorphous solid. $^1$H NMR (300 MHz, CDCl$_3$): δ 8.41 (d, 1H), 7.84 (m, 2H), 7.62 (m, 1H), 7.33 (m, 2H), 7.20 (m, 1H), 7.14 (t, 1H), 6.81 (m, 1H), 6.70 (m, 2H), 5.29 (s, 2H), 5.25 (s, 2H), 3.80 (s, 2H), 2.52 (s, 3H). MS (ESI) 430 (M+H)$^+$.

EXAMPLE 103a

2-[3-(5-Cyclobutyl-[1,2,4]oxadiazol-3-ylmethoxy)-phenoxymethyl]-6-methyl-benzoic acid The title compound is prepared using essentially the same procedure used in example 103 except using 2-[3-(5-Cyclobutyl-[1,2,4]oxadiazol-3-ylmethoxy)-phenoxymethyl]-6-methyl-benzaldehyde (example 102a) in place of 2-methyl-6-[3-(3-methyl-4-oxo-3,4-dihydro-quinazolin-2-ylmethoxy)-phenoxymethyl]-benzaldehyde. $^1$H NMR (300 MHz, DMSO) δ 7.10 (m, 4H), 6.68 (s, 1H), 6.60 (m, 2H), 5.19 (s, 2H), 5.13 (s, 2H), 3.86 (m, 1H), 2.36 (m, 4H), 2.28 (s, 3H), 2.08 (m, 1H), 1.96 (m, 1H). MS (ESI) 395 (M+H)$^+$.

EXAMPLE 104

5-Phenyl-2-methylpyridine

To a cooled (−70° C.) solution of 3-phenylpyridine (1.43 mL, 10.0 mmoles) in diethyl ether (7.5 mL) is added dropwise methyllithium (LiBr complex, 1.5 M in diethyl ether, 7.33 mL, 11.0 mmoles). After letting warm to room temperature over 16 hours the reaction is cooled (0° C.) and quenched with distilled water (5 mL). The reaction is then extracted with methylene chloride, the organic layer isolated and concentrated, and the resulting residue purified by column chromatography (silica, 3:1 hexane: EtOAc) to yield the title compound as a pale yellow oil. MS(ESI) 170 (M+H)$^+$.

Synthesis of a compound of Formula (VI)

A compound of Formula (VI) is prepared in a multi-step synthesis illustrated in the below scheme. The key starting material is quinaldine. In the first stage it is chlorinated to form 2-chloromethylquinoline which, without isolation, is reacted with hydroquinone to form the intermediate 4-(quinolin-2-yl-methoxy)phenol (VIII). This intermediate is then treated with α,α'-dichloro-o-xylene to form 2-[4-quinolin-2-yl-methoxy)phenoxymethyl]benzyl chloride, which is converted in situ to 2-[4-quinolin-2-yl-methoxy) phenoxymethyl]phenylacetonitrile (IX), the penultimate precursor to (VI).

(XI) is converted to (VI) crude, in a reaction with sodium azide and ammonium chloride which transforms the nitrile group into the tetrazole ring. The purification of the final product is accomplished by recrystallization of the crude material from methanol to afford pure (VI).

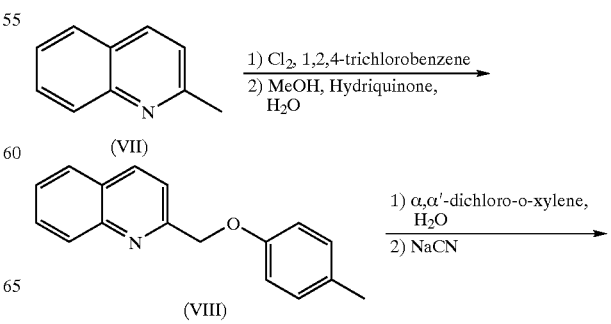

-continued

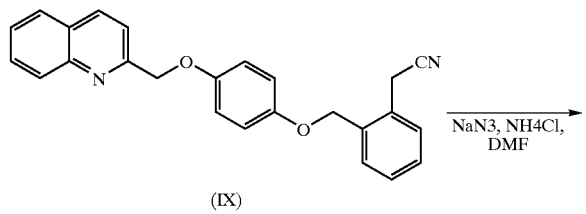

(IX)

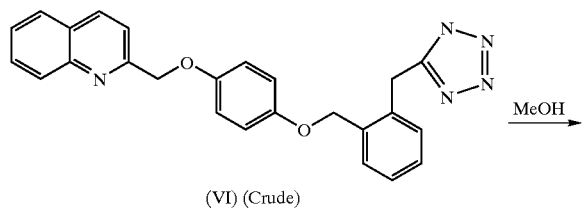

(VI) (Crude)

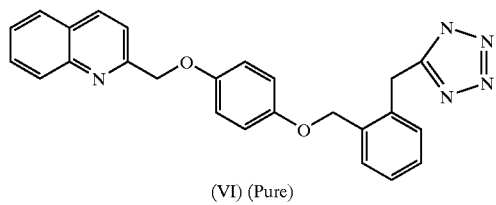

(VI) (Pure)

Solid Phase Synthesis of a Compound of Formula:

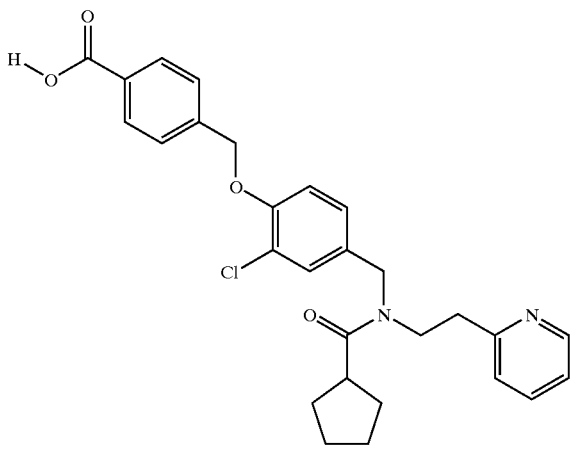

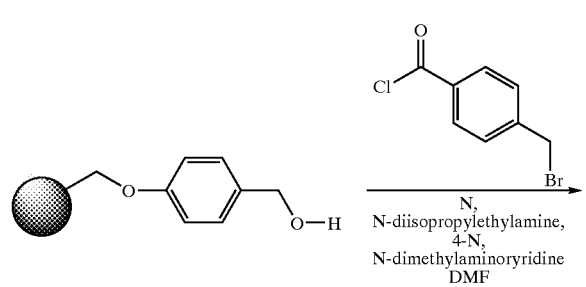

-continued

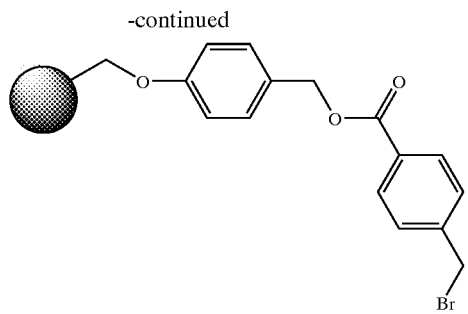

A 1L round bottom flask is charged with 4-(bromomethyl) benzoic acid (32.26 g, 150.0 mmole) and dichloromethane (650 mL). A stir bar is carefully added and the reaction flask is immersed in an ice-water bath. After approximately 15 minutes, oxallyl chloride (15.7 mL, 180 moles) is added. After approximately 1.5 minutes, N,N-dimethylformaide (500 mL, cat.) is added. The reaction began to bubble. After stirring for 1.5 hours, the ice-water bath is removed. After stirring for 3 hours at ambient temperature, the effervescence has ceased. At the end of this period, the stirbar is removed from the reaction mixture and the reaction solvent is removed in vacuo. After the solvent has been removed, more dichloromethane is added to the reaction flask and this too is removed in vacuo.

A three neck 3L round bottom flask is charged with dry N,N-dimethylformamide (1.3 L), N,N-diisopropylethylamine (39.19 mL, 225 mmoles), 4-N,N-dimethylaminopyridine (3.67 g, 30 mmole) and MicroKANS [1456, 15 mg of Wang resin (1.7 mmole/g loading) per MicroKANs, 25.5 micromoles/microKAN, 37.1 mmoles]. The flask is fitted with an overhead stirring apparatus. After stirring for approximately 15 minutes, a solution of the acid chloride as prepared above in dry N,N-dimethylformamide (200 mL) is transferred into the reaction flask. After 14 hours, the reaction solvent is removed. DMF (1.5 L) is added to the reaction flask. The flask was allowed to stir for approximately 15 minutes and the solvent is drained. The MicroKANs are washed, stirred for 20 minutes and drained in the following sequence repeatedly: DMF (2×6 L), THF (3×6 L), dichloromethane (3×6 L) and ether (2×6 L). After the final washing the MicroKANs are dried by blowing a stream of nitrogen through the flask with intermittent agitation. After sufficient drying, the MicroKANs are sorted for the next reaction.

2. Phenol Displacement:

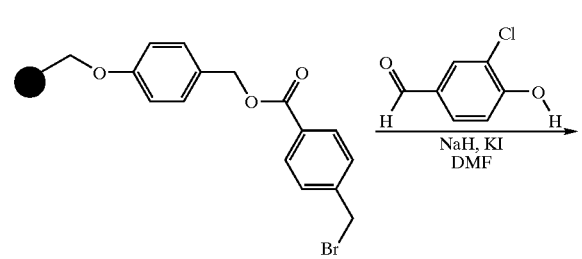

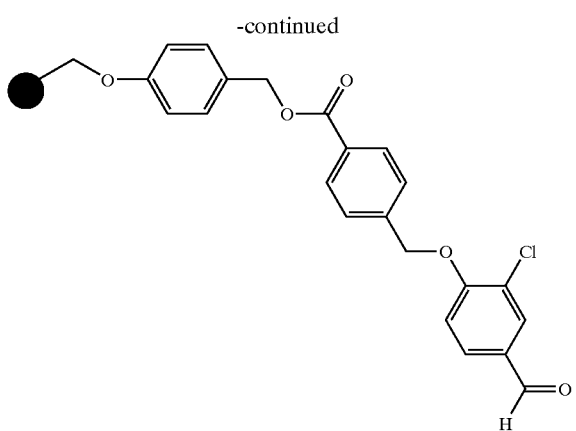

A three neck 3L round bottom flask is charged with 3-chloro-4-hydroxybenzaldehyde (21.9 g, 140 mmoles) and DMF (1.5 L). The reaction flask is fitted with an overhead stirrer and immersed in an ice-water bath. After approximately 15 minutes sodium hydride (60% dispersion in oil, 6.48 g, 180 mmoles) is carefully added. After approximately 30 minutes, the ice-water bath is removed and the reaction allowed to stir at ambient temperature for 1 hour. At the end of this time, the MicroKANs [1274, 25.5 micromoles/microKAN, 32.5 mmoles] and potassium iodide (1.0 g) are added to the reaction mixture. The reaction flask is immersed into an oil bath which is heated to 60° C. After 14 hours, the reaction flask is removed from the oilbath and allowed to cool to ambient temperature. The reaction solvent is removed. DMF (1.2 L) is added to the reaction flask. The flask is allowed to stir for approximately 15 minutes and the solvent is drained. DMF:water (1:1, 1.2 L) is added to the reaction flask. The flask is allowed to stir for approximately 15 minutes and the solvent is drained. This sequence is repeated at least three times or until the effluent from the washing is clear, the reaction flasks are washed repeatedly in the following sequence: THF (2×4 L), dichloromethane (1×4 L) then, methanol (1×4 L), dichloromethane (1×4 L) then methanol (1×4 L), dichloromethane (1×4 L) then methanol (1×4 L), dichloromethane (1×4 L) and ether (1×4 L). After the final washing the MicroKANs are dried by blowing a stream of nitrogen through the flask with intermittent agitation. After sufficient drying, the MicroKANs are sorted for the next reaction.

3. Reductive Amination:

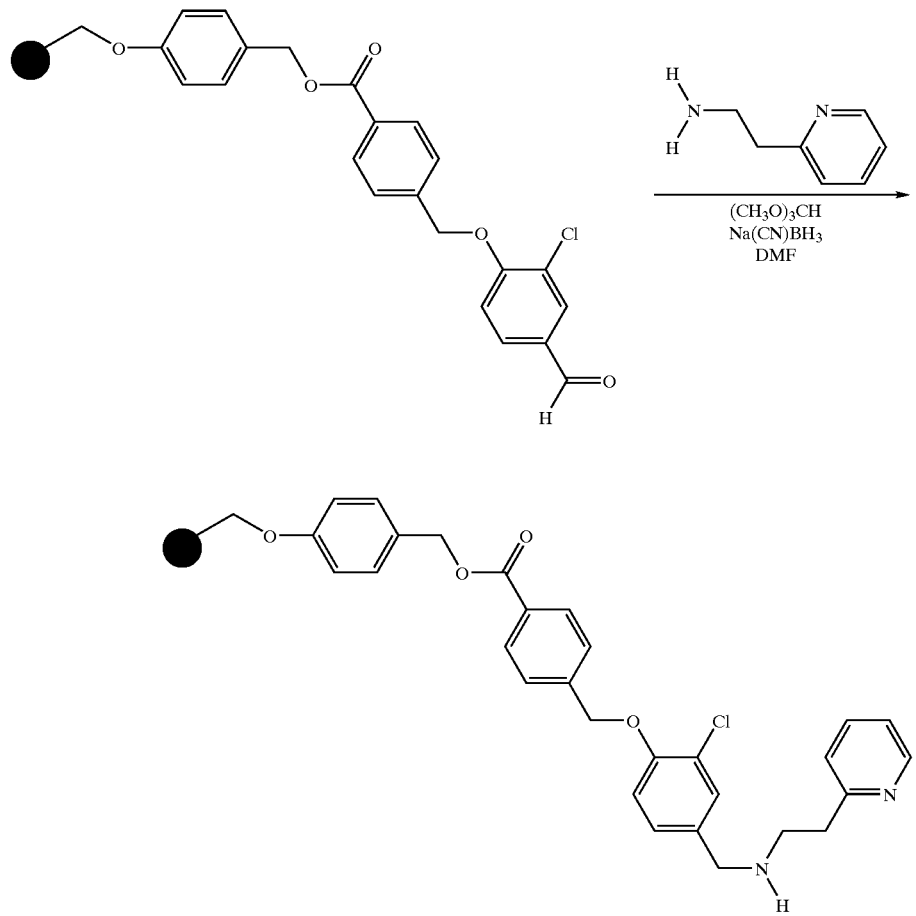

A three neck 2 L round bottom flask is charged with the MicroKANs [784, 25.5 micromoles/microKAN, 20.0 mmoles], trimethylorthoformate (850 mL) and 2-(2-aminoethyl)pyridine 20.79 g, 170 mmoles). The reaction flask is fitted with an overhead stirrer. After 2 hours, sodium cyanoborohydride (21.37 g, 340 mmoles) is added. After approximately 10 minutes, acetic acid (17.0 mL, 297 mmoles) is added. After stirring for an additional hour, the reaction flask is drained. Methanol (800 mL) is added to the flask. After stirring for approximately 10 minutes, the flask is drained the reaction flask is washed repeatedly in the following sequence: DMF (3×4 L), dichloromethane (1×4 L) then methanol (1×4 L), dichloromethane (1×4 L) then methanol (1×4 L), dichloromethane (1×4 L) then methanol (1×4 L), dichloromethane (1×4 L) and ether (1×4 L). After the final washing the microKANS are dried by blowing a stream of nitrogen through the flask with intermittent agitation. After sufficient drying, the MicroKANs are sorted for the next reaction.

4. Acylation:

A three neck 2 L round bottom flask is charged with the MicroKANs [784, 15 mg of resin (1.7 mmole/g loading) per MicroKAN, 25.5 micromoles/microKAN, 20.0 mmoles], and dichloromethane (800 mL). The reaction flask is fitted with an overhead stirrer. N,N-diisopropylethylamine (20.9 mL, 120 mmoles) and 4-N,N-dimethylaminopyridine (195 mg, 1.6 mmoles) are added. After approximately 15 minutes, the cyclopentanecarbonyl chloride (10.6 g, 80.0 mmoles) is added. The reaction was allowed to stir for 61 hours, the reaction flask is drained. Dichloromethane (800 mL) is added to the reaction flask. After stirring for approximately 10 minutes, the flask is drained. This is repeated. The MicroKANs from all of the acylation reactions are randomly combined into two separate large flasks and washed repeatedly in the following sequence: dichloromethane (1×4 L), THF (2×4 L), dichloromethane (1×4 L) then methanol (1×4 L), dichloromethane (1×4 L) then methanol (1×4 L), dichloromethane (1×4 L) then methanol (1×4 L), dichloromethane (1×4 L) and ether (1×4 L).

5. Cleavage:

The MicroKAN is sorted into individual wells of IRORI AccuCleave 96 cleavage station. The well is charged with dichloromethane (600 mL) and then with a TFA: dichloromethane mixture (1:1, 600 mL). After agitating for approximately forty minutes, the reaction well is drained into 2 mL microtube in an 96-well format. The reaction well is again charged with dichloromethane (600 mL). After manual agitation, this too is drained into the 2 mL microtube in an 96-well format. The cleavage cocktail is removed in vacuo using a Savant Speedvac. The concentrated products from the cleavage mother plates are reconstituted with THF and transferred into two daughter plates utilizing a Packard MultiProbe liquid handler. The daughter plates are concentrated in vacuo utilizing a Genie Vac.

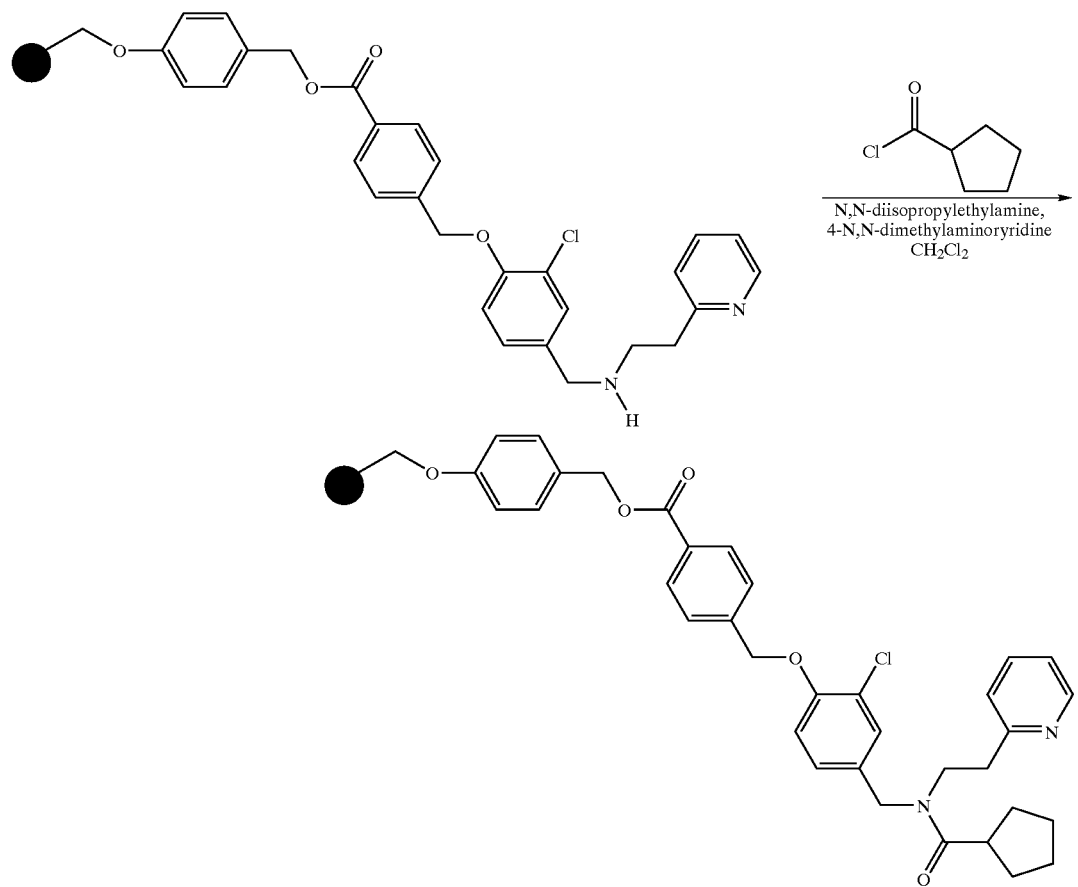

Analytical: MS:m/z 493 (M+).

The methods described above are used to prepare the following compounds of this invention.

5-[2-(4-(2-quinolinylmethoxy)phenoxymethyl)benzyl]tetrazole (M.P. 108–111° C.)
CALC: C, 59.87; H, 5.96; N, 13.96 FOUND: C, 59.67, 60.01; H, 5.62, 5.63; N,. 13,73, 13.77

5-[4-Methoxy-3-(3-(2-quinolinylmethoxy)phenoxymethyl)phenyl]tetrazole (M.P. 184–87° C.)
CALC: C, 67.63; H, 4.88; N, 15.78 FOUND: C, 67.18; H, 5.13; N, 15.40

5-[3-(4-(2-quinolinylmethyloxy)phenoxymethyl)phenyl]tetrazole (M.P. 176–177° C.)
CALC: C, 69.63; H, 4.75; N, 16.92 FOUND: C, 69.58, 69.64; H, 5.00, 4.98; N, 16.66, 16.63

5-[3-Methoxy-4-(4-(2-quinolinylmethyloxy)benzyloxy)phenyl]tetrazole (M.P. 195–97° C.)
CALC: C, 67.63; H, 4.88; N, 15.77 FOUND: C, 67.27; H, 4.89; N, 15.41

5-[4-(3-(2-quinolinylmethyloxy)phenoxymethyl)-3methoxyphenyl]tetrazole (M.P. 189–91° C.)
CALC: C, 66.95; H, 4.95; N, 15.61 FOUND: C, 66.48; H, 5.14; N, 14.93

5-[3-(4-(2-quinolinylmethyloxy)phenoxymethyl)benzyl]tetrazole (M.P. 139–44° C.)
CALC: C, 70.53; H, 5.03; N, 16.45 FOUND: C, 70.33, 70.54; H, 5.25, 5.36; N, 16.38, 16.41

5-[4-(4-(2-quinolinylmethyloxy)phenoxymethyl)benzyl]tetrazole (M.P. 167–71° C.)
CALC: C, 67.33; H, 5.31; N, 15.70 FOUND: C, 67.54, 67.67; H, 5.33, 5.33; N, 15.48, 15.52

5-[4-Methoxy-3-(4-(2-quinolinylmethyloxy)phenyl]methyloxy)phenyl]tetrazole (M.P. 210–13° C.)
CALC: C, 68.33; H, 4.82; N, 4.90 FOUND: C, 68.32; H, 4.90; N, 14.79

4-[3-(2-Quinolinylmethyloxy)phenoxymethyl]phenoxyacetic acid (M.P. 164 (dec))
CALC: C, 69.27; H, 5.35; N, 3.23 FOUND: C, 69.53, 69.65; H, 5.11, 5.05; N, 3.21, 3.12

5-[2-(4-(2-Quinolinylmethyloxy)phenoxymethyl)phenoxymethyl]tetrazole (M.P. 183–85° C.)
CALC: C, 65.63; H, 5.08; N, 15.31 FOUND: C, 65.77, 65.52; H, 4.99, 5.03; N, 14.92, 15.03

4-[4-(2-Quinolinylmethyloxy)phenoxymethyl]phenoxyacetic acid (176° C. (dec))
CALC: C, 71.50; H, 5.16; N, 3.34 FOUND: C, 71.10, 71.17; H, 5.27, 5.33; N, 3.37, 3.34

4-[3-(2-Quinolinylmethyloxy)phenoxymethyl]phenylacetic acid (M.P. 158–60° C.)
CALC: C, 75.17; H, 5.30; N, 3.51 FOUND: C, 74.89; H, 5.36; N, 3.37

2-[3-(3-(2-Quinolinylmethyloxy)phenoxymethyl)phenoxy]pentanoic acid (M.P. 133–35° C.)
CALC: C, 73.51; H, 5.95; N, 3.06 FOUND: C, 73.35, 73.60; H, 5.95, 5.98; N, 3.08, 3.05

2-[3-(2-Quinolinylmethyloxy)phenoxymethyl]phenoxyacetic acid (M.P. 169–172° C.)
CALC: C, 72.28; H, 5.10; N, 3.37 FOUND: C, 69.34, 69.69; H, 5.10, 5.13; N, 3.00, 3.08 CALC: C, 69.27; H. 5.35; N. 3.23 (as Hydrate)

2-[4-(2-Quinolinylmethyloxy)phenoxymethyl]cinnamic acid (M.P. 175–178° C.)
CALC: C, 75.90; H. 5.14; N. 3.40 FOUND: C, 73.92; H. 5.20; N. 3.01 CALC: C, 74.27; H. 5.27; N, 3.33 (as Hydrate)

6-Acetyl-2-propyl-3-[3-(2-quinolinylmethyloxy)-benzyloxy]phenoxyacetic acid (M.P. 153–58° C.)
CALC: C, 72.13; H, 5.85; N, 2.90 FOUND: C, 71.68, 72.08; H, 5.88, 5.83; N, 2.65, 2.70

2-[2-(4-(7-Chloroquinolin-2-ylmethyloxy)-phenoxymethyl)phenoxy]propionic acid (M.P. 169–173° C.)
CALC: C, 67.32; H, 4.78; N, 3.02; CI, 7.64 FOUND: C, 65.18; H, 4.90; N, 2.84; CI, 8.33 CALC: C, 65.41; H, 4,96; N, 2.93; CI, 7.42 (as HYDRATE)

2-[4-(2-Quinolinylmethyloxy)phenoxymethyl]phenylacetic acid (M.P. 181–83° C.)
CALC: C, 75.17; H, 5.30; N, 3.51 FOUND: C, 75.12, 74.96; H, 5.50, 5.49; N, 3.16, 3.16

3-[3-(2-Quinolinylmethyloxy)phenoxymethyl]phenoxyacetic acid (M.P. 146–51° C.)
CALC: C, 72.28; H. 5.10; N. 3.37 FOUND: C, 71.82, 71.80; H. 5.24, 5.23; N, 2.98, 3.00 CALC: C, 71.50; H, 5.16; N, 3.34 (as HYDRATE)

2-[4-(2-Quinolinylmethyloxy)phenoxymethyl]phenoxyacetic acid (M.P. 153–57° C.)
CALC: C, 72.28; H, 5.10; N, 3.37 FOUND: C, 72.30, 71.72; H, 5.39, 5.30; N, 2.94, 2.89

5-[2-(4-(7-Chloroquinolin-2-ylmethyloxy)-phenoxymethyl)benzyl]tetrazole (M.P. 159–63° C.)
CALC: C, 65.57; H, 4.40; N, 15.29 FOUND: C, 64.16; H, 4.72; N, 14.98 CALC: C, 64.30; H, 4.53; N, 14.99 (as HYDRATE)

2-Carbomethoxy-5-[3-(2-quinolinylmethyloxy)-phenoxymethyl]phenoxyacetic acid (M.P. 187–89° C.)
CALC: C, 68.49; H, 4.90; N, 2.95 FOUND: C, 66.71; H, 4.96; N, 2.70 CALC: C, 66.59; H, 5.07; N, 2.87(as HYDRATE)

2-[3-(2-Quinolinylmethyloxy)phenoxymethyl]-6-methylphenoxyacetic acid (M.P. 149–53° C.)
CALC; C, 72.71; H, 5.40; N, 3.26 FOUND: C, 71.23; H, 5.46; N, 3.08 CALC: C, 71.22; H, 5.51; N, 3.19 (as HYDRATE)

2-[3-(3-(2-Quinolinylmethyloxy)phenoxymethyl)phenoxy]glutaric acid (M.P. 129–30° C.)
CALC: C, 69.00; H, 5.17; N, 2.87 FOUND: C, 58.19; H, 4.93; N, 2.23 CALC: C, 58.23; H, 5.17; N, 2.43 (as HYDRATE)

2-[3-(2-Quinolinylmethyloxy)phenoxymethyl]benzylmalonic acid (M.P. 164–65° C.)
CALC: C, 70.89; H, 4.08; N, 3.06 FOUND: C, 70.51, 70.61; H, 5.03, 5.24; N, 3.03, 2.90

2-[2-(3-(2-Quinolinylmethyloxy)phenoxymethyl)phenoxy]pentanoic acid (M.P. 118–20° C.)
CALC: C, 73.51; H, 5.95; N, 3.06 FOUND: C, 73.26; H, 6.07; N, 2.79

2-[4-(2-Quinolinylmethyloxy)phenoxymethyl]-6-methylphenoxy acetic acid (M.P.-151–53° C.)
CALC: C, 72.71; H, 5.40; N, 3.26 FOUND: C, 71.41; H, 5.58; N, 3.03 CALC: C, 71.22; H, 5.51; N, 3.19 (as HYDRATE)

2-[2-(4-(2-Quinolinylmethyloxy)phenoxymethyl)phenoxy]pentanoic acid (M.P. 85–92° C.)
CALC: C, 73.51; H, 5.95; N, 3.06 FOUND: C, 71.73, 71.79; H, 5.96, 5.91; N, 3.06, 2.83 CALC: C, 72.09; H, 6.05; N, 3.00 (as HYDRATE)

2-Carbomethoxy-5-[4-(2-quinolinylmethyloxy)-phenoxymethyl]phenoxyacetic acid (M.P. 149–51° C.)
CALC: C, 68.49; H, 4.90; N, 2.95 FOUND: C, 68.00, 68.08; H, 4.98, 5.04; N, 2.90, 2.90

2-[2-(4-(2-Quinolinylmethyloxy)phenoxymethylphenoxy]propionic acid (M.P. 161–64° C.)
CALC: C, 72.71; H, 5.40; N, 3.26 FOUND: C, 70.96, 71.10; H, 5.51, 5.58; N, 3.08, 3.10 CALC: C, 71.22; H, 5.52; N, 3.19 (as HYDRATE)

2-[2-(3-(2-Quinolinylmethyloxy)phenoxymethyl)phenoxy] glutaric acid (M.P. 83° C. dec)
CALC: C, 68.98; H, 5.17; N, 2.87 FOUND: C, 64.10, 63.75; H, 4.89, 4.92; N, 2.64, 2.69 CALC: C, 63.74; H, 5.63; N, 2.65(as HYDRATE)

2-(3-[2-Quinolinylmethyloxy]benzyloxy)phenoxyacetic acid (M.P. 153–55° C.)
CALC: C, 72.28; H. 5.10; N. 3.37 FOUND: C, 71.75; H. 5.14; N. 3.38 CALC: C, 71.50; H. 5.16; N. 3.34 (as HYDRATE)

2-(2-[4-(2-Quinolinylmethyloxy)phenoxymethyl]4chlorophenoxy)propionic acid (M.P. 196–99° C.)
CALC: C, 67.32; H, 4.78; N. 3.02 FOUND: C, 67.40, 67.43; H, 4.89, 4.94; N, 3.01, 3.13

2-(2-[3-(2-Quinolinylmethyloxy)phenoxymethyl]4chlorophenoxy)propionic acid (M.P. 169–71° C.)
CALC: C, 67.32; H, 4,78; N, 3.02 FOUND: C, 65.47; H, 5.31; N, 2.78 CALC: C, 65.41; H, 4.96; N, 2.93 (as HYDRATE)

2-(2-[3-(2-Quinolinylmethyloxy)phenoxymethyl]4chlorophenoxy)pentanoic acid (M.P. 14445° C.)
CALC: C, 68.36; H, 5,33; N, 2.85 FOUND: C, 67.74, 67.86; H, 5.39, 5.47; N, 2.91, 2.84 CALC: C, 67.74; H, 5.38; N, 2.82 (as HYDRATE)

2-(2-[4-(2-Quinolinylmethyloxy)phenoxymethyl]4-chlorophenoxy)pentanoic acid (M.P. 155–56° C.)
CALC: C, 68.36; H, 5.33; N, 2.85 FOUND: C, 65.96; H, 5.59; N, 2.66 CALC: C, 65.95; H, 5.53; N, 2.75 (as HYDRATE)

2-(2-[4-(2-Quinolinylmethyloxy)phenoxymethyl]4-chlorophenoxy)pentanoic acid (M.P. 155–56° C.)
CALC: C, 68.36; H, 5.33; N, 2.85 FOUND: C, 66.15; H, 5.58; N, 2.68 CALC: C, 65.95; H, 5.53; N, 2.75 (as HYDRATE)

2-(2-[4-(2-Quinolinylmethyloxy)phenoxymethyl]-6-chlorophenoxy)pentanoic acid (M.P. 161–62° C.)
CALC: C, 68.36; H, 5.33; N, 2.85 FOUND: C, 68.15; H, 5.36; N, 2.72

2-(2-[3-(2-Quinolinylmethyloxy)phenoxymethyl]-6-chlorophenoxy)pentanoic acid (M.P. 169–70° C.)
CALC: C, 68.36; H, 5.33; N, 2.85 FOUND: C, 68.10; H, 5.39; N, 2.72

2-(2-[3-(2-Quinolinylmethyloxy)phenoxymethyl]-6-chlorophenoxy)-4-methylpentanoic acid (M.P. 164–66° C.)
CALC: C, 68.84; H, 5.58; N, 2.77 FOUND: C, 68.84; H, 5.70; N, 2.69

2-(2-[4-(2-Quinolinylmethyloxy)phenoxymethyl]-6-chlorophenoxy)$_4$-methylpentanoic acid (M.P. 167–69° C.)
CALC: C, 68.84; H, 5.58; N, 2.77 FOUND: C, 68.78; H, 5.67; N, 2.68

5-[3-(3-(2-quinolinylmethyloxy)benzyloxy)-4-methoxyphenyl]tetrazole (M.P. 204–07° C.)
CALC: C, 67.63; H, 4.88; N, 15.78 FOUND: C, 67.11; H, 5.15; N, 15.86

N-[3-Methoxy-4-(3-(2-quinolinylmethyloxy)benzyloxy) benzoyl)benzene sulfonamide hydrochloride (M.P. dec. 88)
CALC: C, 62.99; H, 4.60; N. 4.74 FOUND: C, 63.88; H, 5.13; N, 4.80

5-Carboxy-2-(3-(2-quinolinylmethyloxy)phenoxymethyl) phenoxy acetic acid (M.P. 226–28° C.)
CALC: C, 61.90; H, 5.18; N, 2.77 FOUND: C, 61.62; H, 5.11; N, 2.67

5-[3-Methoxy-4-(3-(2-quinolinylmethyloxy)benzyloxy) phenyl]tetrazole (M.P. 204–05° C.)
CALC: C, 67.67; H, 5.14; N, 15.87 FOUND: C, 67.63; H, 4.88; N, 15.78

5-(4-(3-(2-Quinolinylmethyloxy)benzyloxy)phenyl)tetrazole (M.P. 233–36° C.)
CALC: C, 69.58; H, 4.73; N, 16.91 FOUND: C, 69.59; H, 4.89; N, 16.91

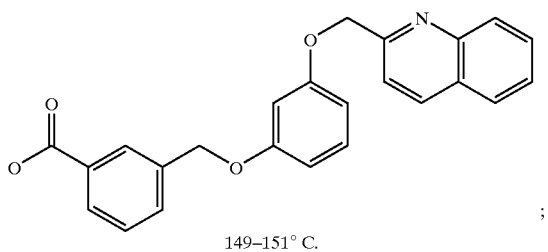

149–151° C.

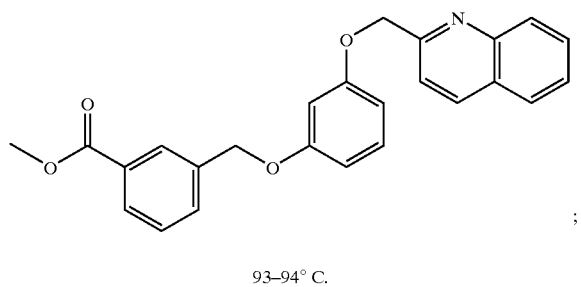

93–94° C.

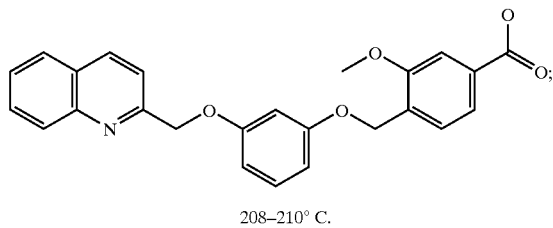

208–210° C.

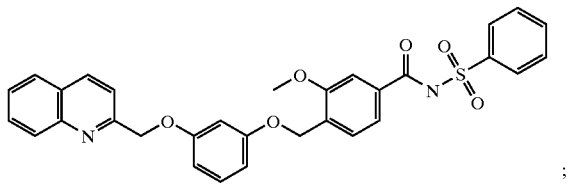

156–158° C.

-continued
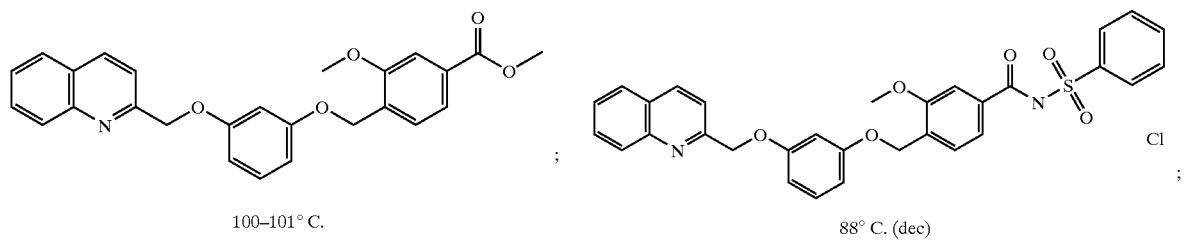
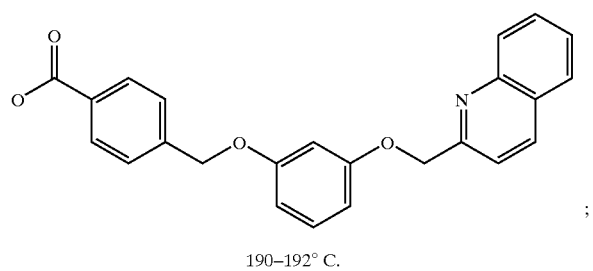
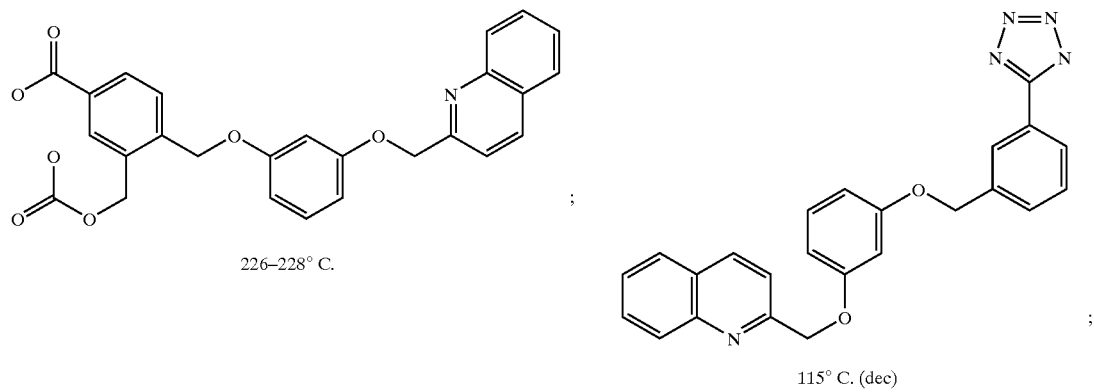
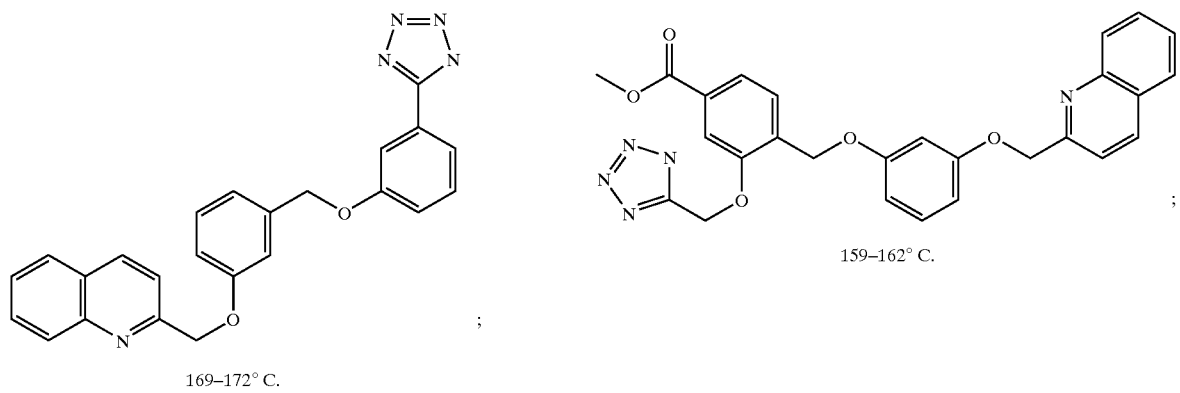

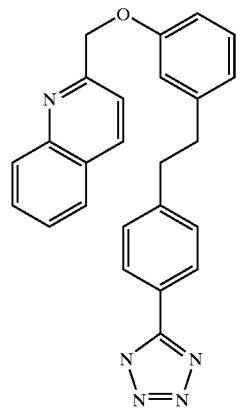
91° C.
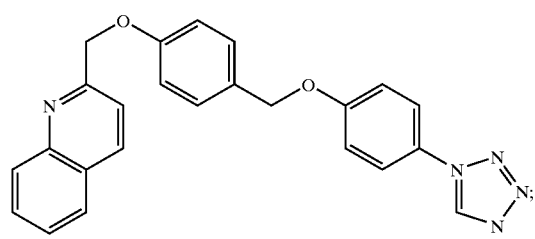
210-213° C.
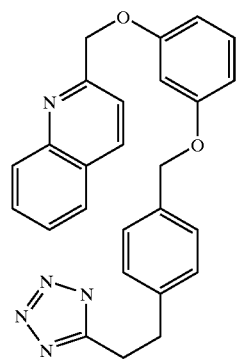
154–156° C.
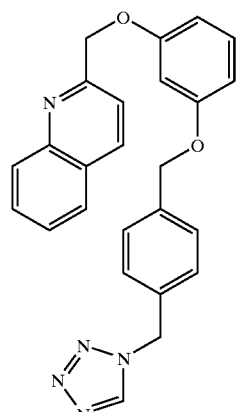
149–151° C.
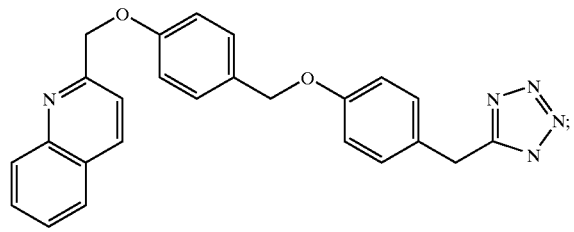
179–181° C.
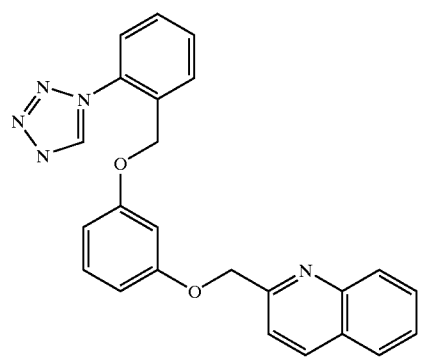
166-170° C.
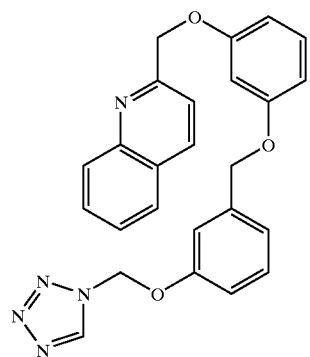
135–138° C.
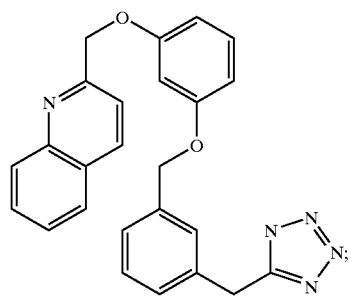
161–164° C.

-continued
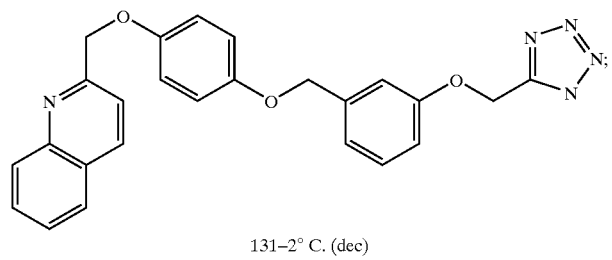
131–2° C. (dec)
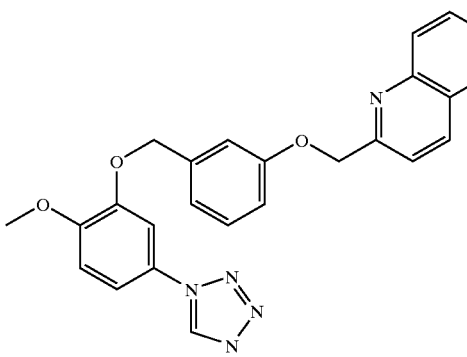
204–207° C.
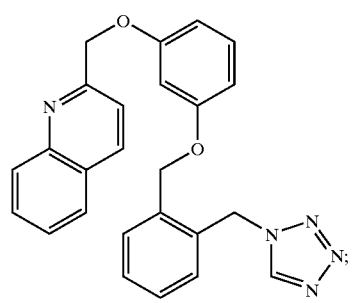
144–147° C.
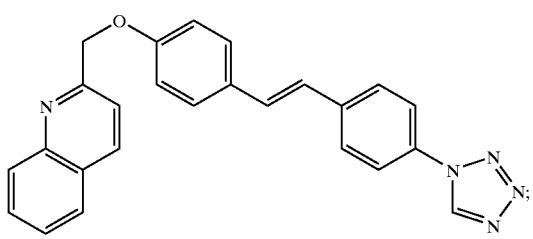
241–243° C.
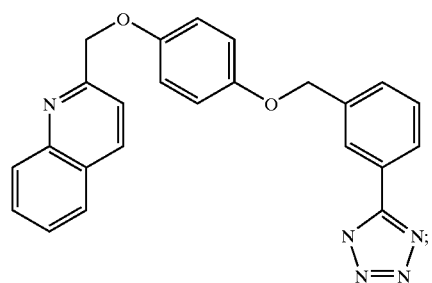
174–175° C.
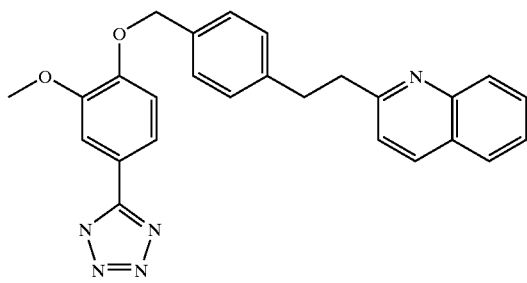
195–197° C.
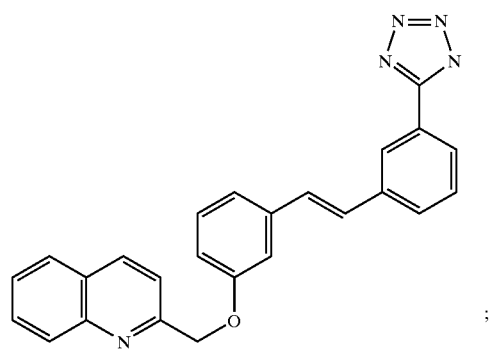
117–118° C.
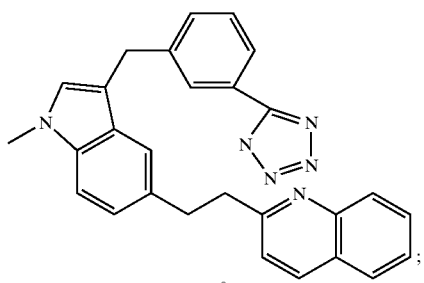
78–80° C.

-continued
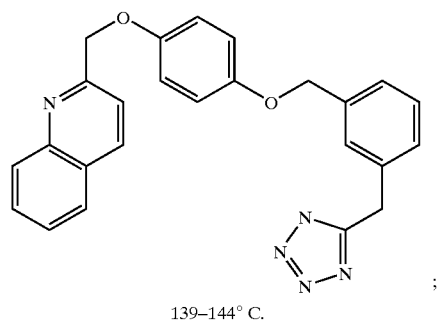
139–144° C.
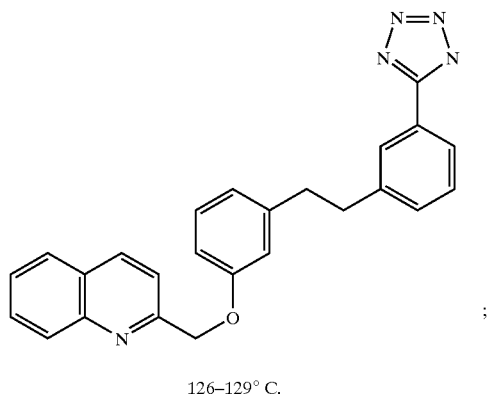
126–129° C.
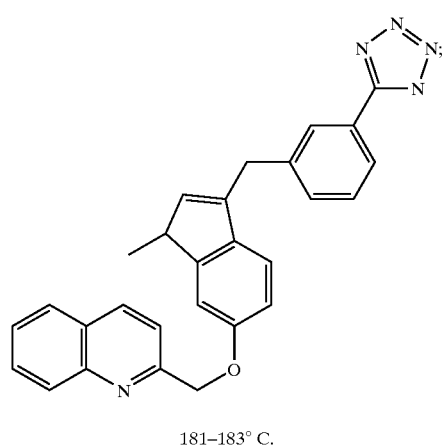
181–183° C.
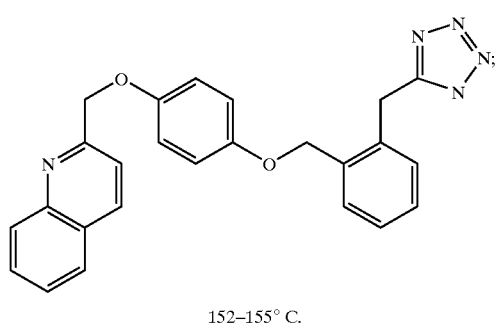
152–155° C.
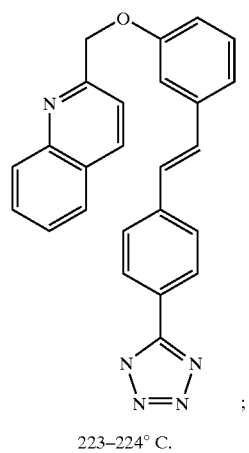
223–224° C.
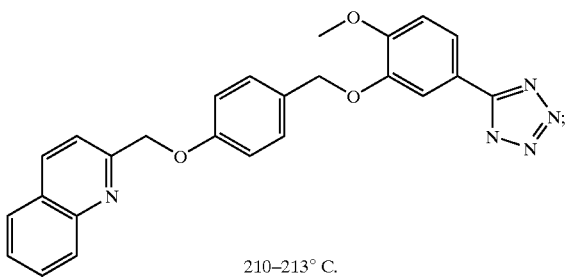
210–213° C.
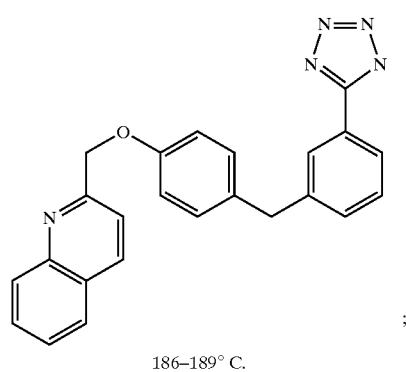
186–189° C.
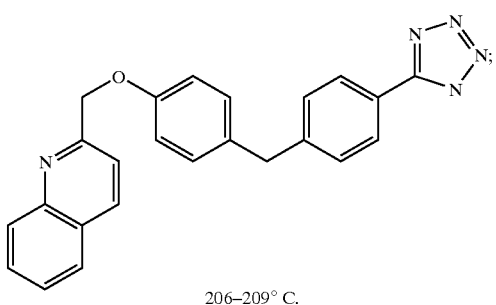
206–209° C.

-continued
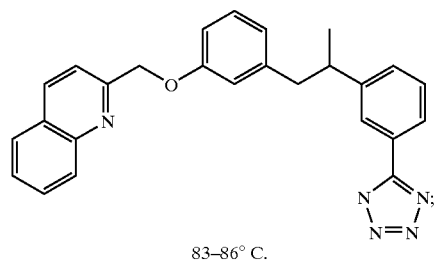
83–86° C.
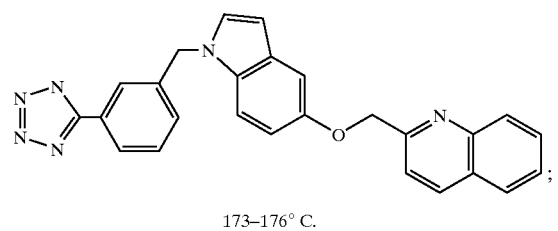
173–176° C.
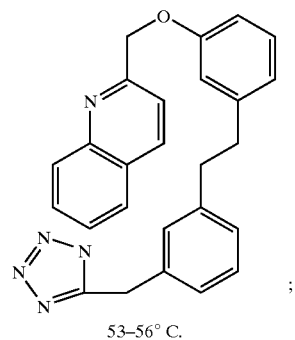
53–56° C.
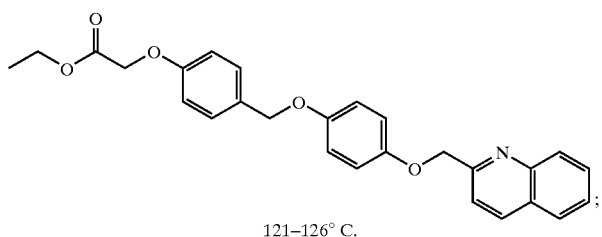
121–126° C.
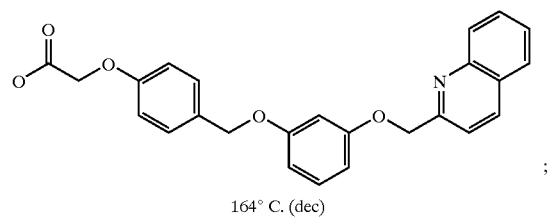
164° C. (dec)
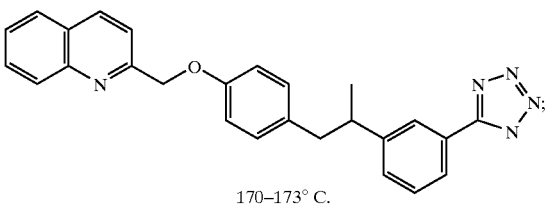
170–173° C.
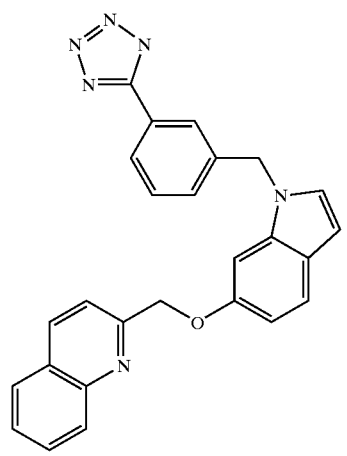
220–221° C.
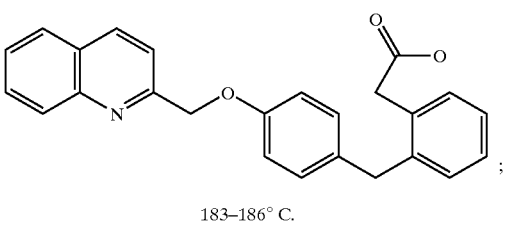
183–186° C.
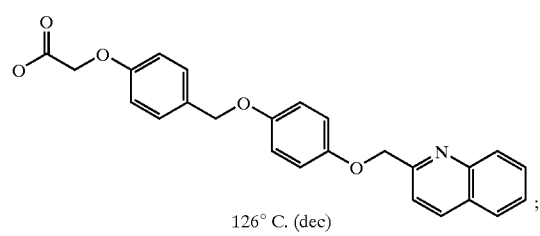
126° C. (dec)
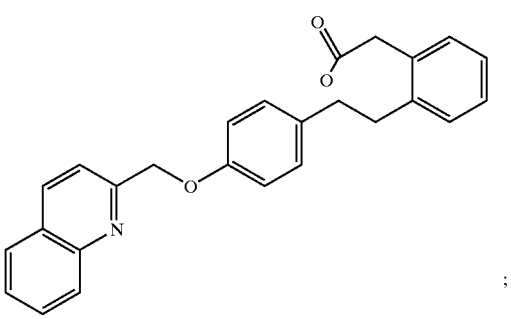
174–176° C.

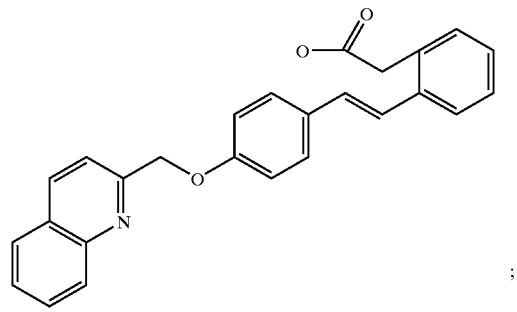
183–185° C.
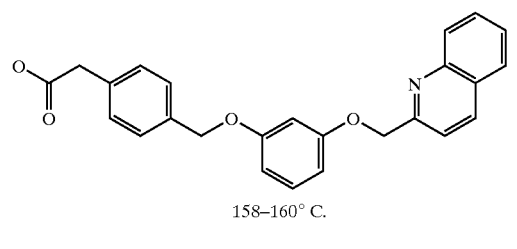
158–160° C.
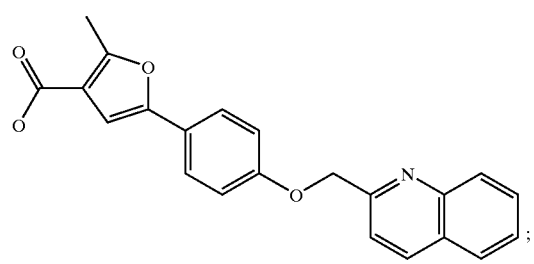
230–231° C.
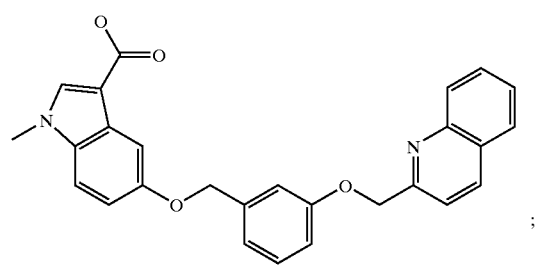
197–199° C.
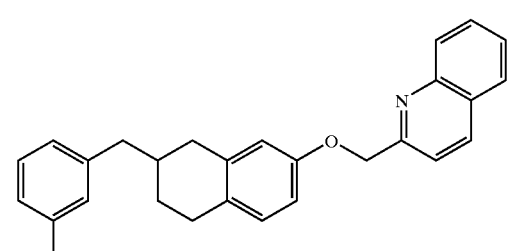
162–164° C.
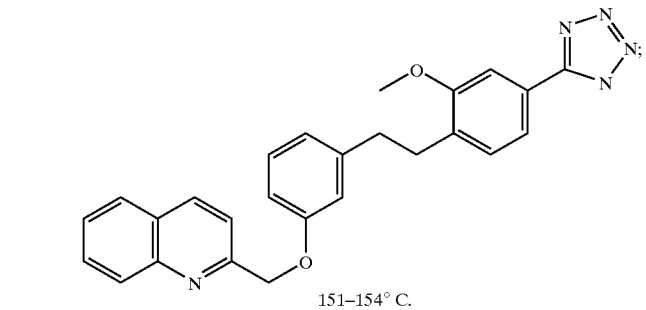
151–154° C.
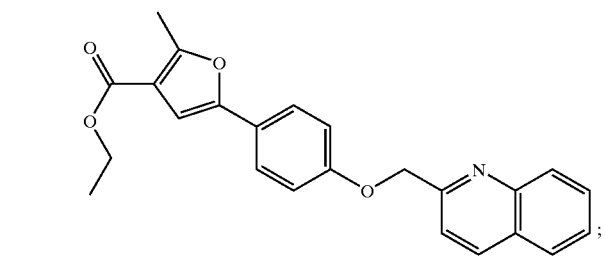
110° C.
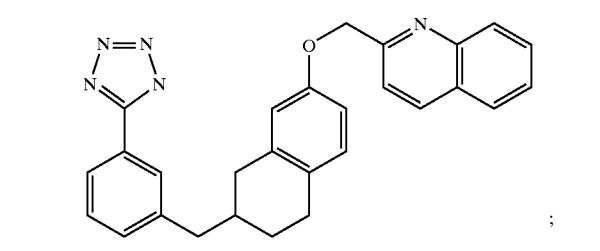
116–118° C.
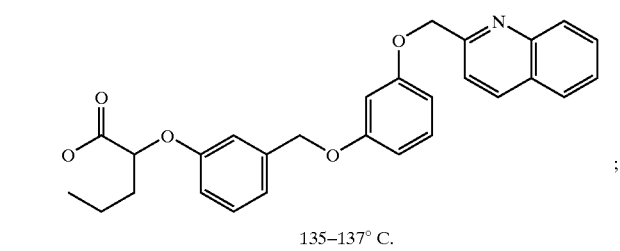
135–137° C.
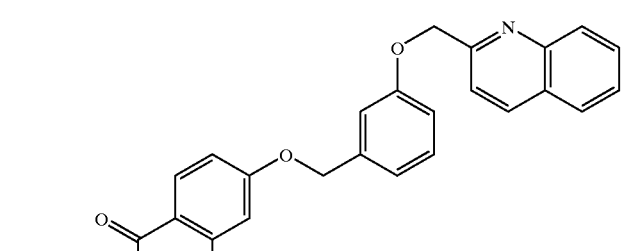
123–124° C.

-continued
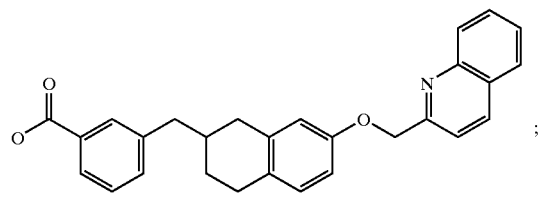
156–158° C.
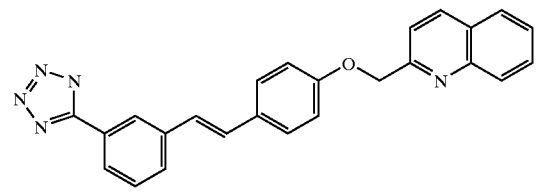
50–51° C.
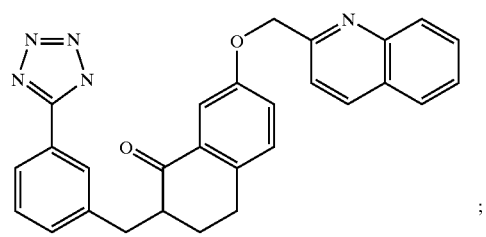
187–188° C.
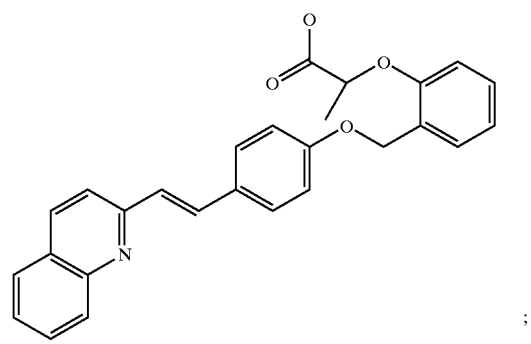
201–203° C.
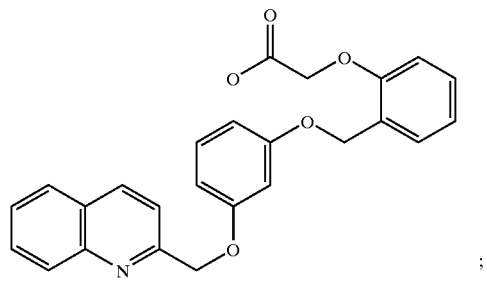
169–172° C.
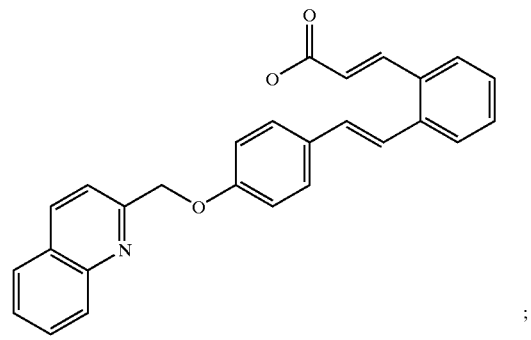
195–197° C.
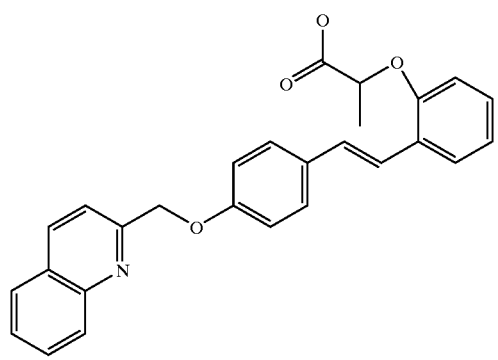
96–97° C.
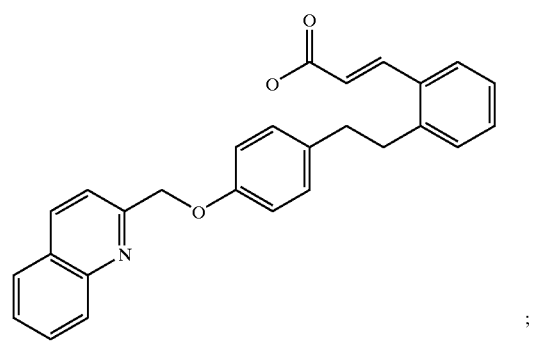
206–209° C.

-continued
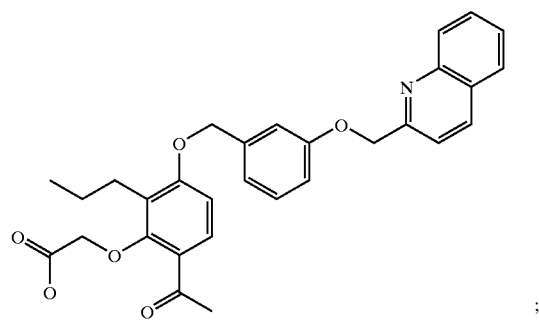
153–158° C.
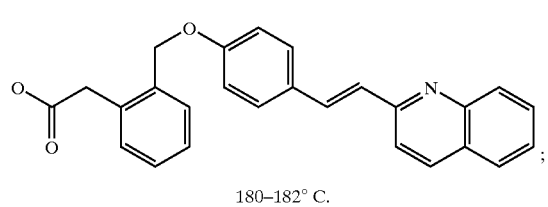
180–182° C.
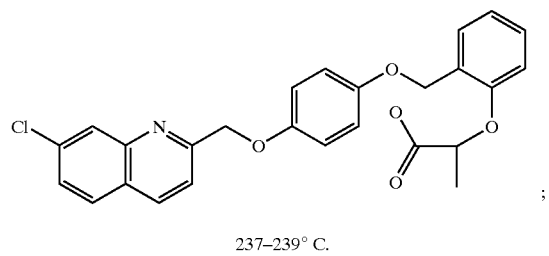
237–239° C.
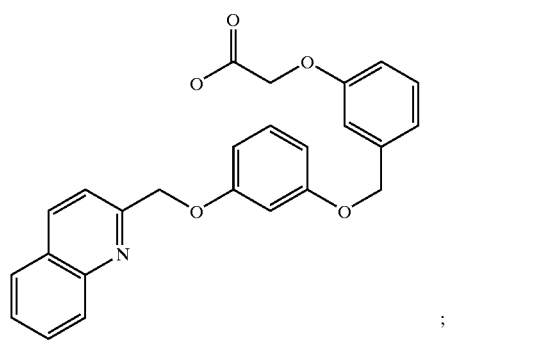
146–151° C.
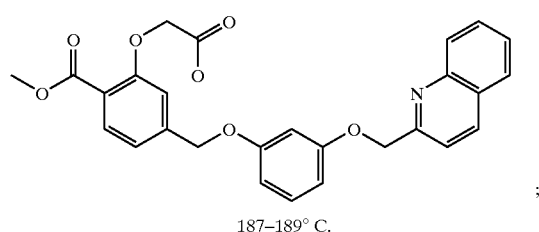
187–189° C.
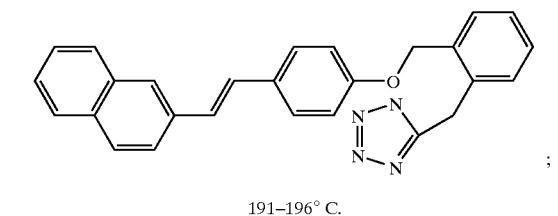
191–196° C.
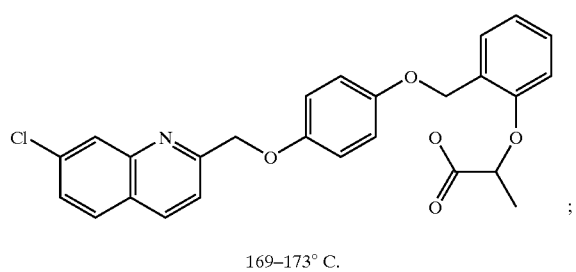
169–173° C.
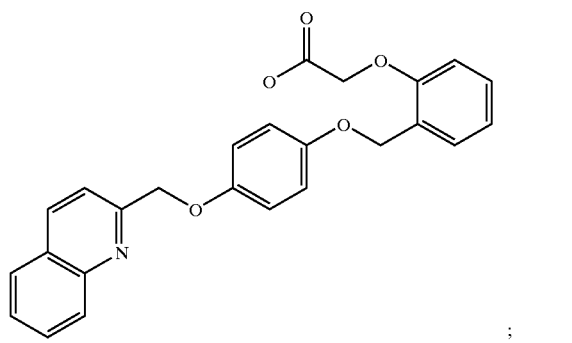
153–157° C.
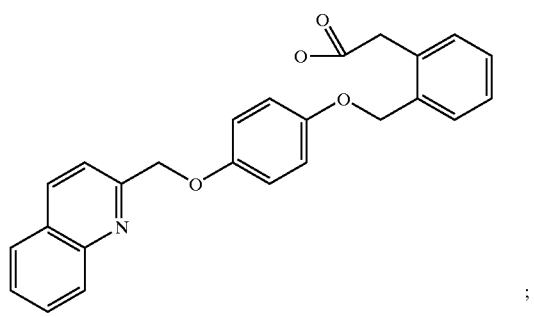
181–183° C.
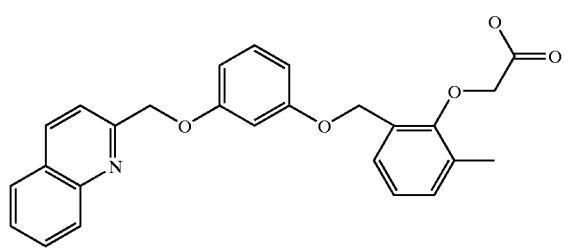
149–153° C.

-continued
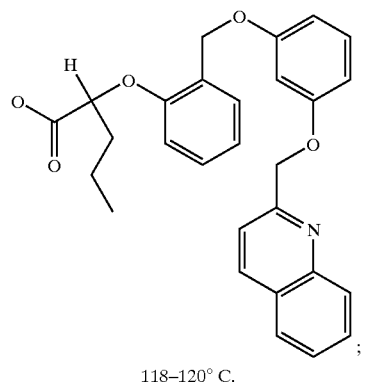
118–120° C.
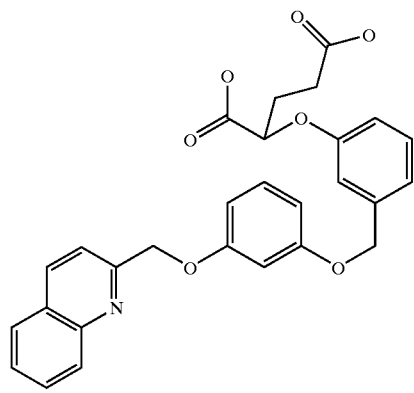
129–130° C.
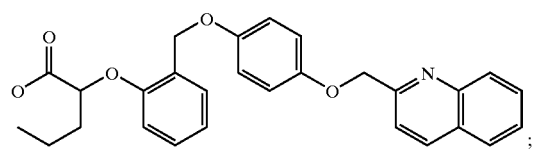
85–92° C.
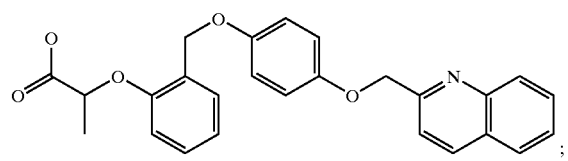
161–164° C.
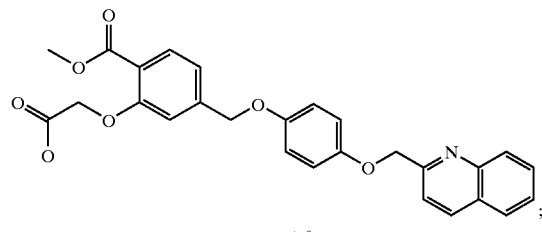
149–151° C.
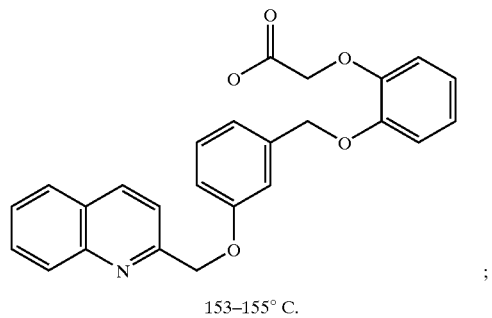
153–155° C.
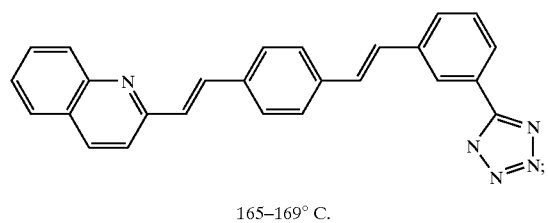
165–169° C.
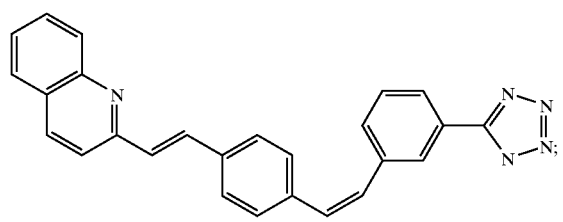
189–193° C.
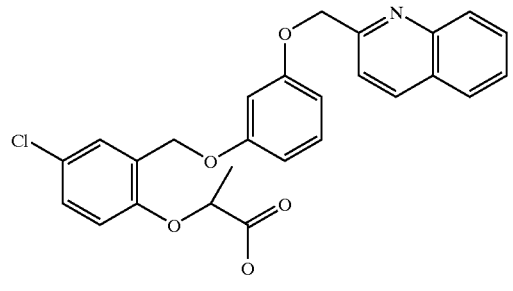
169–171° C.
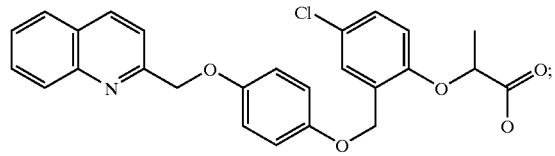
196–199° C.

-continued
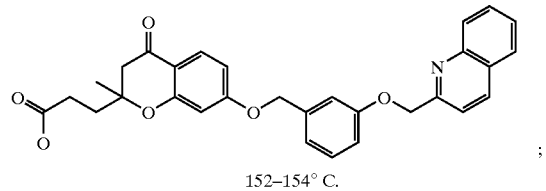
152–154° C.
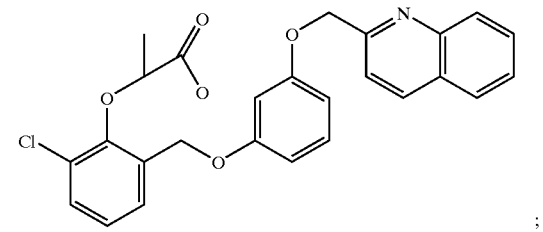
156–159° C.
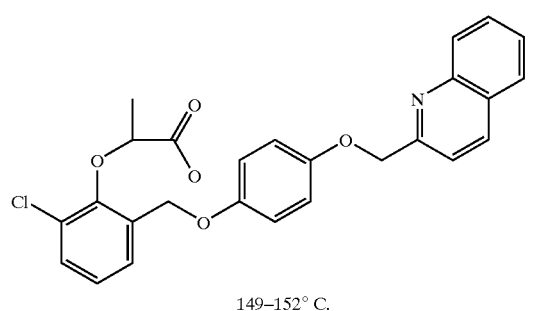
149–152° C.
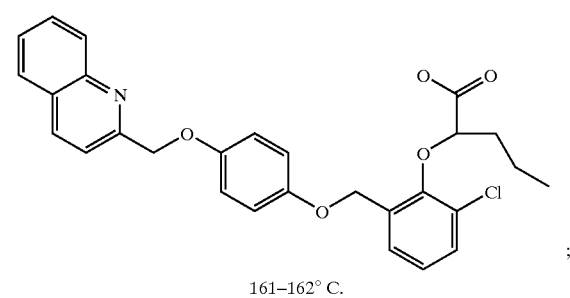
161–162° C.
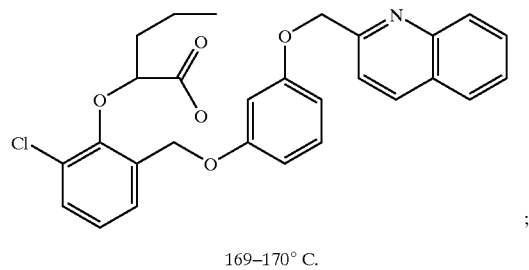
169–170° C.
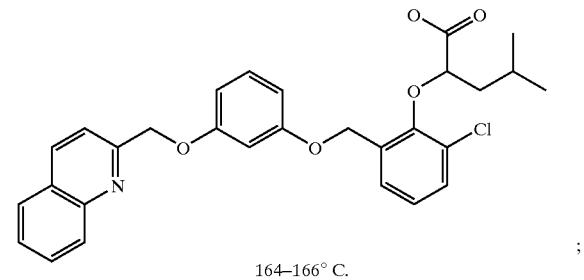
164–166° C.
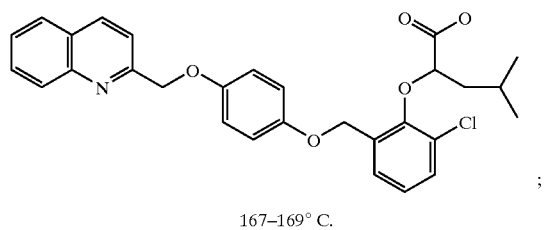
167–169° C.
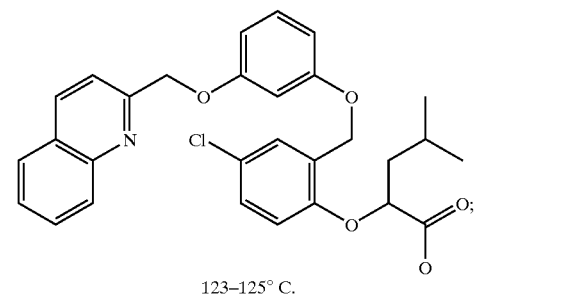
123–125° C.
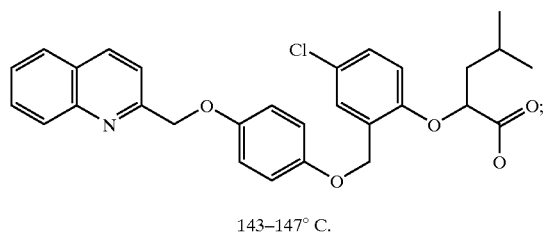
143–147° C.
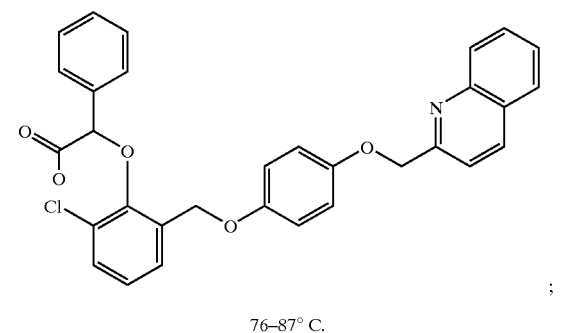
76–87° C.

-continued
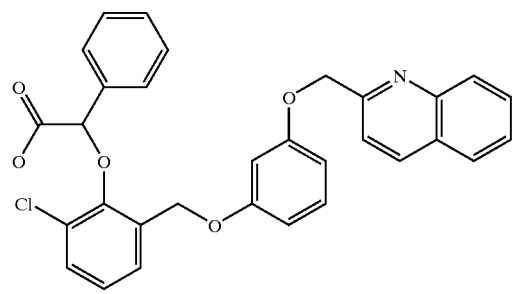
156–157° C.
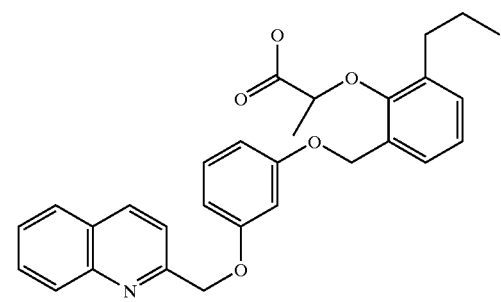
150–157° C.
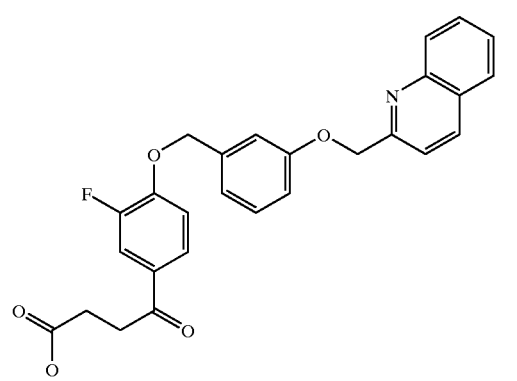
145–147° C.
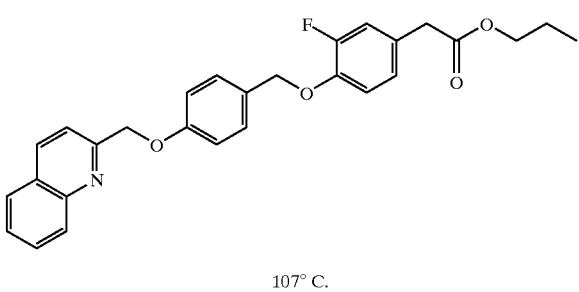
107° C.
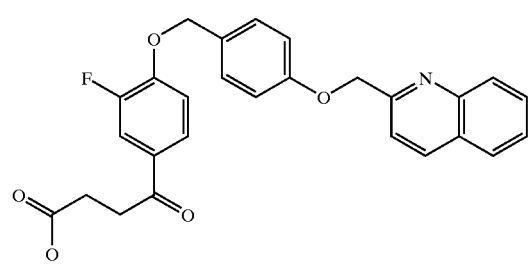
187° C. (dec)
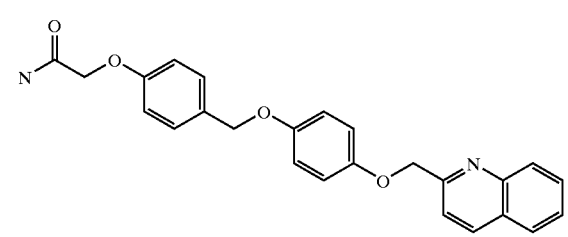
182–184° C.
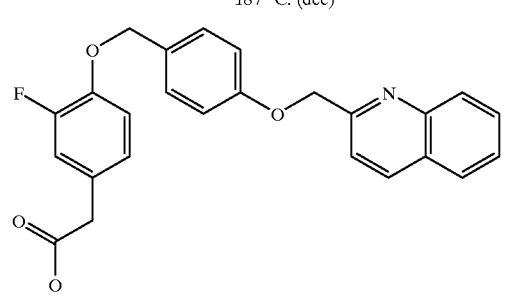
173–4° C. (dec)
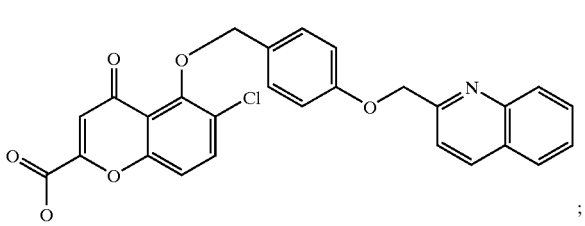
173–5° C. (dec)
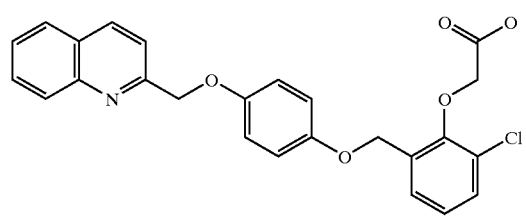
188–191° C.
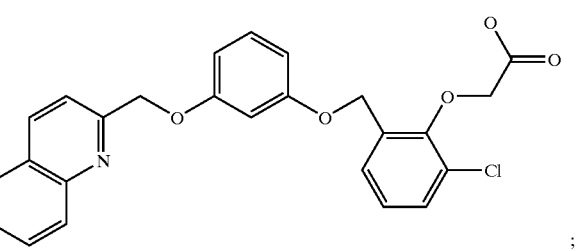
179–181° C.

-continued
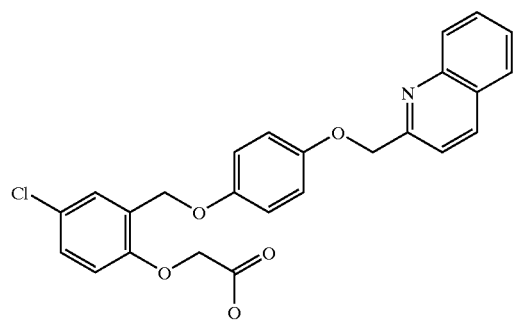
177–180° C.
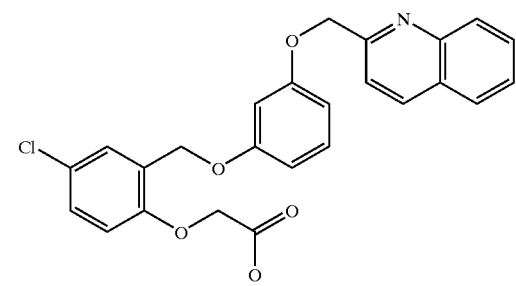
189–191° C.
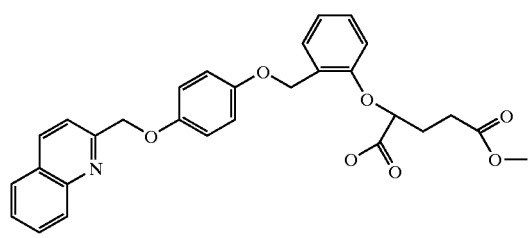
oil; CHN calc.
C30H29NO7+0.5
H2O: C 68.89, H
5.76, N 2.67; found
C 68.68, H 5.71, N
2.86
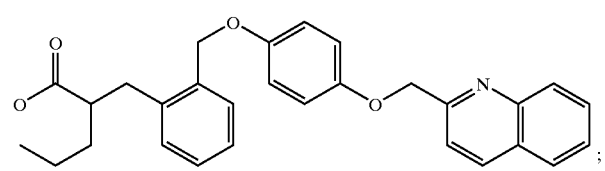
128–132° C.
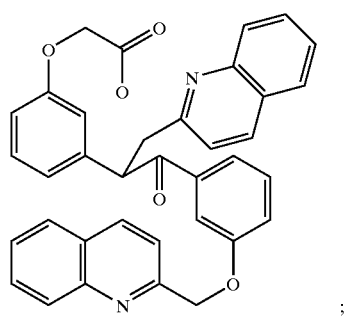
104–106° C.
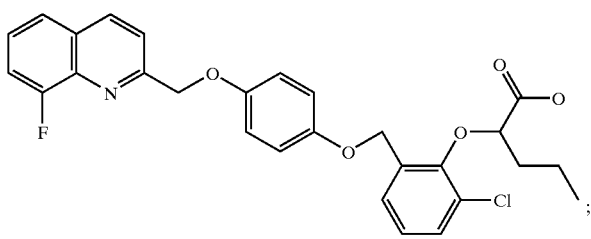
173–177° C.
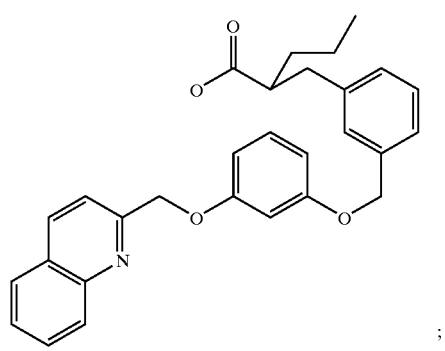
CHN calc.
C29H29NO +
0.75 H2O:
C 64.26, H 6.55,
N 2.99;
found C 73.97,
H 6.31, N 2.89
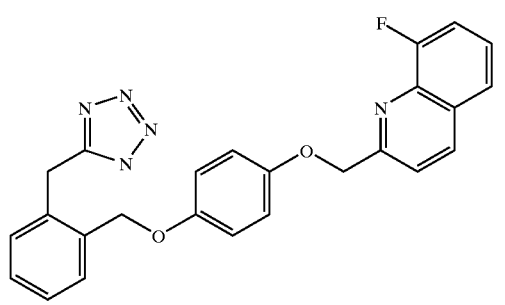
150–153° C.

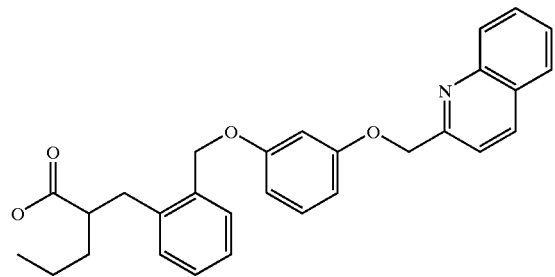

101–103° C.

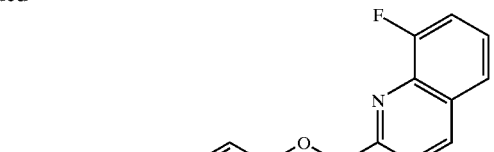

40–45° C.

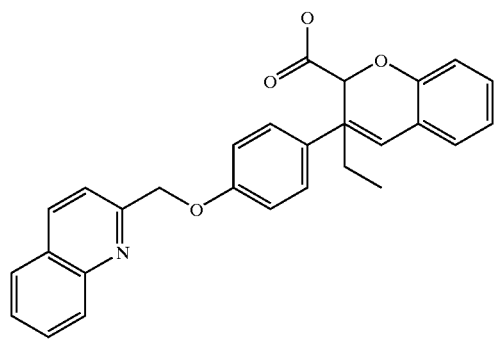

103–106° C.

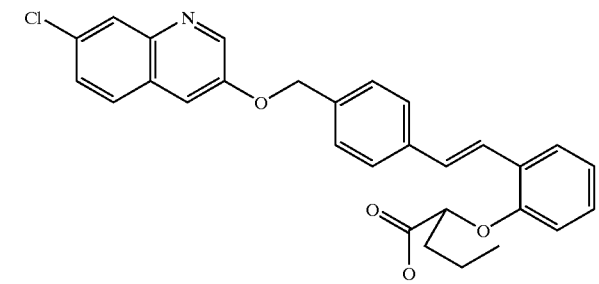

60–63° C.

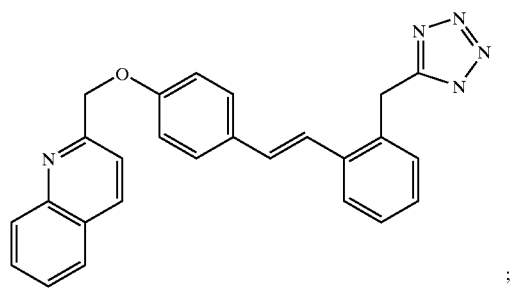

138–140° C.

Using a combination of the above Examples, various compounds may be made within the scope of this invention.

Compounds according to the invention exhibit marked pharmacological activities according to tests described in the literature which tests results are believed to correlate to pharmacological activity in humans and other mammals. The following pharmacological test results are typical characteristics of compounds of the present invention.

The compounds of the present invention have potent activity as PPAR ligand receptor binders and possess anti-diabetic, anti-lipidemic, anti-hypertensive, and an ti-arterio-sclerotic activity and are also anticipated to be effective in the treatment of diabetes, obesity and other related diseases.

hPPARα Binding Assay

The activity of the compounds of the invention as PPARα modulators may be examined in several relevant in vitro and in vivo preclinical assays, for example benchmarking with a known PPARα modulator, for example, [$^3$H]-GW2331 (2-(4-[2-(3-[2,4-Difluorophenyl]-1-heptylureido)-ethyl]phenoxy)-2-methylbutyric acid). (S. Kliewer, et al. Proc. Natl. Acad. Sci. USA 94 (1997).

Human peroxime proliferator-activated receptor a ligand binding domain(hPPARα-LBD):

A binding assay for PPARα could be carried out by the following procedure: cDNAs encoding the putative ligand binding domain of human PPARα (amino acids 167468) (Sher,T., Yi, H.-F., McBride, 0. W.& Gonzalez, F. J. (1993) Biochemistry 32, 5598–5604) are amplified by PCR (Polymerase Chain Reaction) and inserted in frame into the BamHI site of pGEX-2T plasmid (Pharmacia). The soluble fraction of GST-hPPARα fusion proteins or glutathione S-transferase (GST) alone are overexpressed in E. coli BL21(DE3)pLysS cells and purified from bacteria extracts as described in (S. Kliewer, et al. Proc. Natl. Acad. Sci. USA 94 (1997), 4318–4323).

Gel-Filtration Assays: 30 ml of 90 nM GST-hPPARα-LBD is mixed with 20 ml of 50 nM $^3$H-GW2331 with or without 5 ml of 10 mM test compounds in the binding buffer containing 10 mM Tris, 50 mM KCl, 0.05% Tween 20 and 10 mM DTT. The reaction mixtures are incubated in 96-well plates for 2 h at room temperature. 50 ml of the reaction mixtures are then loaded on a 96-well gel filtration block (following manufacture instructions)(EdgeBioSystems). The block placed on top of a clean 96-well plate is centrifuged at 1,500 rpm for 2 min. The block is discarded. 100 ml of Scintillation fluid is added to each well of the 96-well plate. After overnight equilibration, the plate is counted in the Microbeta counter (Wallac.).

Homogenous Scintillation Proximity Binding Assay. For the Scarchard analysis, glutathione coated SPA beads (1.5 mg/ml)(Amersham) are mixed with GST-hPPARα-LBD (10 mg/ml) in the binding buffer. The resulting slurry is incubated at room temperature with agitation for 15 min. 20 ml of the slurry is then added in 30 ml of binding buffer containing various amount $^3$H-GW2331(10~500 nM). Nonspecific binding is determined in the present of 100 mM of GW2331. For the competition binding assay, 20 ml of the slurry is then added in 30 ml of the binding buffer containing 75 nM of $^3$H-GW2331 and 0.03–20 mM of the test compounds. For the control experiments, the glutathione coated SPA beads (1.5 mg/ml) are coated with GST proteins (10 mg/ml). 20 ml of the slurry are mixed with 30 ml of 75 nM of $^3$H-GW2331 with or without 10 mM of GW2331. The above experiments are all performed in a 96-well plates. The sealed plates with the reaction mixtures are allowed to equilibrate for 2 h and counted in the Microbeta counter (Wallac.).

hPPARγ Binding Assay

The activity of the compounds of the invention as PPARγ modulators may be examined in several relevant in vitro and in vivo preclinical assays, for example benchmarking with a known PPARγ modulator, for example, [$^3$H]-BRL 49853 (Lehman L. J. et al, J. Biol. Chem. 270, 12953–12956; Lehman L. J. et al, J. Biol. Chem. 272, 3406–3410 (1997), and Nichols, J. S.; et al Analytical Biochemistry 257, 112–119(1998)).

Human Peroxime Proliferator-Activated Receptor a Ligand Binding Domain(hPPARγ-LBD).

A binding assay for PPARγ could be carried out by the following procedure: cDNAs encoding the putative ligand binding domain of human PPARγ (amino acids 176477) (Green, M. E. et al. Gene expression 281–299(1995)) are amplified by PCR (polymerase chain reaction) and inserted in frame into the BamHI site of pGEX-2T plasmid (Pharmacia). The soluble fraction of GST-hPPARγ fusion proteins or glutathione S-transferase (GST) alone are overexpressed in E. coli BL21 (DE3)pLysS cells and purified from bacteria extracts.

Binding Assay: The fusion proteins, GST-PPARγ-LBD in PBS (5 mg/100 ml/well) are incubated in the glutathione coated 96 well plates for 4 hours. Unbound proteins are then discarded and the plates are washed two times with the wash buffer (10 mM Tris, 50 mM KCl and 0.05% Tween-20). 100 ml of reaction mixtures containing 60 nM of $^3$H-BRL-49853 and 10 mM of the testing compounds (10 ml of 0.1 mM compounds from each well of the child plates) in the binding buffer (10 mM Tris, 50 mM KCl and 10 mM DTT) are added and incubated at room temperature for 2.5 h. The reaction mixtures are discarded and the plates are washed two times with the wash buffer. 100 ml of scintillation fluid is added to each well and plates are counted on β-counter.

hPPARδ Binding Assay

The activity of the compounds of the invention as PPARδ modulators may be examined in several relevant in vitro and in vivo preclinical assays (See references WO 97/28149; Brown P. et al Chemistry & Biology, 4, 909–18, (1997)), for example benchmarking with a known PPARδ modulator, for example [$^3$H$_2$] GW2433 or [$^3$H$_2$] Compound X

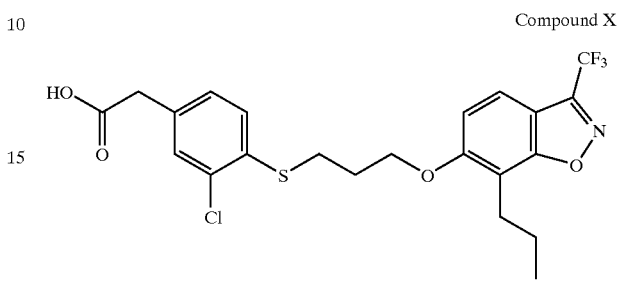

Compound X

The hPPARδ binding assay comprises the steps of:

(a) preparing multiple test samples by incubating separate aliquots of the receptor hPPARδ with a test compound in TEGM containing 5–10% COS-1 cell cytoplasmic lysate and 2.5 nM labeled ([$^3$H]Compound X, 17 Ci/mmol) for a minimum of 12 hours, and preferably for about 16 hours, at 4° C., wherein the concentration of the test compound in each test sample is different, and preparing a control sample by incubating a further separate aliquot of the receptor hPPARδ under the same conditions but without the test compound; then (b) removing unbound ligand by adding dextran/gelatin-coated charcoal to each sample while maintaining the samples at 4° C. and allowing at least 10 minutes to pass, then (c) subjecting each of the test samples and control sample from step (b) to centrifugation at 4° C. until the charcoal is pelleted; then (d) counting a portion of the supernatant fraction of each of the test samples and the control sample from step (c) in a liquid scinitillation counter and analyzing the results to determine the IC$_{50}$ of the test compound.

In the hPPARδ binding assay, preferably at least four test samples of varying concentrations of a single test compound are prepared in order to determine the IC$_{50}$.

The compounds useful according to the invention can be administered to a patient in a variety of forms adapted to the chosen route of administration, i.e., orally, or parenterally. Parenteral administration in this respect includes administration by the following routes: intravenous, intramuscular, subcutaneous, intraocular, intrasynovial, transepthelially including transdermal, opthalmic, sublingual and buccal; topically including opthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be from about 2% to about 6% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropyl-cellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds useful according to this invention may be administered to a patient alone or in combination with pharmaceutically acceptable carriers, as noted above, the proportion of which is determined by the solubility and chemical nature of the compound, chosen route of administration and standard pharmaceutical practice.

The physician will determine the dosage of the present therapeutic agents which will be most suitable for prophylaxis or treatment and it will vary with the form of administration and the particular compound chosen, and also, it will vary with the particular patient under treatment. He will generally wish to initiate treatment with small dosages by small increments until the optimum effect under the circumstances is reached. The therapeutic dosage will generally be from 0.1 to 100 mM/day or from about 0.1 mg to about 50 mg/kg of body weight per day, or 10 mg to about 50 mg/kg of body weight per day, or more preferably 30 mg to about 50 mg/kg of body weight per day, and higher, although it may be administered in several different dosage units. Higher dosages are required for oral administration.

The compounds useful according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

One skilled in the art will readily appreciate that the present invention is well adapted to carry out the objects of the invention and obtain the ends and advantages mentioned, as well as those inherent therein. The compounds, compositions and methods described herein are presented as representative of the preferred embodiments, or intended to be exemplary and not intended as limitations on the scope of the present invention.

What is claimed is:

1. A compound of formula I (I)

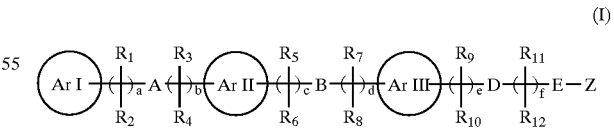

wherein:

is quinoxalinyl, quinazolinyl, benzoxazolyl, benzimidazolyl, benzothiazolyl, benzofuranyl, benzothiophenyl, oxazolyl, thiazolyl, oxadiazolyl, isoxazolyl, imidazolyl, pyrazolyl, thiadiazolyl, triazolyl, pyridyl, pyrimidinyl, pyrazinyl or pyridazinyl, which is optionally substituted by one or more ring system substituents;

and

are, independently, aryl, which are optionally substituted by one or more ring system substituents;

A is —O—, —S—, —SO—, —SO$_2$—, —NR$_{13}$—, —C(O)—, —N(R$_{14}$)C(O)—, —C(O)N(R$_5$)—, —N(R$_{14}$)C(O)N(R$_{15}$)—, —C(R$_{14}$)=N—, a chemical bond,

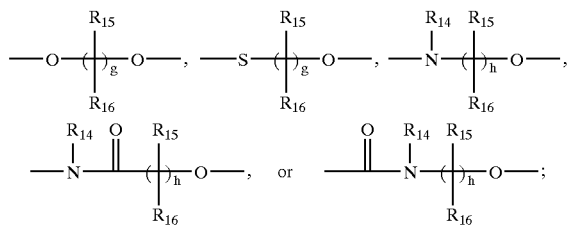

B is —O—, —S—, —SO—, —SO$_2$—, ethynylene, —C(O)—, —N(R$_{18}$)C(O)—, or —C(O)NR$_{18}$—;

D is —O—, —S—, —NR$_{19}$—, a chemical bond, ethynylene, —N(R$_{20}$)C(O)—, —C(O)—, or —C(O)N(R$_{20}$)—;

E is a chemical bond or an ethylene group;

a is 0–4;
b is 0–4;
c is 0–4;
d is 0–5;
e is 0–4;
f is 0–6;
g is 1–4;
h is 1–4;

R$_1$, R$_3$, R$_5$, R$_7$, R$_9$, and R$_{11}$, are independently hydrogen, halogen, alkyl, carboxyl, alkoxycarbonyl or aralkyl;

R$_2$, R$_4$, R$_6$, R$_8$, R$_{10}$ and R$_{12}$, are independently —(CH$_2$)$_q$—X;

q is 0–3;

X is hydrogen, halogen, alkyl, alkenyl, cycloalkyl, heterocyclyl, aryl, heteroaryl, aralkyl, heteroaralkyl, hydroxy, alkoxy, aralkoxy, heteroaralkoxy, carboxyl, alkoxycarbonyl, tetrazolyl, acyl, acylHNSO$_2$—, —SR$_{23}$, Y$^1$Y$^2$N— or Y$^3$Y$^4$NCO—;

Y$^1$ and Y$^2$ are independently hydrogen, alkyl, aryl, aralkyl or heteroaralkyl, or one of Y$^1$ and Y$^2$ is hydrogen or alkyl and the other of Y$^1$ and Y$^2$ is acyl or aroyl;

Y$^3$ and Y$^4$ are independently hydrogen, alkyl, aryl, aralkyl or heteroaralkyl;

Z is R$_{21}$O$_2$C—, R$_{21}$OC—, cyclo-imide, —CN, R$_{21}$O$_2$SHNCO—, R$_{21}$O$_2$SHN—, (R$_{21}$)$_2$NCO—, R$_{21}$O—2,4-thiazolidinedionyl, or tetrazolyl; and R$_{21}$ is hydrogen, alkyl, aryl, cycloalkyl, or aralkyl;

R$_{13}$, R$_{19}$ and R$_{23}$ are independently R$_{22}$OC—, R$_{22}$NHOC—, hydrogen, alkyl, aryl, heteroaryl, cycloalkyl, heterocyclyl, heteroaralkyl, or aralkyl;

R$_{14}$, R$_{15}$, R$_{16}$, R$_{18}$ and R$_{20}$ are independently hydrogen, alkyl, aralkyl, carbonyl, or alkoxycarbonyl;

or R$_{14}$, and R$_{15}$ taken together with the carbon and nitrogen atoms through which they are linked form a 5 or 6-membered azaheterocyclyl group; and R$_{22}$ is hydrogen, alkyl, aryl, heteroaryl, cycloalkyl, heterocyclyl, heteroaralkyl, or aralkyl; or a pharmaceutically acceptable salt thereof, an N-oxide thereof, a hydrate thereof or a solvate thereof;

wherein

"alkyl," when used to designate an alkyl group per se or when used as an alkyl component of any other group, is an aliphatic hydrocarbon group which is straight or branched having 1 to about 20 carbon atoms and is optionally substituted by one or more alkyl group substituents;

"aryl" is an aromatic monocyclic or multicyclic ring system of about 6 to about 14 carbon atoms, which is optionally substituted by one or more ring system substituents;

"heteroaryl" is an aromatic monocyclic or multicyclic ring system of about 5 to about 14 carbon atoms, in which at least one of the carbon atoms in the ring system is replaced by nitrogen, oxygen or sulfur, which is optionally substituted by one or more ring system substituents;

"heterocyclyl" is a non-aromatic saturated monocyclic or multicyclic ring system of 3 to about 10 carbon atoms, in which at least one of the carbon atoms in the ring system is replaced by nitrogen, oxygen or sulfur, which is optionally substituted by one or more ring system substituents;

"heteroaralkyl" is a heteroaryl-alkyl group, wherein the heteroaryl and alkyl groups are as defined above;

an "alkyl group substituent" is halo, carboxy, cycloalkyl, cycloalkenyl, heterocyclyl, heterocyclenyl, aryl, alkoxy, alkoxycarbonyl, aralkoxycarbonyl, heteroaralkoxycarbonyl, or Y$^1$Y$^2$NCO—, wherein Y$^1$ and Y$^2$ are independently hydrogen, alkyl, aryl, aralkyl or heteroaralkyl, or Y$^1$ and Y$^2$ taken together with the nitrogen atom to which Y$^1$ and Y$^2$ are attached form heterocyclyl wherein the substituents may contain further alkyl group substituents or ring system substituents as recited herein; and a "ring system substituent" is alkyl, cycloalkyl, heterocyclyl, aryl, heteroaryl, aralkyl, heteroaralkyl, hydroxy, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, fused cycloalkyl, fused cycloalkenyl, fused heterocyclyl, fused heterocyclenyl, arylazo, heteroarylazo, R$^a$R$^b$N—, R$^c$R$^d$NCO—, R$^c$O$_2$CN—, or R$^c$R$^d$NSO$_2$— wherein R$^a$ and R$^b$ are independently hydrogen, alkyl, aryl, aralkyl or heteroaralkyl, or one of R$^a$ and R$^b$ is hydrogen or alkyl and the other of R$^a$ and R$^b$ is aroyl or heteroaroyl, and R$^c$ and R$^d$ are independently hydrogen, alkyl, aryl, heteroaryl, cycloalkyl, cycloalkenyl, heterocyclyl, heterocyclenyl, aralkyl or heteroaralkyl and, where the ring is cycloalkyl, cycloalkenyl, heterocyclyl or heterocyclenyl, the ring system substituent may also include methylene, oxo and thioxo on carbon atoms thereof wherein the substituents may contain further alkyl group substituents or ring system substituents as recited herein.

2. A compound according to claim 1 wherein

is optionally substituted quinoxalinyl, quinazolinyl, benzoxazolyl, benzimidazolyl, benzothiazolyl, oxazolyl, thiazolyl, oxadiazolyl, isoxazolyl, imidazolyl, pyrazolyl, thiadiazolyl, triazolyl, pyridyl, pyrimidinyl, pyrazinyl or pyridazinyl.

3. A compound according to claim 1 wherein a=1, 2 or 3; $R_1$ and $R_2$ are hydrogen; A is —O—; and b=0.

4. A compound according to claim 1 wherein c=0 or 1; $R_5$ and $R_6$ are hydrogen; B is —O—; and d=0 or 1.

5. A compound according to claim 1 wherein e=0; f=0 or 1; D and E is a chemical bond; Z is tetrazolyl, $NH_2CO$— or —$CO_2R_{21}$; and $R_{21}$ is hydrogen or lower alkyl.

6. A compound according to claim 1 wherein e=0; f=0 or 1; D is —O— or a chemical bond; E is a chemical bond; and Z is tetrazolyl, $NH_2CO$— or —$CO_2R_{21}$;

and $R_{21}$ is hydrogen or lower alkyl.

7. A compound according to claim 1 wherein

is an unsubstituted quinozalin-2-yl, 3-substituted quinozalin-2-yl, 6-substituted quinozalin-2-yl or 3,6-disubstituted quinozalin-2-yl; unsubstituted quinozolin-2-yl, 4-substituted quinazolin-2-yl or 6-substituted quinazolin-2-yl; 2-substituted-oxazol-4-yl or 2,5 disubstituted-oxazol-4-yl; 4-substituted oxazol-2-yl or 4,5-disubstituted-oxazol-2-yl; 2-substituted thiazol-4-yl or 2,5-disubstituted thiazol-4-yl; 4-substituted thiazol-2-yl or 4,5-disubstituted-thiazol-2-yl; 5-substituted-[1,2,4]oxadiazol-3-yl; 3-substituted-[1,2,4] oxadiazol-5-yl; 5-substituted-imidazol-2-yl or 3,5-disubstituted-imidazol-2-yl; 2-substituted-imidazol-5-yl or 2,3-disubstituted-imidazol-5-yl; 3-substituted-isoxazol-5-yl; 5-substituted-isoxazol-3-yl; 5-substituted-[1,2,4] thiadiazol-3-yl; 3-substituted-[1,2,4]-thiadiazol-5-yl; 2-substituted-[1,3,4]-thiadiazol-5-yl; 2-substituted-[1,3,4]-oxadiazol-5-yl; 1-substituted-pyrazol-3-yl; 3-substituted-pyrazol-5-yl; 3-substituted-[1,2,4]-triazol-5-yl; 1-substituted-[1,2,4]-triazol-3-yl; 3-substituted pyridin-2-yl, 5-substituted pyridin-2-yl, 6-substituted pyridin-2-yl or 3,5-disubstituted pyridin-2-yl; 3-substituted pyrazin-2-yl, 5-substituted pyrazin-2-yl, 6-substituted pyrazin-2-yl or 3,5 disubstituted-pyrazin-2-yl; 5-substituted pyrimidin-2-yl or 6-substituted-pyrimidin-2-yl; 6-substituted-pyridazin-3-yl or 4,6-disubstituted-pyridazin-3-yl; unsubstituted-benzothiazol-2-yl or 5-substituted-benzothiazol-2-yl; unsubstituted benzoxazol-2yl or 5-substituted-benzoxazol-2yl; unsubstituted-benzimidazol-2-yl or 5-substituted-benzimidazol-2-yl; unsubstituted-thiophen-2-yl, 3-substituted-thiophen-2-yl, 6-substituted-thiophen-2-yl or 3,6-disubstituted-thiophen-2-yl; unsubstituted-benzofuran-2-y, 3-substituted-benzofuran-2-yl, 6-substituted-benzofuran-2-yl or 3,6-disubstituted-benzofuran-2-yl; 3-substituted-benzofuran-6-yl or 3,7-disubstituted-benzofuran-6-yl.

8. A compound according to claim 7 wherein

is substituted by a substituent selected from the group consisting of phenyl, substituted-phenyl, thienyl, substituted thienyl, cycloalkyl, straight or branched lower alkyl, fluoro, chloro, alkoxy, aralkyloxy, trifluoromethyl and trifluoromethyloxy.

9. A compound according to claim 1 wherein $R_1$ and $R_2$ are hydrogen; a=1; A is —O—; and b=0.

10. A compound of formula (Ia)

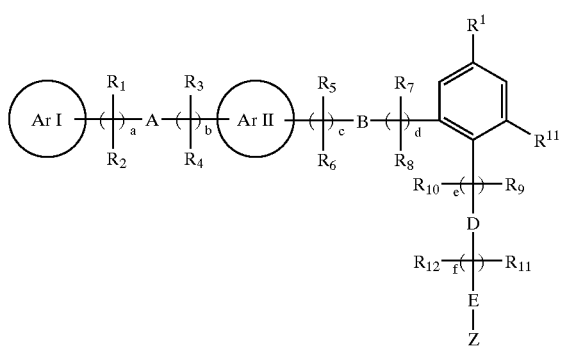

(Ia)

wherein:

is quinoxalinyl, quinazolinyl, benzoxazolyl, benzimidazolyl, benzothiazolyl, benzofuranyl, benzothiophenyl, oxazolyl, thiazolyl, oxadiazolyl, isoxazolyl, imidazolyl, pyrazolyl, thiadiazolyl, triazolyl, pyridyl, pyrimidinyl, pyrazinyl or pyridazinyl, which is optionally substituted by one or more ring system substituents;

is aryl, which is optionally substituted by one or more ring system substituents;

A is —O—, —S—, —SO—, —SO$_2$—, —NR$_{13}$—, —C(O)—, —N(R$_{14}$)C(O)—, —C(O)N(R$_{15}$)—, —N(R$_{14}$)C(O)N(R$_{15}$)—, —C(R$_{14}$)=N—, a chemical bond,

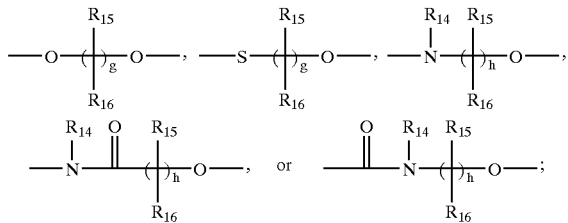

B is —O—, —S—, —SO—, —SO$_2$—, ethynylene, —C(O)—, —N(R$_{18}$)C(O)—, or —C(O)NR$_{18}$—;

D is —O—, —S—, —NR$_{19}$—, a chemical bond, ethynylene, —N(R$_{20}$)C(O)—, —C(O)—, or —C(O)N(R$_{20}$)—;

E is a chemical bond or an ethylene group;

a is 0–4;
b is 0–4;
c is 0–4;
d is 0–5;
e is 0–4;
f is 0–6;
g is 1–4;
h is 1–4;

R$_1$, R$_3$, R$_5$, R$_7$, R$_9$, and R$_{11}$, are independently hydrogen, halogen, alkyl, carboxyl, alkoxycarbonyl or aralkyl;

R$_2$, R$_4$, R$_6$, R$_8$, R$_{10}$ and R$_{12}$, are independently —(CH$_2$)$_q$—X;

q is 0–3;

X is hydrogen, halogen, alkyl, alkenyl, cycloalkyl, heterocyclyl, aryl, heteroaryl, aralkyl, heteroaralkyl, hydroxy, alkoxy, aralkoxy, heteroaralkoxy, carboxyl, alkoxycarbonyl, tetrazolyl, acyl, acylHNSO$_2$—, —SR$_{23}$, Y$^1$Y$^2$N— or Y$^3$Y$^4$NCO—;

Y$^1$ and Y$^2$ are independently hydrogen, alkyl, aryl, aralkyl or heteroaralkyl, or one of Y$^1$ and Y$^2$ is hydrogen or alkyl and the other of Y$^1$ and Y$^2$ is acyl or aroyl;

Y$^3$ and Y$^4$ are independently hydrogen, alkyl, aryl, aralkyl or heteroaralkyl;

Z is R$_{21}$O$_2$C—, R$_{21}$OC—, cyclo-imide, —CN, R$_{21}$O$_2$SHNCO—, R$_{21}$O$_2$SHN—, (R$_{21}$)$_2$NCO—, R$_{21}$O-2,4-thiazolidinedionyl, or tetrazolyl;

R' and R'' are, independently, hydrogen or ring system substituents;

R$_{21}$ is hydrogen, alkyl, aryl, cycloalkyl, or aralkyl;

R$_{13}$, R$_{19}$ and R$_{23}$ are independently R$_{22}$OC—, R$_{22}$NHOC—, hydrogen, alkyl, aryl, heteroaryl, cycloalkyl, heterocyclyl, heteroaralkyl, or aralkyl;

R$_{14}$, R$_{15}$, R$_{16}$, R$_{18}$ and R$_{20}$ are independently hydrogen, alkyl, aralkyl, carbonyl, or alkoxycarbonyl;

or R$_{14}$, and R$_{15}$ taken together with the carbon and nitrogen atoms through which they are linked form a 5 or 6-membered azaheterocyclyl group; and R$_{22}$ is hydrogen, alkyl, aryl, heteroaryl, cycloalkyl, heterocyclyl, heteroaralkyl, or aralkyl; or a pharmaceutically acceptable salt thereof, an N-oxide thereof, a hydrate thereof or a solvate thereof;

wherein

"alkyl," when used to designate an alkyl group per se or when used as an alkyl component of any other group, is an aliphatic hydrocarbon group which is straight or branched having 1 to about 20 carbon atoms and is optionally substituted by one or more alkyl group substituents;

"aryl" is an aromatic monocyclic or multicyclic ring system of about 6 to about 14 carbon atoms, which is optionally substituted by one or more ring system substituents;

"heteroaryl" is an aromatic monocyclic or multicyclic ring system of about 5 to about 14 carbon atoms, in which at least one of the carbon atoms in the ring system is replaced by nitrogen, oxygen or sulfur, which is optionally substituted by one or more ring system substituents;

"heterocyclyl" is a non-aromatic saturated monocyclic or multicyclic ring system of 3 to about 1.0 carbon atoms, in which at least one of the carbon atoms in the ring system is replaced by nitrogen, oxygen or sulfur, which is optionally substituted by one or more ring system substituents;

"heteroaralkyl" is a heteroaryl-alkyl group, wherein the heteroaryl and alkyl groups are as defined above;

an "alkyl group substituent" is halo, carboxy, cycloalkyl, cycloalkenyl, heterocyclyl, heterocyclenyl, aryl, alkoxy, alkoxycarbonyl, aralkoxycarbonyl, heteroaralkoxycarbonyl, or Y$^1$Y$^2$NCO—, wherein Y$^1$ and Y$^2$ are independently hydrogen, alkyl, aryl, aralkyl or heteroaralkyl, or Y$^1$ and Y$^2$ taken together with the nitrogen atom to which Y$^1$ and Y$^2$ are attached form heterocyclyl wherein the substituents may contain further alkyl group substituents or ring system substituents as recited herein; and a "ring system substituent" is alkyl, cycloalkyl, heterocyclyl, aryl, heteroaryl, aralkyl, heteroaralkyl, hydroxy, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, fused cycloalkyl, fused cycloalkenyl, fused heterocyclyl, fused heterocyclenyl, arylazo, heteroarylazo, R$^a$R$^b$N—, R$^c$R$^d$NCO—, R$^c$O$_2$CN—, or R$^c$R$^d$NSO$_2$— wherein R$^a$ and R$^b$ are independently hydrogen, alkyl, aryl, aralkyl or heteroaralkyl, or one of R$^a$ and R$^b$ is hydrogen or alkyl and the other of R$^a$ and R$^b$ is aroyl or heteroaroyl, and R$^c$ and R$^d$ are independently hydrogen, alkyl, aryl, heteroaryl, cycloalkyl, cycloalkenyl, heterocyclyl, heterocyclenyl, aralkyl or heteroaralkyl and, where the ring is cycloalkyl, cycloalkenyl, heterocyclyl or heterocyclenyl, the ring system substituent may also include methylene, oxo and thioxo on carbon atoms thereof wherein the substituents may contain further alkyl group substituents or ring system substituents as recited herein.

11. A compound according to claim 10 wherein
a=1 or 2;
A is —O—;
b=0;
$R_1$, $R_2$, $R_7$ and $R_8$ are independently hydrogen;

is optionally substituted phenyl;
c=0;
B is —O—;
d=1;
e=0;
f=0;
D and E are a chemical bond;
R' is hydrogen, halo or benzyloxy;
R" is lower alkyl;
Z is —$CO_2H$.

12. A compound according to claim 10 wherein:
a=1;
A is —O—;
b=0;
c=0–1;
B is —O—;
d=0 or 1, wherein c+d=1 or 2;
e=0;
f=0;
D and E are a chemical bond;
R' is hydrogen, aralkoxy, or halo;
R" is lower alkyl;
Z is —$CO_2H$.

13. A compound according to claim 10 wherein:
a=1;
A is —O—;
b=0;
c=0;
B is —O—;
d=1;
e=0;
f=0;
D and E are a chemical bond;
R' is hydrogen;
R" is lower alkyl;
Z is —$CO_2H$.

14. A compound according to claim 10 wherein:
a=1;
A is —O—;
b=0;
c=0;
B is —O—;
d=1;
e=0;
f=0;
D and E are a chemical bond;
R' is hydrogen;
R" is methyl;
Z is —$CO_2H$.

15. A compound according to claim 10 wherein:

is optionally substituted quinoxalinyl, quinazolinyl, benzoxazolyl, benzimidazolyl, benzothiazolyl, oxazolyl, thiazolyl, oxadiazolyl, isoxazolyl, imidazolyl, pyrazolyl, thiadiazolyl, triazolyl, pyridyl, pyrimidinyl, pyrazinyl or pyridazinyl;

is optionally substituted phenyl;
a=1;
A is —O—;
b=0;
c=0;
B is —O—;
d=1;
e=0;
f=0;
D and E are a chemical bond;
R' is hydrogen;
R" is lower alkyl;
Z is $CO_2H$.

16. A pharmaceutical composition comprising a pharmaceutically acceptable amount of the compound according to claim 1 and a pharmaceutically acceptable carrier.

17. A method of treating a patient suffering from a physiological disorder capable of being modulated by a compound according to claim 1 having PPAR ligand binding activity, comprising administering to the patient a pharmaceutically effective amount of the compound, or a pharmaceutically acceptable salt thereof.

18. A method according to claim 17 wherein the physiological disorder is associated with a physiological detrimental blood level of insulin, glucose, free fatty acids (FFA), or triglycerides.

19. The method according to claim 18, wherein the physiological disorder is hyperglycemia.

20. The method according to claim 19, wherein the hyperglycemia is diabetes.

21. The method according to claim 19, wherein the hyperglycemia is Type II diabetes.

22. The method according to claim 18, wherein the physiological disorder is hyperinsulinism.

23. The method according to claim 22, wherein the hyperinsulinism is Syndrome X.

24. The method according to claim 18, wherein the physiological disorder is insulin resistance.

25. The method according to claim 18, wherein the physiological disorder is a cardiovascular condition.

26. The method according to claim 25, wherein the cardiovascular condition is atherosclerosis.

27. The method according to claim 18, wherein the physiological disorder is hyperlipidemia.

28. The method according to claim 18, wherein the physiological disorder is hypertension.

29. The method according to claim 18, wherein the physiological disorder is an eating disorder.

30. The method according to claim 17 wherein the mediating is agonistic.

31. The method according to claim 17 wherein the mediating is antagonistic.

32. A method for mediating the activity of PPAR-γ receptor comprising contacting said PPAR-γ receptor with a compound of according to claim 1.

33. A pharmaceutical composition comprising a pharmaceutically acceptable amount of the compound according to claim 10 and a pharmaceutically acceptable carrier.

34. A method of treating a patient suffering from a physiological disorder capable of being modulated by a compound according to claim 10 having PPAR ligand binding activity, comprising administering to the patient a pharmaceutically effective amount of the compound, or a pharmaceutically acceptable salt thereof.

35. A method according to claim 34 wherein the physiological disorder is associated with a physiological detrimental blood level of insulin, glucose, free fatty acids (FFA), or triglycerides.

36. The method according to claim 34, wherein the physiological disorder is hyperglycemia.

37. The method according to claim 36, wherein the hyperglycemia is diabetes.

38. The method according to claim 36, wherein the hyperglycemia is Type II diabetes.

39. The method according to claim 34, wherein the physiological disorder is hyperinsulinism.

40. The method according to claim 39, wherein the hyperinsulinism is Syndrome X.

41. The method according to claim 34, wherein the physiological disorder is insulin resistance.

42. The method according to claim 34, wherein the physiological disorder is a cardiovascular disorder.

43. The method according to claim 42, wherein the cardiovascular disorder is atherosclerosis.

44. The method according to claim 34, wherein the physiological disorder is hyperlipidemia.

45. The method according to claim 34, wherein the physiological disorder is hypertension.

46. The method according to claim 34, wherein the physiological disorder is an eating disorder.

47. The method according to claim 34 wherein the mediating is agonistic.

48. The method according to claim 34 wherein the mediating is antagonistic.

49. A method for mediating the activity of PPAR receptor comprising contacting said PPAR receptor with a compound of according to claim 10.

50. A compound as claimed in claim 1, wherein the optional ring system substituents for Ar I are selected from the group consisting of phenyl, substituted-phenyl, thienyl, substituted thienyl, cycloalkyl, straight or branched lower alkyl, fluoro, chloro, alkoxy, aralkyloxy, trifluoromethyl and trifluoromethyloxy.

51. A compound as claimed in claim 11, wherein R" is methyl.

52. A compound as claimed in claim 12, wherein R" is methyl.

53. A compound as claimed in claim 1, wherein the compound is or a pharmaceutically acceptable salt, hydrate or solvate thereof.

54. A compound as claimed in claim 1, wherein the compound is or a pharmaceutically acceptable salt, hydrate or solvate thereof.

55. A compound as claimed in claim 1, wherein the compound is
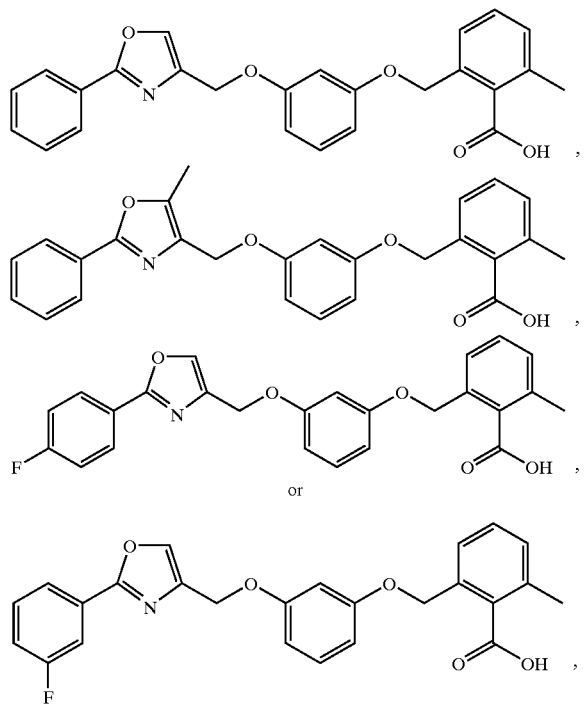
or
56. A compound as claimed in claim 1, wherein the compound is
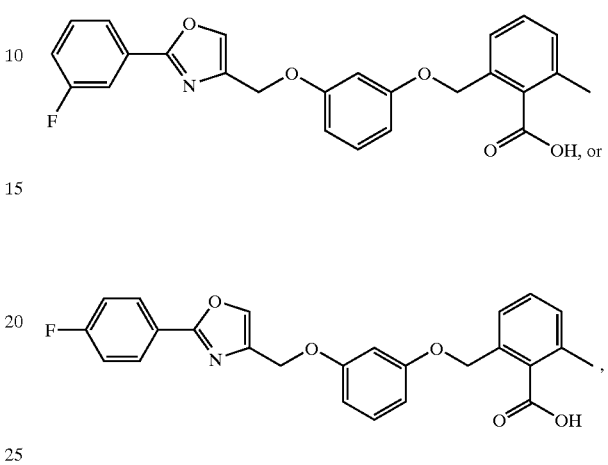
or a pharmaceutically acceptable salt, hydrate or solvate thereof.
* * * * *

UNITED STATES PATENT AND TRADEMARK OFFICE
CERTIFICATE OF CORRECTION

PATENT NO. : 7,005,440 B1
DATED : February 28, 2006
INVENTOR(S) : Zaid Jayyosi et al.

It is certified that error appears in the above-identified patent and that said Letters Patent is hereby corrected as shown below:

Column 263,
Line 25, "–C(O)N($R_5$)–," should read -- –C(O)N($R_{15}$)–, --.

Signed and Sealed this

Ninth Day of May, 2006

JON W. DUDAS
*Director of the United States Patent and Trademark Office*